United States Patent
Ichimura et al.

(10) Patent No.: US 6,525,212 B1
(45) Date of Patent: Feb. 25, 2003

(54) BIS(AMINOSTYRYL)BENZENE COMPOUNDS AND SYNTHETIC INTERMEDIATES THEREOF, AND PROCESS FOR PREPARING THE COMPOUNDS AND INTERMEDIATES

(75) Inventors: Mari Ichimura; Shinichiro Tamura; Tadashi Ishibashi; Ichinori Takada, all of Kanagawa (JP)

(73) Assignee: Sony Corporation (JP)

( * ) Notice: Subject to any disclaimer, the term of this patent is extended or adjusted under 35 U.S.C. 154(b) by 0 days.

(21) Appl. No.: 09/704,960

(22) Filed: Nov. 2, 2000

Related U.S. Application Data

(63) Continuation-in-part of application No. 09/455,724, filed on Dec. 6, 1999.

(30) Foreign Application Priority Data

Dec. 7, 1998 (JP) ............................ 10-347561
Nov. 2, 1999 (JP) ............................ 11-312069

(51) Int. Cl.[7] .................... C07C 205/35; C07C 209/78; C07C 217/76; C07C 253/30; C07C 255/60
(52) U.S. Cl. .................. 558/418; 558/419; 558/421; 564/429; 564/434
(58) Field of Search ................ 558/418, 419, 558/421; 564/429, 434

(56) References Cited

U.S. PATENT DOCUMENTS 6,022,998 A * 2/2000 Kawaguchi et al. ........ 564/434

FOREIGN PATENT DOCUMENTS

JP 11273859 A2 * 10/1998

OTHER PUBLICATIONS

Paul G. Stecher et al, The Merck Index, eighth edition, 1968, Rahway, NJ,, pp. 1226–1227.*

* cited by examiner

*Primary Examiner*—Mukund J. Shah
*Assistant Examiner*—Thomas McKenzie
(74) *Attorney, Agent, or Firm*—Sonnenschein Nath & Rosenthal

(57) ABSTRACT

A bis(aminostyryl)benzene compound of the following general formula [I] is provided

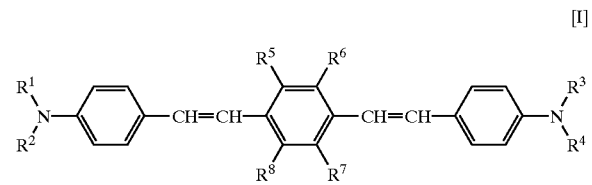

wherein $R^2$ and $R^3$ independently represent an unsubstituted aryl group, and $R^1$ and $R^4$ independently represent an aryl group, and $R^5$ to $R^8$ independently represent a cyano group or the like. A process for the preparation thereof is described wherein a 4-(N,N-diarylamino)benzaldehyde and a diphosphonic acid ester or diphosphonium salt are, for example, subjected to condensation reaction. Intermediates of the bis(aminostyryl)benzene compound are also described.

21 Claims, 40 Drawing Sheets

Example 27

Example 28

Example 31

Example 32

Example 40

Example 41

BIS(AMINOSTYRYL)BENZENE COMPOUNDS AND SYNTHETIC INTERMEDIATES THEREOF, AND PROCESS FOR PREPARING THE COMPOUNDS AND INTERMEDIATES

RELATED APPLICATION DATA

This application is a continuation-in-part of application Ser. No. 09/455,724 filed Dec. 6, 1999. This application claims priority to Japanese Application Nos. P10-347561 filed Dec. 7, 1998, and P11-312069 filed Nov. 2, 1999. All of the forgoing applications are incorporated herein by reference to the extent permitted by law.

BACKGROUND OF THE INVENTION

This invention relates to bis(aminostyryl)benzene compounds which are suitable for use as an organic luminescent material capable of developing a desired luminescent color and to synthetic intermediates thereof. The invention also relates to a process for preparing such compounds and intermediates as mentioned above.

As a candidate for flat panel displays which make use of spontaneous light, have a high response speed and have no dependence on an angle of field, attention has been recently paid to an organic electroluminescent device (EL device), and an increasing interest has been taken in organic luminescent materials for the EL device. The first advantage of the organic luminescent material resides in that the optical properties of the material can be controlled, to an extent, depending on the molecular design, so that it is possible to realize a full color organic luminescent device wherein three primary color luminescences of red, blue and green can be all created by use of the respective organic luminescent materials.

The bis(aminostyryl)benzene compound of the following general formula (A) is able to develop blue to red strong luminescences in a visible region depending on the type of introduced substituent

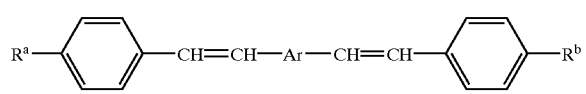

[A]

wherein Ar represents an aryl group which may have a substituent, $R^a$ and $R^b$, respectively, represent a hydrogen atom, a saturated or unsaturated hydrocarbon group, an aryl group which may have a substituent, a cyano group, a halogen atom, a nitro group or an alkoxy group and may be the same or different. Hence, this compound is utilizable not only as a material for an organic electroluminescent device, but also in various fields. These materials are sublimable in nature, with the attendant advantage that they can be formed as a uniform amorphous film according to a process such as vacuum deposition. Nowadays, although optical properties of a material can be predicted to some extent by calculation of its molecular orbital, it is as a matter of course that a technique of preparing a required material in a high efficiency is most important from the industrial standpoint.

Up to now, a large number of compounds including those of the above general formula (A) have been prepared for use as an organic luminescent material. The fluorescence or luminescence of these materials mostly covers blue to green colors, and only a few of materials which develop yellow to red luminescence has been reported [Technical Investigation Report of The Association of Electric Information Communication, organic Electronics, 17, 7 (1992), inorganic and organic Electroluminescent 96 Berlin, 101(1996) and the like]. In addition, there has never been established any process of preparing such materials in a high efficiency.

SUMMARY OF THE INVENTION

Accordingly, an object of the invention is to provide compounds, which are suitable for use as an organic luminescent material capable of developing intense luminescence which is particularly yellow to red in color, and synthetic intermediates thereof.

Another object of the invention is to provide a process for preparing the compounds and their intermediates in a high efficiency.

We made intensive studies in order to solve the above-stated problems of the prior art, and as a result, found that bis(aminostyryl)benzene compounds of the general formulae [I], [II], [III] and [IV] are able to develop intense lumninescence and are suitable as a luminescent material of yellow to red colors. At the same time, we established general and highly efficient preparation thereof.

More particularly, there is provided, according to the invention, a bis(aminostyryl)benzene compound of the following general formula [I], [II], [III] or [IV] (which may be hereinafter referred to as first compound of the invention):

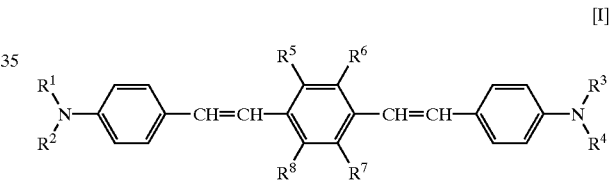

[I]

wherein $R^2$ and $R^3$ independently represent an unsubstituted aryl group, and $R^1$ and $R^4$ independently represent an aryl group represented by the following general formula (1)

(1)

in which $R^9$, $R^{10}$, $R^{11}$, $R^{12}$ and $R^{13}$ may be the same or different and at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^5$, $R^6$, $R^7$ and $R^8$ may be the same or different and at least one thereof represents a member selected from a cyano group and a nitro group, and the others independently represent a hydrogen atom, a cyano group, a nitro group or a halogen atom;

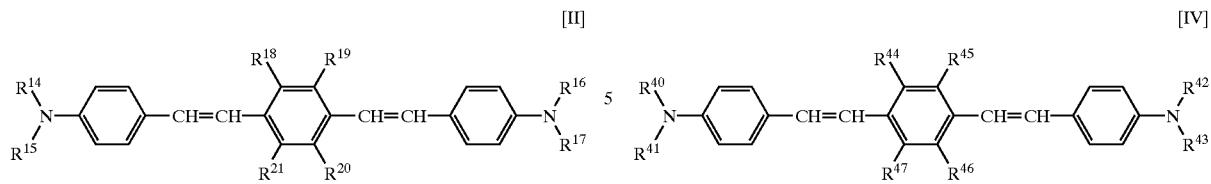

wherein $R^{14}$, $R^{15}$, $R^{16}$ and $R^{17}$ may be the same or different and independently represent an aryl group of the following general formula (2)

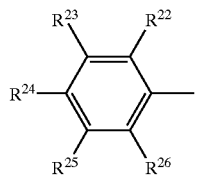

in which $R^{22}$, $R^{23}$, $R^{24}$, $R^{25}$ and $R^{26}$ may be the same or different, and at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{18}$, $R^{19}$, $R^{20}$ and $R^{21}$ may be the same or different and at least one thereof represents a member selected from a cyano group and a nitro group, and the others independently represent a hydrogen atom, a cyano group, a nitro group or a halogen atom;

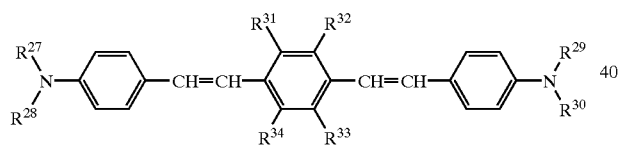

wherein at least one of $R^{27}$, $R^{28}$, $R^{29}$ and $R^{30}$ represents an aryl group of the following general formula (3) and the others independently represent an unsubstituted aryl group

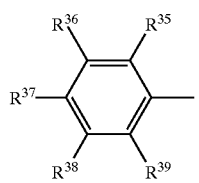

in which $R^{35}$, $R^{36}$, $R^{37}$, $R^{38}$ and $R^{39}$ may be the same or different and at least one thereof is a group selected from a dialkylamino or dialkenylamino group whose alkyl or alkenyl moiety has from 1 to 4 carbon atoms, a dicyclohexylamino group, and a diphenylamino group, and the others represent a hydrogen atom, and $R^{31}$, $R^{32}$, $R^{33}$ and $R^{34}$ may be the same or different and at least one thereof represents a group selected from a cyano group and a nitro group, and the others independently represent a hydrogen atom, a cyano group, a nitro group or a halogen atom; or

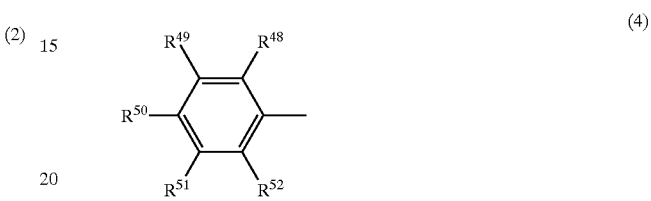

wherein $R^{41}$ and $R^{42}$ may be the same or different and independently represent an aryl group of the following general formula (4)

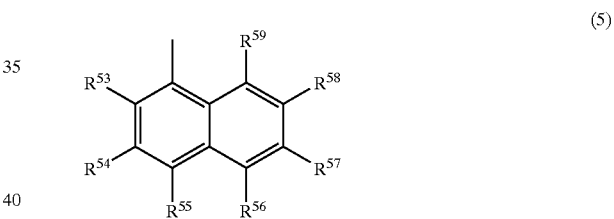

in which $R^{48}$, $R^{49}$, $R^{50}$, $R^{51}$ and $R^{52}$ may be the same or different and independently represent a hydrogen atom provided that at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{40}$ and $R^{43}$ may be the same or different and independently represent an aryl group of the following general formula (5)

in which $R^{53}$, $R^{54}$, $R^{55}$, $R^{56}$, $R^{57}$, $R^{58}$ and $R^{59}$ may be the same or different and independently represent a hydrogen atom, or at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{44}$, $R^{45}$, $R^{46}$ and $R^{47}$ may be the same or different and at least one thereof represents a member selected from a cyano group and a nitro group, and the others independently represent a hydrogen atom, a cyano group, a nitro group or a halogen atom.

The first compound of the invention can be effectively utilized as an organic luminescent material capable of developing yellow to red luminescence. These compounds are ones which have a high glass transition point and a high melting point and are excellent in electric, thermal and chemical stabilities. In addition, they are amorphous in nature, are capable of readily forming a vitreous state and can be thus subjected to vacuum deposition.

DETAILED DESCRIPTION OF THE PREFERRED EMBODIMENTS

Figure 1:
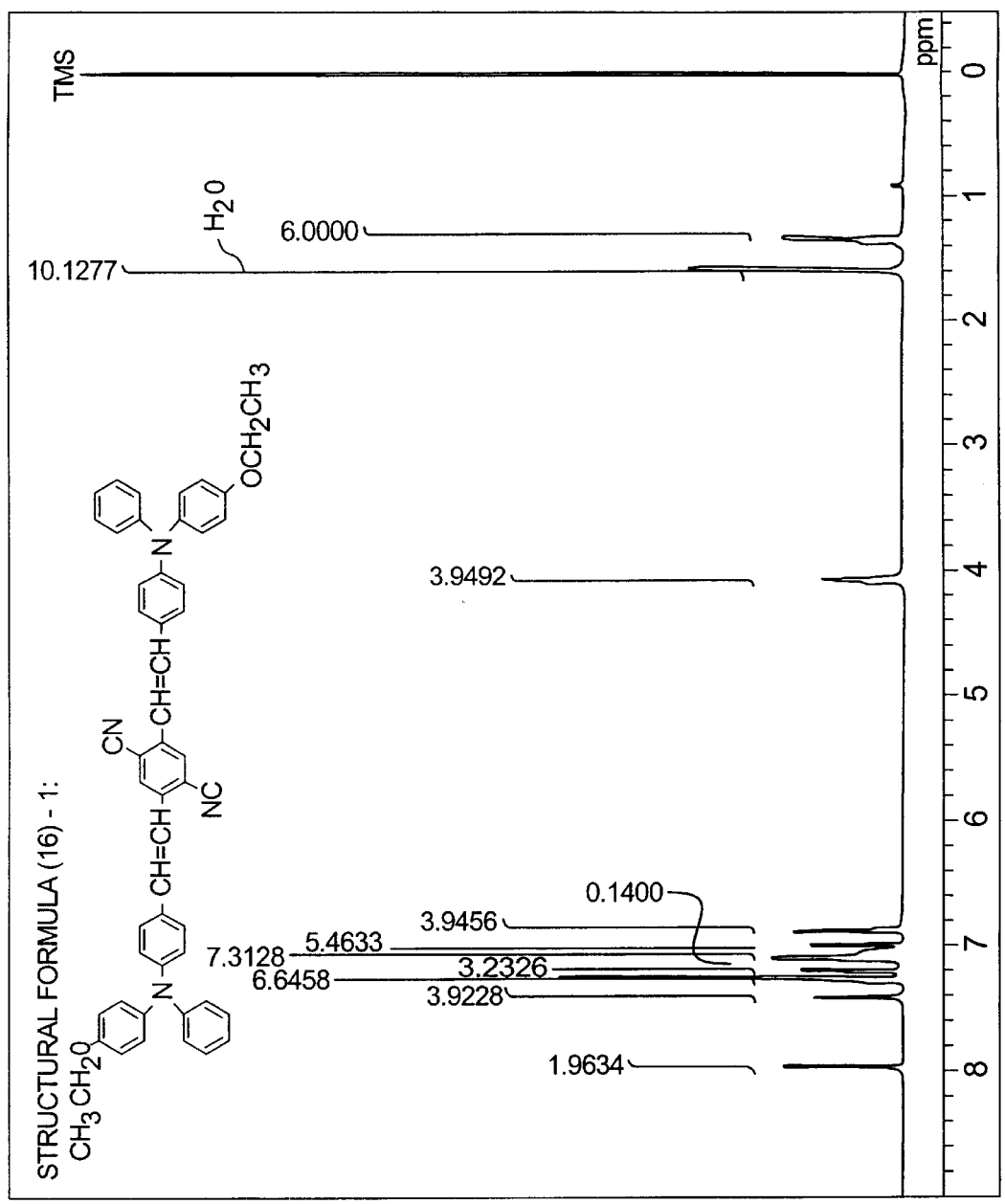
FIG. 1 is an $^1$HNMR spectral diagram of a bis (aminostyryl)benzene compound of structural formula (16)-1 of the invention.

The first inventive compounds are preferably those of the following general formula

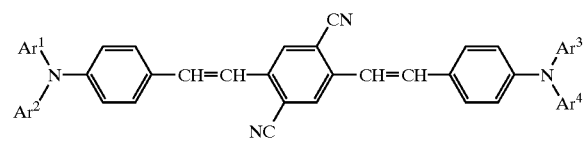

wherein $Ar^1$, $Ar^2$, $Ar^3$ and $Ar^4$ may be the same or different and independently represent an aryl group which may have a substituent, and if a substituent is present, such an aryl group is one selected from those aryl groups of the following general formulas (6), (7), (8) and (9)

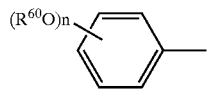
(6)

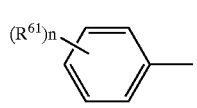
(7)

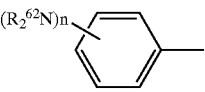
(8)

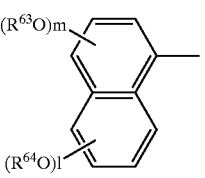
(9)

wherein $R^{60}$ represents an alkyl or alkenyl group having from 1 to 4 carbon atoms, a cyclohexyl group or a phenyl group, provided that where $Ar^1$, $Ar^2$, $Ar^3$ and $Ar^4$ are all the aryl group of the general formula (6), $R^{60}$ represents an alkyl or alkenyl group having from 1 to 4 carbon atoms, a cyclohexyl group or a phenyl group, $R^{61}$ and $R^{62}$ independently represent an alkyl or alkenyl group having from 1 to 4 carbon atoms, a cyclohexyl group or a phenyl group, $R^{63}$ and $R^{64}$ may be the same or different and independently represent an alkyl or alkenyl group having from 1 to 4 carbon atoms, a cyclohexyl group or a phenyl group, n is an integer of 0 to 5, m is an integer of 0 to 3, and l is an integer of 0 to 4.

More particularly, the first inventive compound is preferably one represented by the following general formula (9), (10), (11), (12), (13), (14), (15) or (15'):

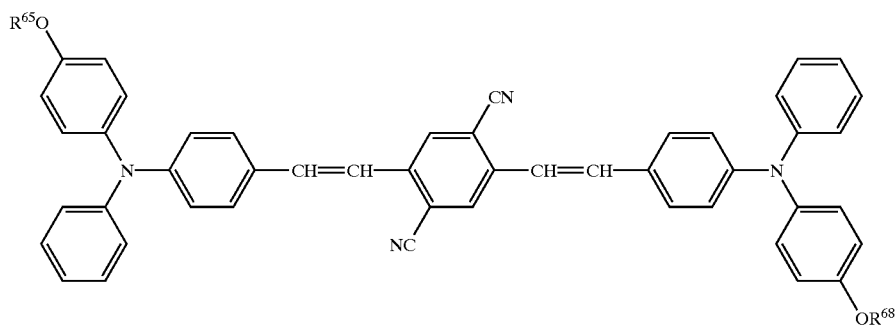
(10)

wherein $R^{65}$ represents an alkyl or alkenyl group having from 1 to 4 carbon atoms, a cyclohexyl group or a phenyl group;

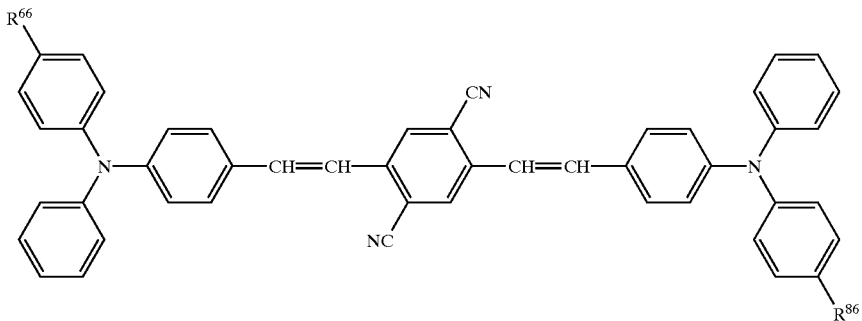
(11)
wherein $R^{66}$ represents an alkyl or alkenyl group having from 1 to 4 carbon atoms, a cyclohexyl group or a phenyl group;
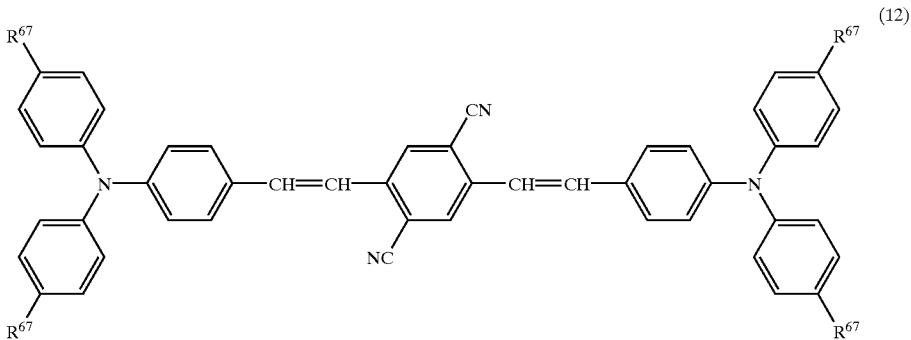
(12)
wherein $R^{67}$ represents an alkyl or alkenyl group having from 1 to 4 carbon atoms, a cyclohexyl group or a phenyl group;
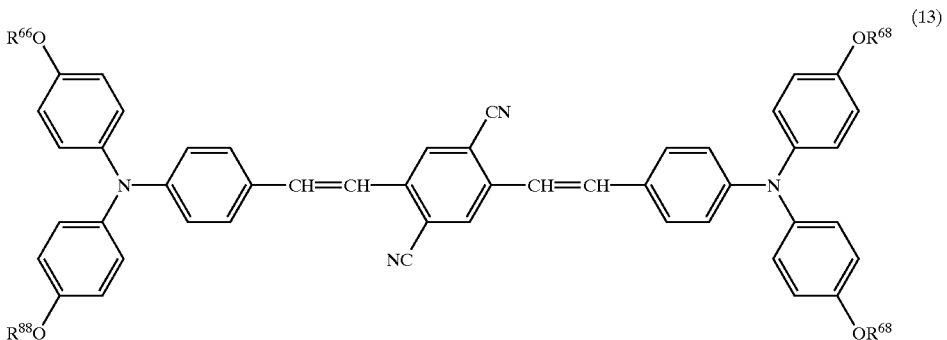
(13)
wherein $R^{68}$ represents an alkyl or alkenyl group having from 1 to 4 carbon atoms, a cyclohexyl group or a phenyl group;

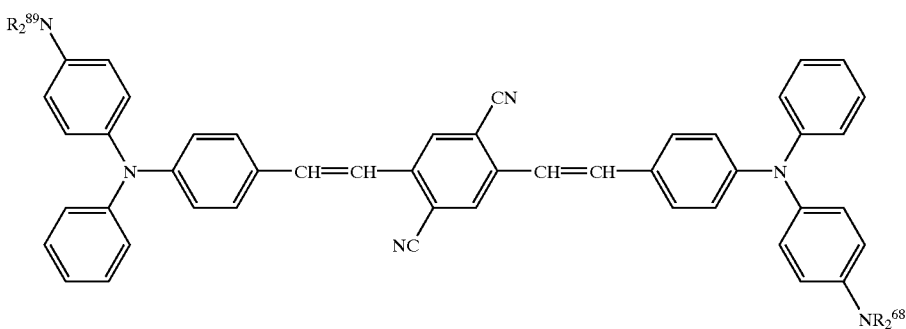

(14)

wherein $R^{69}$ represents an alkyl or alkenyl group having from 1 to 4 carbon atoms, a cyclohexyl group or a phenyl group;

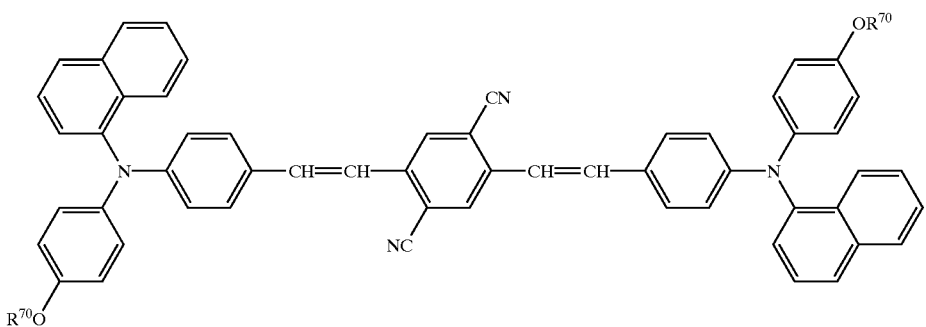

(15)

wherein $R^{70}$ represents an alkyl or alkenyl group having from 1 to 4 carbon atoms, a cyclohexyl group or a phenyl group; or

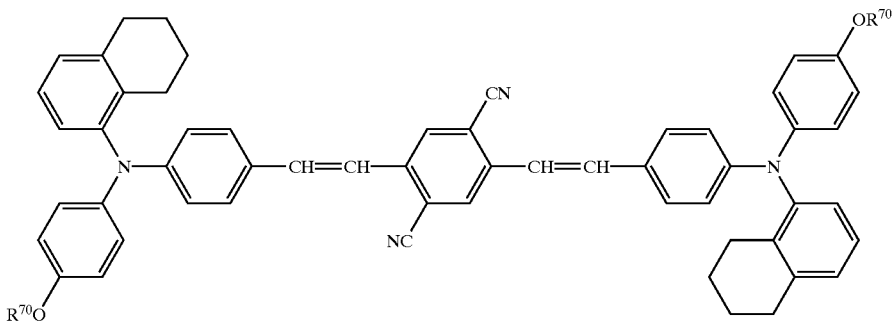

(15')

wherein $R^{70}$ represents an alkyl or alkenyl group having from 1 to 4 carbon atoms, a cyclohexyl group or a phenyl group.

More specific examples of the first inventive compounds include those of the following structural formulas (16)-1, (16)-2, (16)-3, (16)-4, (16)-5, (16)-6, (16)-7, (16)-8, (16)-9, (16)-10, (16)-11, (16)-12 and (16)-13:

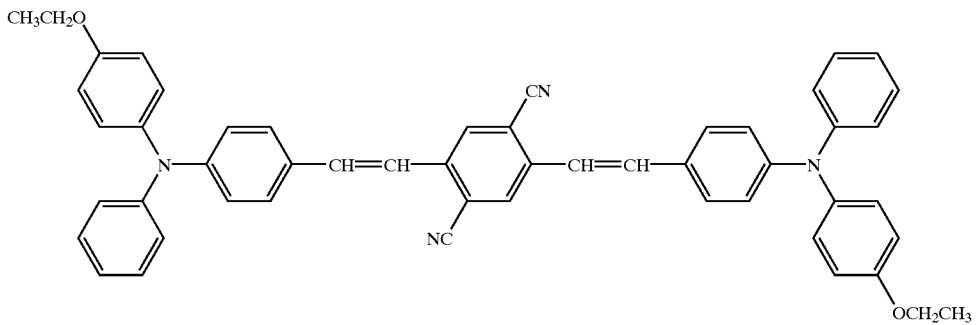
(16)-1
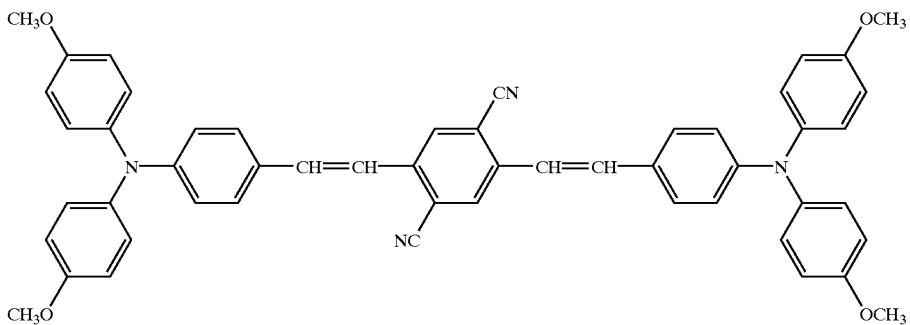
(16)-2
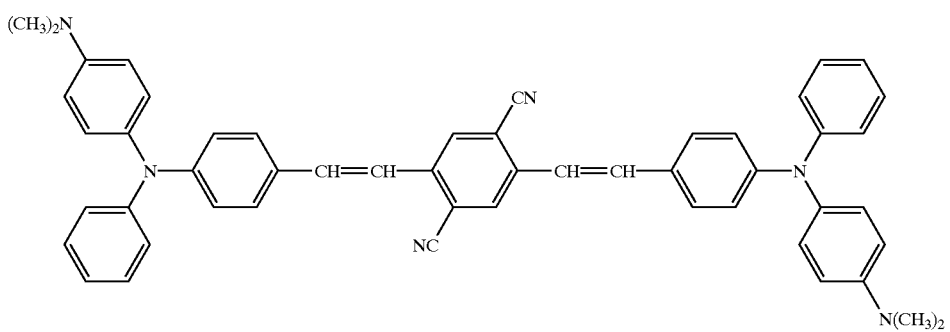
(16)-3
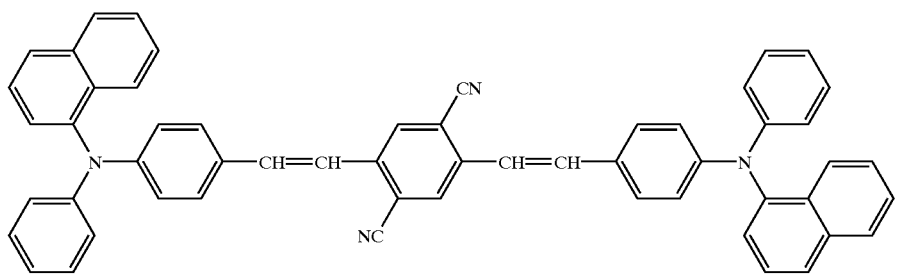
(16)-4
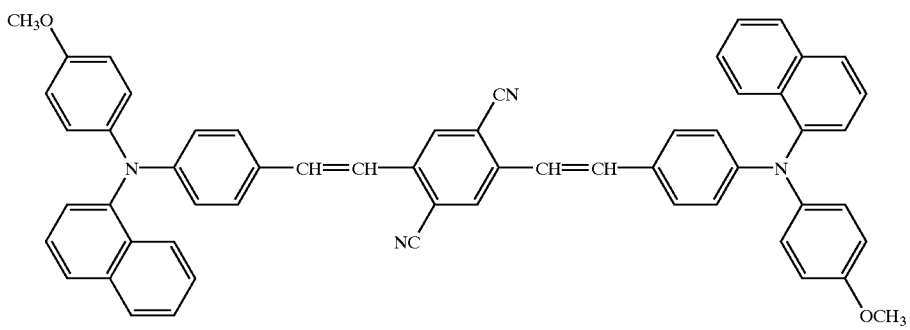
(16)-5

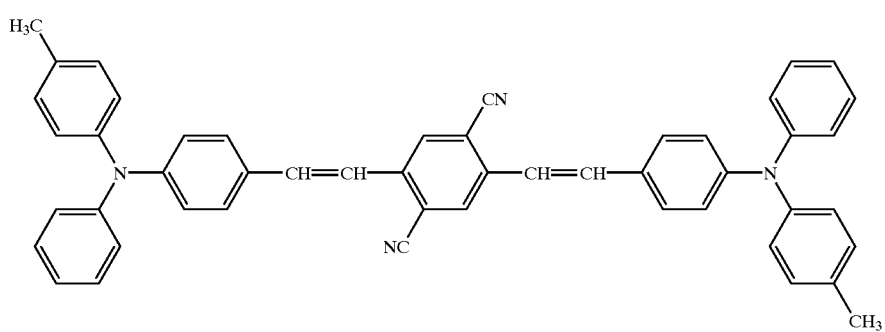
(16)-6
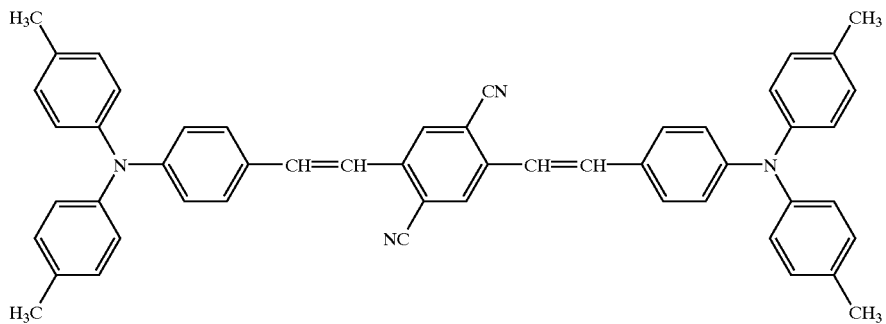
(16)-7
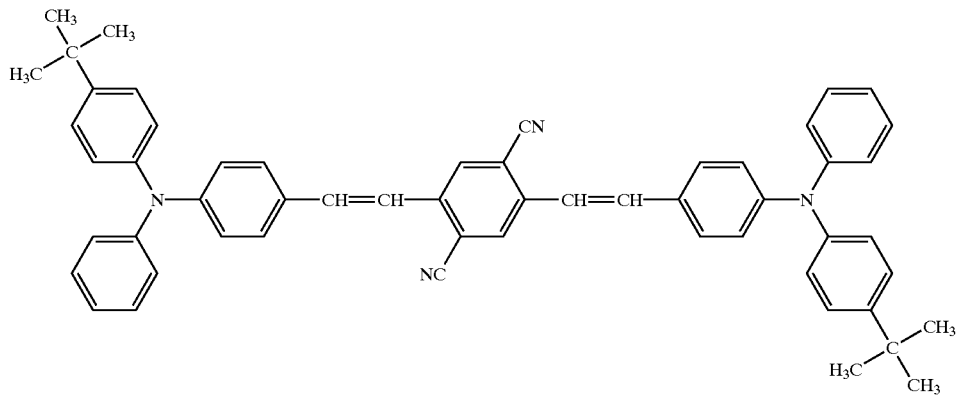
(16)-8
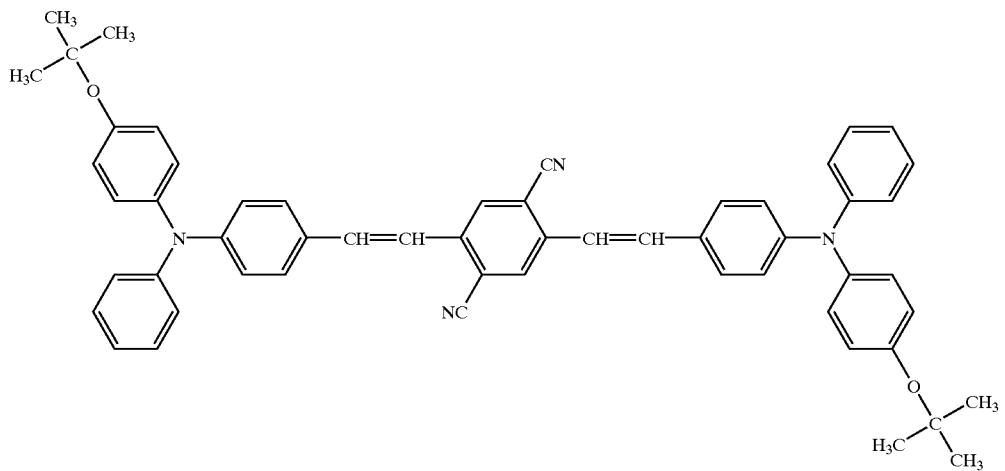
(16)-9

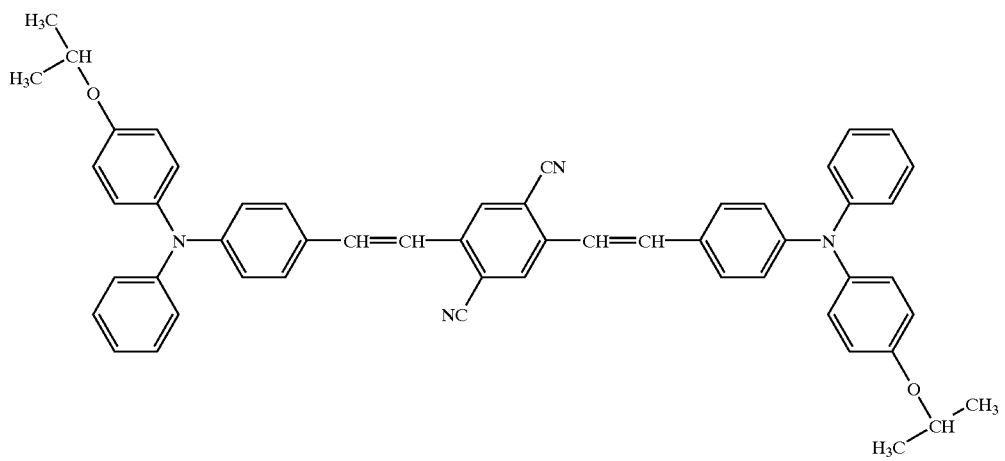
(16)-10
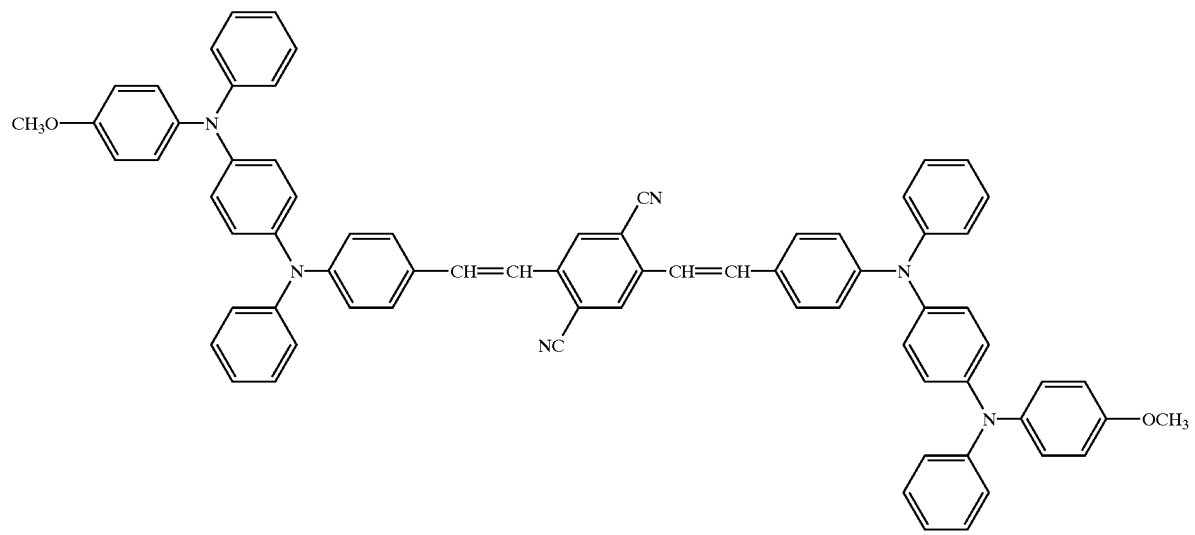
(16)-11
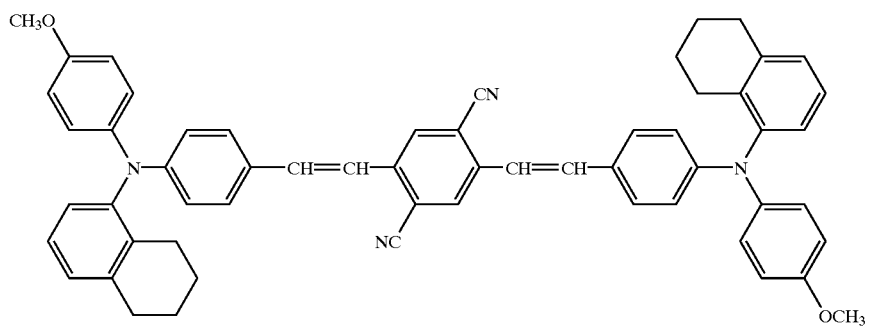
(16)-12

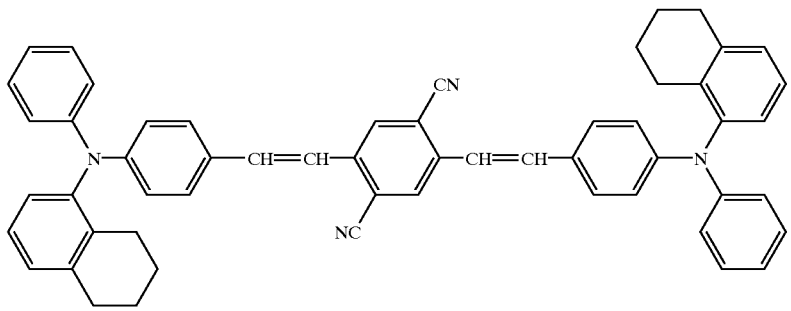
Besides, mention is made of the following compounds:
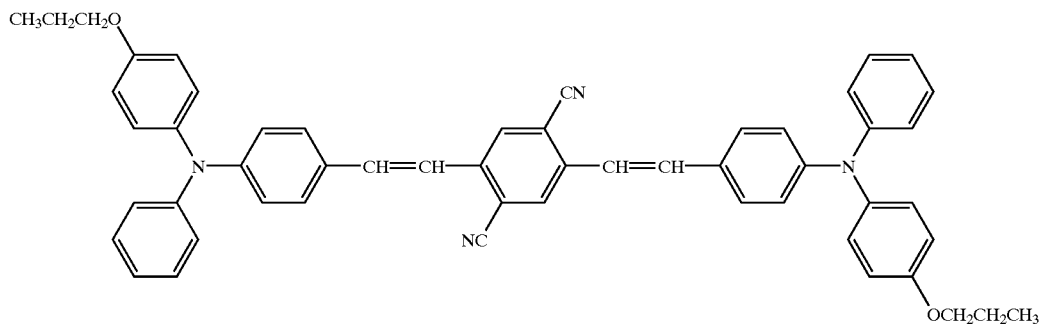
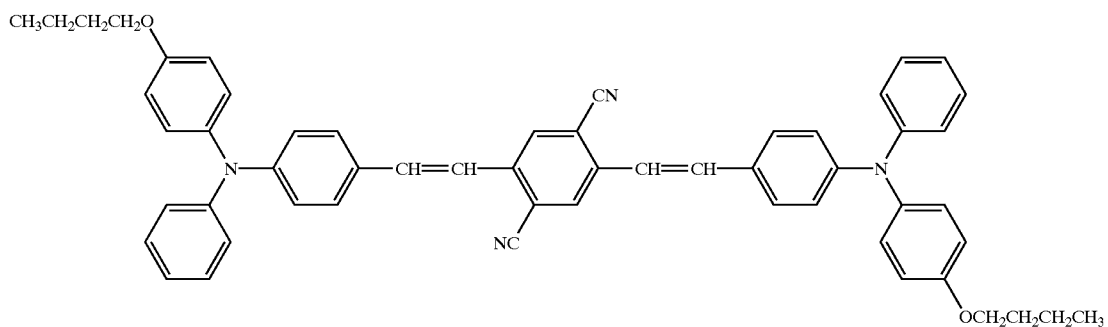
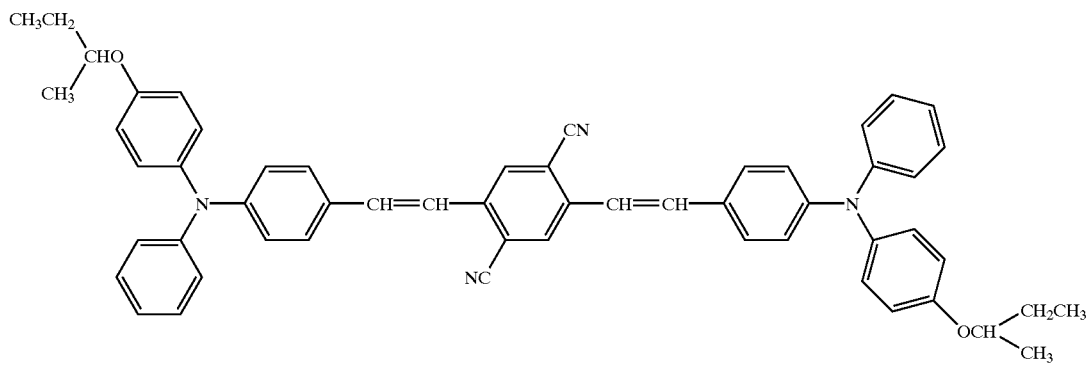

-continued
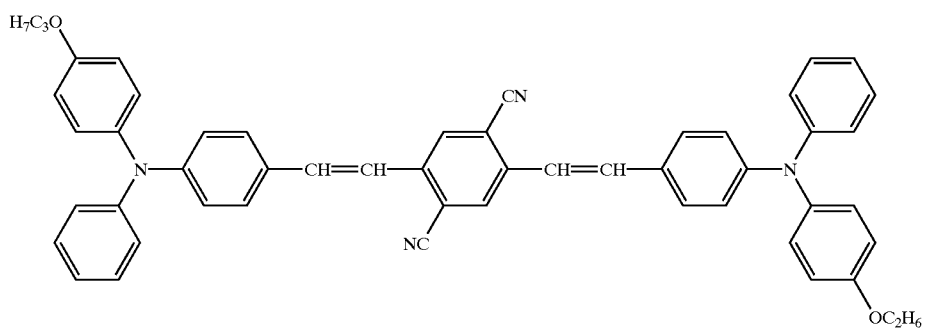
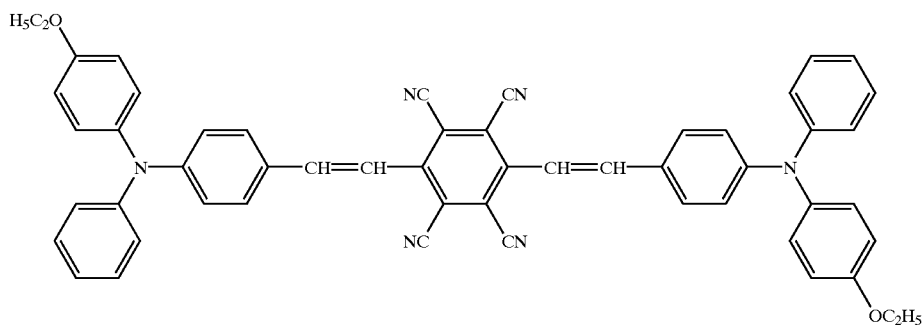
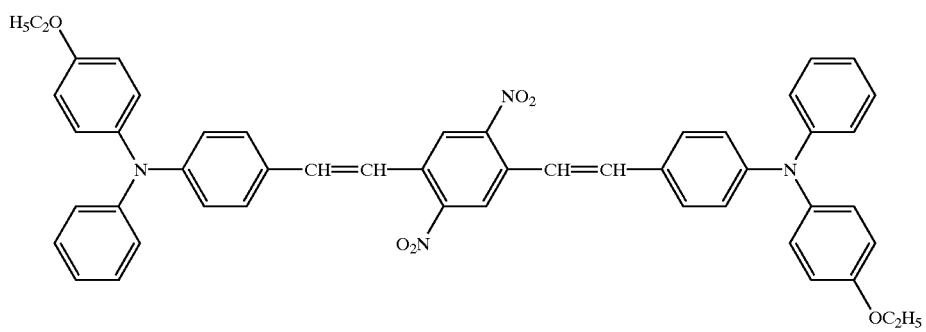
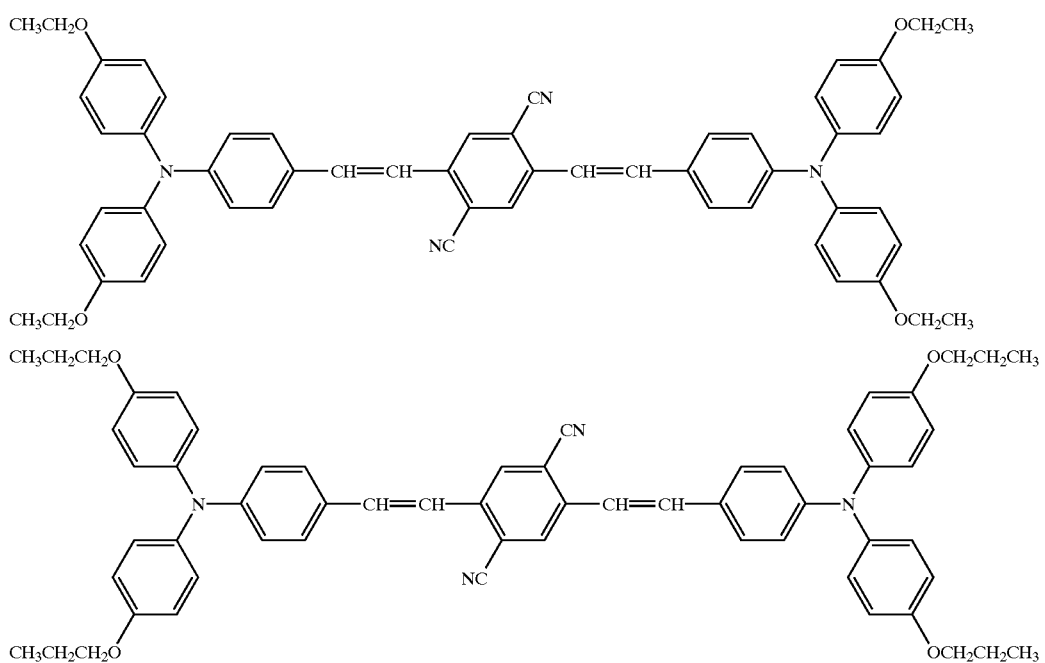

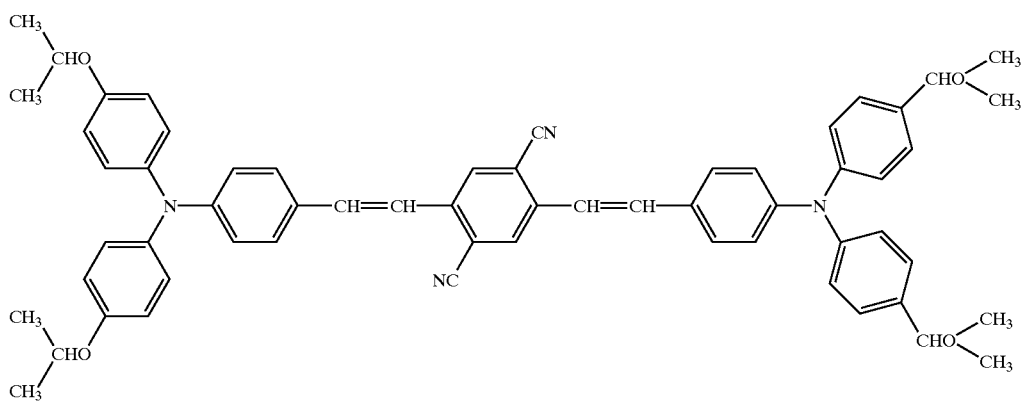
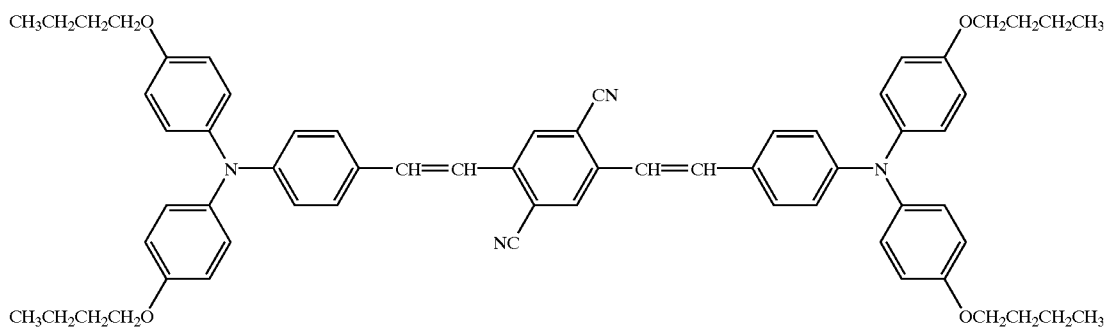
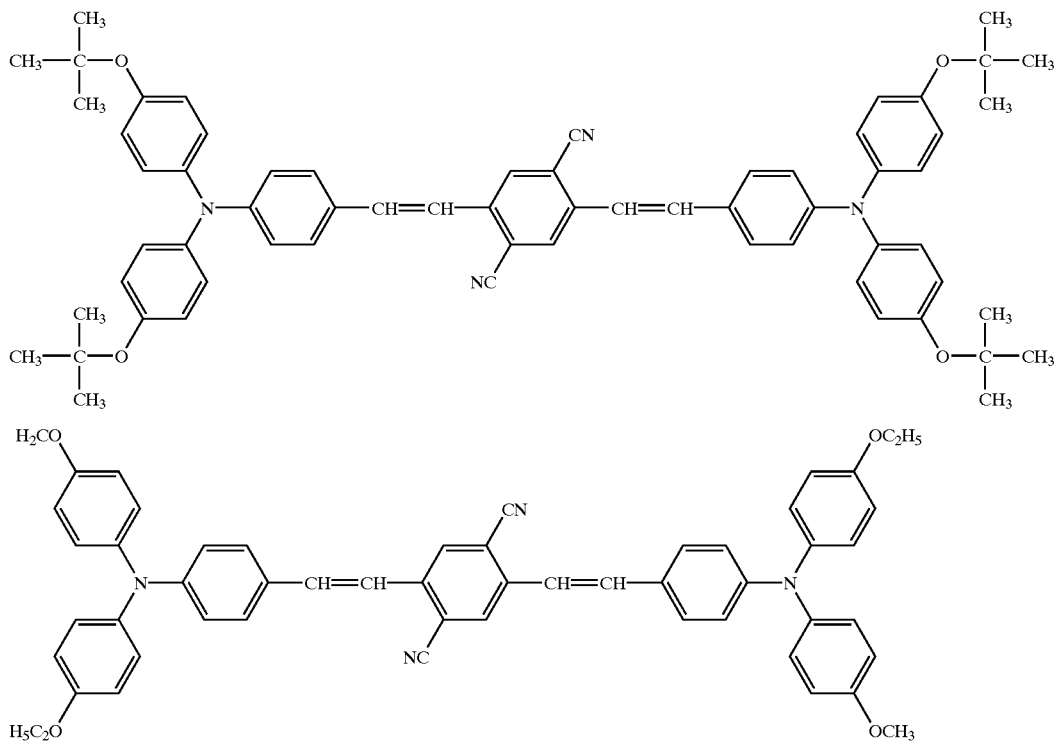

-continued
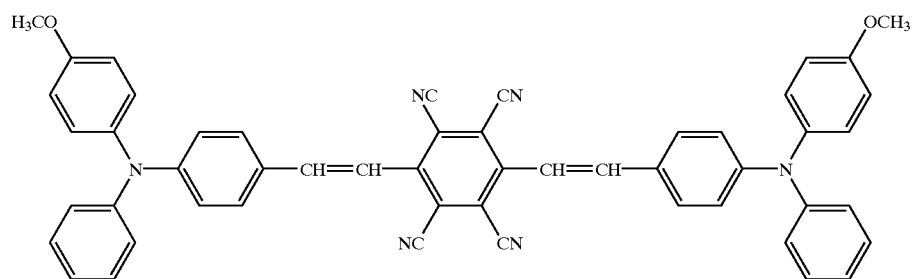
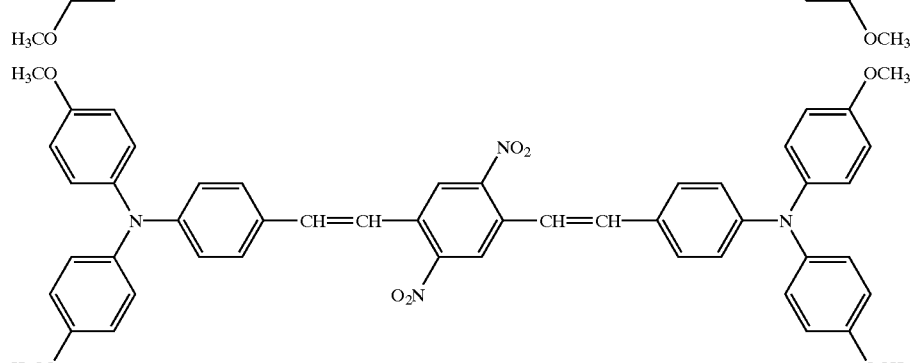
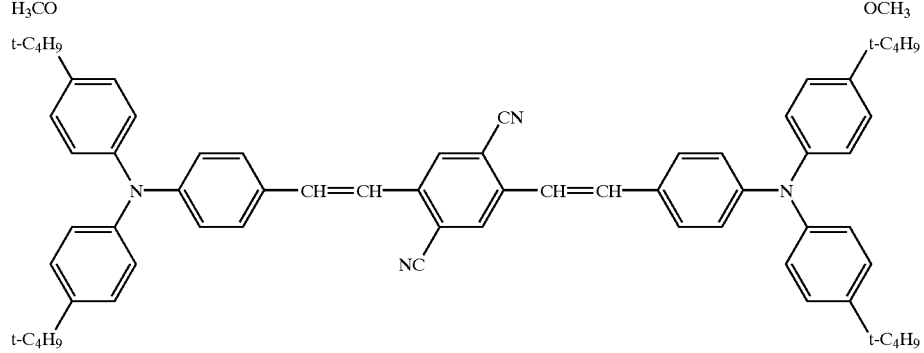
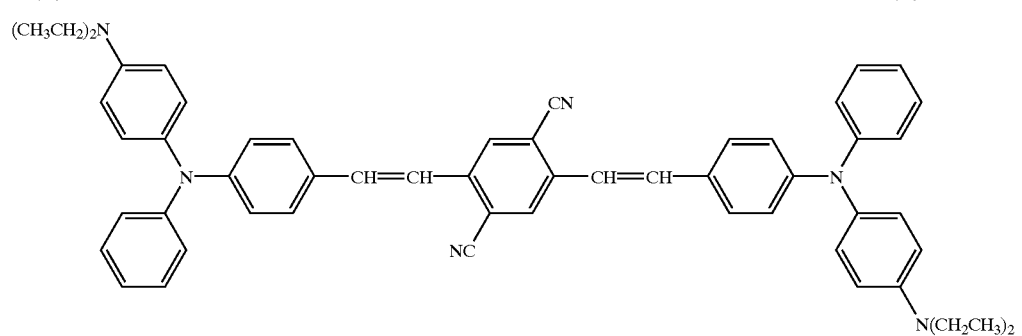
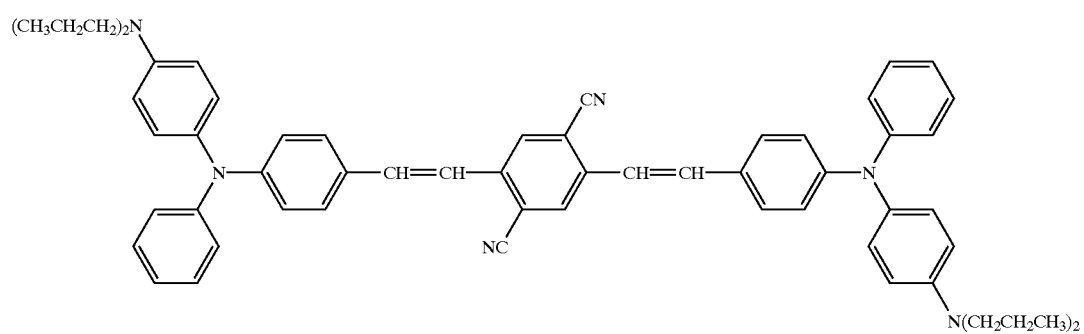

-continued
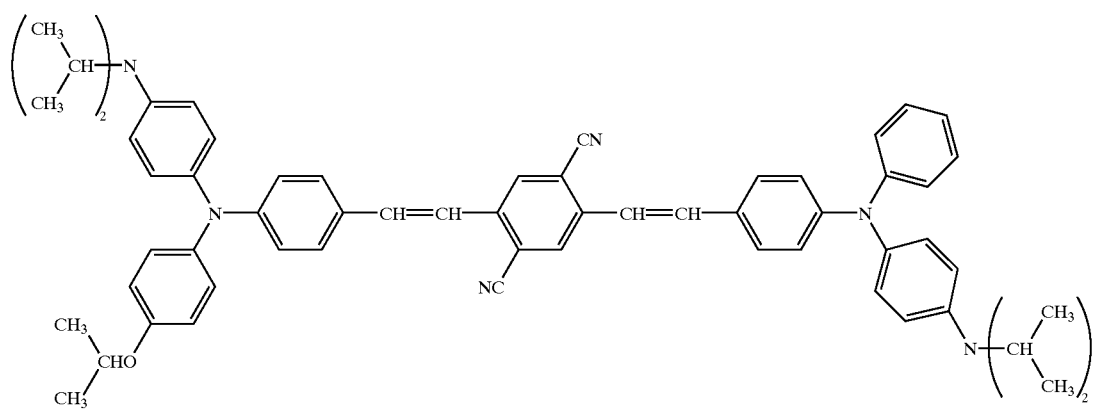
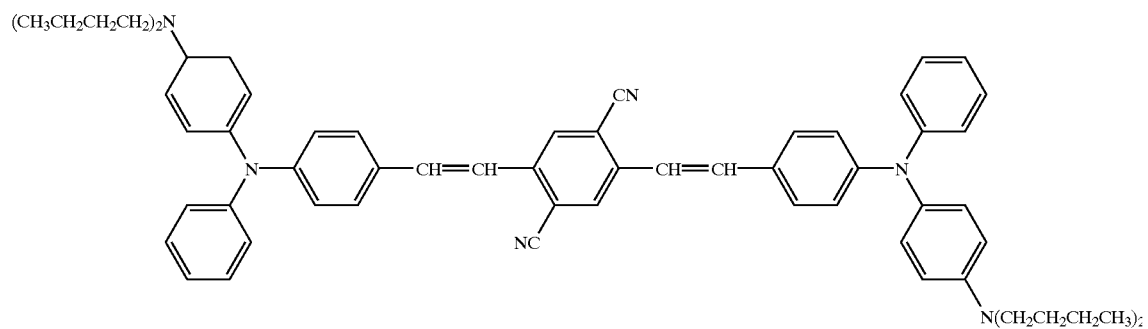
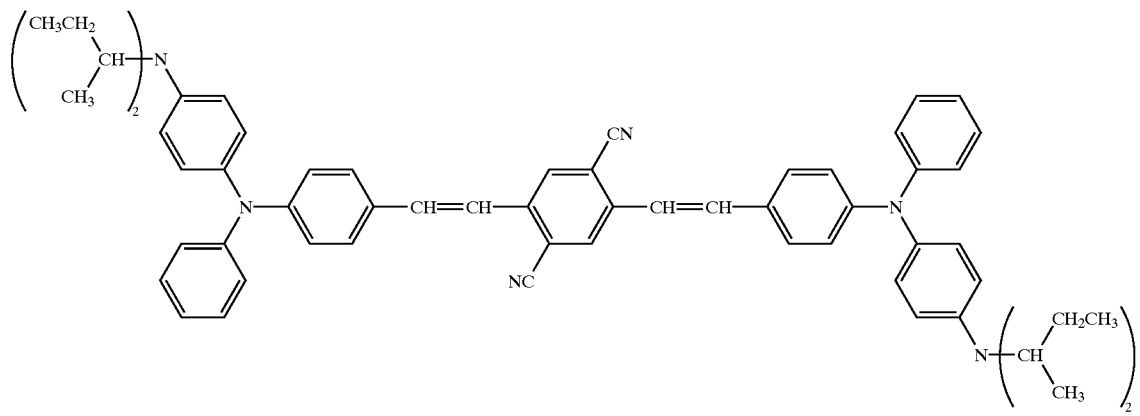
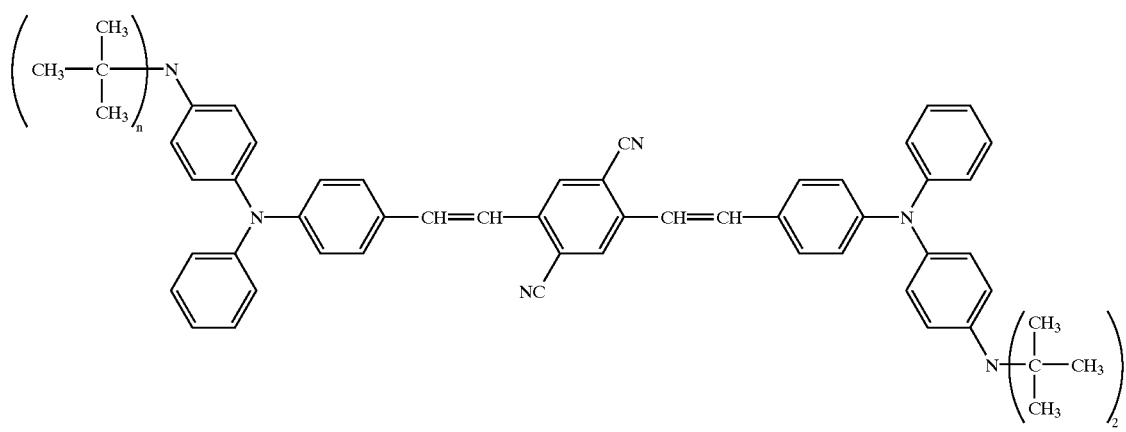

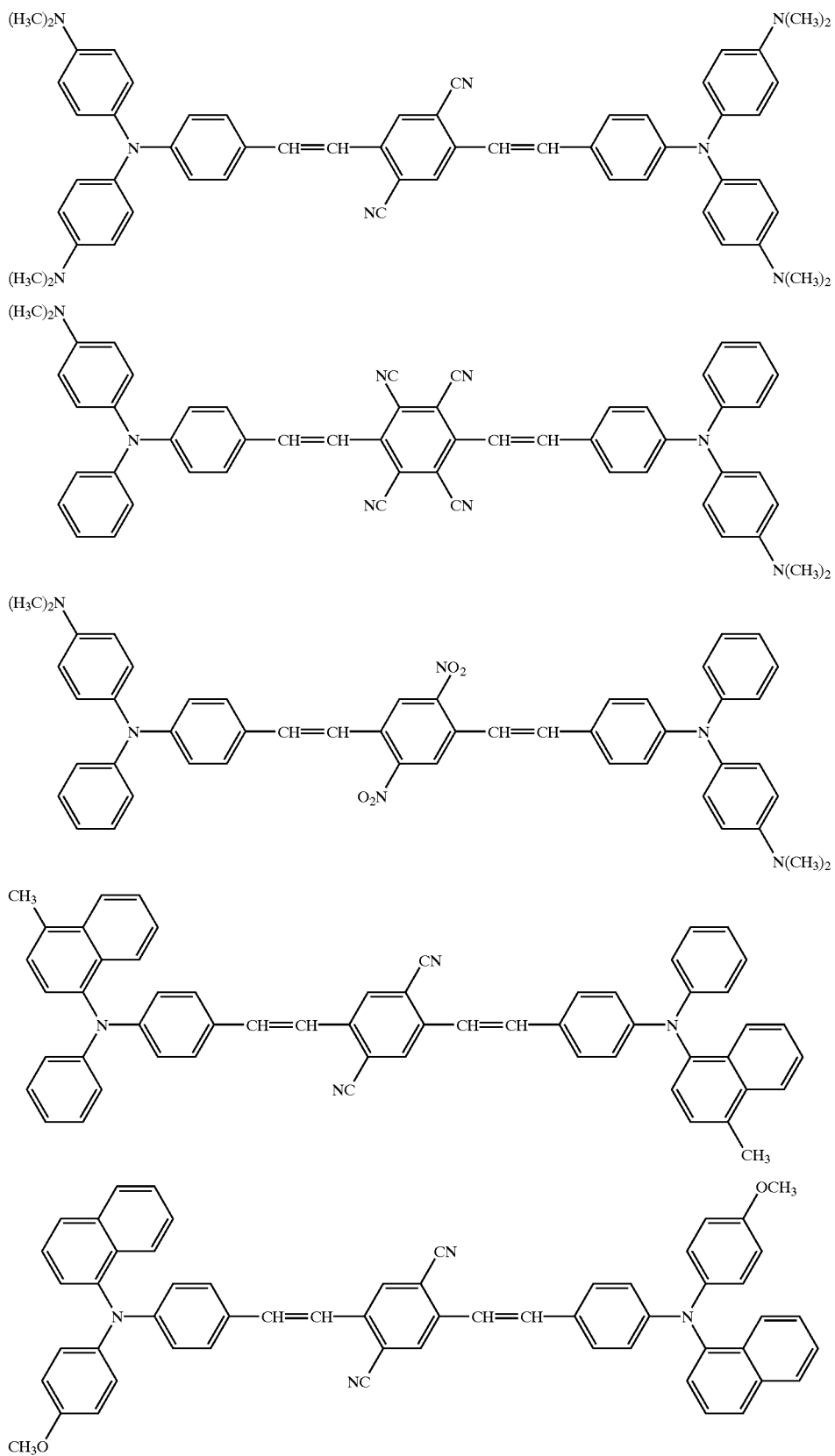

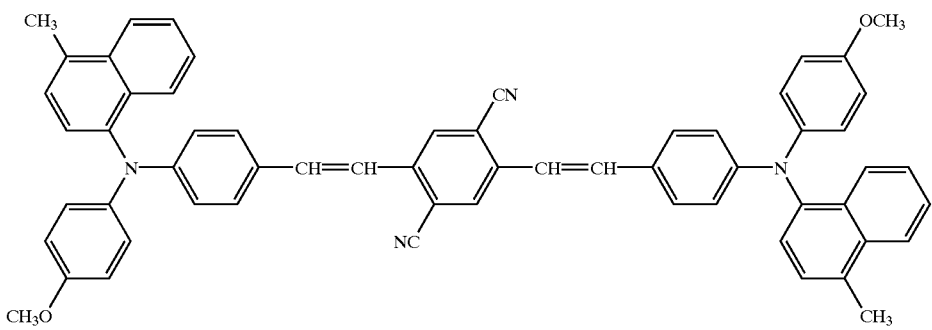
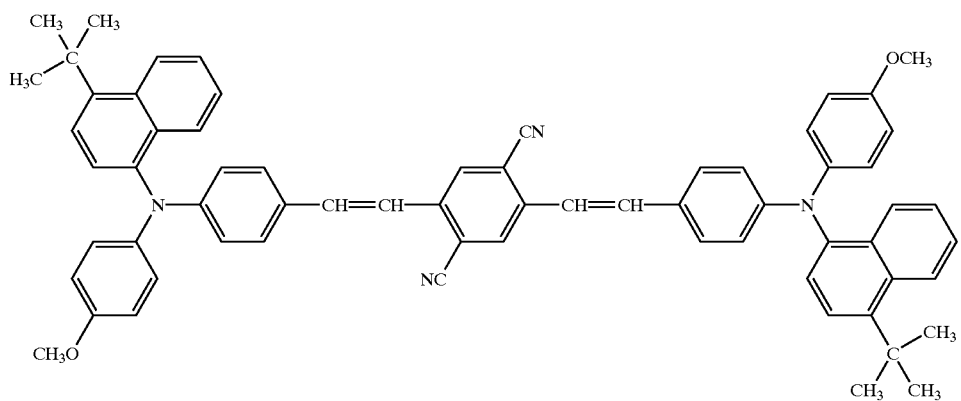
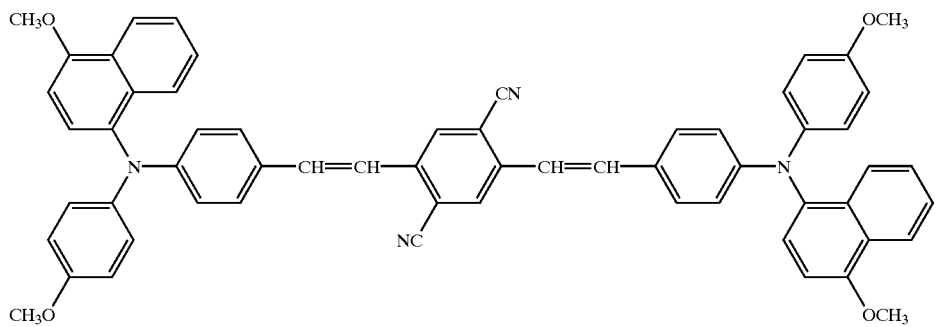
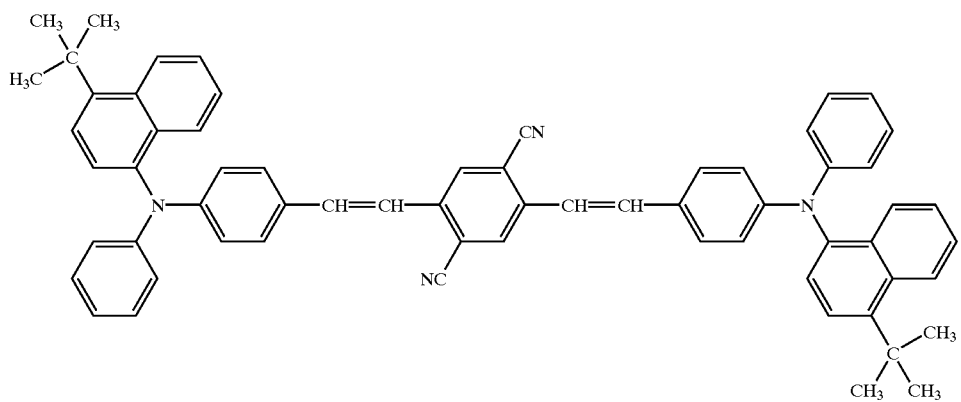

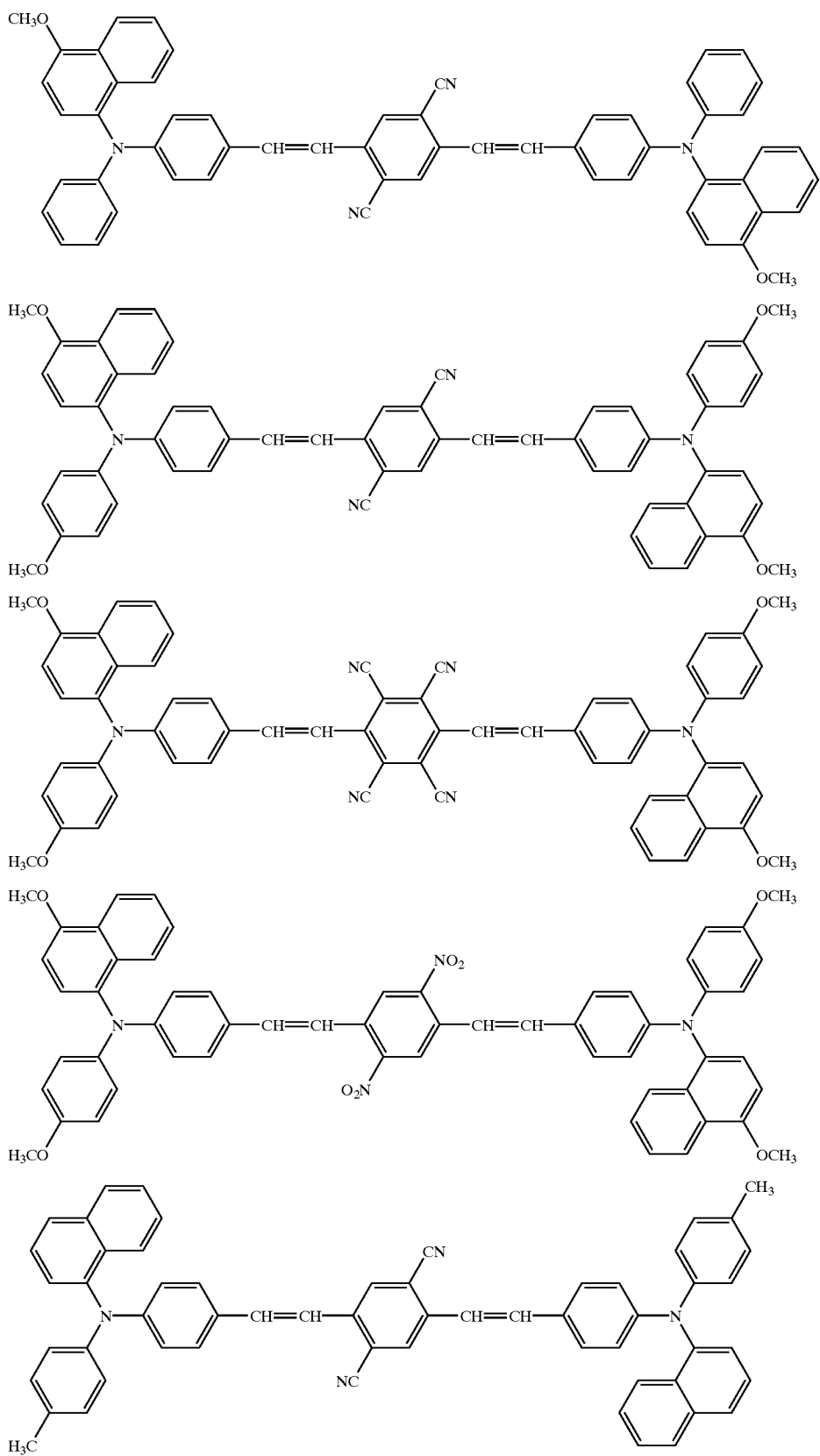

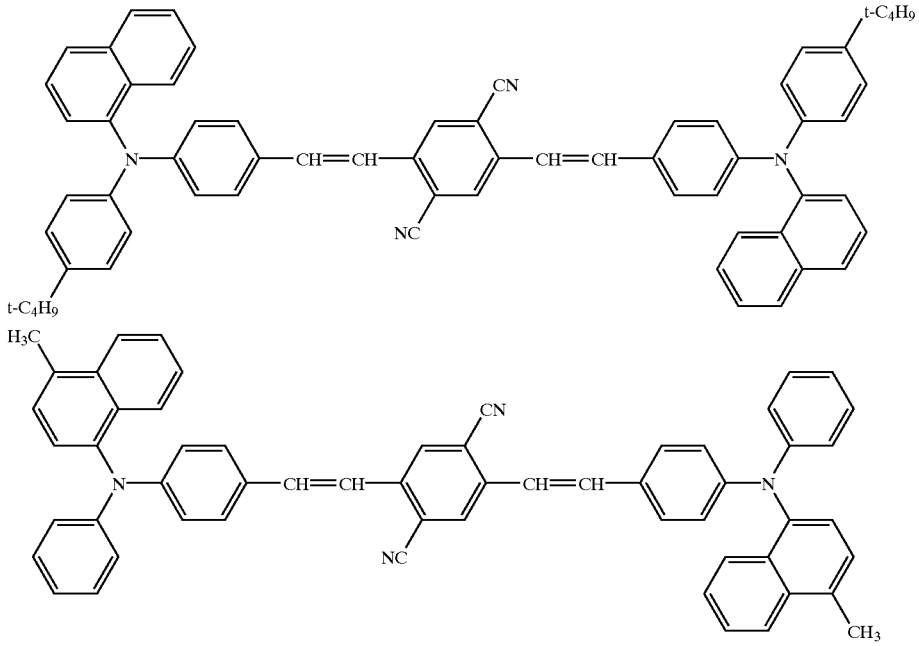

When a bulky substituent group, such as t-butyl, is introduced as in the above structural formula (16)-8 or (16)-9, there is the possibility of improving characteristic properties as set out below, (1) The strong intramolecular interaction is so weakened as to realize a stable amorphous film.
(2) The hopping site distance of holes can be kept away to appropriately control hole transport properties.

Further, the invention also provides a bis(aminostyryl) benzene compound of the following general formula [XIX] (hereinafter referred to as second inventive compound)

may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{94}$, $R^{95}$, $R^{96}$ and $R^{97}$ may be the same or different and at least one thereof represents a fluorine atom and the others independently represent a hydrogen atom, a cyano group, a nitro group or a halogen atom.

The second inventive compound can be effectively utilized as an organic luminescent material exhibiting green to red luminescence, and has a high glass transition point and melting point. The compound is electrically, thermally or

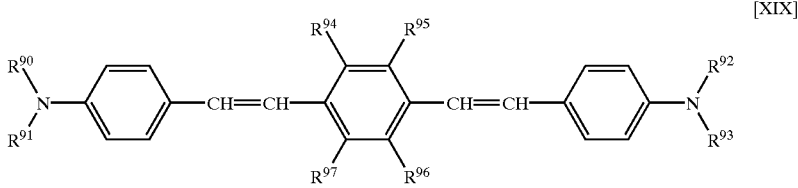

[XIX]

wherein $R^{90}$, $R^{91}$, $R^{92}$ and $R^{93}$ are groups, which may be the same or different, and at least one thereof represents an aryl group of the following general formula (40) and the others independently represent an unsubstituted aryl group chemically stable and is amorphous in nature and is able to readily form a vitreous state. Thus, the compound can be vacuum deposited.

The second inventive compound should preferably be of the following general formula [XX]

(40)

[XX]

wherein $R^{98}$, $R^{99}$, $R^{100}$, $R^{101}$ and $R^{102}$ may be the same or different and at least one thereof is a member selected from an alkoxy group having from 1 to 4 carbon atoms, which wherein $R^{90}$, $R^{91}$, $R^{92}$ and $R^{93}$, respectively, have the same meanings as defined above, and at least one of $R^{90}$, $R^{91}$, $R^{92}$ and $R^{93}$ represents an aryl group of the following general formula (41) and the others independently represent an unsubstituted aryl group

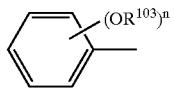
(41)

wherein at least one of $R^{103}$'s represents an alkyl or alkenyl group having from 1 to 4 carbon atoms, a cyclohexyl group or a phenyl group and the other represents a hydrogen atom, and n is an integer of 0 to 5.

Preferably, a compound of the following general formula (42) is mentioned

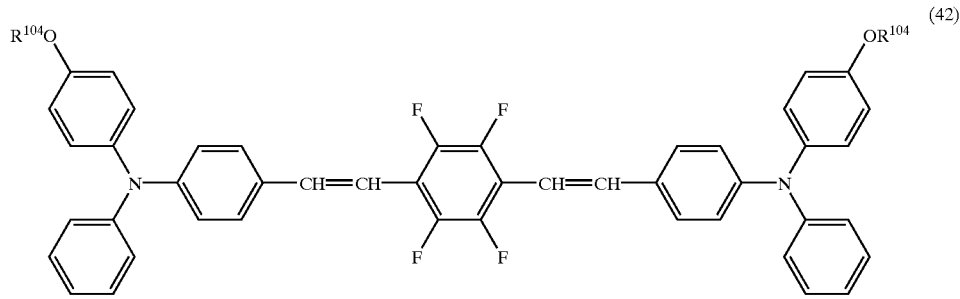
(42)

wherein at least one of $R^{104}$'s represents an alkyl or alkenyl group having from 1 to 4 carbon atoms, a cyclohexyl group or a phenyl group and the others independently represent a hydrogen atom, if present.

Specific examples of the second inventive compound include those of the following structural formulas (40)-1, (40)-2, (40)-3, (40)-4, (40)-5, (40)-6 and (40)-7

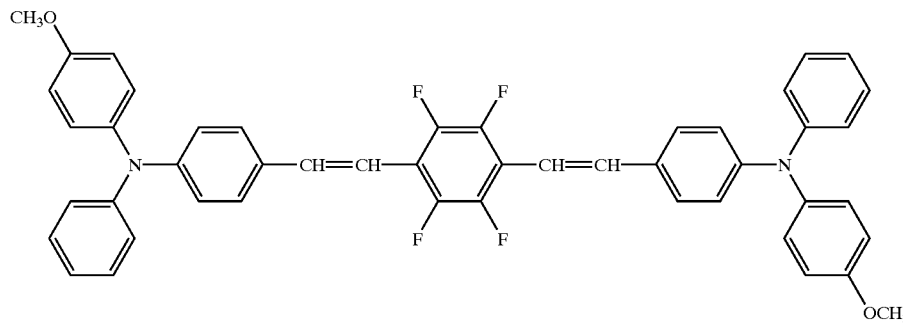
(40)-1

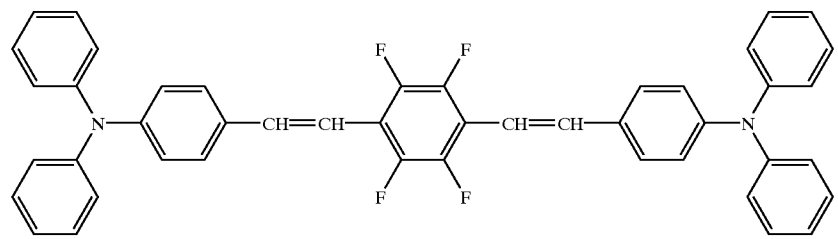
(40)-2

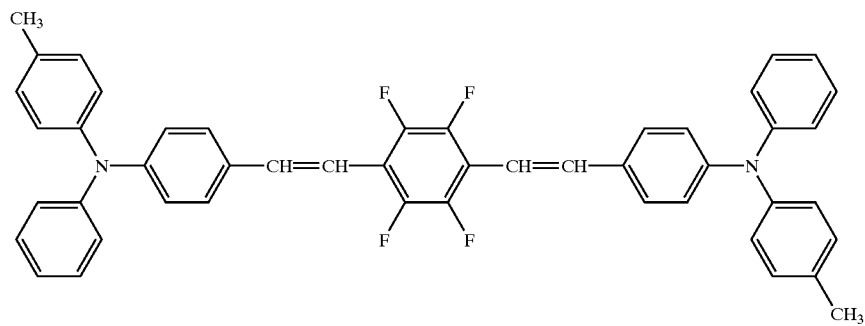
(40)-3

-continued

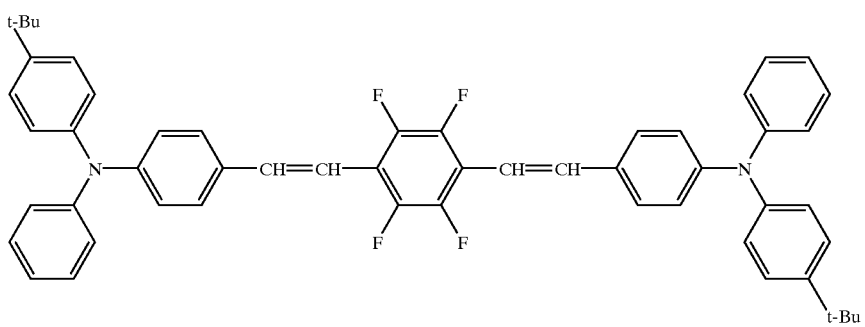
(40)-4

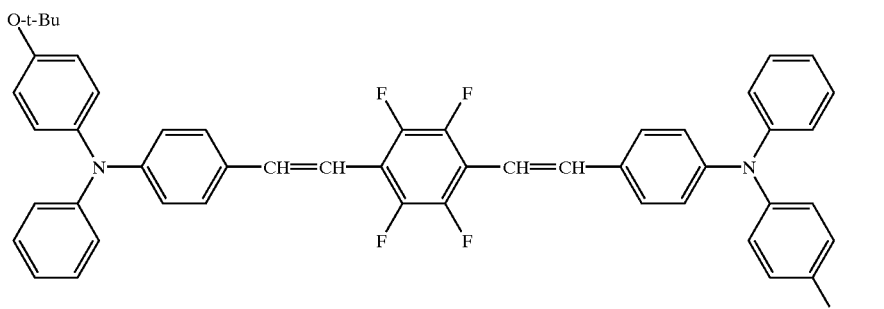
(40)-5

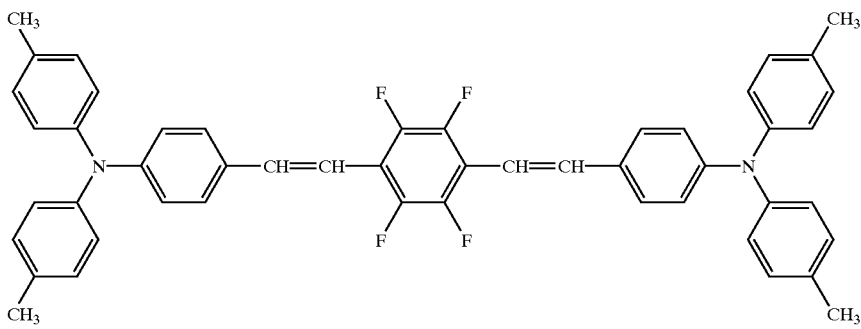
(40)-6

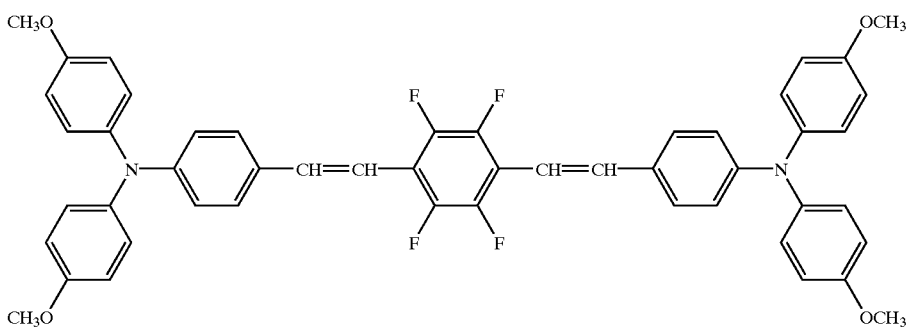
(40)-7

To prepare the first inventive compound in a high efficiency, the invention also provides a process for preparing the bis(aminostyryl)benzene compound of the afore-indicated general formula [I], [II], [III] or [IV], which comprises subjecting at least one of 4-(N,N-diarylamino)benzaldehyde of the following general formulas [V] or [VI] to condensation with a diphosphonic acid ester of the following general formula [VII] or a diphosphonium salt of the following general formula [VIII] (hereinafter referred to as first inventive preparation process):

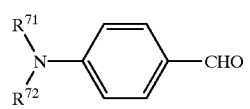
[V]

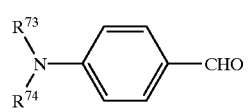
[VI]

wherein $R^{71}$ and $R^{72}$ independently represent an aryl group corresponding to or as defined before with respect to $R^1$, $R^2$, $R^{14}$, $R^{15}$, $R^{27}$, $R^{28}$, $R^{40}$ or $R^{41}$, and $R^{73}$ and $R^{74}$ independently represent an aryl group corresponding to or as defined before with respect to $R^3$, $R^4$, $R^{16}$, $R^{17}$, $R^{29}$, $R^{30}$, $R^{42}$ or $R^{43}$; and

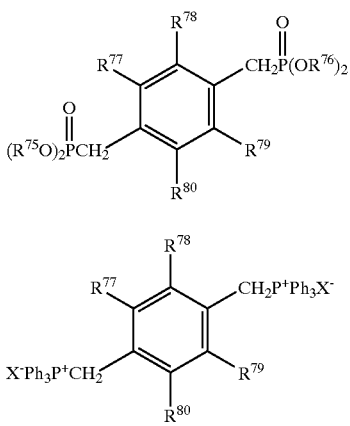

wherein $R^{75}$ and $R^{76}$ may be the same or different and independently an alkyl or alkenyl group having from 1 to 4 carbon atoms, a cyclohexyl group or a phenyl group, $R^{77}$, $R^{78}$, $R^{79}$ and $R^{80}$ independently represent a group corresponding to or defined before with respect to $R^5$, $R^6$, $R^7$, $R^8$, $R^{18}$, $R^{19}$, $R^{20}$, $R^{21}$, $R^{31}$, $R^{32}$, $R^{33}$, $R^{34}$, $R^{44}$, $R^{45}$, $R^{46}$ or $R^{47}$, and x represents a halogen atom.

More particularly, in the first inventive process, the condensation is carried out according to the Wittig-Horner reaction or Wittig reaction wherein the diphosphonic acid ester and/or diphosphonium salt indicated above is treated with a base in a solvent to form carbo anions, followed by condensation of the carbo anions with the 4-(N,N-diarylamino)benzaldehyde.

For instance, in order to obtain a bis(aminostyryl)benzene compound of the following general formula [I']

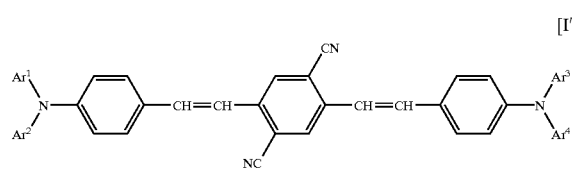

wherein $Ar^1$, $Ar^2$, $Ar^3$ and $Ar^4$, respectively, have the same meanings as defined before, at least one of 4-(N,N-diarylamino)benzaldehydes of the following general formulas (17) and (18) is condensed with a diphosphonic acid ester of the following general formula (19) or a diphosphonium salt of the following general formula (20)

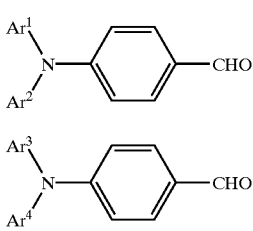

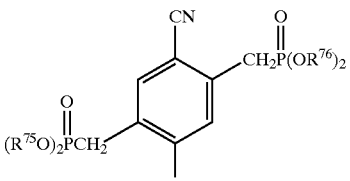

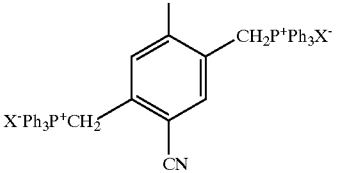

wherein $Ar^1$, $Ar^2$, $Ar^3$, $Ar^4$, $R^{75}$, $R^{76}$ and X, respectively, have the same meanings as defined before.

The reaction sequence of the condensation is, for example, as shown in the following Reaction Scheme 1.

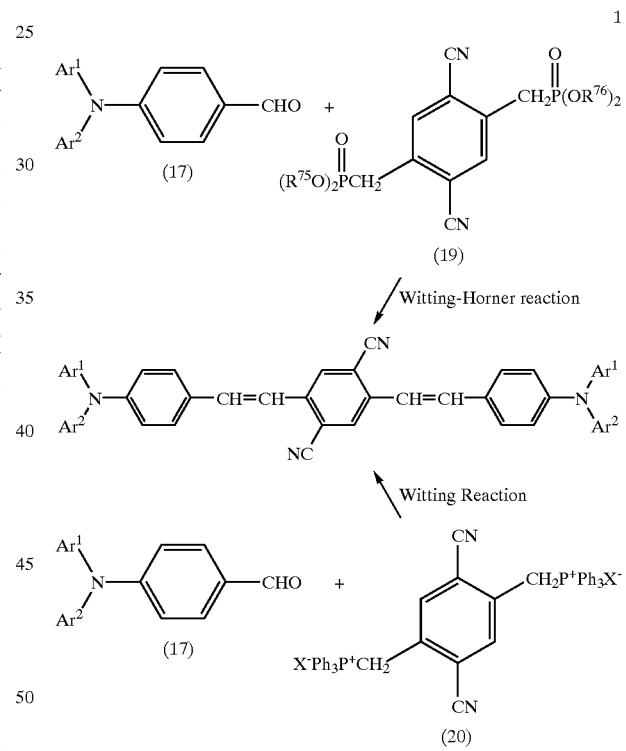

The above reactions start from the formation of a carbo anion by treating the compound of the general formula (19) or (20) with a base in an appropriate solvent, and are completed through condensation of the carbo anion with the aldehyde of the general formula (17). The possible combinations of the bases and the solvents are considered to be ones mentioned below.

More particularly, such combinations include sodium hydroxide/water, sodium carbonate/water, potassium carbonate/water, sodium ethoxide/ethanol or dimethylformamide, sodium methoxide/methanol-diethyl ether mixed solvent or dimethylformamide, triethylamine/ethanol, diglyme, chloroform or nitromethane, pyridine/methylene chloride or nitromethane, 1,5-diazabicyclo[4,3, 0]non-5-ene/dimethylsulfoxide, potassium t-butoxide/ dimethylsulfoxide or tetrahydrofuran, butyl lithium/diethyl ether, tetrahydrofuran, benzene or dimethylformamide, phenyl lithium/diethyl ether or tetrahydrofuran, sodium amide/ ammonia, sodium hydride/dimethylformamide or tetrahydrofuran, triethyl sodium/diethyl ether or tetrahydrofuran, and the like.

The reaction proceeds at a relatively low temperature of −30° C. to 30° C. and is selective, so that purification of the intended product through chromatography is easy. In addition, the first inventive compound represented by the general formula [I'] exhibits high crystallinity, and thus, purity can be improved by re-crystallization. The manner of the recrystallization is not critical, and it is simple to use a procedure wherein the product is dissolved in acetone, to which hexane is added, with the attendant advantage that the subsequent removal of the solvent through distillation is easy. The reaction may be effected at normal temperatures to 30° C. at normal pressures for 3 to 24 hours.

According to the first inventive preparation process, there can be obtained the bis(aminostyryl)benzene compounds of the afore-indicated general formulas (10), (11), (12), (13), (14) and (15). More particularly, there can be obtained the bis(aminostyryl)benzene compounds of the afore-indicated structural formulas (16)-1, (16)-2, (16)-3, (16)-4, (16)-5, (16)-6, (16)-7, (16)-8 and (16)-9.

The invention also provides, as a process for preparing the second inventive compound in a high efficiency, a process for preparing a bis(aminostyryl)benzene compound wherein at least one of 4-(N,N-diarylamino)benzaldehydes of the following general formulas [V'] and [VI'] is subjected to condensation reaction with a diphosphonic acid ester of the following general formula [VII'] or a diphosphonium salt of the following general formula [VIII'] (hereinafter referred to as second inventive process)

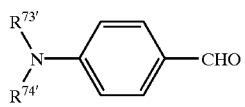

[V']

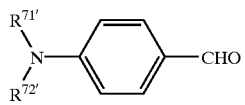

[VI']

wherein $R^{71}$ and $R^{72}$ independently represent an aryl group corresponding to or as defined before with respect to $R^{90}$ or $R^{91}$, and $R^{73}$ and $R^{74}$ independently represent an aryl group corresponding to or as defined before with respect to $R^{92}$ or $R^{93}$, and

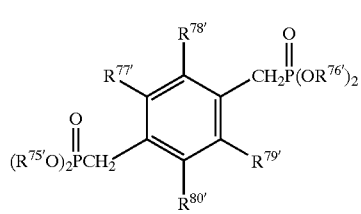

[VII']

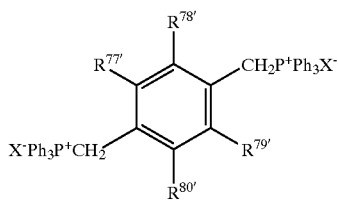

[VIII']

wherein $R^{75}$ and $R^{76}$ may be the same or different and independently represent an alkyl or alkenyl group having from 1 to 4 carbon atoms, a cyclohexyl group or a phenyl group, $R^{77}$, $R^{78}$, $R^{79}$ and $R^{80}$ independently represent a group corresponding to or defined before with respect to $R^{94}$, $R^{95}$, $R^{96}$ or $R^{97}$, and X represents a halogen atom.

More particularly, in the second inventive process, the condensation is carried out according to the Wittig-Horner reaction or Wittig reaction wherein the diphosphonic acid ester and/or diphosphonium salt indicated above is treated with a base in a solvent to form carbo anions, followed by condensation of the carbo anions with the 4-(N,N-diarylamino)benzaldehyde.

The reaction sequence of the condensation is, for example, as shown in the following Reaction Scheme 1'.

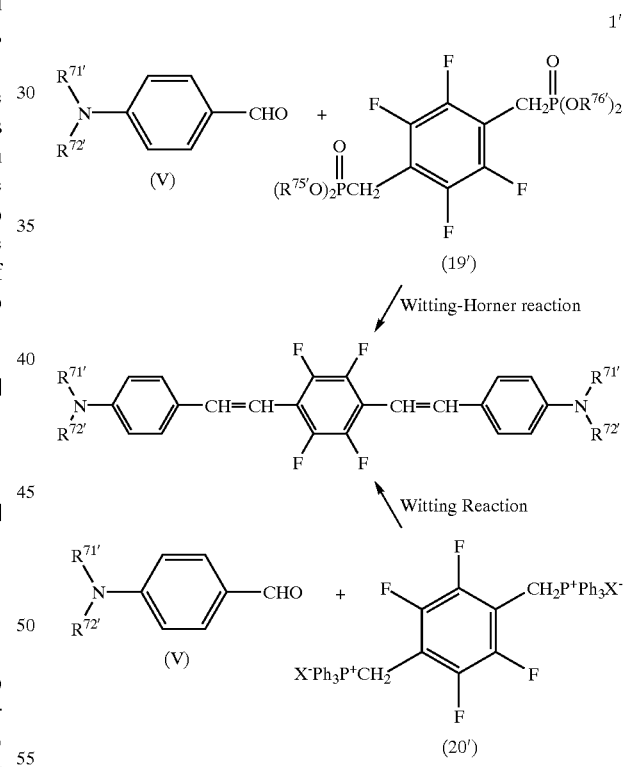

The above reactions start from the formation of a carbo anion by treating the compound of the general formula (19') or (20') with a base in an appropriate solvent, and are completed through condensation of the carbo anion with the aldehyde of the general formula [V'] The combinations of the bases and the solvents are considered to be ones mentioned hereinbefore.

The reaction proceeds at a relatively low temperature of −30° C. to 30° C. and is selective, so that purification of the intended product through chromatography is easy. In addition, the second inventive compound exhibits high crystallinity, and thus, purity can be improved by re-crystallization. The manner of the re-crystallization is not critical, and it is simple to use a procedure wherein the product is dissolved in acetone, to which hexane is added, with the attendant advantage that the subsequent removal of the solvent through distillation is easy. The reaction may be effected at normal temperatures to 30° C. at normal pressures for 3 to 24 hours.

According to the second inventive preparation process, there can be obtained the bis(aminostyryl)benzene compounds of the afore-indicated structural formulas (40)-1, (40)-2, (40)-3, (40)-4, (40)-5, (40)-6 and (40)-7.

The invention also provides various compounds suitable as synthetic intermediates of the first inventive compounds.

More particularly, mention is made of 4-(N,N-diarylamino)benzaldehyde, which is used as a synthetic intermediate for bis(aminostyryl)benzene compounds represented firstly by the general formulas [V] and [VI], and by the general formulas [I], [II], [III] and [IV].

This synthetic intermediate (hereinafter referred to as inventive synthetic intermediate 1) is represented by the afore-indicated general formula (17) or (18), and more particularly, by the following general formula (21), (22), (23), (24), (25), (26) or (26'), with its specific examples including those represented by the following structural formulas (27)-1, (27)-2, (27)-3, (27)-4, (27)-5, (27)-6, (27)-7, (27)-8, (27)-9, (27)-10, (27)-11, (27)-12, (27)-13, (27)-14 and (27)-15:

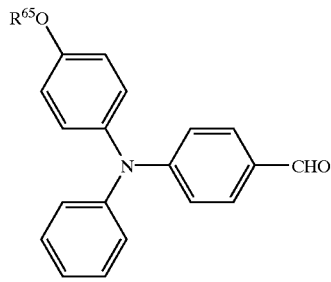
(21)

wherein $R^{65}$ an alkyl or alkenyl group having from 1 to 4 carbon atoms, a cyclohexyl group or a phenyl group;

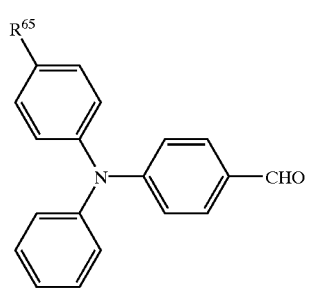
(22)

wherein $R^{66}$ an alkyl or alkenyl group having from 1 to 4 carbon atoms, a cyclohexyl group or a phenyl group;

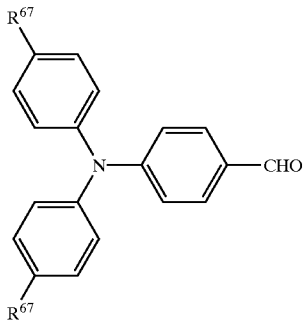
(23)

wherein $R^{67}$ an alkyl or alkenyl group having from 1 to 4 carbon atoms, a cyclohexyl group or a phenyl group;

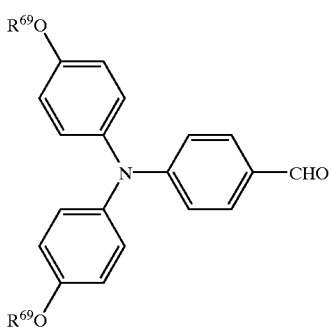
(24)

wherein $R^{68}$ an alkyl or alkenyl group having from 1 to 4 carbon atoms, a cyclohexyl group or a phenyl group;

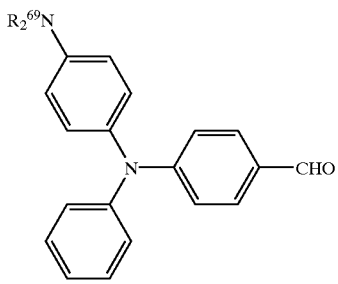
(25)

wherein $R^{69}$ an alkyl or alkenyl group having from 1 to 4 carbon atoms, a cyclohexyl group or a phenyl group;

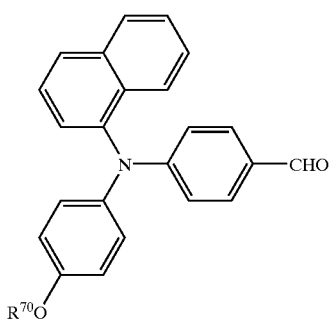
(26)

wherein $R^{70}$ an alkyl or alkenyl group having from 1 to 4 carbon atoms, a cyclohexyl group or a phenyl group;

(26')
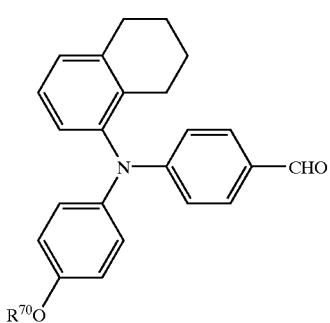
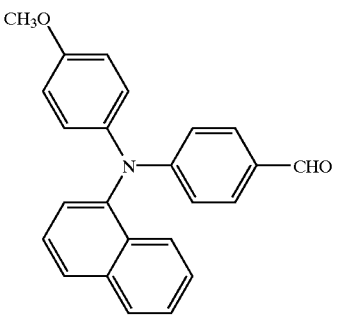
(27)-5
wherein $R^{70}$ an alkyl or alkenyl group having from 1 to 4 carbon atoms, a cyclohexyl group or a phenyl group;
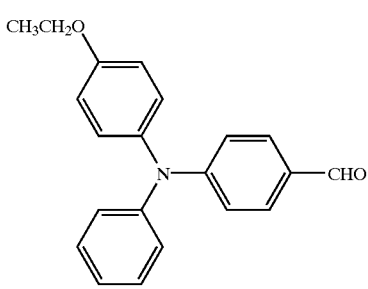
(27)-1
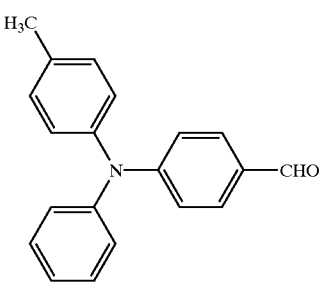
(27)-6
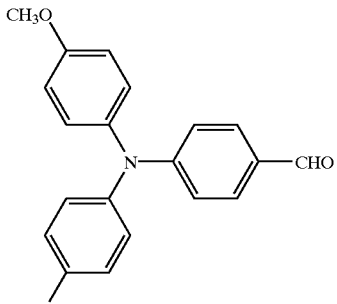
(27)-2
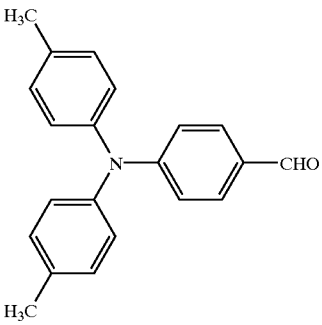
(27)-7
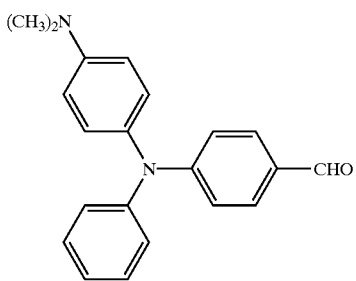
(27)-3
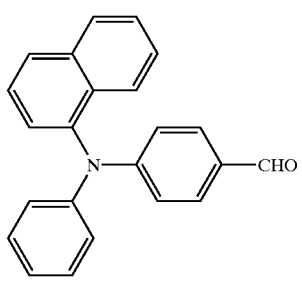
(27)-4
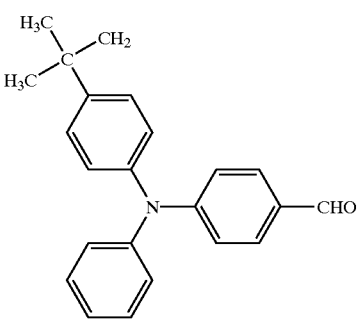
(27)-8

-continued (27)-9
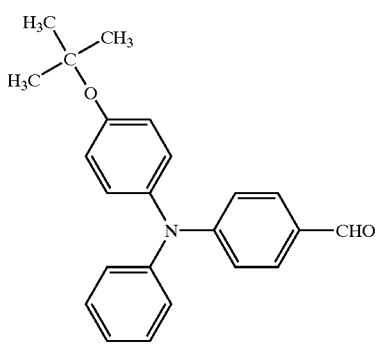

(27)-10
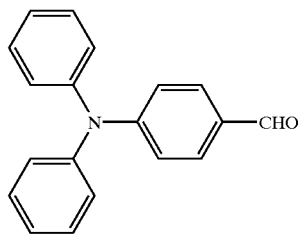

(27)-11
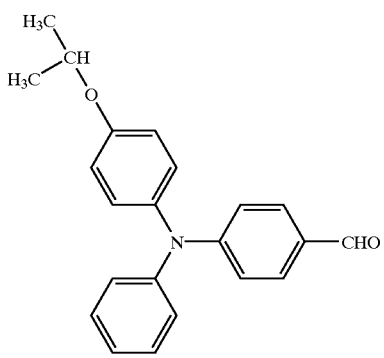

(27)-12
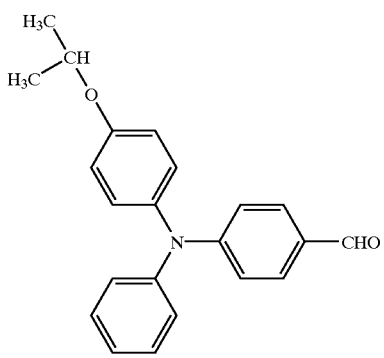

(27)-13
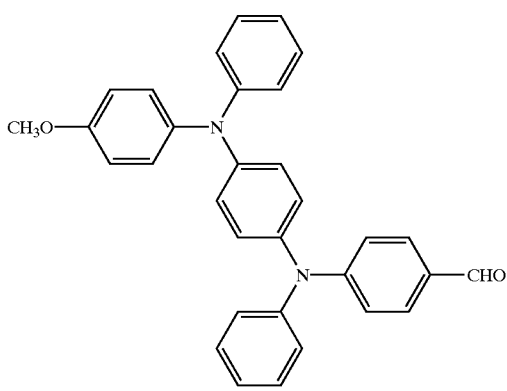

-continued (27)-14
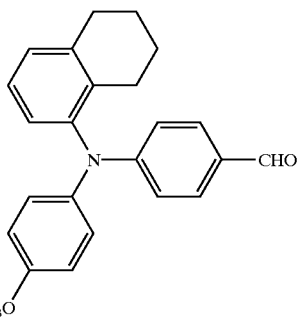

(27)-15
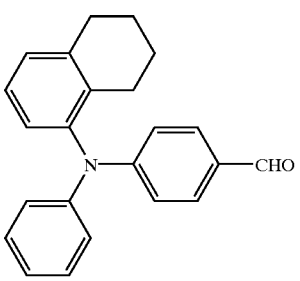

Furthermore, the invention provides various compounds suitable as synthetic intermediates of the second inventive compounds.

More particularly, mention is made of 4-(N,N-diarylamino)benzaldehyde, which is used as a synthetic intermediate for the bis(aminostyryl)benzene compounds represented by the general formula [V'] or [VI'], or [XIX].

This synthetic intermediate (hereinafter referred to as inventive synthetic intermediate 1') is represented by the following general formula (43), and more particularly, by the following structural formula (41)-1, (41)-2, (41)-3, (41)-4, (41)-5, (41)-6 or (41)-7:

(43)
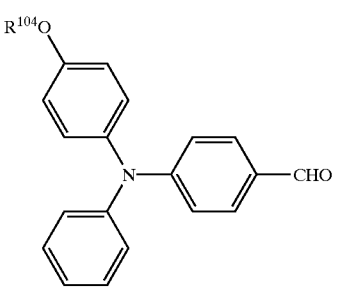

wherein at least one of $R^{104}$'s an alkyl or alkenyl group having from 1 to 4 carbon atoms, a cyclohexyl group or a phenyl group and the others independently represent a hydrogen atom, if present;

(41)-1
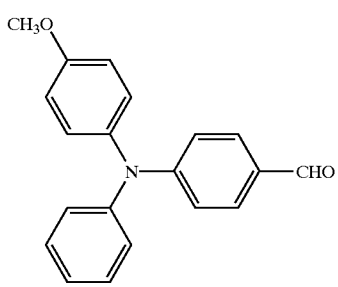

(41)-2
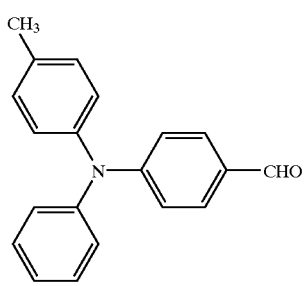

(41)-3
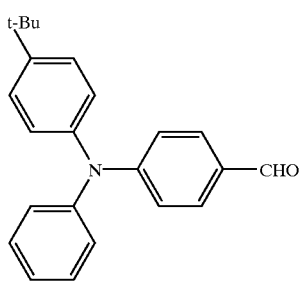

(41)-4
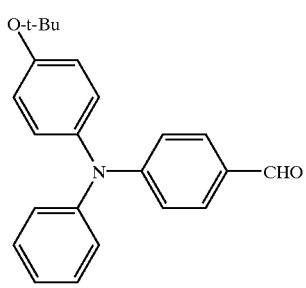

(41)-5

(41)-6
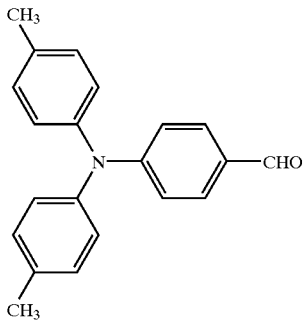

(41)-7
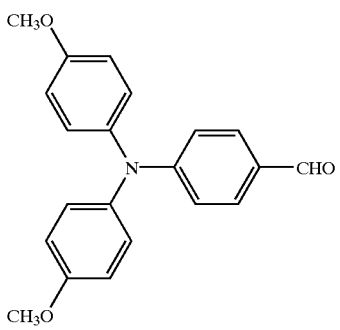

The inventive synthetic intermediate 1 or 1' can be led from a synthetic intermediate serving as a precursor in the following manner.

A triarylamine (hereinafter referred to as inventive synthetic intermediate 2), which is represented by the following general formula [IX] or [X], or by the following general formula [IX'] or [X'] and is used as a synthetic intermediate of the bias(aminostyryl)benzene compound of the afore-indicated general formula [I], [II], [III] or [IV], or a triarylamine (hereinafter referred to as inventive synthetic intermediate 2'), which is used as a synthetic intermediate for the bis(aminostyryl)benzene compound of the afore-indicated general formula [XIX], is formylated with an adduct of dimethylformamide and phosphorus oxychloride to obtain a 4-(N,N-diarylamino)benzaldehyde of the afore-indicated general formula [V] or [VI], or [V'] or [VI'], which serves as the synthetic intermediate 1 or 1' for the bis(aminostyryl) benzene compound. The formylation reaction may be carried out at room temperature (20° C.) to 80° C. at normal pressures for 3 to 24 hours.

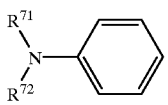
[IX]

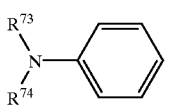
[X]

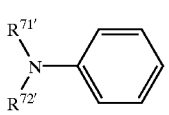
[IX']

-continued

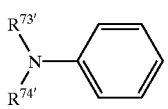
[X']

wherein $R^{71}$ and $R^{72}$ independently represent an aryl group corresponding to or defined before with respect to $R^1$, $R^2$, $R^{14}$, $R^{15}$, $R^{27}$, $R^{28}$, $R^{40}$ or $R^{41}$, $R^{71'}$ and $R^{72'}$ independently represent an aryl group corresponding to $R^{90}$ or $R^{91}$, $R^{73}$ and $R^{74}$ independently represent an aryl group corresponding to or defined before with respect to $R^3$, $R^4$, $R^{16}$, $R^{17}$, $R^{29}$, $R^{30}$, $R^{42}$ or $R^{43}$, and $R^{73'}$ and $R^{74'}$ independently represent an aryl group corresponding to $R^{92}$ or $R^{93}$.

The above inventive synthetic intermediate 2 or 2' is generally represented by the afore-indicated general formula [IX] or [X], or [IX'] or [X'], and particularly represented by the following general formula (28) or (29) and more particularly represented by the following general formula (30), (31), (32), (33), (33), (34) or (35) with its specific examples including those of the following structural formulas (36)-1, (36)-2, (36)-3, (36)-3, (36)-4, (36)-5, (36)-6, (36)-7, (36)-8, (36)-9, (36)-10 and (36)-11:

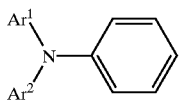
(28)

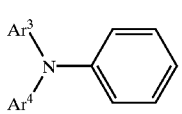
(29)

wherein $Ar^1$, $Ar^2$, $Ar^3$ and $Ar^4$, respectively, have the same meanings as defined before;

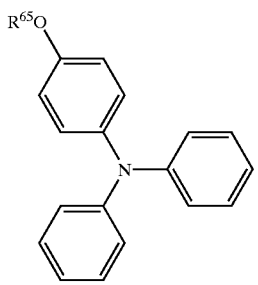
(30)

wherein $R^{65}$ an alkyl or alkenyl group having from 1 to 4 carbon atoms, a cyclohexyl group or a phenyl group;

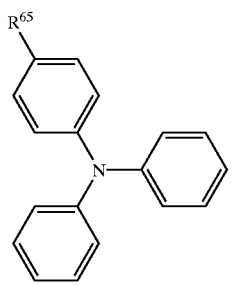
(31)

wherein $R^{66}$ an alkyl or alkenyl group having from 1 to 4 carbon atoms, a cyclohexyl group or a phenyl group;

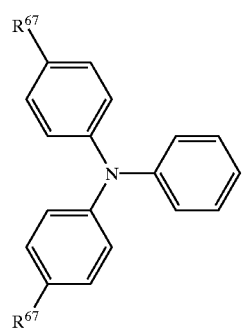
(32)

wherein $R^{67}$ an alkyl or alkenyl group having from 1 to 4 carbon atoms, a cyclohexyl group or a phenyl group;

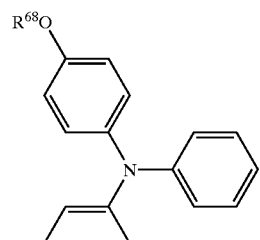
(33)

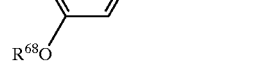

wherein $R^{68}$ an alkyl or alkenyl group having from 1 to 4 carbon atoms, a cyclohexyl group or a phenyl group;

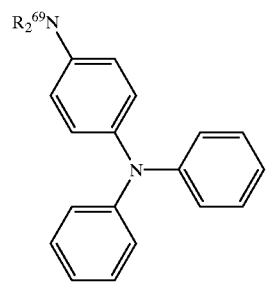
(34)

wherein $R^{69}$ an alkyl or alkenyl group having from 1 to 4 carbon atoms, a cyclohexyl group or a phenyl group;

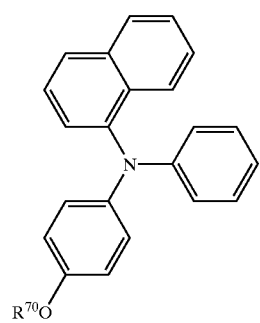
(35)

wherein $R^{70}$ represents an alkyl or alkenyl group having from 1 to 4 carbon atoms, a cyclohexyl group or a phenyl group;

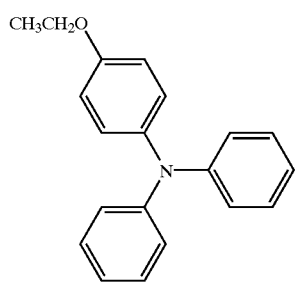

(36)-11

[structure: triphenylamine]

The inventive synthetic intermediate 2 or 2' of the following general formula [IX] or [X], or [IX'] or [X'] can be synthesized in the following manner.

The diarylamine of the following general formula [XI] or [XI'] and the halogenated benzene of the following general formula [XII] or [XII'] are subjected to coupling in the presence of a catalyst and a base, or the diarylamine of the following general formula [XII] or [XIII'] and the halogenated aryl compound of the following general formula [XIV] or [XIV'] are subjected to coupling in the presence of a catalyst and a base, thereby obtaining a triarylamine as the synthetic intermediate 2 or 2':

[IX]

[structure with $R^{64}$, $R^{65}$ and $Ar^1$, $Ar^2$]

[X]

[structure with $R^{66}$, $R^{67}$ and $Ar^3$, $Ar^4$]

[IX']

[structure with $R^{71'}$, $R^{72'}$]

[X']

[structure with $R^{73'}$, $R^{74'}$]

[XI]

$R^{71}$\N—H or $R^{73}$\N—H
$R^{72}$/          $R^{74}$/

[XII]

X—[phenyl]

[XI']

$R^{71'}$\N—H or $R^{73'}$\N—H
$R^{72'}$/          $R^{74'}$/

[XII']

X—[phenyl]

[XIII]

$R^{71}$\N—[phenyl]  or  $R^{73}$\N—[phenyl]
H/                       H/

[XIV]

X—$R^{72}$  or  X—$R^{74}$

[XIII']

$R^{71'}$\N—[phenyl]  or  $R^{73'}$\N—[phenyl]
H/                         H/

[XIV']

X—$R^{72'}$  or  X—$R^{74'}$

In the above general formulas [I'] and [X], [IX'] and [XI], [XI] and [XII], [XI'], and [XII'], [XIII] and [XIV], and [XIII'] and [XIV'] $R^{71}$ and $R^{72}$ independently represent an aryl group corresponding to or defined before with respect to $R^1$, $R^2$, $R^{14}$, $R^{15}$, $R^{27}$, $R^{28}$, $R^{40}$ or $R^{41}$, $R^{71'}$ and $R^{72'}$ independently represent an aryl group corresponding to or defined before with respect to $R^{90}$ or $R^{91}$ defined before, $R^{73}$ and $R^{74}$ independently represent an aryl group corresponding to or defined before with respect to $R^3$, $R^4$, $R^{16}$, $R^{17}$, $R^{29}$, $R^{30}$, $R^{42}$ or $R^{43}$, $R^{73'}$ and $R^{74'}$ independently represent an aryl group corresponding to or defined before with respect to $R^{92}$ or $R^{93}$ defined before, and X represents a halogen atom.

The catalyst used for the synthetic reaction of the inventive synthetic intermediate 2 or 2' includes, Cu, CuX, $CuX_2$, CuO, $Pd(CH_3COO)_2$, $Pd(PR_3)_4$ and the like, in which R represents a phenyl group or an alkyl group). The base includes $K_2CO_3$, $Ca_2CO_3$, NaOH, BuONa, PrONa, $C_2H_5ONa$, $CH_3ONa$ or the like. This reaction is favorably carried out at a reaction temperature of 100 to 200° C. at normal pressures for a reaction time of 1 to 48 hours in a solvent such as dimethylformamide, dimethylsulfoxide, nitrobenzene, dichlorobenzene, xylene or the like.

The invention also provides, as a synthetic intermediate for the first and second inventive compounds, a diphosphonic acid ester of the afore-indicated general formula [VII] or [VII'] or a diphosphonium salt of the afore-indicated general formula [VIII] or [VIII'] (hereinafter referred to as inventive synthetic intermediate 3).

This synthetic intermediate 3 is represented by the following general formula (19) or (20) or by the following general formula (19') or (20'):

(19)

[structure: benzene ring with two CN and two $CH_2P(O)(OR^{76})_2$ groups]

(20)

[structure: benzene ring with two CN and two $CH_2P^+Ph_3X^-$ groups]

-continued

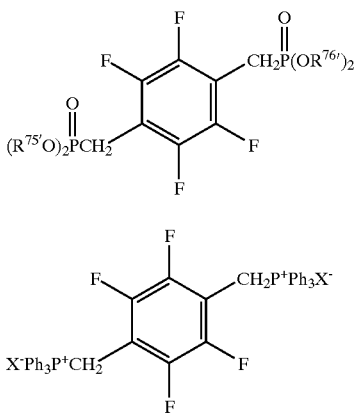

(19')

(20')

wherein $R^{75}$, $R^{76}$, $R^{75'}$ and $R^{76'}$, respectively, have the same meanings as defined before.

The inventive synthetic intermediate 3 can be derived from a synthetic intermediate serving as a precursor in the following manner.

A halogenated aryl compound of the following general formula [XV] or [XV'] and a trialkyl phosphite of the following general formula [XVI] or triphenylphosphine (PPh$_3$) are reacted to obtain a diphosphinic acid ester of the aforeindicated general formula [VII] or [VII'] or a diphosphonium salt of the afore-indicated general formula [VIII] or [VIII'] as synthetic intermediate 3. This reaction is favorably carried out at a reaction temperature of 120 to 160° C. at normal pressures for a time of 30 minutes to 12 hours in a solvent-free condition or in an excess solvent such as a trialkyl phosphite or xylene

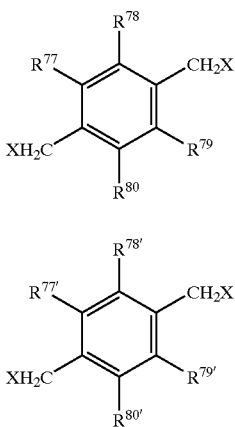

[XV]

[XV']

wherein $R^{77}$, $R^{78}$, $R^{79}$ and $R^{80}$ may be the same or different provided that at least one of them is a cyano group or a nitro group and the others independently represent a hydrogen atom, a cyano group, a nitro group or a halogen atom, $R^{77'}$, $R^{78'}$, $R^{79'}$ and $R^{80'}$ may be the same or different and independently represent a group selected from a hydrogen atom and a halogen atom provided that at least one of them is a fluorine atom, and X represents a halogen atom; and $P(OR^{81})_3$ or $P(OR^{82})_3$   [XVI]

wherein $R^{81}$ and $R^{82}$ may be the same or different and independently an alkyl or alkenyl group having from 1 to 4 carbon atoms, a cyclohexyl group or a phenyl group and, respectively, correspond to the group defined with respect to $R^{75}$ or $R^{76}$, or $R^{75'}$ or $R^{76'}$.

Moreover, the invention provides a halogenated aryl compound of the afore-indicated general formula [XV] or [XV'] (hereinafter referred to as inventive synthetic intermediate 4) as a synthetic intermediate for preparing the synthetic intermediate 3.

The inventive synthetic intermediate 4 is obtained by reacting a xylene compound of the following general formula [XVII] or [XVII'] with an N-halogenated succinimide of the general formula [XVIII] under irradiation of light. For example, the reaction is performed in a solvent, such as carbon tetrachloride, chloroform, benzene or the like, under irradiation of light of a 100 to 500 W light source, such as a high pressure mercury lamp, a low pressure mercury lamp, a xenon lamp, a halogen lamp or the like, at a temperature of 20 to 60° C. under a normal pressure for a reaction time of 30 minutes to 48 hours.

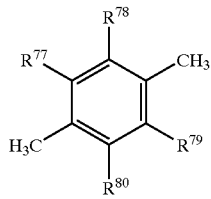

[XVII]

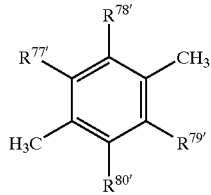

[XVII']

wherein $R^{77}$, $R^{78}$, $R^{79}$ and $R^{80}$ may be the same or different provided that at least one of them is a cyano group or a nitro group and the others independently represent a hydrogen atom, a cyano group, a nitro group or a halogen atom, and $R^{77'}$, $R^{78'}$, $R^{79'}$ and $R^{80'}$ are, respectively, groups which may be the same or different and are selected from a hydrogen atom and a halogen atom provided that at least one of them is a fluorine atom; and

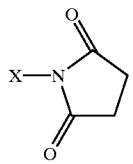

[XVIII]

wherein X represents a halogen atom.

The reactions for obtaining the respective synthetic intermediates 1 to 4 stated above can be shown according to the following reaction scheme 2 and also the reaction scheme 3 or 3':

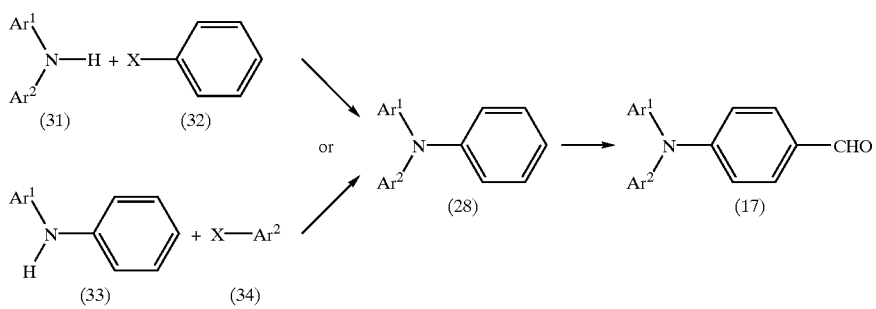

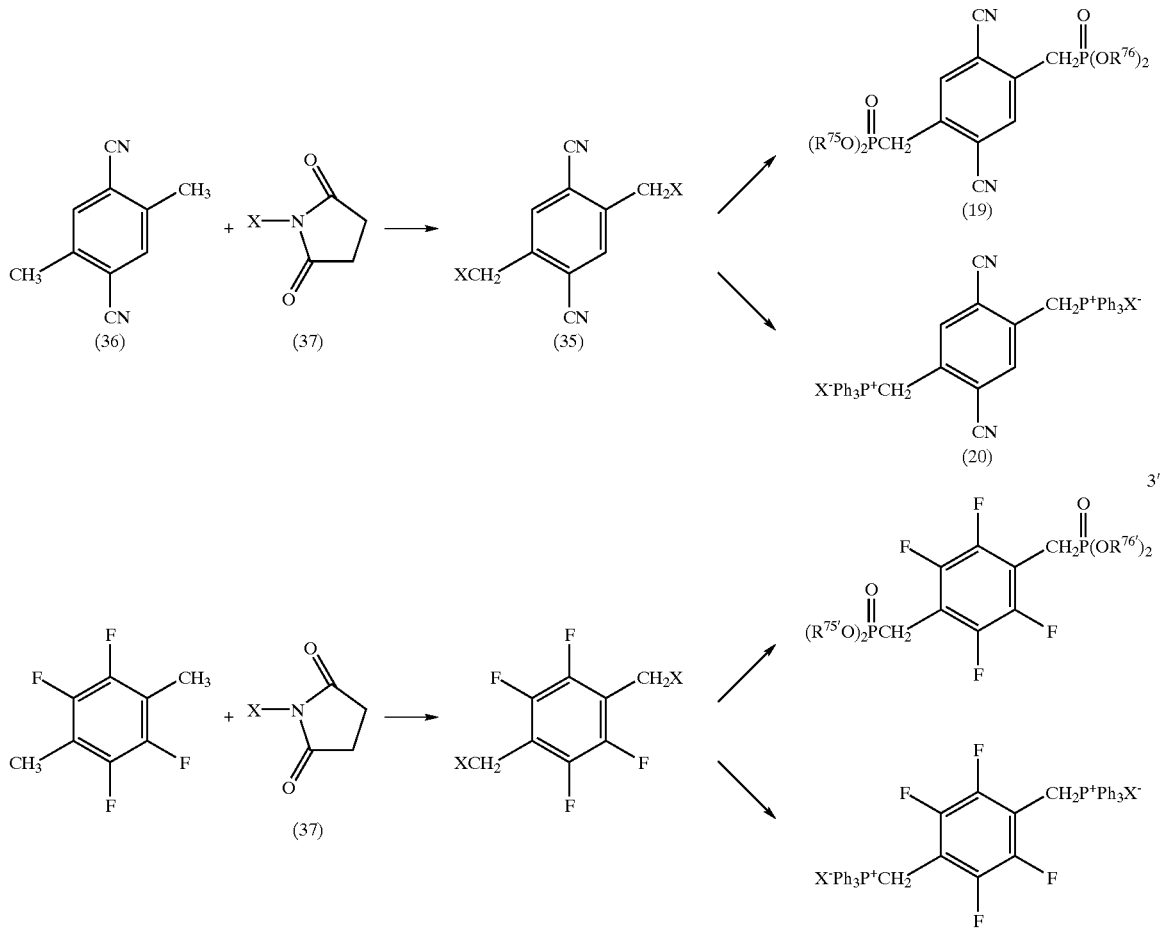

The invention further provides a more preferred compound suitable as a synthetic intermediate for the inventive first and second compounds.

More particularly, this synthetic intermediate consists of an acetal compound of the following general formula (44), (45) or (46) (hereinafter referred to as inventive synthetic intermediate 5):

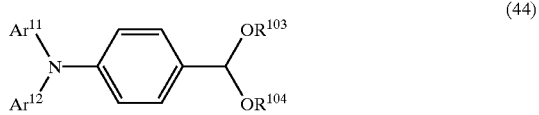

(44)

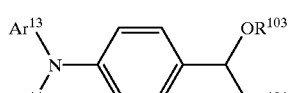

(45)

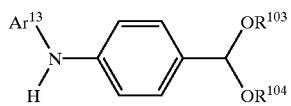

(46)

wherein $Ar^{11}$, $Ar^{12}$, $Ar^{13}$ and $Ar^{14}$ may be the same or different and independently represent an aryl group of the following general formula (47)

(47)

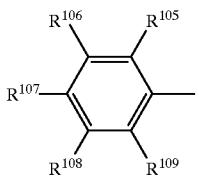

wherein $R^{105}$, $R^{106}$, $R^{107}$, $R^{108}$ or $R^{109}$ may be the same or different and independently represent a group selected from a hydrogen atom, an alkyl or alkenyl group having from 1 to 4 carbon atoms, a cyclohexyl group, a phenyl group, an alkoxy group having from 1 to 4 carbon atoms, which may be saturated or may have a double bond, a cyclohexyloxy group, a phenoxy group, a dialkylamino or dialkenylamino group whose alkyl or alkenyl moiety has from 1 to 4 carbon atoms, a dicyclohexylamino group, and a diphenylamino group, and $R^{103}$ and $R^{104}$ independently represent an alkyl or alkenyl group having from 1 to 4 carbon atoms, a cyclohexyl group or a phenyl group provided that $R^{103}$ and $R^{104}$ may take a structure joined through a carbon chain.

To obtain the acetal compound of the general formula (44) for the preparation of the inventive synthetic intermediate 5, an amine compound of the following general formula (48) and an acetal compound of the following general formula (49) are subjected to coupling reaction in the presence of a catalyst and a base

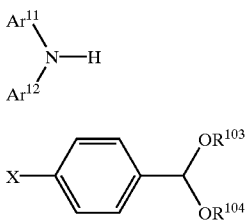

(48)

(49)

wherein $Ar^{11}$, $Ar^{12}$, $R^{103}$ and $R^{104}$, respectively, have the same meanings as defined above, and X represents a halogen atom.

In order to obtain the acetal compound of the afore-indicated general formula (45), an acetal compound of the following general formula (49') and an aryl compound of the following general formula (50) are subjected to coupling reaction in the presence of a catalyst and a base (49')

(50)

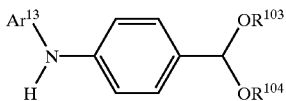

wherein $Ar^{13}$, $Ar^{14}$, $R^{103}$ and $R^{104}$, respectively, have the same meanings as defined before, and x represents a halogen atom.

To obtain an acetal compound of the afore-indicated general formula (46), an amine compound of the following general formula (51) and an acetal compound of the following general formula (52) are subjected to coupling reaction in the presence of a catalyst and a base

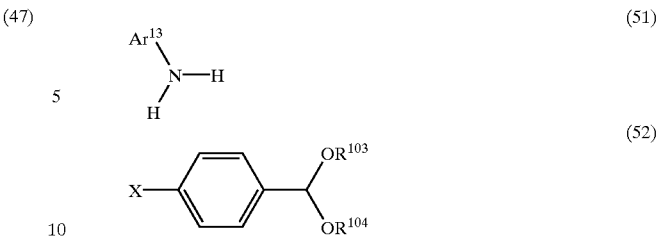

(51)

(52)

wherein $Ar^{13}$, $R^{103}$ and $R^{104}$, respectively, have the same meanings as defined before, and X represents a halogen atom.

The catalyst used for the coupling reactions may be one wherein a Pd(O)-phosphine complex defined before serves as an active species:

Pd(O)-phosphine complex
wherein Pd(O) may be added to as a reagent for Pd(O), Pd(I) or Pd(II), and the phosphine represents a tertiary phosphine of the following general formula (53) or (54)

 (53)

 (54)

wherein $R^{105}$ and $R^{106}$ independently represent an alkyl or alkenyl group having from 1 to 4 carbon atoms, a cyclehexyl group or a phenyl group, and Q represents a hydrocarbon group or may take a crosslinking structure represented by the following general formula (55) or (56):

 (55)

 (56)

wherein G represents an oxygen atom, a sulfur atom, an amino group, a hydrocarbon group or a metal atom. and $Ar^{15}$ and $Ar^{16}$ independently represent an aryl group which may have a substituent group.

Next, the inventive synthetic intermediate 5, i.e. the acetal compound of the following general formula (44), (45) or (46), is subjected to acetal exchange in a ketone solvent in the presence of an acid or base catalyst to conveniently obtain a 4-(N,N-diarylamino)benzaldehyde compound of the following general formula (57), (58) or (59)

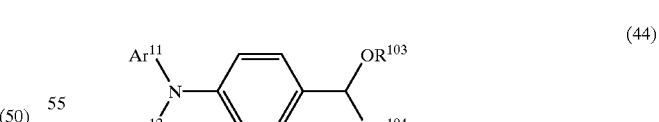 (44)

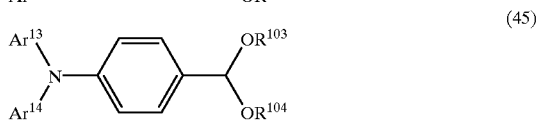 (45)

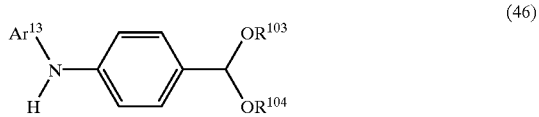 (46)

wherein $Ar^{11}$, $Ar^{12}$, $Ar^{13}$ and $Ar^{14}$ are groups which may be the same or different and independently represent an aryl group of the following general formula (47)

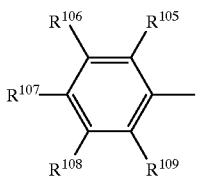
(47)

wherein $R^{105}$, $R^{106}$, $R^{107}$, $R^{108}$ or $R^{109}$ may be the same or different and independently represent a group selected from a hydrogen atom, an alkyl or alkenyl group having from 1 to 4 carbon atoms, a cyclohexyl group, a phenyl group, an alkoxy group having from 1 to 4 carbon atoms, which may be saturated or may have a double bond, a cyclohexyloxy group, a phenoxy group, a dialkylamino or dialkenylamino group whose alkyl or alkenyl moiety has from 1 to 4 carbon atoms, a dicyclohexylamino group, and a diphenylamino group, $R^{103}$ and $R^{104}$ independently represent an alkyl or alkenyl group having from 1 to 4 carbon atoms, a cyclohexyl group or a phenyl group provided that $R^{103}$ and $R^{104}$ may take a structure joined through a hydrocarbon chain

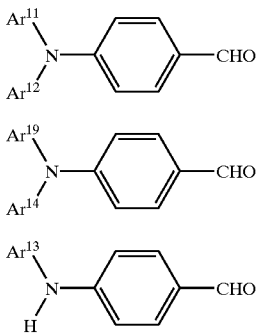

(57)

(58)

(59)

wherein $Ar^{11}$, $Ar_{12}$, $Ar^{13}$ and $Ar^{14}$, respectively, have the same meanings as defined before.

Specific examples of the compound of the above general formula (44) include those indicated below

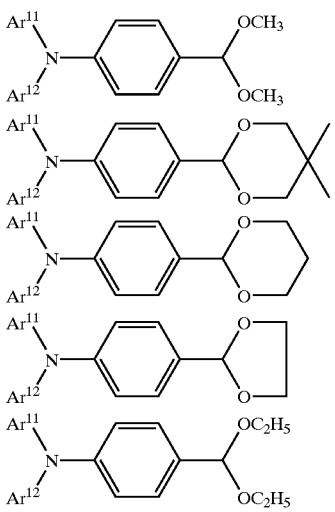

-continued

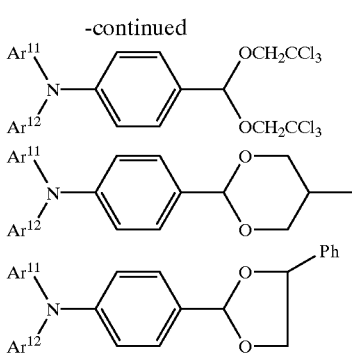

The combinations of the acid catalyst and the solvent include, for example, sulfuric acid/methanol. hydrochloric acid/methanol, DCC—$SnCl_4$/oxalic acid/alcohol, trifluoroacetic acid/dimethoxymethane/nitromethane, p-toluenesulfonic acid/dimethoxymethane/methanol, hydrochloric acid/tetramethoxysilane/methanol, p-toluenesulfonic acid/acetone, trifluoroacetic acid/chloroform/water, tetrachlorotitanium/lithium iodide/diethyl ether, acetic acid/water, formic acid/pentane, acetic acid/zinc-silver/tetrahydrofuran, pyridinium p-toluenesulfonate/acetone-water, silica gel/water-methylene chloride, and the like.

When a palladium catalyst ($Pd(CH_3COO)_2$) is used as the catalyst for the coupling reactions, the yield for the coupling reaction can be improved. Moreover, when such a catalyst as indicated below is applied to a less reactive system, the yield can be improved.

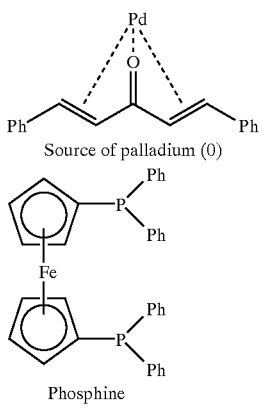

Source of palladium (0)

Phosphine

=palladium(O)bis(dibenzylidene acetone)

In this regard, it should be noted that the catalysts indicated below were not used in examples appearing hereinafter.

It is sufficient that palladium is in the form of Pd(O) in the reaction system, and with the $Pd(CH_3COO)_2$—$PPh_4$ system, it is considered that PD(II) is reduced with $PPh_4$, thereby causing Pd(O) to occur. In this connection, it has been generally accepted as preferred that phosphine is bulky around phosphorus and the bihedral angle of C—P—C is large, and the specific structure of the active species in the Pd(O)-phosphine reaction system is not known at the present stage.

A typical combination of the palladium catalyst is one created from a Pd complex, a tertiary phosphine, a base and a xylene solvent, all refluxed for 2 to 10 hours.

The benzaldehyde of the afore-indicated general formula (57) or (58) may be ones, like the afore-indicated synthetic intermediate 1 or 1', represented by the afore-indicated structural formulas (27)-1, (27)-2, (27) -3, (27)-4, (27)-5, (27)-6, (27)-7, (27)-8, (27)-9, (27)10, and (27)-11.

In order to obtain the inventive synthetic intermediate 1 or 1'of the afore-indicated general formula [V] or [VI], or [V'] or [VI'], a phosphorus oxychloride (POCl₃)-dimethylformamide (DMF) adduct has been used to convert the tertiary amine of the synthetic intermediate 2 or 2' into an aldehyde. This method may present such a problem as mentioned below.

When the tertiary amine has a substituent such as a cyano group and thus, assumes an electron-attracting property, the phosphorus oxychoride-dimethylformamide adduct is unlikely to react.

Instance 1)

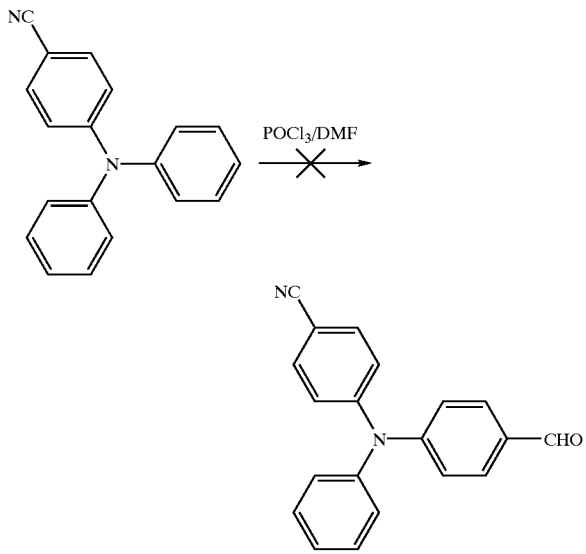

In the method using the phosphorus oxychoride-dimethylformamide adduct, when there are two or more active sites, the positional selectivity of the reaction is low.

Instance 2)

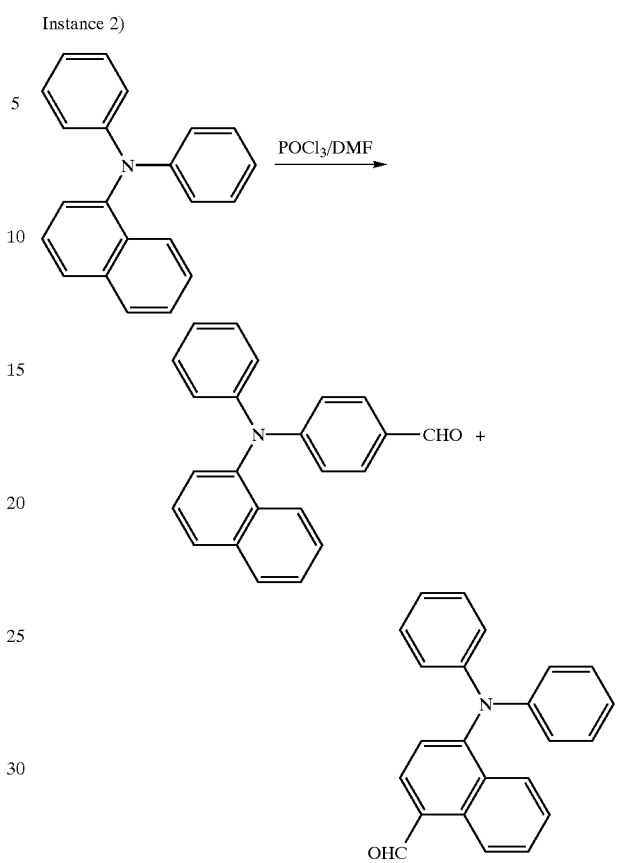

To avoid this, the acetal compound of the afore-indicated general formula (49), (49') or (52) is used for reaction with the compound of the general formula (48), (50) or (51), there can be readily prepared an intended aldehyde in good positional selectivity. The method of preparing the inventive compound including the above reaction may be shown, for example, in the following reaction scheme 4, 5 or 6.

(1) Preparation of a bis(aminostyryl)benzene Compound (Structural Formula (16)-9)

4

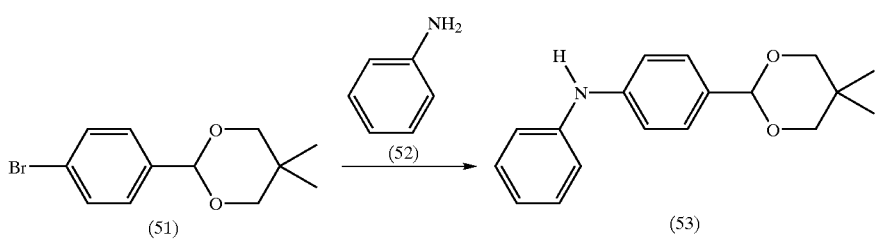

-continued
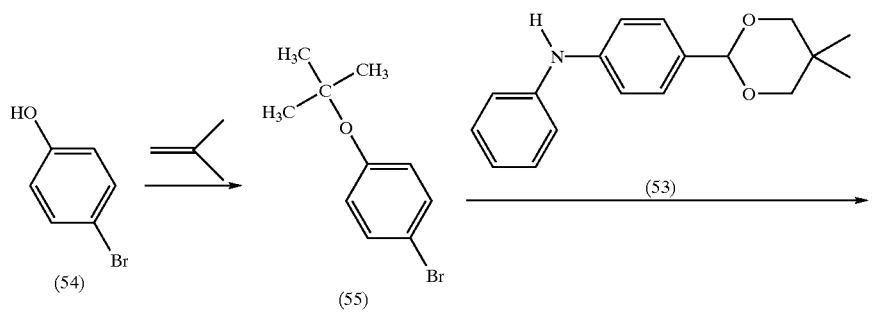
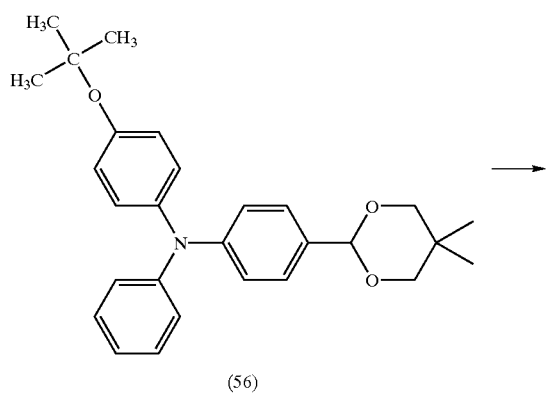
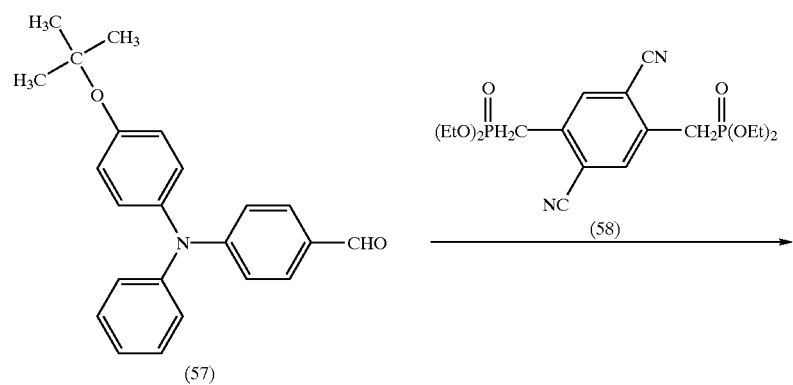
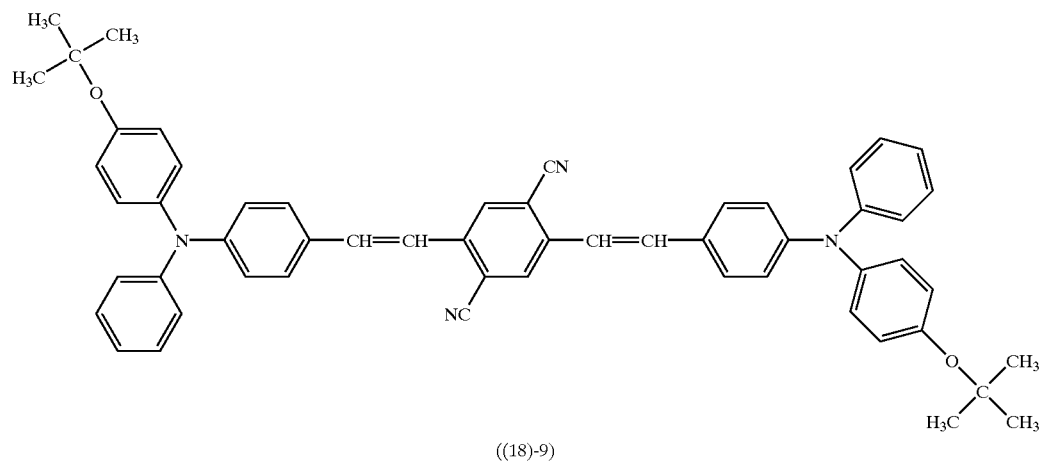

(2) Preparation of a bis(aminostyryl)benzene Compound
Structural Formula (16)-8
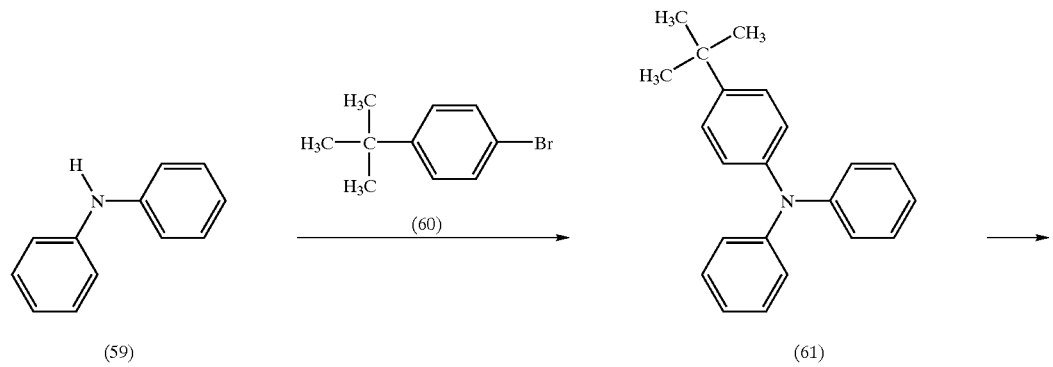
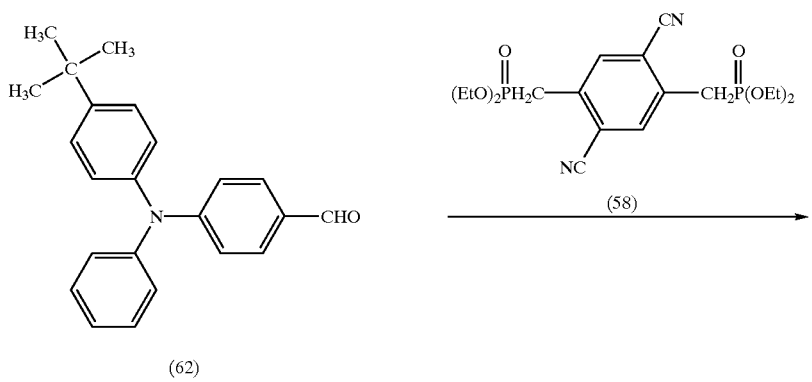
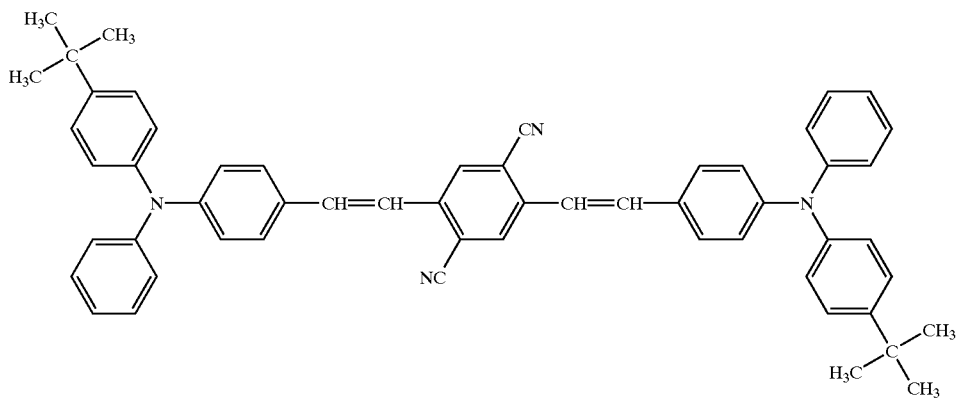
((16)-8)

(3) Preparation of a bis(aminostyryl)benzene Compound (Structural Formula (16)-3)

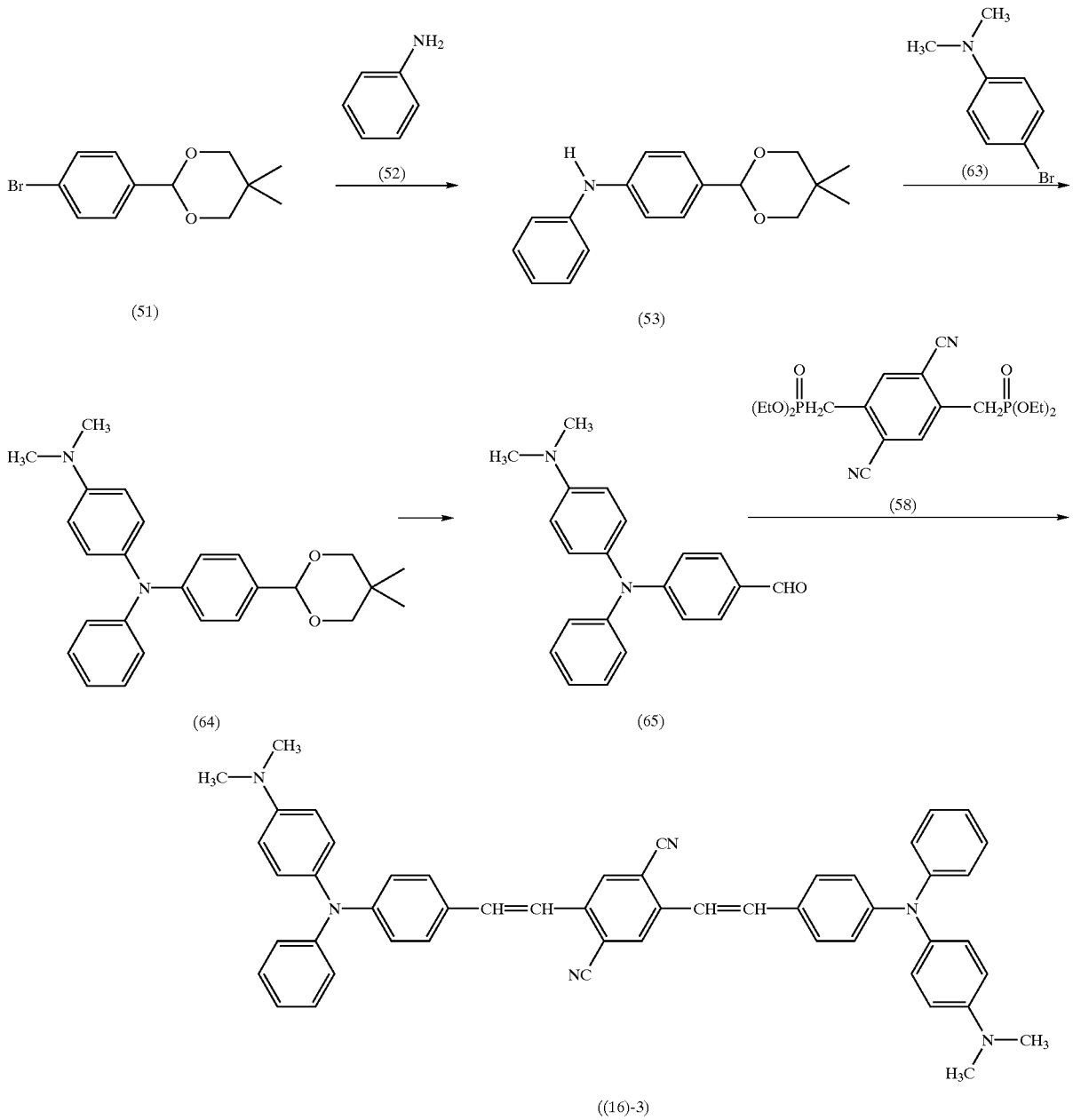

Reaction scheme 6

FIGS. 45 to 48 are, respectively, views showing organic electroluminescent devices (EL devices) using the compounds of the invention as an organic luminescent material.

Figure 45:
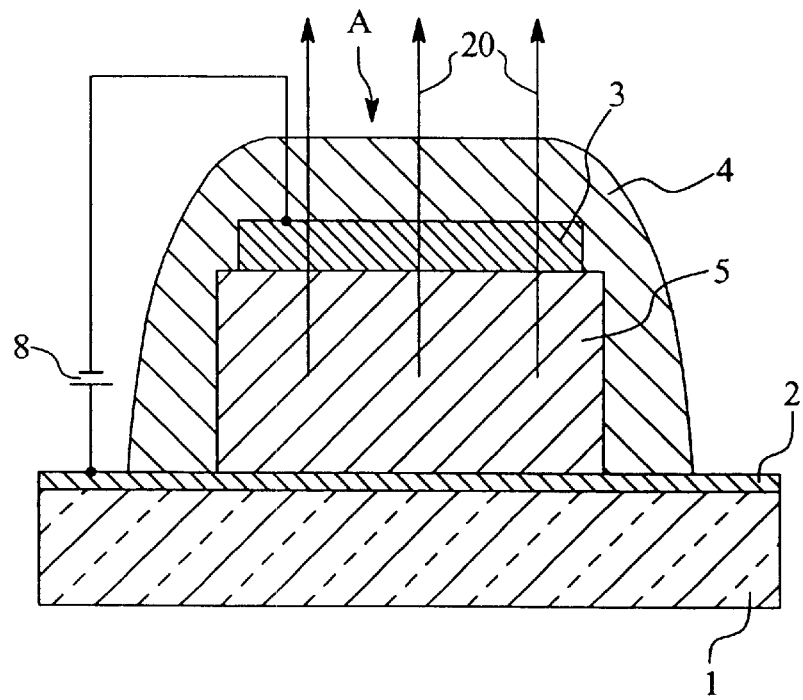
FIG. 45 is a schematic sectional view showing an essential part of an organic electroluminescent device according to one embodiment of the invention.
Figure 46:
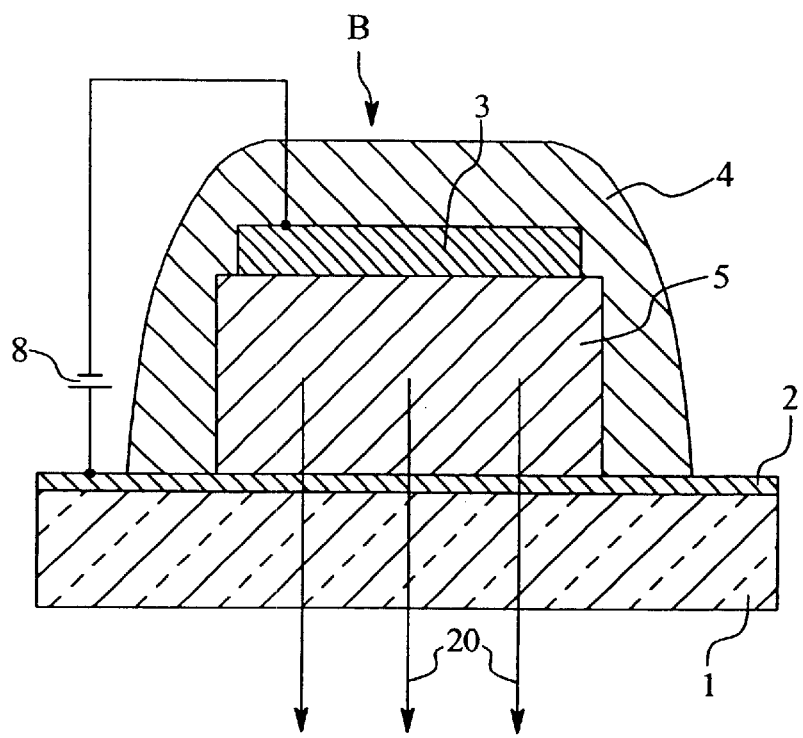
FIG. 46 is a schematic sectional view showing an essential part of an organic electroluminescent device according to another embodiment of the invention.

FIG. 45 shows organic electroluminescent device A of a transmission type in which luminescent light 20 is transmitted through a cathode 3, and the light can also be observed from a side of a protective layer 4. FIG. 46 shows organic electroluminescent device B of a reflection type wherein light reflected at a cathode 3 can also be obtained as luminescent light 20.

In the figures, reference numeral 1 indicates a substrate for forming an organic electroluminescent device, which may be made of glass, plastics and other appropriate materials. Where the organic electroluminescent device is used in combination with other types of display devices, the substrate 1 may be commonly used. Reference numeral 2 indicates a transparent electrode (anode), for which ITO (indium tin oxide), $SnO_2$ or the like may be used.

Reference numeral 5 indicates an organic luminescent layer, which contains the compound of the invention as a luminescent material. For a layer arrangement for obtaining the organic electroluminescence 20, hitherto known various types of arrangements may be used. As is described hereinafter, if a material for either a hole transport layer or an electron transport layer has luminescent properties, for example, a built-up structure of these thin films may be used.

Further, in order to increase charge transportability within a range satisfying the purposes of the invention, either or both of a hole transport layer and an electron transport layer have a built-up structure of thin films made of plural types of materials, or a thin film composed of a mixture of plural types of materials may be used without limitation. In addition, in order to improve luminescent properties, at least one fluorescent material may be used to provide a structure wherein a thin film of the fluorescent material is sandwiched between the hole transport layer and the electron transport layer. Alternatively. another type of structure may be used wherein at least one fluorescent material is present in the hole transport layer or the electron transport layer, or in both. In these cases, in order to improve a luminescent efficiency, a thin film for controlling the transport of holes or electrons may be incorporated in a layer arrangement.

Where the compounds of the invention have both electron transportability and electron transportability, they can be used as a luminescent layer serving also as an electron transport layer, or as a luminescent layer serving as a hole transport layer in the device arrangement. Moreover, it is possible to provide an arrangement wherein the compound of the invention is formed as a luminescent layer sandwiched between the electron transport layer and the hole transport layer.

It will be noted that in FIGS. 45 and 46, reference numeral 3 indicates a cathode, and an electrode material therefor may be made of an alloy of an active metal such as Li, Mg, Ca or the like, and a metal such as Ag, Al, In or the like. Alternatively, a built-up structure of thin films of these metals may also be used. In the transmission-type organic electroluminescent device, an optical transmission required for an intended application can be obtained by controlling a cathode thickness. In the figures, reference numeral 4 indicates a sealing/protecting layer, and when an organic electroluminescent device is wholly covered therewith, its effect increases. Appropriate materials may be used for this purpose provided that air tightness is ensured. Reference numeral 8 indicates a drive power supply for current charge.

In the organic electroluminescent device of the invention, the organic layer may have an organic built-up structure (single hetero structure) wherein a hole transport layer and an electron transport layer are built up and wherein the compound of the invention is used as a material for forming the hole transport layer or electron transport layer. Alternatively, the organic layer may have an organic built-up structure (double hetero structure) wherein a hole transport layer, a luminescent layer and an electron transport layer are successively built up, and the luminescent layer is formed of the compound of the invention.

An example of an organic electroluminescent device having such an organic built-up structure is shown. More particularly, FIG. 47 shows organic electroluminescent device C having a single hetero structure which comprises a built-up structure including, on an optically transparent substrate 1, an optically transparent anode 2, an organic layer 5a consisting of a hole transport layer 6 and an electron transport layer 7, and a cathode 3 superposed successively in this order, and the built-up layer structure is sealed with the protective layer 4.

Figure 47:
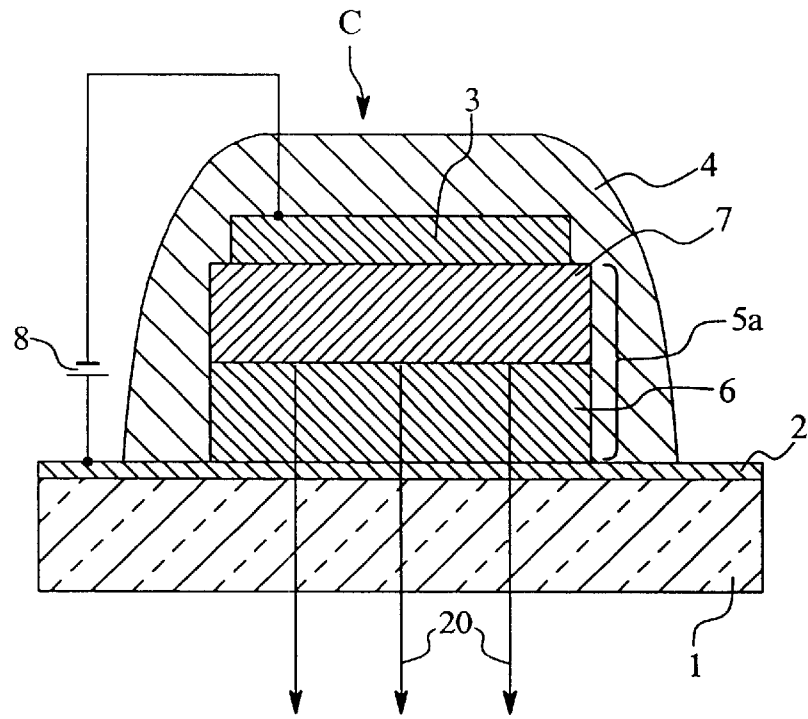
FIG. 47 is schematic sectional view showing an essential part of an organic electroluminescent device according to a further embodiment of the invention.

With such a layer arrangement as shown in FIG. 47 wherein a luminescent layer is omitted, luminescence or light 20 with a given wavelength is emitted from the interface between the hole transport layer 6 and the electron transport layer 7. This luminescence is observed from the side of the substrate 1.

Figure 48:
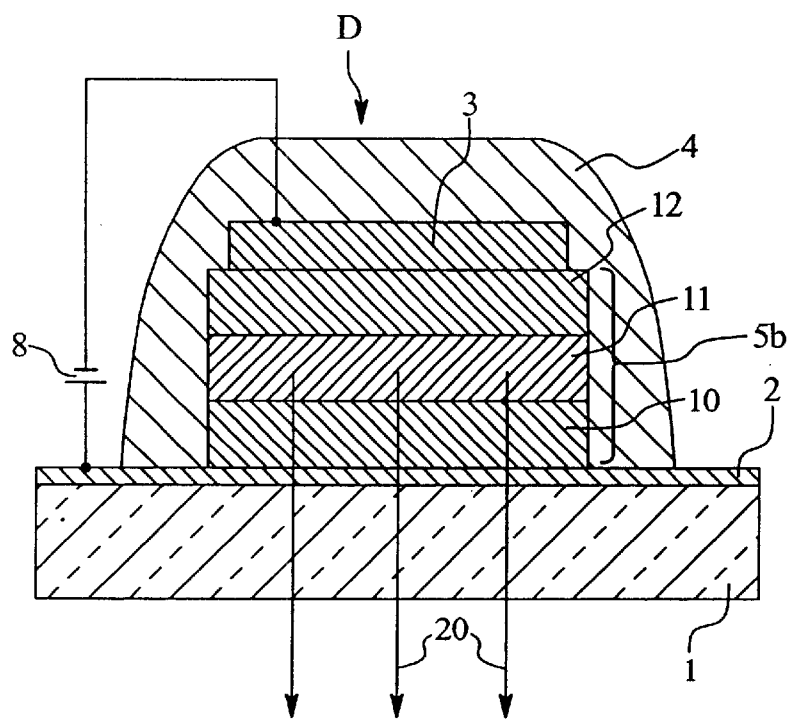
FIG. 48 is a schematic sectional view showing an essential part of an organic electroluminescent device according to a still further embodiment of the invention.

FIG. 48 shows organic electroluminescent device D having a double hetero structure which comprises a built-up structure including, on an optically transparent substrate 1, an optically transparent anode 2, an organic layer 5b consisting of a hole transport layer 10, a luminescent layer 11 and an electron transport layer 12, and a cathode 3 superposed successively in this order, the built-up structure being sealed with a protective layer 4.

In the organic electroluminescent device shown in FIG. 48, when a DC voltage is applied between the anode 2 and the cathode 3, the holes injected from the anode 2 arrives at the luminescent layer 11 via the hole transport layer 10. and the electrons injected from the anode 3 also arrives at the luminescent layer 11 via the electron transport layer 12. Eventually, the electrons/the holes are re-combined in the luminescent layer to generate singlet excitons, thereby causing luminescence with a given wavelength to be generated from the singlet excitons.

In the above-stated organic electroluminescent devices C and D, optically transparent materials such as, for example, glass, plastics and the like may be appropriately used as the substrate 1. Where the devices are used in combination with other types of display devices, or where the built-up structures shown in FIGS. 47 and 48 are arranged in the form of a matrix, the substrate may be commonly used. Both of the devices C and D may have a structure of either a transmission type or a reflection type.

The anode 2 consists of a transparent electrode, for which ITO (indium tin oxide), $SnO_2$ or the like may be used. In order to improve a charge injection efficiency, a thin film made of an organic material or an organometallic compound may be provided between the anode 2 and the hole transport layer 6 (or the hole transport layer 10). It will be noted that where the protective layer 4 is formed of a conductive material such as a metal, an insulating film may be provided at the sides of the anode 2.

The organic layer 5a of the organic electroluminescent device C consists of a built-up organic layer of the hole transport layer 6 and the electron transport layer 7. The compound of the invention may be contained in either or both of these layers to provide a luminescent hole transport layer 6 or electron transport layer 7. The organic layer 5b of the organic electroluminescent device D consists of a built-up organic layer of the hole transport layer 10, the luminescent layer 11 containing the compound of the invention, and the electron transport layer 12. The layer 5b may take other various types of built-up structures. For instance, either or both of the hole transport layer and the electron transport layer may have luminescent properties.

Especially, it is preferred that the hole transport layer 6 or electron transport layer 7, and the luminescent layer 11, respectively, are comprised of a layer made of the compound of the present invention. These layers may be formed of the compound of the invention alone, or may be formed through co-deposition of the compound of the invention and other type of hole or electron transport material (e.g. an aromatic amine, a pyrazoline or the like). Moreover, in order to improve the hole transportability in the hole transport layer. a hole transport layer, which consists of a plurality of hole transport materials being built up, may be formed.

In the organic electroluminescent device C, the luminescent layer may be the electron transport luminescent layer 7. In this case, light may be emitted from the hole transport layer 6 or its interface depending on the voltage applied to from a power supply 8. Likewise, in the organic electroluminescent device D. the luminescent layer may be, aside from the layer 11, the electron transport layer 12 or the hole transport layer 10. For improving the luminescent performance, it is preferred to provide a structure wherein the luminescent layer 11 containing at least one fluorescent material is sandwiched between the hole transport layer and the electron transport layer. Alternatively, a fluorescent material may be contained in the hole transport layer or the electron transport layer, or in both. In this connection, in order to improve a luminescent efficiency, a thin film (such as a hole blocking layer or an exciton-generating layer) for controlling the transport of holes or electrons may be provided in the layer arrangement.

The materials used as the cathode 3 may be alloys of active metals such as Li, Mg, Ca and the like and metals such as Ag, Al, In and the like. Alternatively, a built-up structure of the layers of these metals may also be used. Proper selection in cathode thickness and in type of alloy or metal enables one to fabricate an organic electroluminescent device adapted for its application.

The protective layer 4 acts as a sealing film, and is arranged to wholly cover an organic electroluminescent device therewith, thereby ensuring improved charge injection efficiency and luminescent efficiency. It should be noted that if air tightness is ensured, a material including a single metal such as aluminium, gold, chromium or the like or an alloy thereof may be appropriately selected for this purpose.

The electric current applied to the respective organic electroluminescent devices set out hereinbefore is usually a direct current, but a pulse current or AC current may also be used. The values of current and voltage are not critical provided that they are within ranges not breaking the devices down. Nevertheless, taking into account the power consumption and life of the organic electroluminescent devices, it is preferred to cause luminescence efficiently by use of an electric energy which is as small as possible.

Figure 49:
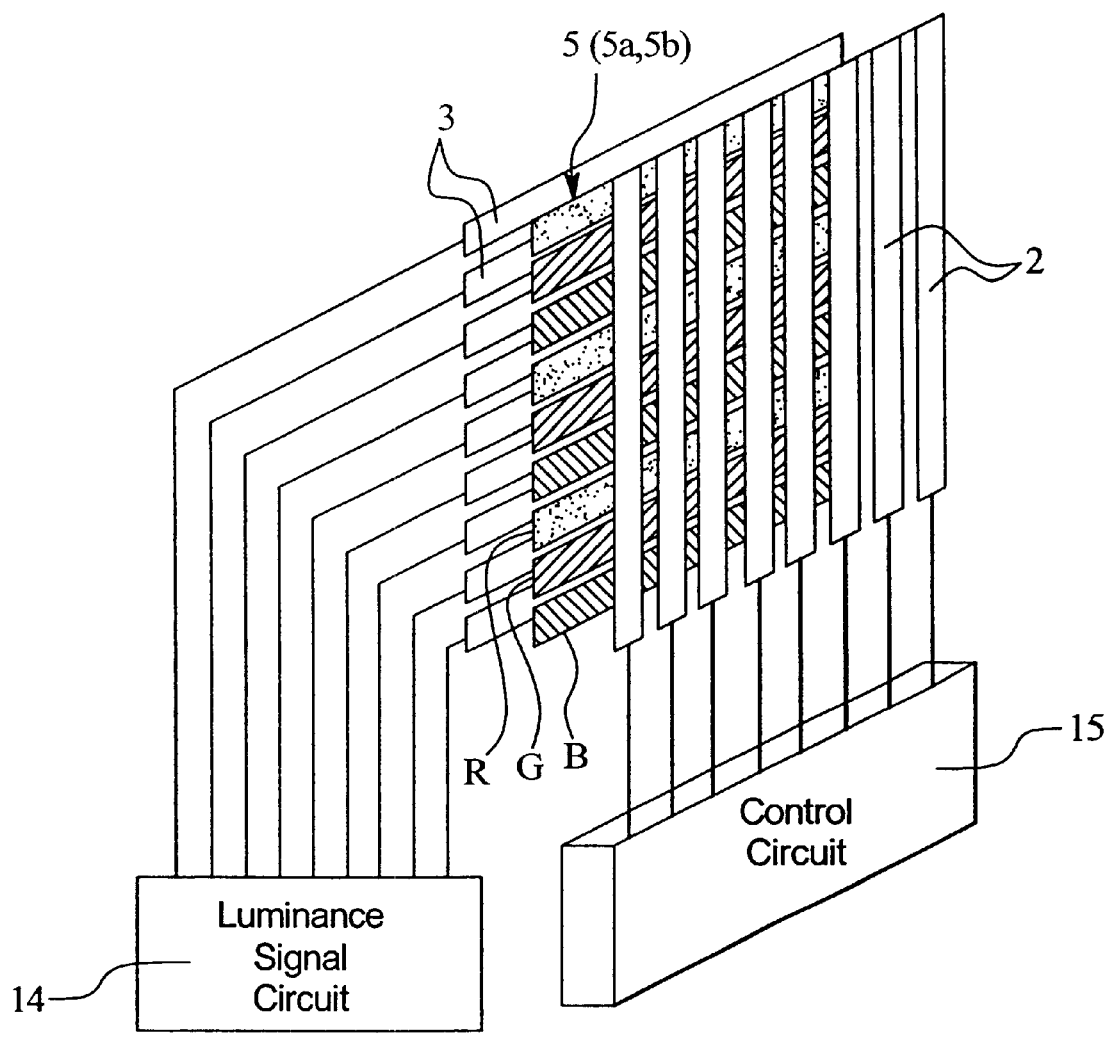
FIG. 49 is a view showing an arrangement of a multicolor or full color flat display using an organic electroluminescent device of the invention.

Next, FIG. 49 shows an arrangement of a flat display, which makes use of an organic electroluminescent device of the invention. As shown in the figure, with the case, for example, of a full color display, organic layers 5 (5a, 5b) capable of generating luminescent three primary colors of red IR), green (G) and blue (B) are arranged between cathodes 3 and anodes 2. The cathodes 3 and the anodes 2 may be provided in the form of stripes in which they are mutually intersected, and are properly selected by means of a luminance signal circuit 14 and a shift register built-in control circuit 15 and applied with a signal voltage thereto. As a result, an organic layer at a position (picture element) where the selected cathode 3 and anode 2 are intersected emits light.

More particularly, FIG. 49 shows, for example, a 8×3 RGB simple matrix wherein a built-up body 5 consisting of a hole transport layer and at least one of a luminescent layer and an electron transport layer is provided between the cathodes 3 and the anodes 2 (see FIG. 47 or 48). The cathodes and anodes are patternized in the form of stripes and are mutually intersected in a matrix, to which signal voltages are applied in time series from the shift register built-in control circuits 15 and 14, thereby causing electroluminescence or light emission at the intersected position. The EL device having such an arrangement may be used not only as a display for letters/symbols, but also as an image reproducing apparatus. Moreover, the striped patterns of the anodes 3 and the cathodes 2 may be arranged for each of red (RX, green (G) and blue (B) colors, thus making it possible to fabricate a solid-state flat panel display of the multicolor or full color type.

The invention is more particularly described by way of examples, which should not be construed as limited the invention thereto.

EXAMPLE 1

Synthetic Example of bis(aminostyryl)benzene Compound (Structural Formula (16)-1)

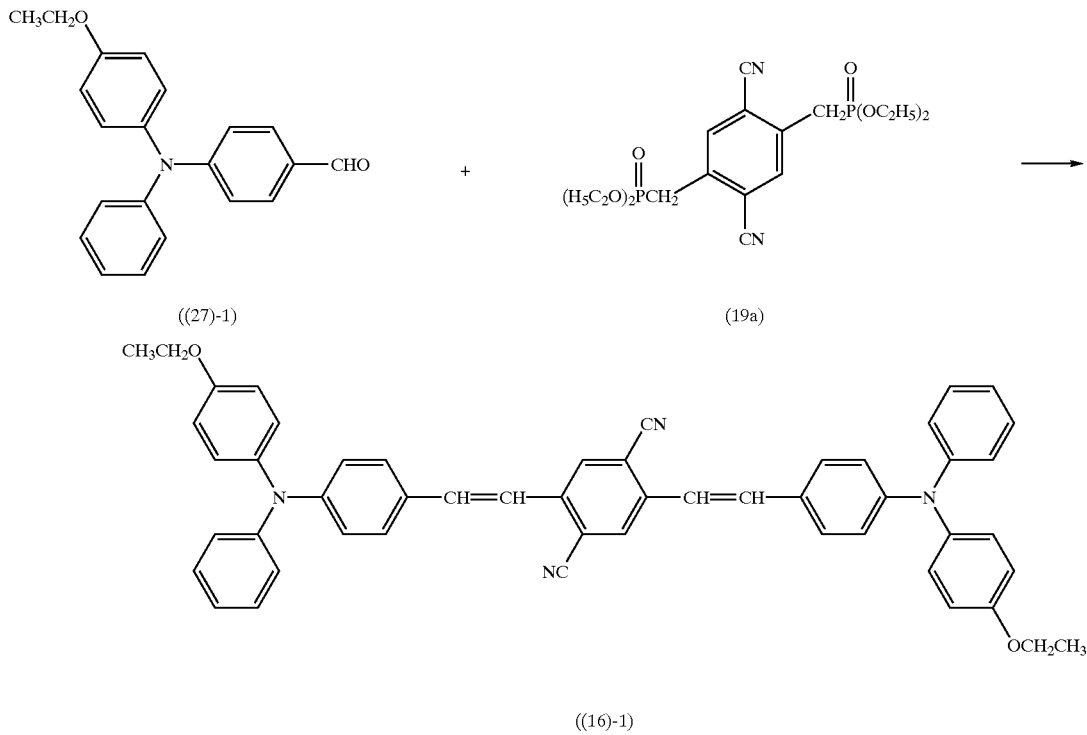

794 mg (4.78 mmols) of triethyl phosphate was dropped in 750 mg (2.39 mmols) of 2,5-di(bromomethyl)-terephthalonitrile, followed by agitation at 125° C. for 30 minutes to obtain diphosphonic acid ester (19a). The ethyl bromide formed by the reaction was distilled off, followed by dissolution in 25 ml of anhydrous tetrahydrofuran (THF) and storage.

NMR (CDCl$_3$) δ (ppm): 1.32. (6H, t), 4.03 (4H, q), 6.93 (4H, d), 6.98–7.22 (22H, m), 7.40 (4H, d), 7.98 (2H, s)

EXAMPLE 2

Synthetic Example of bis(aminostyryl)benzene Compound (Structural Formula (16)-1)

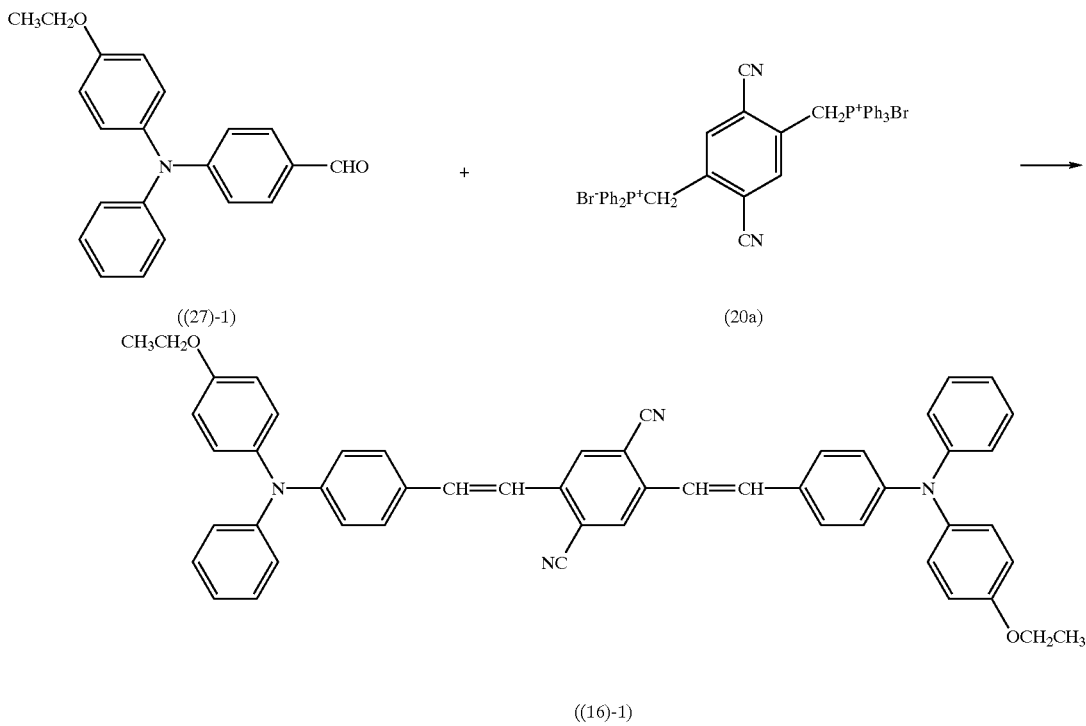

18.5 mmols of sodium hydride was suspended in 70 ml of anhydrous tetrahydrofuran, into which the anhydrous tetrahydrofuran solution of the thus obtained diphosphonic acid ester (19a) (corresponding to 2.39 mmols) was dropped in an atmosphere of nitrogen in 15 minutes, followed by agitation at room temperature for 20 minutes.

Subsequently, an anhydrous tetrahydrofuran solution (40 ml) of 1.78 g (5.60 mmols) of 4-[N-phenyl-N-(4-ethoxyphenyl)amino]benzaldehyde (structural formula (27)-1) was further dropped in the mixture in 15 minutes, and agitated at room temperature for 2.5 hours. The reaction mixture was quenched with a small amount of ice pieces, washed with a saturated saline solution and dried over anhydrous sodium sulfate.

The intended product was purified from the reaction mixture through silica gel chromatography (WAKO-gel C-300, tetrahydrofuran:hexane=1:8) and recrystallized from acetone/hexane to obtain 900 mg of the bis(aminostyryl) benzene compound ((16)-1). The yield was found to be at 51% with a glass transition point of 140° C. and a melting point of 180° C. The visible light absorption maximum of the tetrahydrofuran solution was at 475 nm and the fluorescence maximum wavelength was at 590 nm. The $^1$HNMR spectra of the solution were indicated below and also shown in FIG. 1 (it is to be noted that TMS in this and related figures means a peak of trimethylsilane added as a reference substance at the time of measurement of the $^1$HNMR spectra).

750 mg (2.39 mmols) of 2,5-di(bromomethyl)-terephthalonitrile and 1.38 g (5.26 mmols) of triphenylphosphine were dissolved in xylene and refluxed for 20 hours. The reaction solution was cooled down to room temperature, and the resultant precipitate was separated by filtration and washed with 5 ml of xylene, dried under reduced pressure and dissolved in 25 ml of anhydrous tetrahydrofuran for storage.

18.5 mols of sodium hydride was suspended in 70 ml of anhydrous tetrahydrofuran, into which the anhydrous tetrahydrofuran solution of the thus obtained diphosphonium (20a) (corresponding to 2.39 mmols) was dropped in an atmosphere of nitrogen in 15 minutes, followed by agitation at room temperature for 48 hours.

Subsequently, an anhydrous tetrahydrofuran solution (40 ml) of 1.78 g (5.60 mmols) of 4-[N-phenyl-N-(4-ethoxyphenyl)amino]benzaldehyde ((27)-1) was further dropped in the mixture in 15 minutes, and agitated at room temperature for 2.5 hours. The reaction mixture was quenched with a small amount of ice pieces, washed with a saturated saline solution and dried over anhydrous sodium sulfate.

There was obtained 558 mg of the bis(aminostyryl) benzene compound ((16)-1) by purification through silica gel chromatography (WAKO-gel C-300, tetrahydrofuran:hexane=1:8) and recrystallization from acetone/hexane. The yield was found to be at 31%, with various physical properties being coincident with those of the bis(aminostyryl)benzene compound ((16)-1) obtained in Example 1.

EXAMPLE 3

Synthetic Example of bis(aminostyryl)benzene Compound (Structural Formula (16)-2)

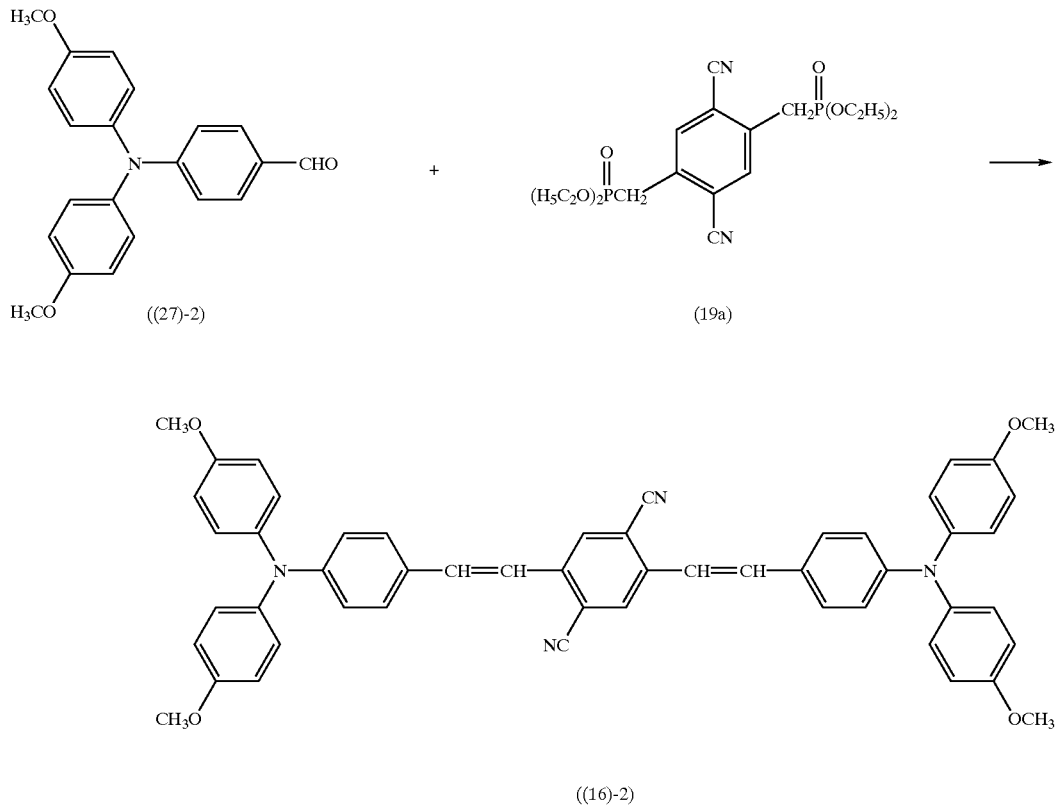

((27)-2)

(19a)

((16)-2)

11.3 mmols of sodium hydride was suspended in 20 ml of anhydrous tetrahydrofuran, into which the anhydrous tetrahydrofuran solution of the diphosphonic acid ester (19) (corresponding to 1.13 mmols) obtained in Example 1 was dropped in an atmosphere of nitrogen in 15 minutes, followed by agitation at room temperature for 20 minutes.

Subsequently, an anhydrous tetrahydrofuran solution (40 ml) of 750 mg (2.25 mmols) of 4-[N,N-di(4-methoxyphenyl)amino]benzaldehyde ((27)-2) was further dropped in the mixture in 15 minutes, and agitated at room temperature for 1 hour. The reaction mixture was quenched with a small amount of ice pieces, washed with a saturated saline solution and dried over anhydrous sodium sulfate.

Figure 2:
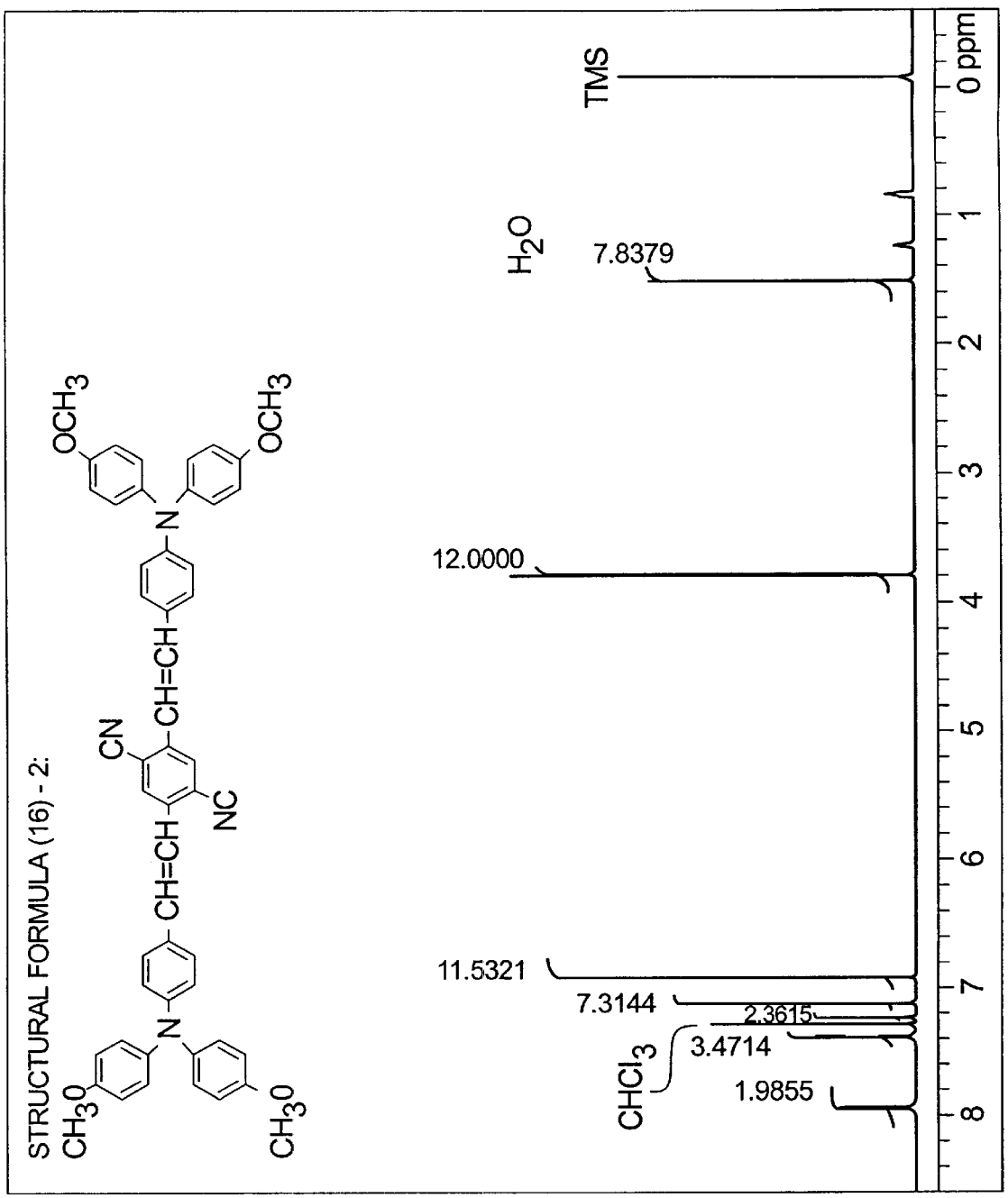
FIG. 2 is an ¹HNMR spectral diagram of a bis (aminostyryl)benzene compound of structural formula (16)-2 of the invention.

The intended product was purified from the reaction mixture through silica gel chromatography (WAK-gel C-300, tetrahydrofuran:hexane=1:8) and recrystallized from acetone/hexane to obtain 488 mg of the bis(aminostyryl) benzene compound ((16) -2). The yield was found to be at 31% with a glass transition point of 130° C. and a melting point of 170° C. The visible light absorption maximum of the tetrahydrofuran solution was at 486 nm and the fluorescence maximum wavelength was at 620 nm. The $^1$HNMR spectra of the solution were indicated below and also shown in FIG. 2.

NMR (CDCl$_3$) δ (ppm): 3.81 (12H, s), 6.84 (12H, m), 7.05 (9H, d), 7.19 (2H, d), 7.39 (4H, d), 7.98 (2H, s).

EXAMPLE 4

Synthetic Example of bis(aminostyryl)benzene Compound (Structural Formula (16)-4))

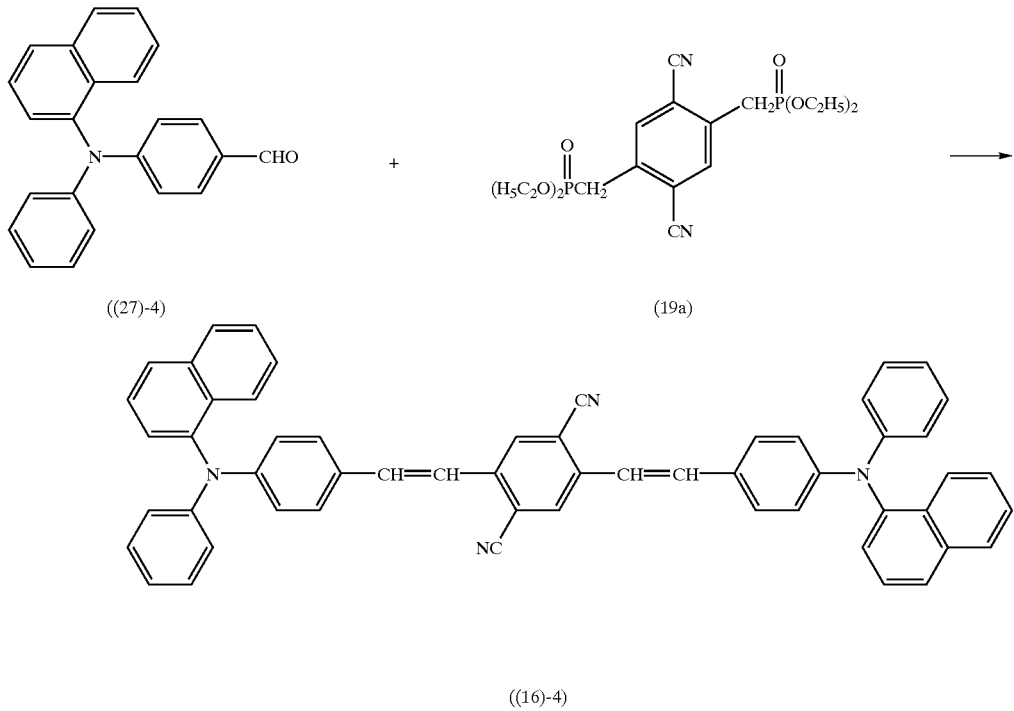

((27)-4)

(19a)

((16)-4)

11.3 mmols of sodium hydride was suspended in 20 ml of anhydrous tetrahydrofuran, into which the anhydrous tetrahydrofuran solution of the diphosphonic acid ester (19a) (corresponding to 1.13 mmols) obtained in Example 1 was dropped in an atmosphere of nitrogen in 15 minutes, followed by agitation at room temperature for 20 minutes.

Subsequently, an anhydrous tetrahydrofuran solution (12 ml) of 728 mg (2.25 mmols) of 4-[N-(1-naphthyl)-N-phenylamino]benzaldehyde ((27)-4) was further dropped in the mixture in 15 minutes, and agitated at room temperature for 2 hours. The reaction mixture was quenched with a small amount of ice pieces, washed with a saturated saline solution and dried over anhydrous sodium sulfate.

Figure 3:
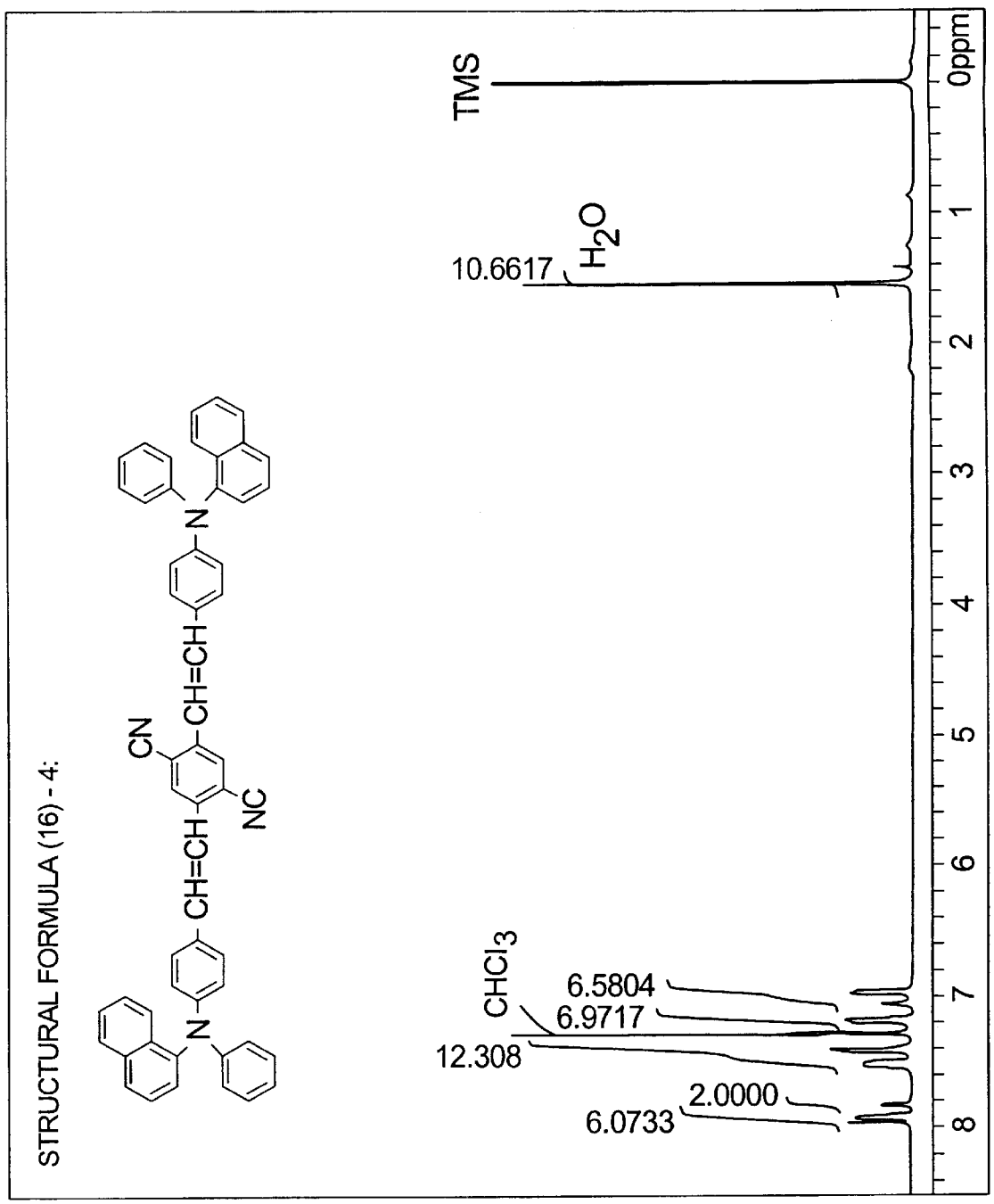
FIG. 3 is an ¹HNMR spectral diagram of a bis (aminostyryl)benzene compound of structural formula (16)-4 of the invention.

The intended product was purified from the reaction mixture through silica gel chromatography (WAKO-gel C-300, tetrahydrofuran:hexane=1:8) and recrystallized from acetone/hexane to obtain 546 mg of the bis(aminostyryl) benzene compound ((16)-4). The yield was found to be at 63%, with a glass transition temperature of 150° C. and a melting point of 210° C. The visible light absorption maximum of the tetrahydrofuran solution was at 461 nm and the fluorescence maximum wavelength was at 550 nm. The $^1$HNMR spectra of the solution were indicated below and also shown in FIG. 3.

NMR (CDCl$_3$) δ (ppm): 6.97 (4H, d), 7.02 (2H, s), 7.25–7.49 (23H, m), 7.81 (2H, d), 7.92 (4H, d), 7.97(2H, s).

EXAMPLE 5

Synthetic Example of bis(aminostyryl)benzene Compound (Structural Formula (16)-5)

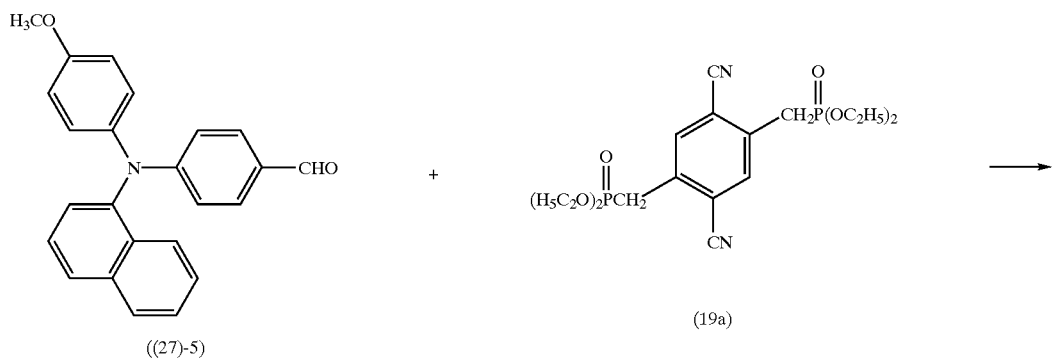

((27)-5)

(19a)

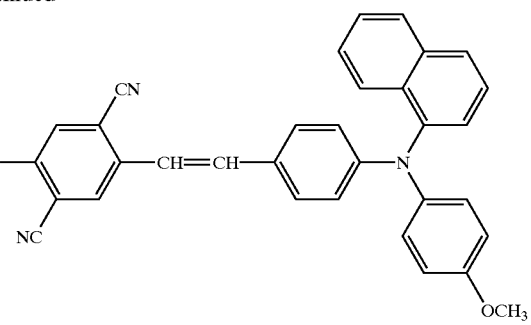

((16)-5)

11.3 mmols of sodium hydride was suspended in 20 ml of anhydrous tetrahydrofuran, into which the anhydrous tetrahydrofuran solution of the diphosphonic acid ester (19a) (corresponding to 1.13 mmols) obtained in Example 1 was dropped in an atmosphere of nitrogen in 15 minutes, followed by agitation at room temperature for 20 minutes.

Subsequently, an anhydrous tetrahydrofuran solution (12 ml) of 761 mg (2.25 mmols) of 4-[N-(1-naphtyl)-N-(4-methoxyphenyl)amino]benzaldehyde ((27)-5) was, further dropped in the mixture in 15 minutes, and agitated at room temperature for 2 hours. The reaction mixture was quenched with a small amount of ice pieces, washed with a saturated saline solution and dried over anhydrous sodium sulfate.

The intended product was purified from the reaction mixture through silica gel chromatography (WAKO-gel C-300, tetrahydrofuran:hexane=1:8) and recrystallized from acetone/hexane to obtain 386 mg of the bis(aminostyryl) benzene compound ((16)-5). The yield was found to be at 43% with a glass transition point of 130° C. and a melting point of 190° C. The visible light absorption maximum was at 465 nm and the fluorescence maximum wavelength was at 555 nm.

EXAMPLE 6

Synthetic Example of 4-[N,N-di(4-methoxyphenyl) amino]benzaldehyde (Structural Formula (27)-2)

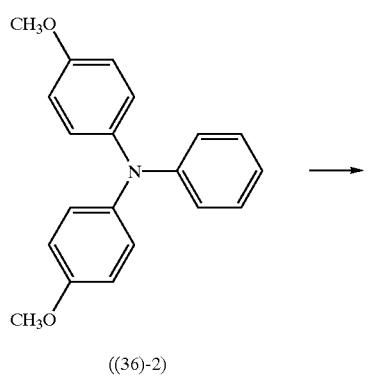

((36)-2)

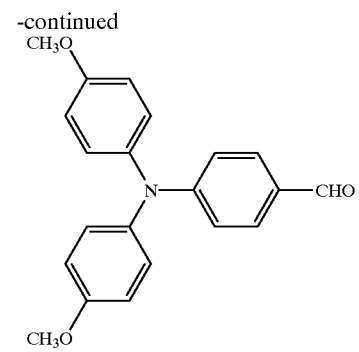

((27)-2)

1.76 g (11.5 mmols) of phosphorus oxychloride was dropped in anhydrous dimethylformamide under agitation at room temperature, into which 25 ml of anhydrous dimethylformamide solution of 1.75 g of N,N-di(4-methoxyphenyl)aniline ((36)-2) was further dropped, following by raising the reaction temperature and agitating at 70° C. for 90 minutes.

The resultant solution was cooled down to room temperature and quenched with a small amount of ice pieces, followed by extraction of the reaction solution with toluene, washing with a saturated saline solution and drying over anhydrous sodium sulfate.

Figure 4:
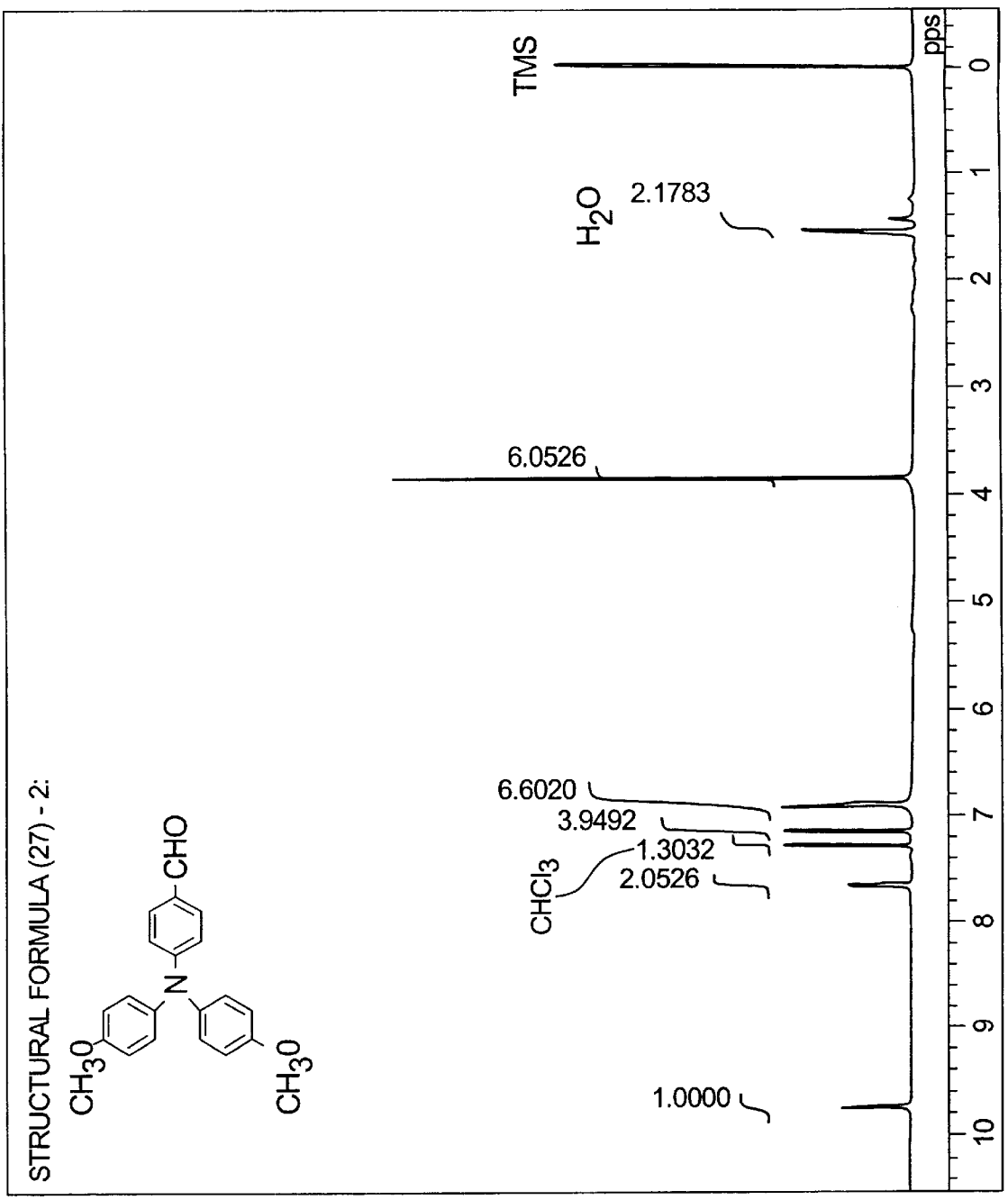
FIG. 4 is an ¹HNMR spectral diagram of 4-[N,N-di(4-methoxyphenyl)amino]benzaldehyde of structural formula (27)-2, which is a synthetic intermediate of the invention.

The intended product was purified from the reaction mixture through silica gel chromatography (WAKO-gel C-300, tetrahydrofuran:hexane=1:4) to obtain 0.750 g of the compound ((27)-2). The yield was found to be at 39%. The $^1$HNMR spectra of the compound were shown in FIG. 4 and also indicated below.

NMR (CDCl$_3$) δ (ppm): 3.81 (6H, s), 6.82 (2H, d), 6.90 (4H, d), 7.13 (4H, d), 7.62 (2H, d), 9.78 (1H, s).

EXAMPLE 7

Synthetic Example of N,N-di(4-methoxyphenyl) aniline (Structural Formula (36)-2)

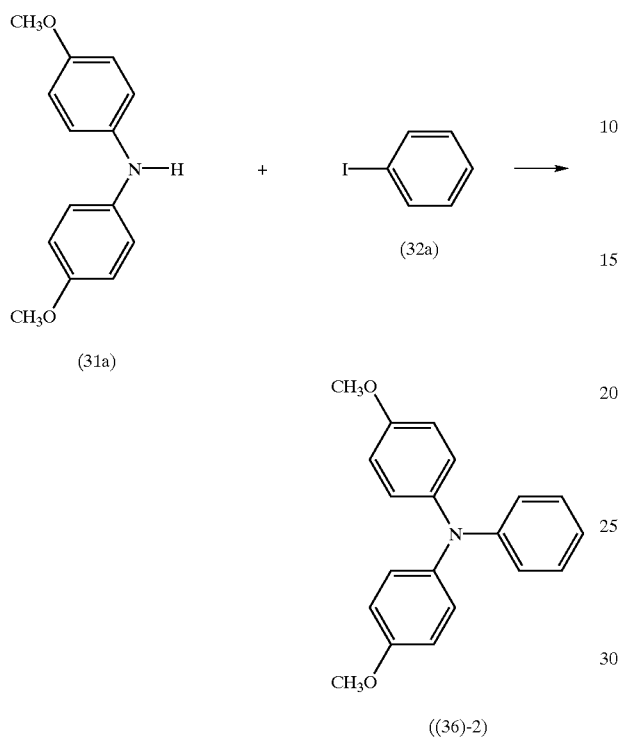

1.00 g (4.46 mmols) of N,N-di(4-methoxyphenyl)amine (31a), 1.00 a (4.90 mmols) of iodobenzene (32a), 0502 g (5.23 mmols) of t-BuONa and 0.010 g (0.044 mmols) of PdG(CH$_3$COO)$_2$ were dissolved in anhydrous xylene, and while refluxing the solution in an atmosphere of nitrogen, 1.0 ml of 0.237 M of P(Bu$^r$)$_3$ was further dropped, followed by refluxing for 4 hours.

Figure 5:
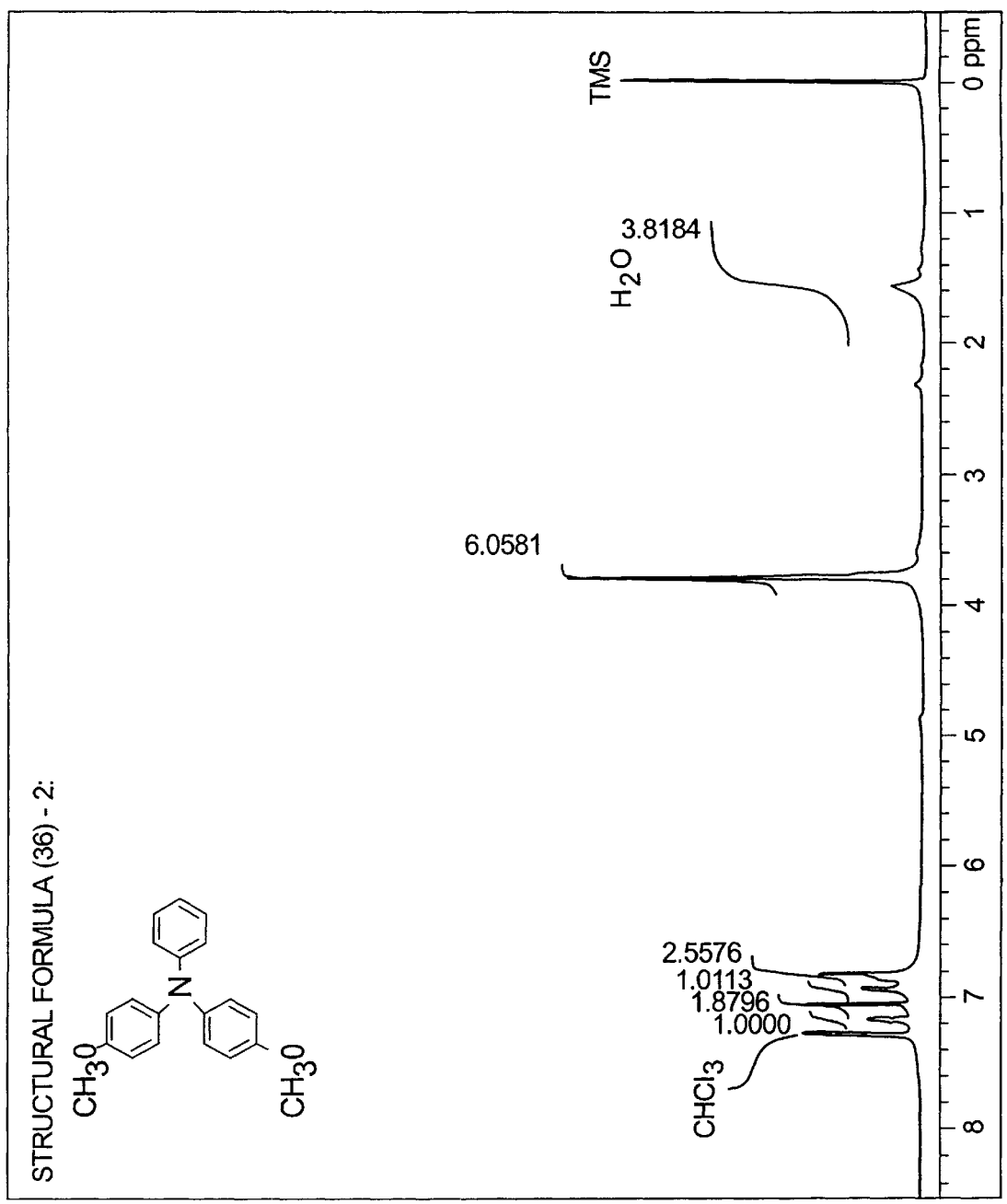
FIG. 5 is an ¹HNMR spectral diagram of N,N-di(4-methoxyphenyl)aniline of structural formula (36)-2, which is a synthetic intermediate of the invention.

The resultant reaction product was purified through silica gel chromatography (WAKO-gel C-300, tetrahydrofuran:hexane=1:4), and the resulting eluate was recrystallized from acetone/hexane to obtain a compound ((36)-2). The yield was 1.17 g (yield of 88%) The $^1$HNMR spectra of the compound were shown in FIG. 5 and also indicated below.

NMR (CDCl$_3$) δ (ppm): 3.80 (6H, s), 6.80 (4H, d), 6.82 (1H, t), 6.92 (2H, d), 7.02 (4H, d), 7.17 (2H, t).

EXAMPLE 8

(Synthetic Example of N-(1-phenyl)-N-(4-ethoxyphenyl)aniline (Structural Formula (36)-1)

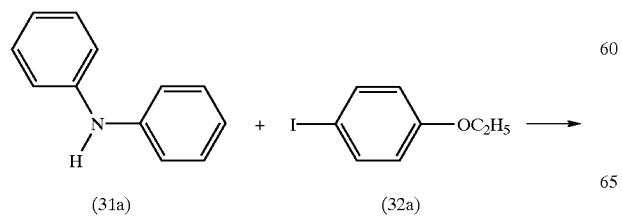

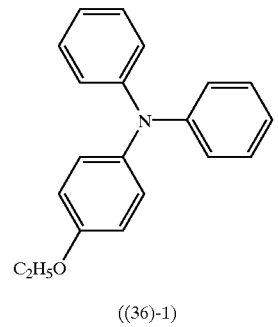

8.20 g (50 mmols) of N,N-di-phenylamine (31), 12.40 g (50 mmols) of iodoanisole (32a), 5.76 g (60 mmols) of t-BuONa and 0.224 g (1.00 mmol) of Pd(CH$_3$COO)$_2$ were dissolved in dichlorobenzene, and while refluxing the resulting solution in an atmosphere of nitrogen, 17 ml of 0.237 M of P(Bu$^r$)$_3$ was further dropped. followed by refluxing for 4 hours.

Figure 6:
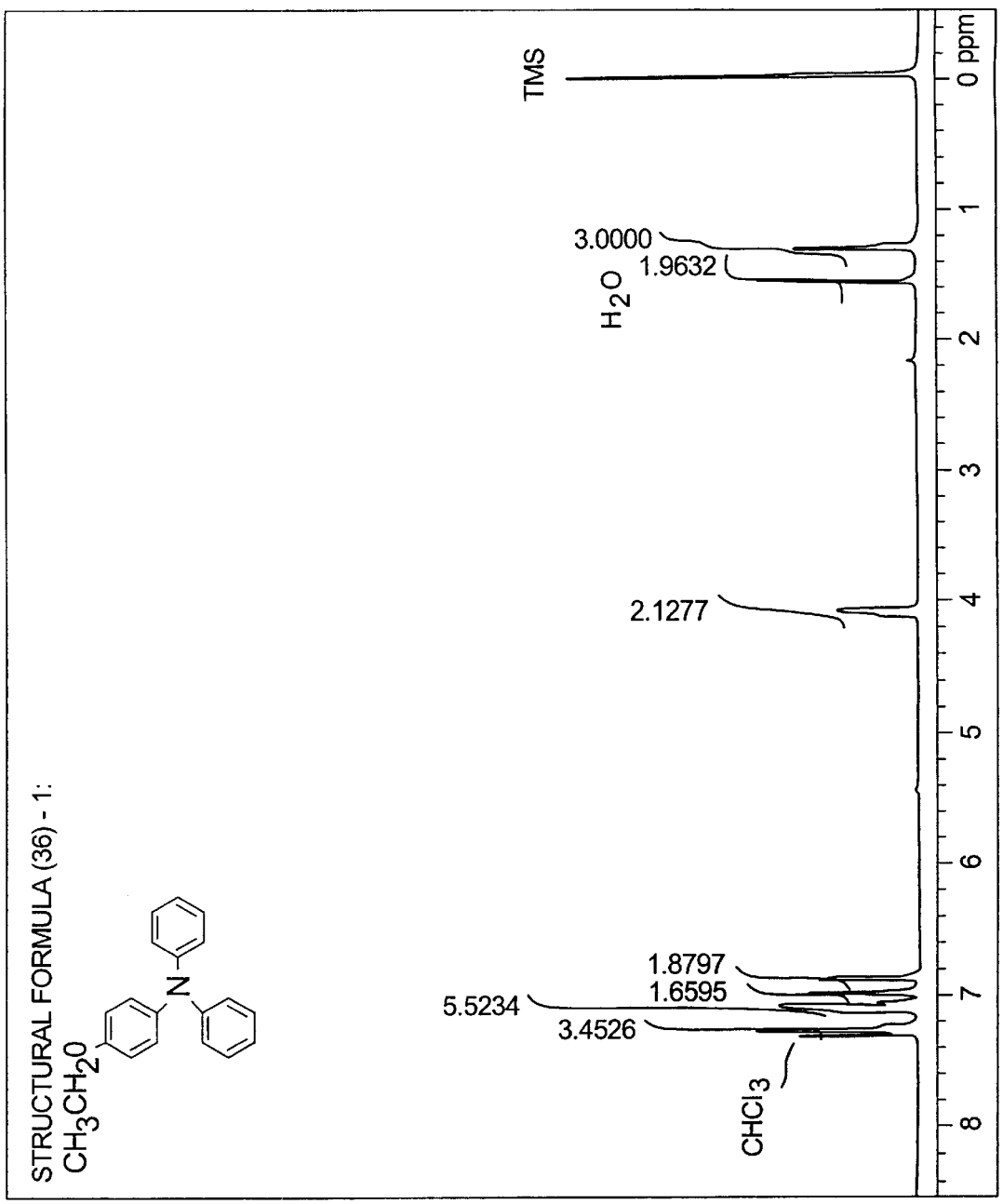
FIG. 6 is an ¹HNMR spectral diagram of N-(1-phenyl)-N-(4-ethoxyphenyl)aniline of structural formula (36)-1, which is a synthetic intermediate of the invention.

The intended product was obtained by purification through column chromatography (alumina, hexane:toluene= 4:1) and recrystallization of the resultant eluate from acetone/hexane. The yield was 10.9 g (yield of 79%). The $^1$HMR spectra of the compound were shown in FIG. 6 and also indicated below.

NMR (CDCl$_3$) δ (ppm): 1.28 (3H, t), 4.02 (2H, q), 6.84 (2H, d), 6.94 (2H, t), 7.03 (4H, d), 7.06 (2H, d), 7.20 (4H, t).

EXAMPLE 9

Synthetic Example of 2,5-di (bromotriphenylphosphomethyl)terephthalonitrile (Structural Formula (20a))

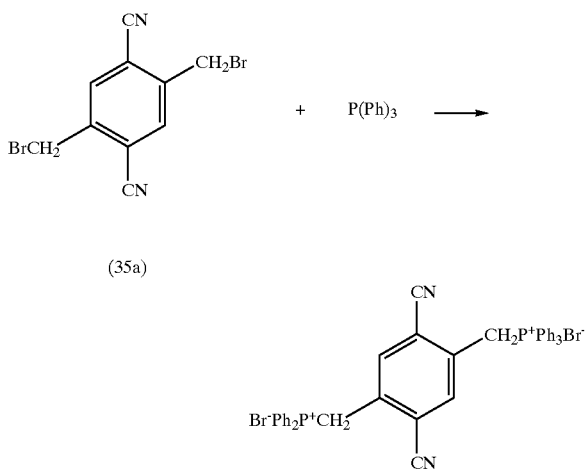

750 mg (2.39 mmols) of 2,5-di(bromomethyl) terephthalonitrile (35a) and 1.38 g (5.26 mmols) of triphenylphosphine were dissolved in xylene and refluxed for 20 hours. The reaction solution was cooled down to room temperature, and the resultant precipitate was separated by filtration, washed with 5 ml of xylene, dried under reduced pressure and dissolved for storage in 25 ml of anhydrous tetrahydrofuran. In this way, there was obtained the diphosphonium (20a) set out in Example 2.

EXAMPLE 10

Synthetic Example of 2,5-di(bromomethyl) terephthalonitrile (Structural Formula (35a))

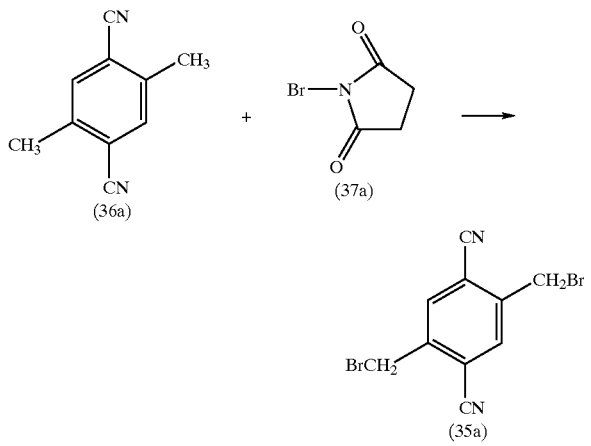

Figure 7:
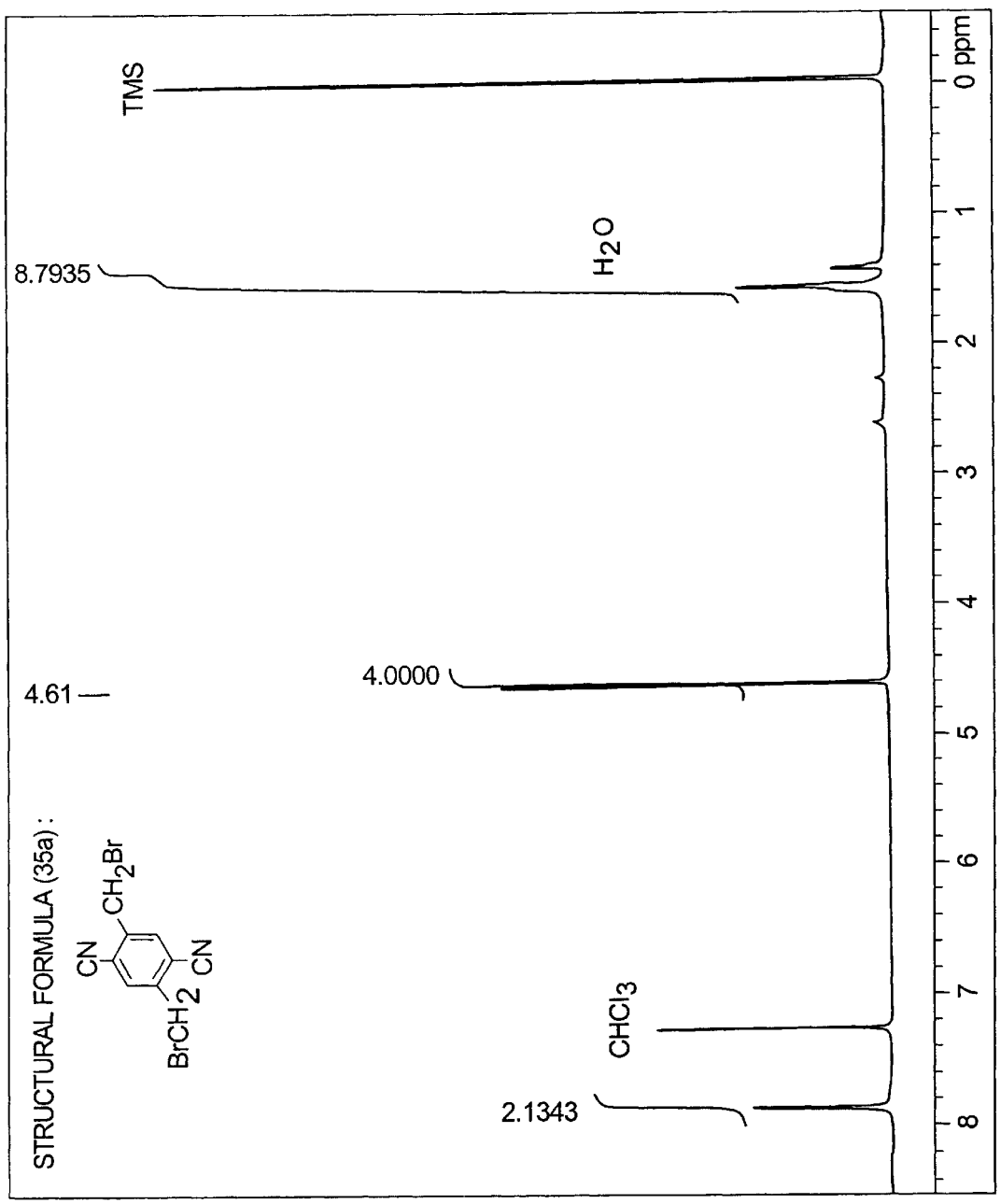
FIG. 7 is an ¹HNMR spectral diagram of 2,5-di (bromomethyl)terephthalonitrile of structural formula (35a), which is a synthetic intermediate of the invention.

1.00 g (6.4 mmols) of 2,5-dimethylterephthalonitrile (36a) and 8.10 g (90 mmols) of N-bromosuccinimide (NBS) (37a) were dissolved in 500 ml of chloroform and refluxed for 48 hours under irradiation with a high pressure mercury lamp (400 W), The solvent was distilled off, and the resultant reaction product was purified through silica gel chromatography (WAKO-gel C-300, tetrahydrofuran:hexane=1:4), and the resultant eluate was recrystallized twice from acetone/hexane to selectively obtain a compound (35a) in the form of white crystals. The yield was 698 mg (yield of 34%). The $^2$HNMR spectra of the compound were shown in FIG. 7 and also indicated below.

NMR (CDCl$_3$) δ (ppm): 4.60 (4H, s), 7.83 (2H, s)

EXAMPLE 11

Synthetic Example of N-(p-toluyl)-N,N-diphenylamine) (Structural Formula (36)-6)

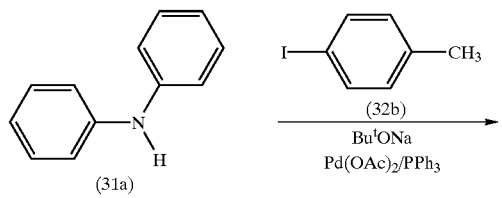

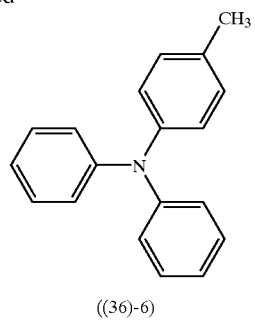

9.70 g (57.3 mmols) of N,N-diphenylamine (31a), 12.5 g (57.3 mmols) of 4-iodotoluene (32b), 6.61 g (68.8, mmols) of t-BuONa, 260 mg (1.15 mmols) of Pd(CH$_3$COO)$_2$ and 1.20 g (4.58 mmols) of triphenylphosphine were dissolved in xylene and refluxed in an atmosphere of nitrogen for 4 hours.

Figure 8:
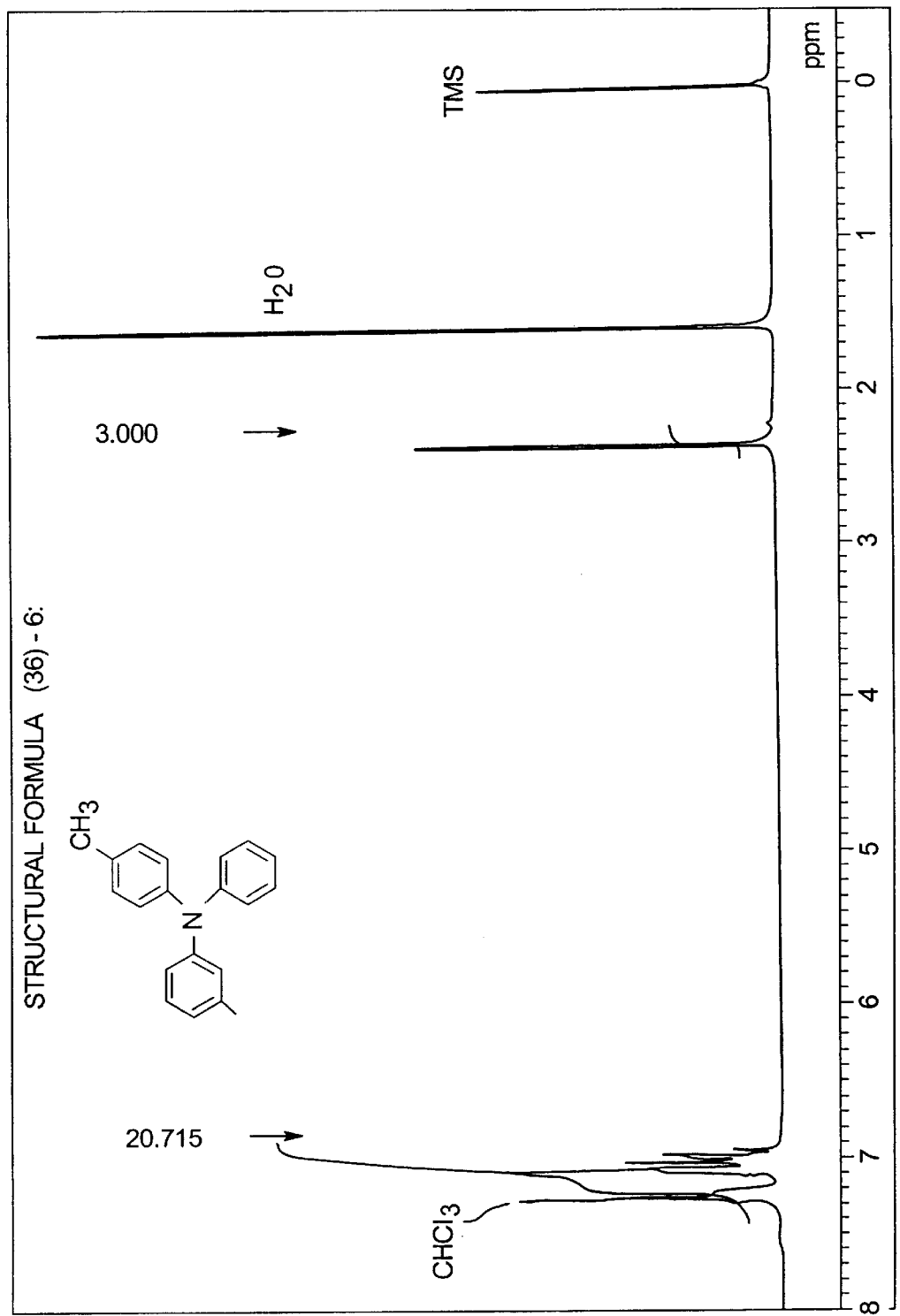
FIG. 8 is an ¹HNMR spectral diagram of N-(p-toluyl)-N, N-diphenylamine of structural formula (36)-6 which is a synthetic intermediate of the invention.

The resultant insoluble matter was separated by filtration, followed by purification through alumina chromatography (300 mesh-sized neutral alumina, tetrahydrofuran:hexane= 1:4). and the resulting eluate was recrystallized from acetone/hexane to quantitatively obtain the intended product ((36)-6). The $^1$HNMR spectra of this product ((36)-6) were shown in FIG. 8 and also indicated below.

NMR (CDCl$_3$) δ (ppm): 2.31 (3H, s), 6.94–7.27 (14H, m).

EXAMPLE 12

(Synthetic Example of 4-[N-(p-toluyl)-N-phenylamino]benzaldehyde (Structural Formula (27)-6)

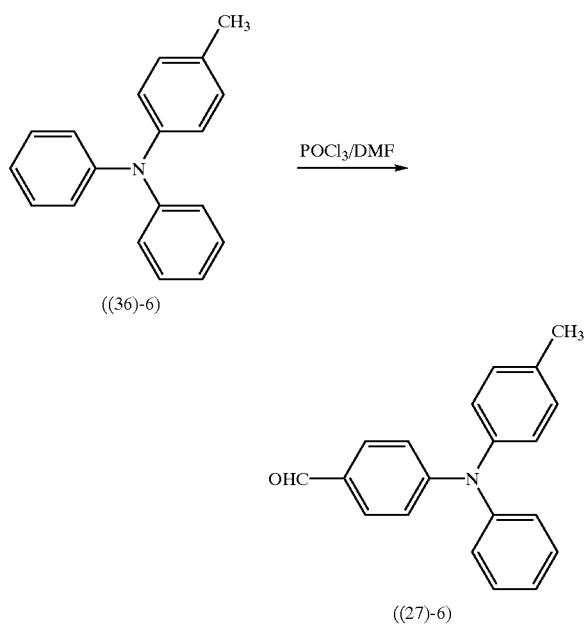

Figure 9:
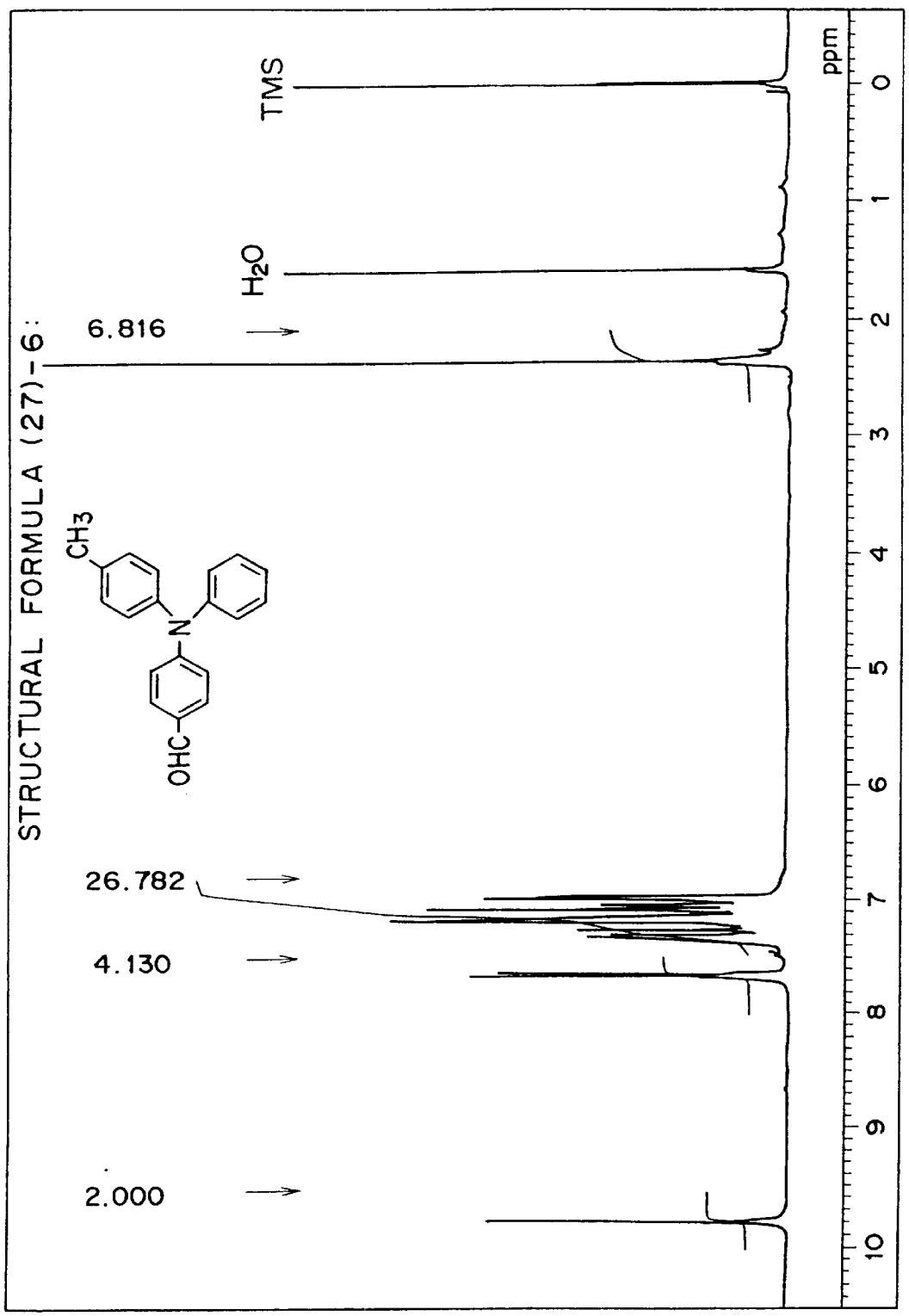
FIG. 9 is an ¹HNMR spectral diagram of 4-[N-(p-toluyl)-N-phenylamino]benzaldehyde of structural formula (27)-6, which is a synthetic intermediate of the invention.
Figure 10:
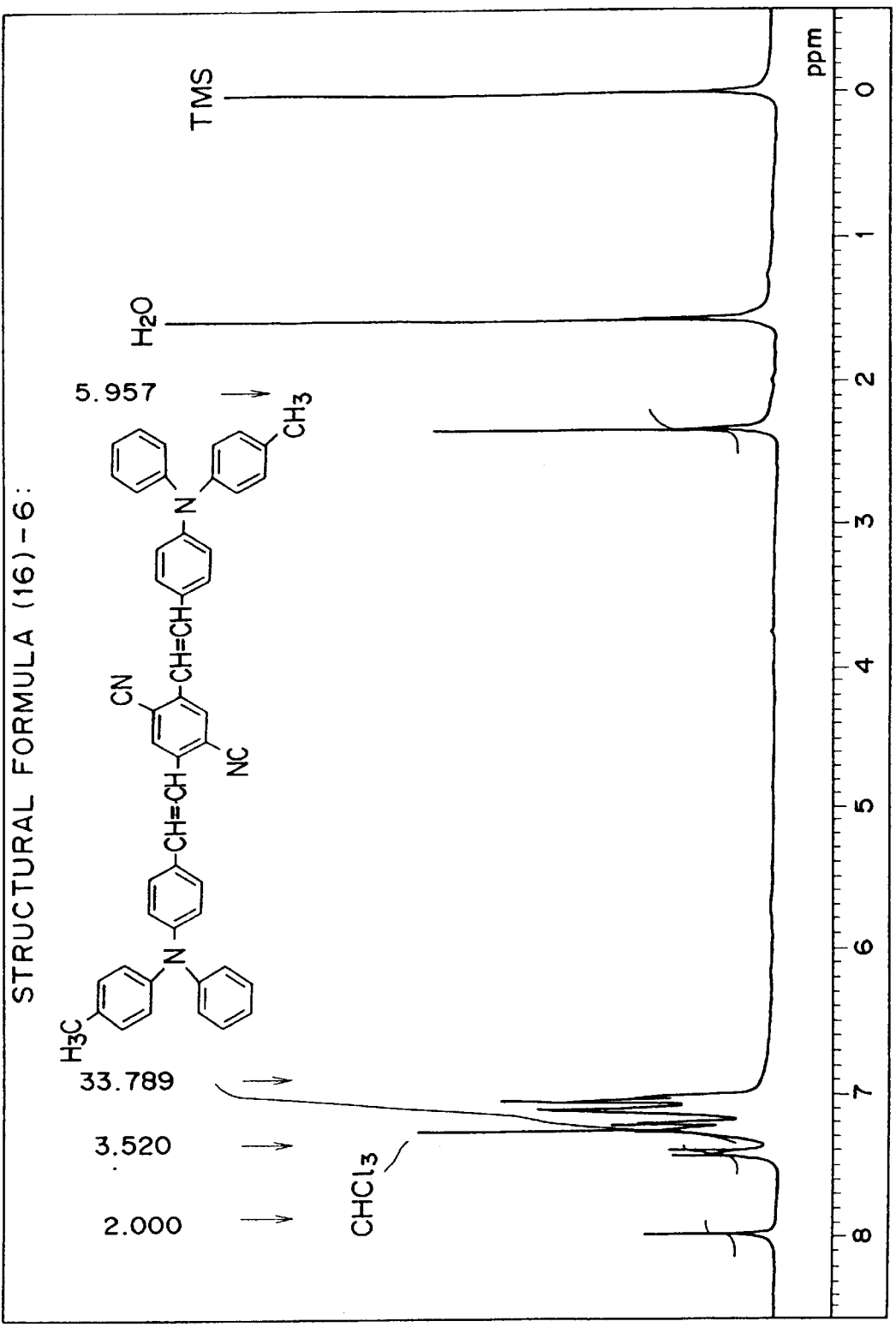
FIG. 10 is an ¹HNMR spectral diagram of a bis (aminostyryl)benzene compound of structural formula (16)-6 of the invention.

596 g (38.9 mmols) of phosphorus oxychloride was dropped in 50 ml of anhydrous dimethylformamide (DMF) under agitation at room temperature, into which 50 ml of an anhydrous dimethylformamide (DMF) solution of 5.04 g (19.4 mmols) of N-(p-toluyl)-N,N-diphenylamine ((36)-6) was further dropped, following by raising the reaction temperature and agitating, at 70° C. for 90 minutes, The resultant solution was cooled down to room temperature and quenched with a small amount of ice pieces, followed by purification through silica gel chromatography (WAKO-gel C-300, tetrahydrofuran:hexane=1:4) to obtain an oily substance ((27)-6) substantially quantitatively. The $^1$HNMR spectra of this product were shown in FIG. 9 and also indicated below.

NMR (CDCl$_3$) δ (ppm): 2.35 (3H, s), 6.96–7.64 (11H, m), 7.66 (2H, d), 9.80 (1H, s).

EXAMPLE 13

Synthetic Example of bis(aminostyryl)benzene Compound (Structural Formula (16)-6)

(aminostyryl)benzene compound ((16)-6) was obtained by purification through silica gel chromatography (WAKO-gel C-300, tetrahydrofuran:hexane=1:4→1:1) and recrystallization from acetone/hexane. The yield was found to be at 49%, and the $^1$HNMR spectra of the solution were shown in rig. 10 and indicated below.

NMR (CDCl$_3$) δ (ppm): 2.34 (6H, s), 7.01–7.30 (26H, m), 7.42 (4H, d), 7.99 (2H, s).

The visible light absorption maximum of a tetrahydrofuran solution of this substance ((16)-6) was at 469 nm and the fluorescent maximum wavelength was at 568 nm.

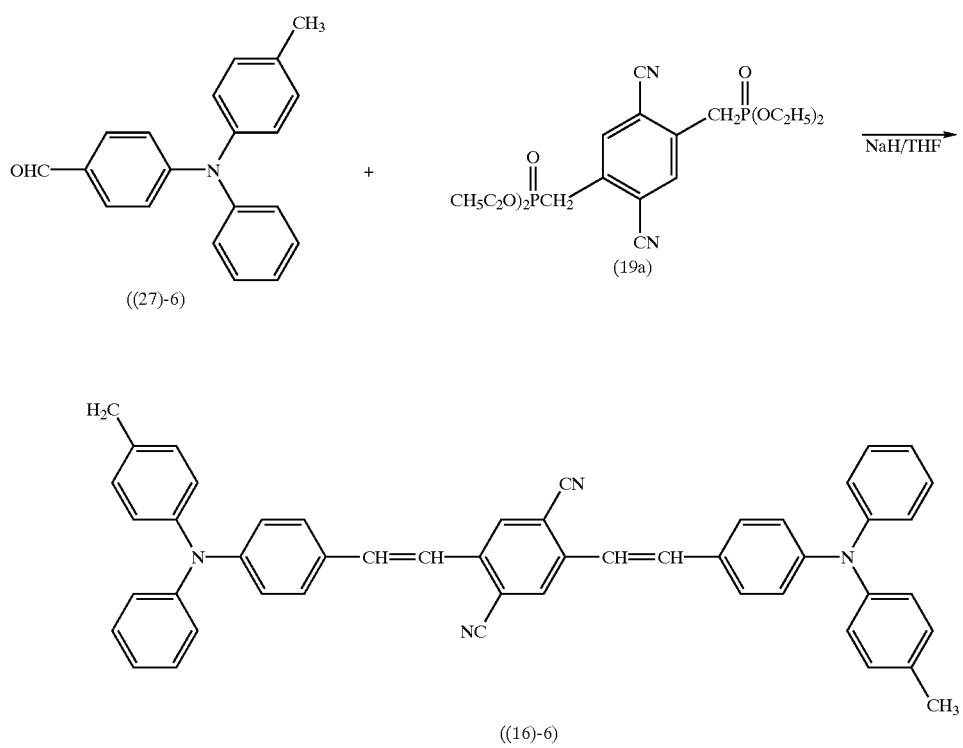

14.5 mmols of sodium hydride was suspended in 20 ml of anhydrous tetrahydrofuran (THF), into which the anhydrous tetrahydrofuran solution of diphosphonic acid ester (19a) (corresponding to 2.33 mmols) was dropped in an atmosphere of nitrogen, followed by agitation for 60 minutes. Subsequently, an anhydrous tetrahydrofuran solution (40 ml) of 1.34 g (4.66 mmols) of 4-[N-(p-toluyl)-N-phenylamino]benzaldehyde ((27)-6) was further dropped in the mixture, and agitated at room temperature for 12 hours.

The reaction mixture was quenched with a small amount of ice pieces, washed with a saturated saline solution and dried over anhydrous sodium sulfate. 0.787 g of the bis

EXAMPLE 14

(Synthetic Example of N,N-di(p-toluyl-N-phenylamine (Structural Formula (36)-7)

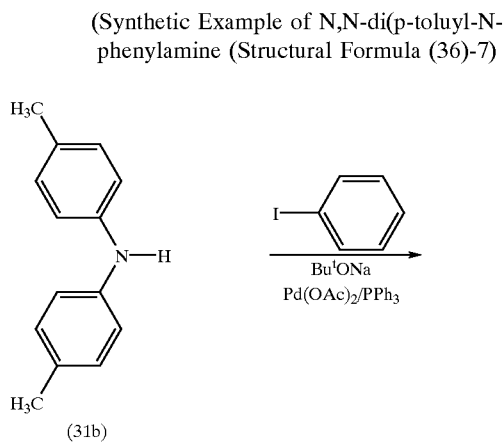

EXAMPLE 15

Synthetic Example of 4-[N,N-di(p-toluyl)amino]benzaldehyde (Structural Formula (27)-7)

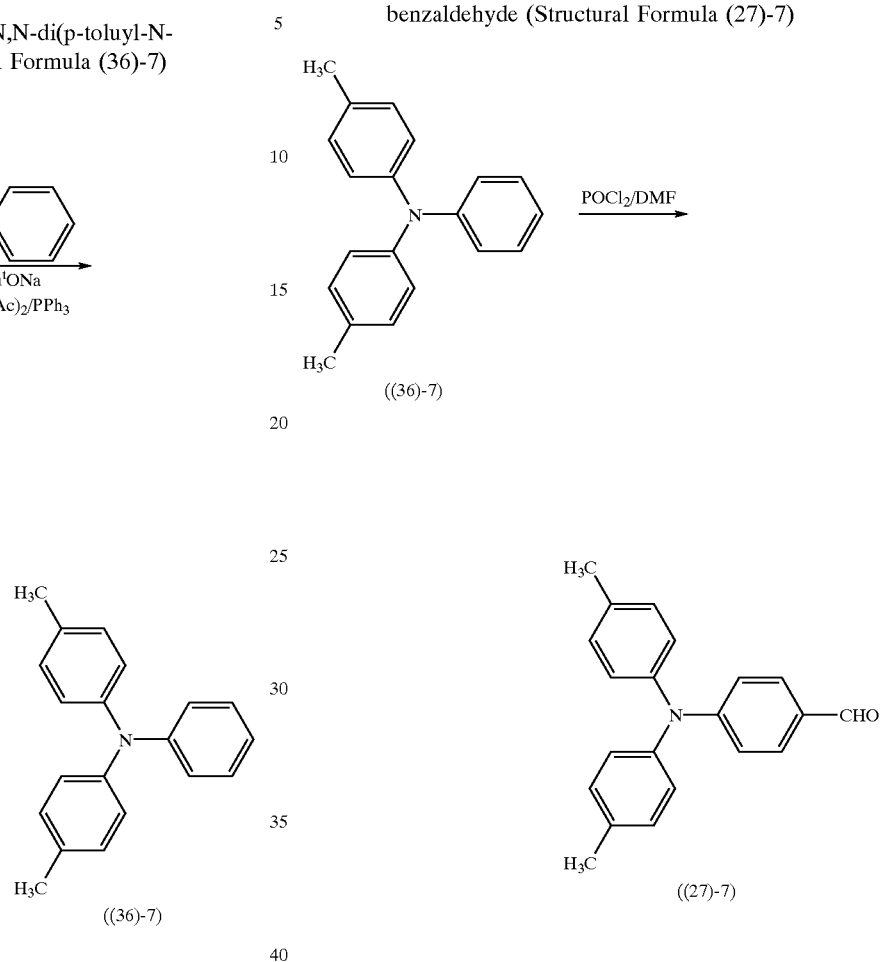

10.0 g (50.7 mmols) of N,N-di(p-toluyl)amine (31b). 10.3 g (50.7 mmols) of 4-iodobenzene, 5.95 g (60.8 mmols) of t-BuONa, 300 mg (1.34 mmols) of Pd(CH$_3$COO)$_2$ and 1.50 g (5.71 mmols) of triphenylphosphine were dissolved in xylene and refluxed in an atmosphere of nitrogen for 4 hours.

Figure 11:
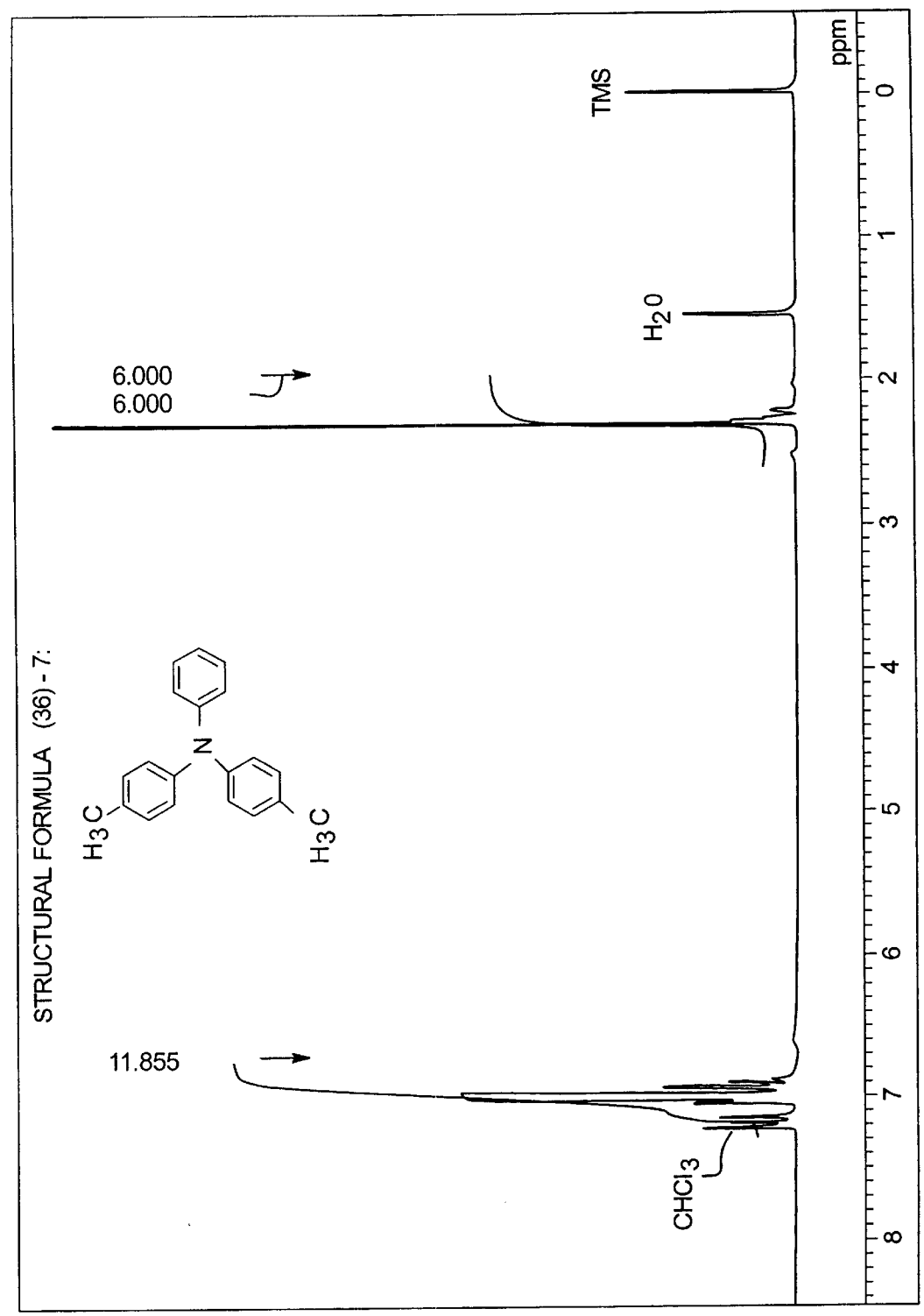
FIG. 11 is an ¹HNMR spectral diagram of N,N-(p-toluyl-N-phenylamine) of structural formula (36)-7, which is a synthetic intermediate of the invention.

The resultant insoluble matter was separated by filtration, followed by purification through alumina chromatography (300 mesh-sized neutral alumina, tetrahydrofuran:hexane= 1:4), and the resulting eluate was recrystallized from acetone/hexane to quantitatively obtain the intended compound ((36)-7). The $^1$HNMR spectra of this product were shown in FIG. 11 and also indicated below.

NMR (CDCl$_3$) δ (ppm): 2.30 (6H, s), 6.90–7.07 (11H, m), 7.16–7,22 (2H, m).

5.90 g (38.4 mmols) of phosphorus oxychloride was dropped in 20 ml of anhydrous dimethylformamide (DMF) under agitation at room temperature, into which 50 ml of anhydrous dimethylformamide solution of 7.00 g (25.6 mmols) of N-di(p-toluyl)-N-phenylamine ((36)-7) was further dropped, following by agitation at room temperature for 24 hours.

Figure 12:
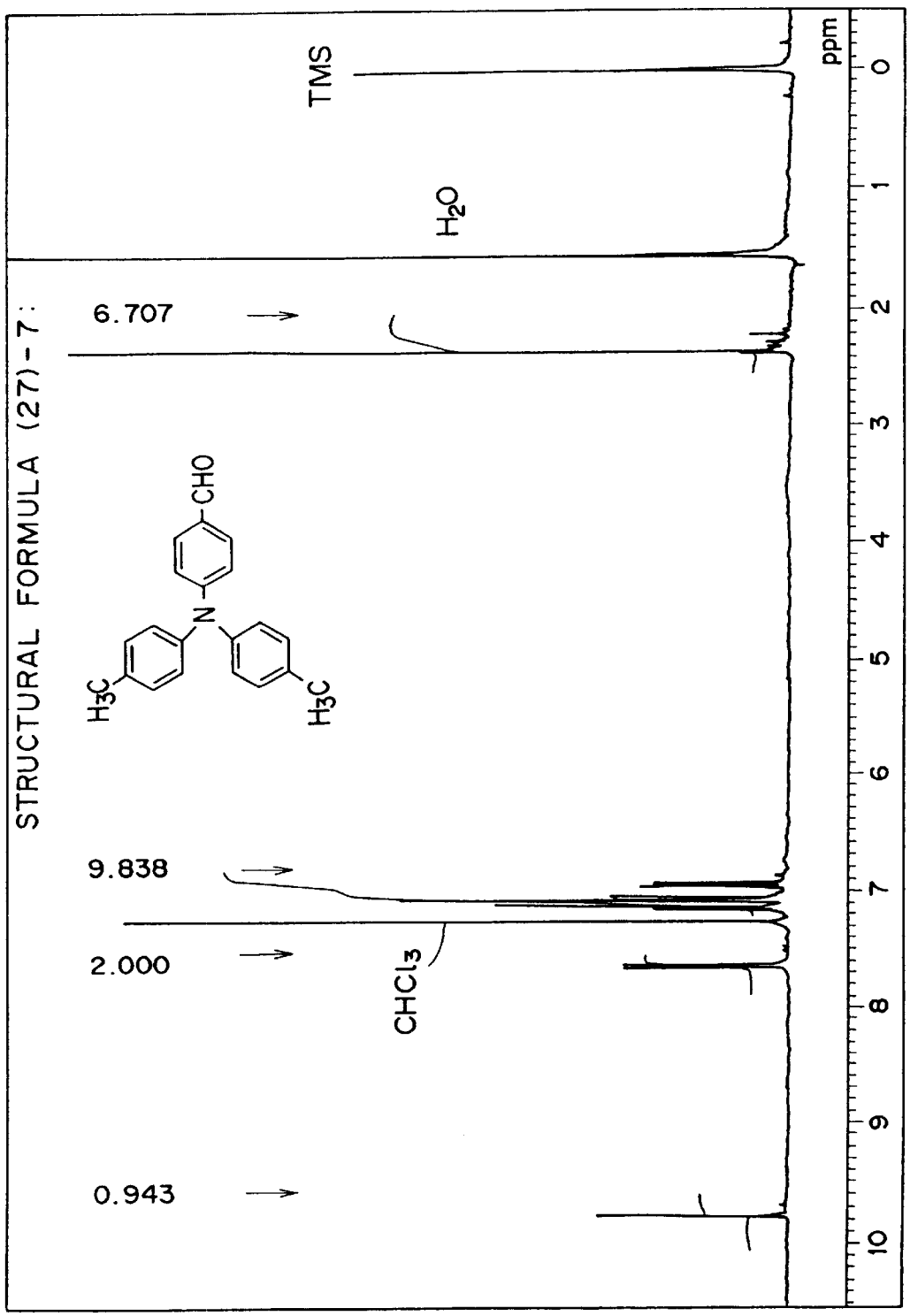
FIG. 12 is an ¹HNMR spectral diagram of 4-[N,N-di(p-toluyl)amino]benzaldehyde of structural formula (27)-7, which is a synthetic intermediate of the invention.

The resultant reaction mixture was quenched with a small amount of ice pieces, extracted with toluene, washed with a saturated saline solution and dried over Na$_2$SO$_4$, followed by purification through silica gel chromatography (WAKO-gel C-300, tetrahydrofuran:hexane=1:4) to obtain an oily substance ((27)-7) substantially quantitatively. The $^1$HNMR spectra of this product were shown in FIG. 12 and also indicated below.

NMR (CDCl$_3$) δ (ppm): 2.35 (6H, s), 6.93 (2H, d), 7.06 (2H, d), 7.15 (4H, d), 7.64 (4H, d), 9.78 (1H, s)

EXAMPLE 16

Synthetic Example of bis(aminostyryl)benzene Compound (Structural Formula (16)-7)

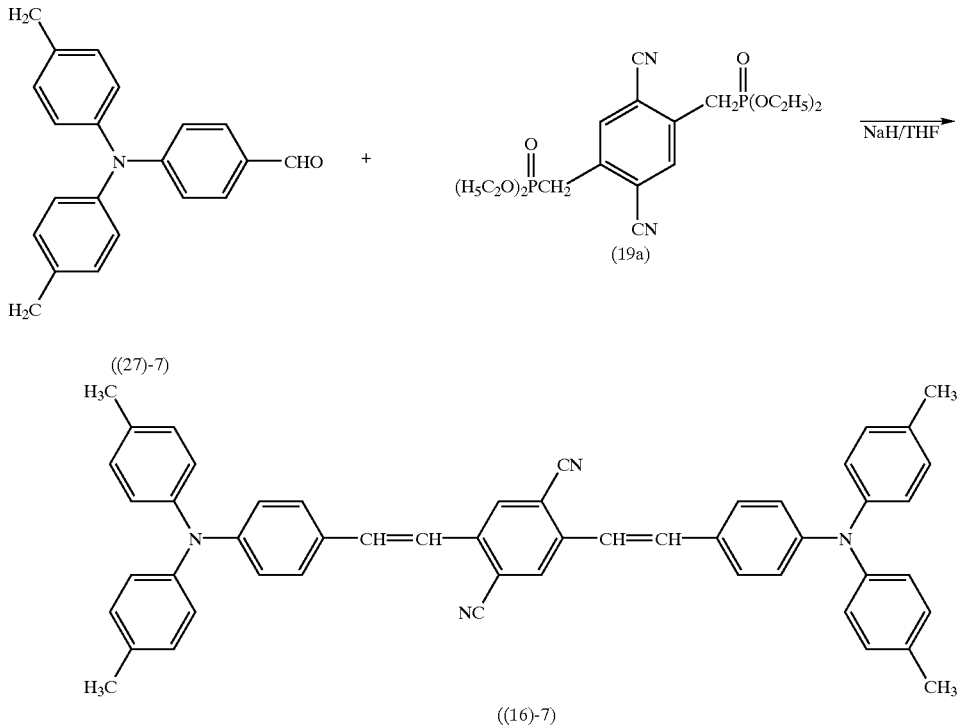

14.3 mmols of sodium hydride was suspended in 20 ml of anhydrous tetrahydrofuran (THF), into which 20 ml of an anhydrous tetrahydrofuran solution of 750 mg (2.39 mmols) of diphosphonic acid ester (19a) was dropped in an atmosphere of nitrogen, followed by further dropping of 25 ml of an anhydrous tetrahydrofuran solution of 4-[N,N-di(p-toluyl)amino]benzaldehyde ((27)-7) (corresponding to 2.39 mmols) and agitation for 48 hours.

Figure 13:
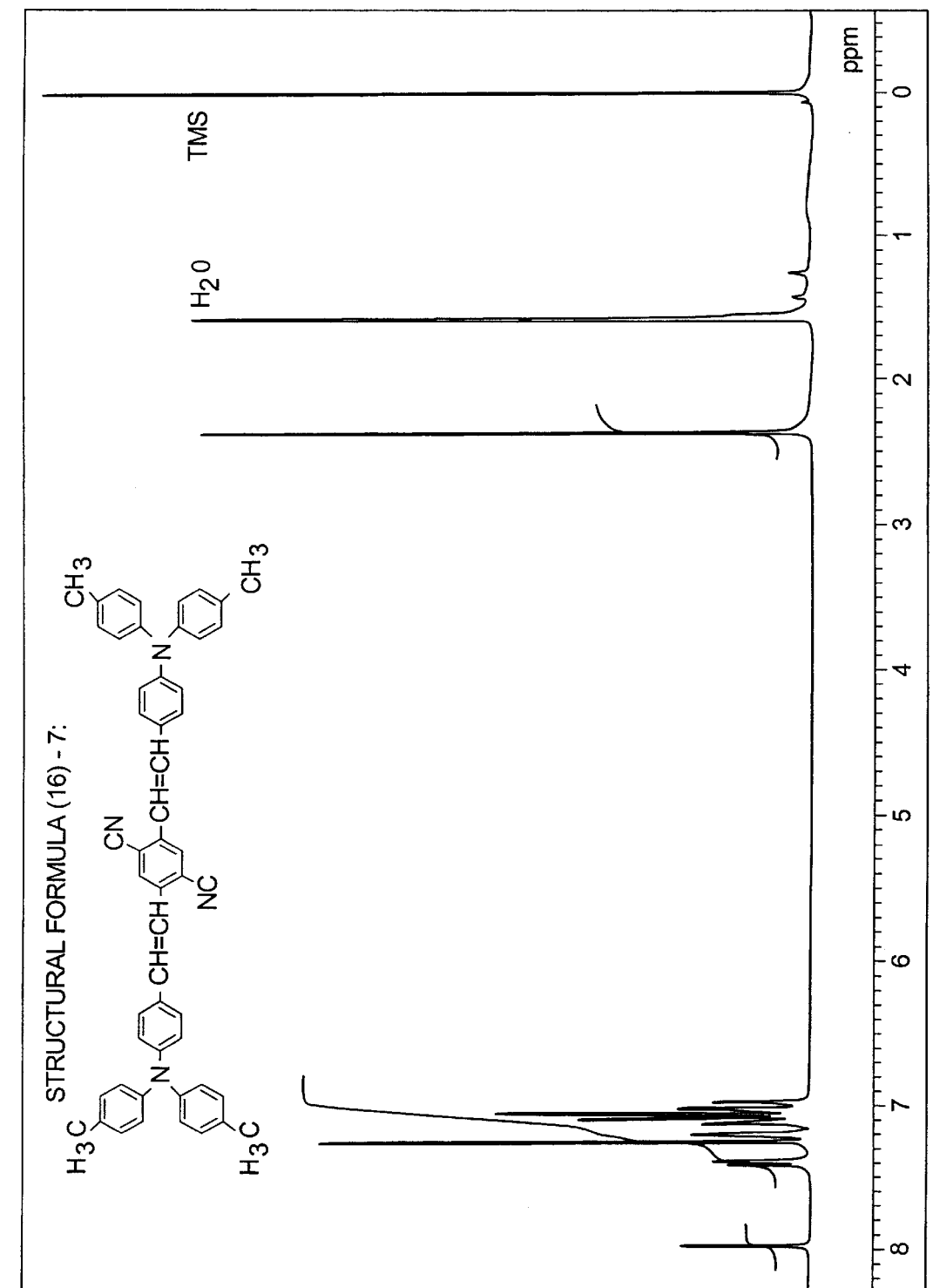
FIG. 13 is an ¹HNMR spectral diagram of a bis (aminostyryl)benzene compound of structural formula (16)-7 of the invention.

The reaction mixture was quenched with a small amount of ice pieces, washed with a saturated saline solution and dried over anhydrous sodium sulfate. 431 mg of the bis(aminostyryl)benzene compound ((16)-7) was obtained by purification through silica gel chromatography (WAKO-gel C-300, tetrahydrofuran:hexane=1:4→1:1) and recrystallization from acetone/hexane. The yield was found to be at 25%, and the $^1$HNMR spectra of the solution were shown in FIG. 13 and indicated below.

NMR (CDCl$_3$) δ (ppm): 2.33 (12H, s), 6.97–7.21 (24H, m), 7.39 (4H, s), 7.97 (2H, s)

The visible light absorption maximum of a tetrahydrofuran solution of this substance was at 476 nm and the fluorescent maximum wavelength was at 590 nm.

EXAMPLE 17

(Synthetic Example of bis(aminostyryl)benzene Compound (Structural Formula (16)-9)

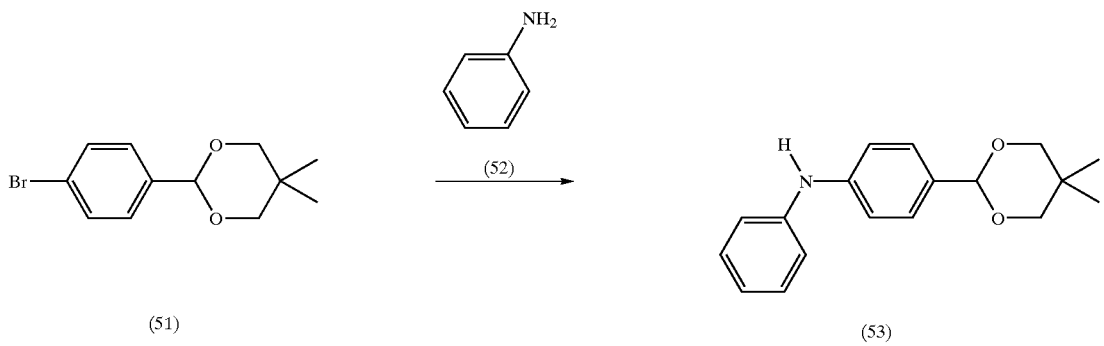

-continued
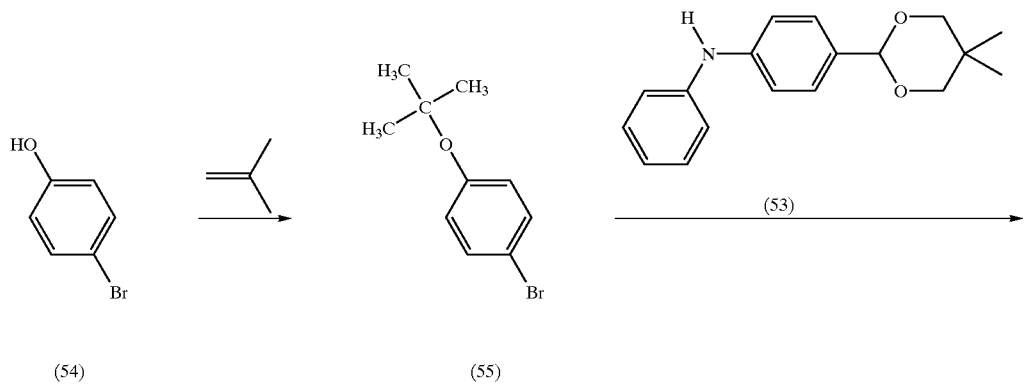
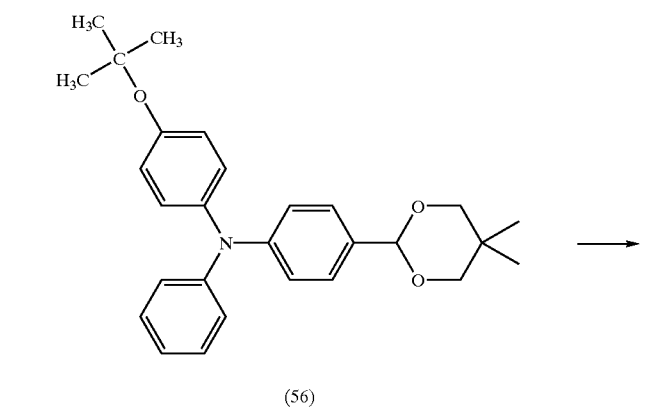
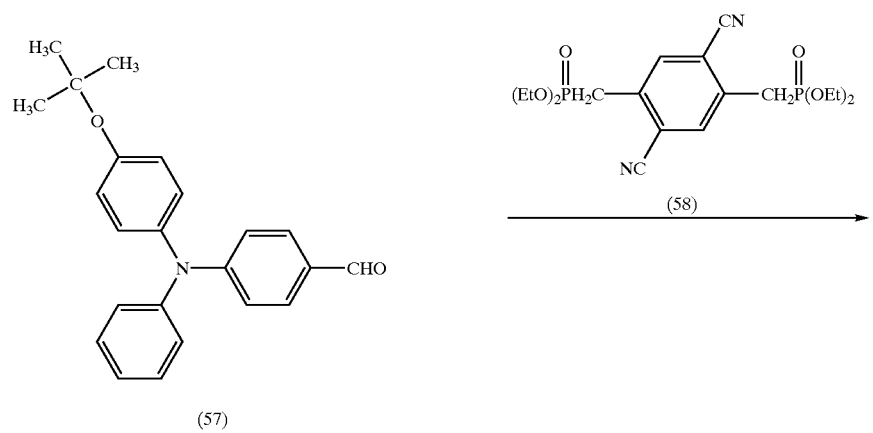

15

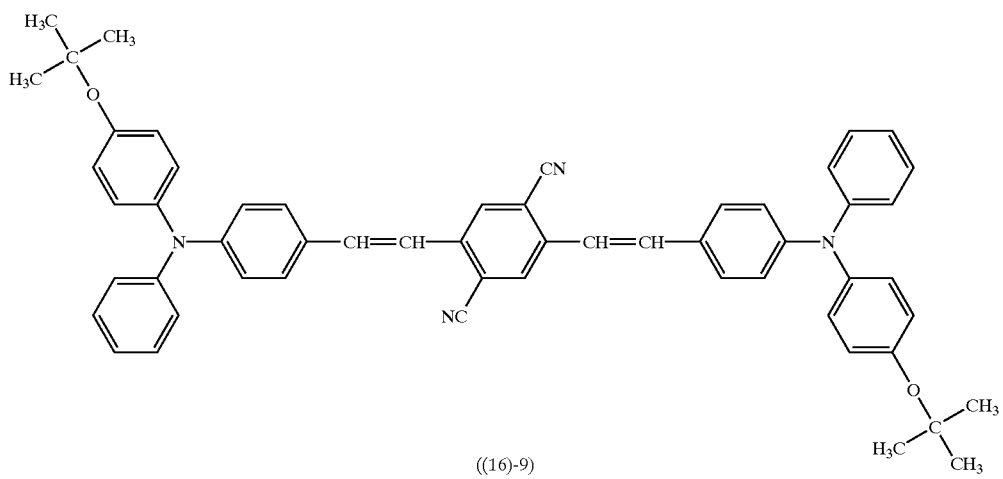

((16)-9)

(1) Preparation of Intermediate (53)

2.75 g (10.2 mmols) of an acetal compound (51), 20 ml (215 mmols) of aniline, 1.00 g (10.4 mmols) of t-BuONa, and 0.022 g (0.047 mmols) of Pd(OAc)$_2$ were dissolved in 150 ml of xylene, into which 2.0 ml (0.20 mmols) of 0.1 M P(t-Bu)$_3$ was further dropped while refluxing in an atmosphere of nitrogen, followed by refluxing for 6 hours. The starting materials were removed by alumina column chromatography (200 mesh, toluene:THP=1:1), followed by removal of excess aniline by distillation under reduced pressure to quantitatively obtain the intermediate (53).

This product was identified as the intended product (53) by measurement with $^1$HNMR and FAB-MS.

$^1$HNMR (CDCl$_3$) δ (ppm): 0.80 (3H, s), 1.30 (3H, s), 3.63 (2H, d), 3.76 (2H, d), 5.34 (1H, s), 5.74 (1H, brs), 6.92 (1H, t), 7.06 (4H, d), 7.26 (2H, t), 7.39 (2H, d).

Figure 14:
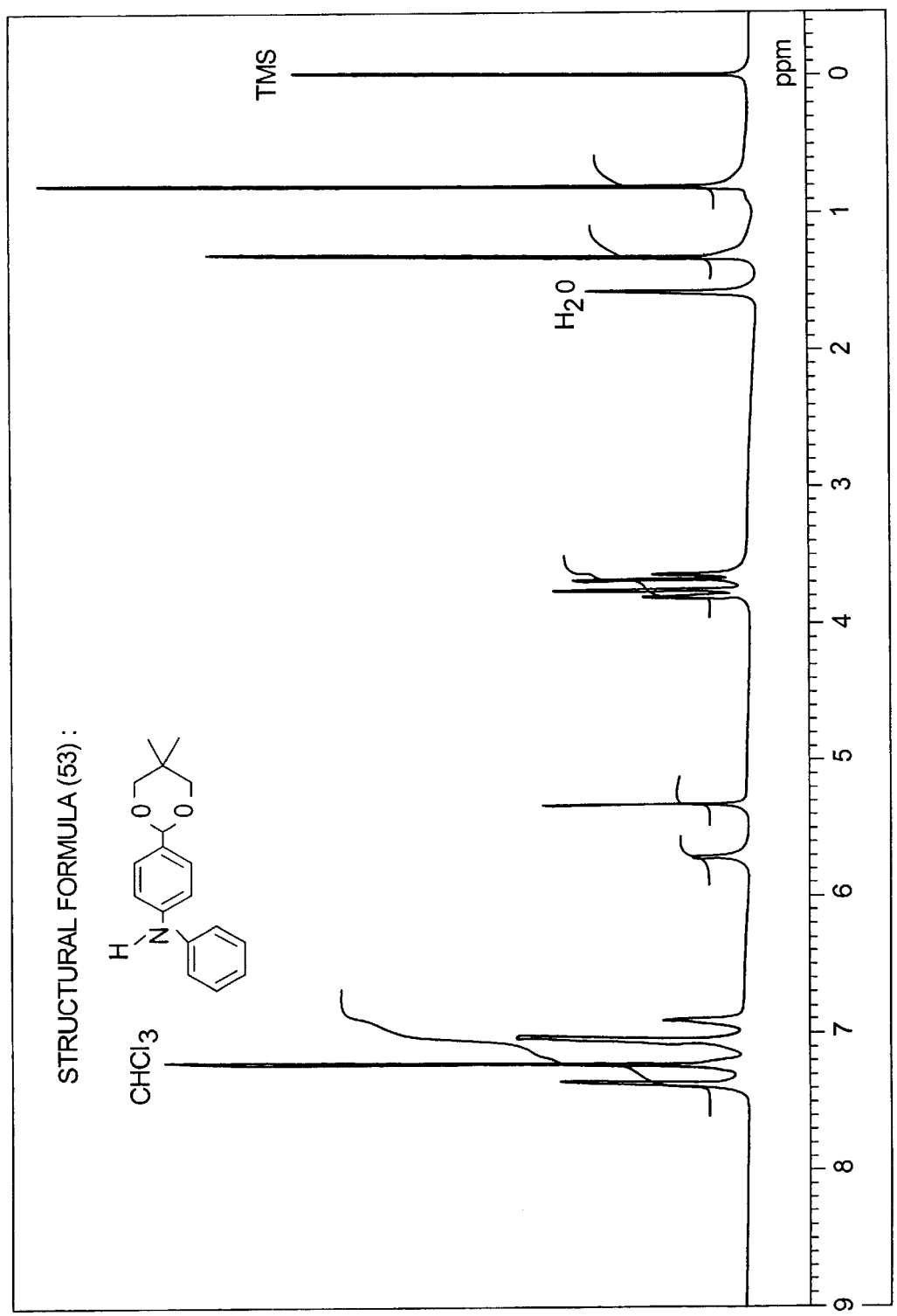
FIG. 14 is an ¹HNMR spectral diagram of an acetal compound of structural formula (53), which is a synthetic intermediate of the invention.

The $^2$HNMR spectra of the intermediate (53) are shown in FIG. 14.

(2) Preparation of Intermediate (55)

5.00 g (28.9 mmols) of compound (54) was dissolved in 50 ml of CHCl$_3$, and cooled down to 0° C., to which 0.2 ml of CF$_3$SO$_3$H was added while agitating in an atmosphere of nitrogen. Thereafter, the solution was gently bubbled with use of an isobutylene gas in 3 hours. 6 ml of NEt$_3$ was added to the solution to neutralize the reaction solution, followed by passage through dried alumina (300 mesh size, toluene) to remove the starting materials, followed by removal of the solvent by distillation to quantitatively obtain the compound (55).

This product was identified as the intended product (55) by measurement with $^1$HNMR and FAB-MS.

$^1$HNMR (CDCl$_3$) δ (ppm): 1.33 (9H, s), 6.86 (2H, d), 7.37 (2H, d).

Figure 15:
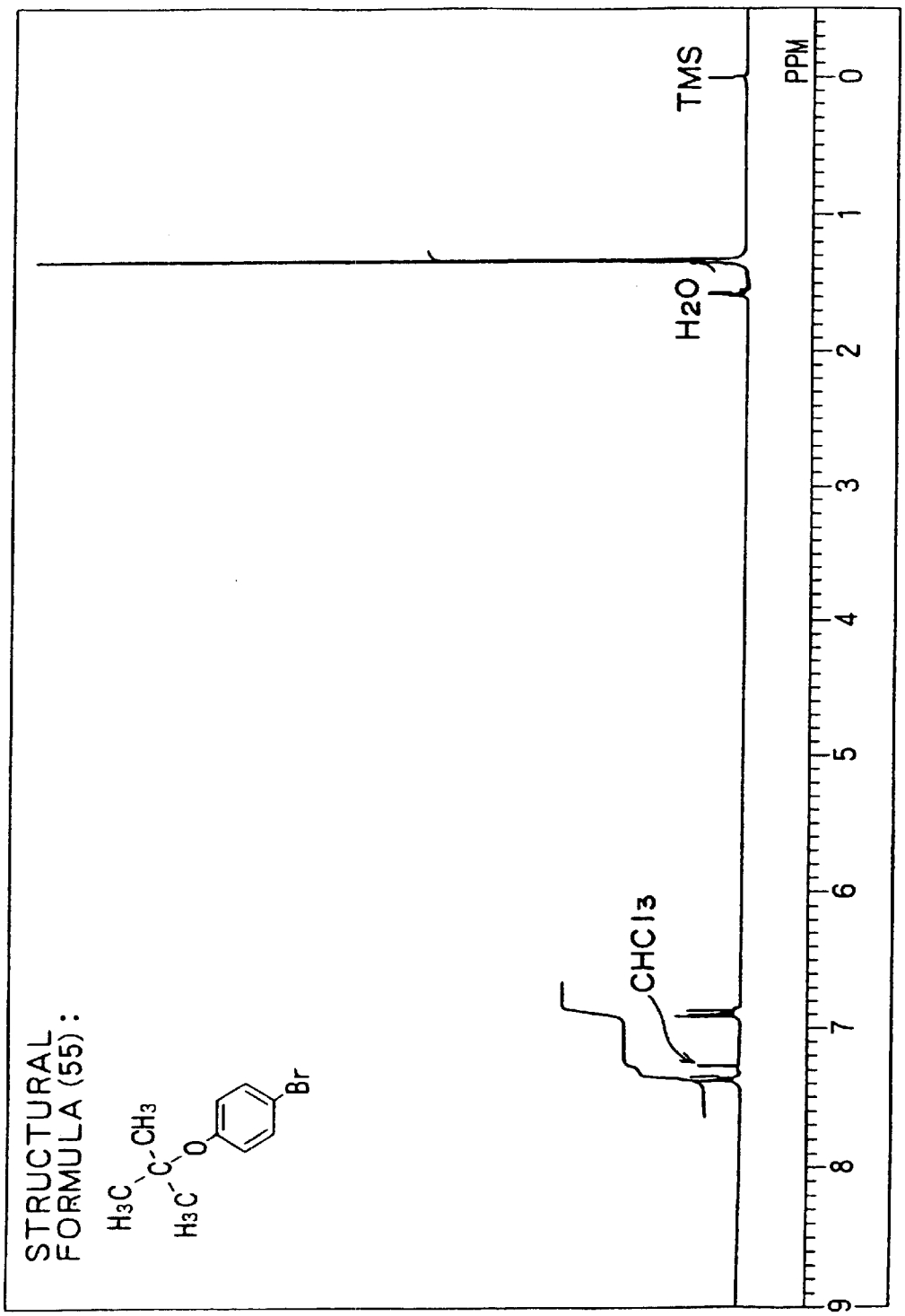
FIG. 15 is an ¹HNMR spectral diagram of an acetal compound of structural formula (55), which is a synthetic intermediate of the invention.

The $^1$HNMR spectra of the intermediate (55) are shown in FIG. 15.

(3) Preparation of Intermediate (56)

0.809 g (3.53 mmols) of compound (55), 1.00 g (3.53 mmols) of compound (53), 0.407 g (4.24 mmols) of t-BuONa and 7.9 mg (0.035 mmols) of Pd(OAc)$_2$ were suspended in 100 ml of xylene, to which 1.4 ml of 0.1 M of P(t-Bu)$_3$ was further added while agitating under refluxing in an atmosphere of nitrogen at 120° C., followed by refluxing for further 4 hours, The reaction solution was allowed to cool, and an insoluble matter was removed and the resultant filtrate was condensed, followed by purification through silica gel chromatography (WAKO-gel C-300, hexane:THF 20:1) and recrystallization from acetone/hexane to obtain 1.44 g of white crystals.

This product was identified as the intended product (56) by measurement with $^1$HNMR and FAB-MS (yield of 95%).

$^1$HNMR (CDCl$_3$) δ (ppm): 0.79 (3H, s), 1.30 (3H, s), 1.34 (9H, s), 3.64 (2H, d), 3.76 (2H, s), 5.34 (1H, s), 6.86 (2H, d), 6.96–7.06 (7H, m), 7.22 (2H, d), 7.36 (2H, d).

Figure 16:
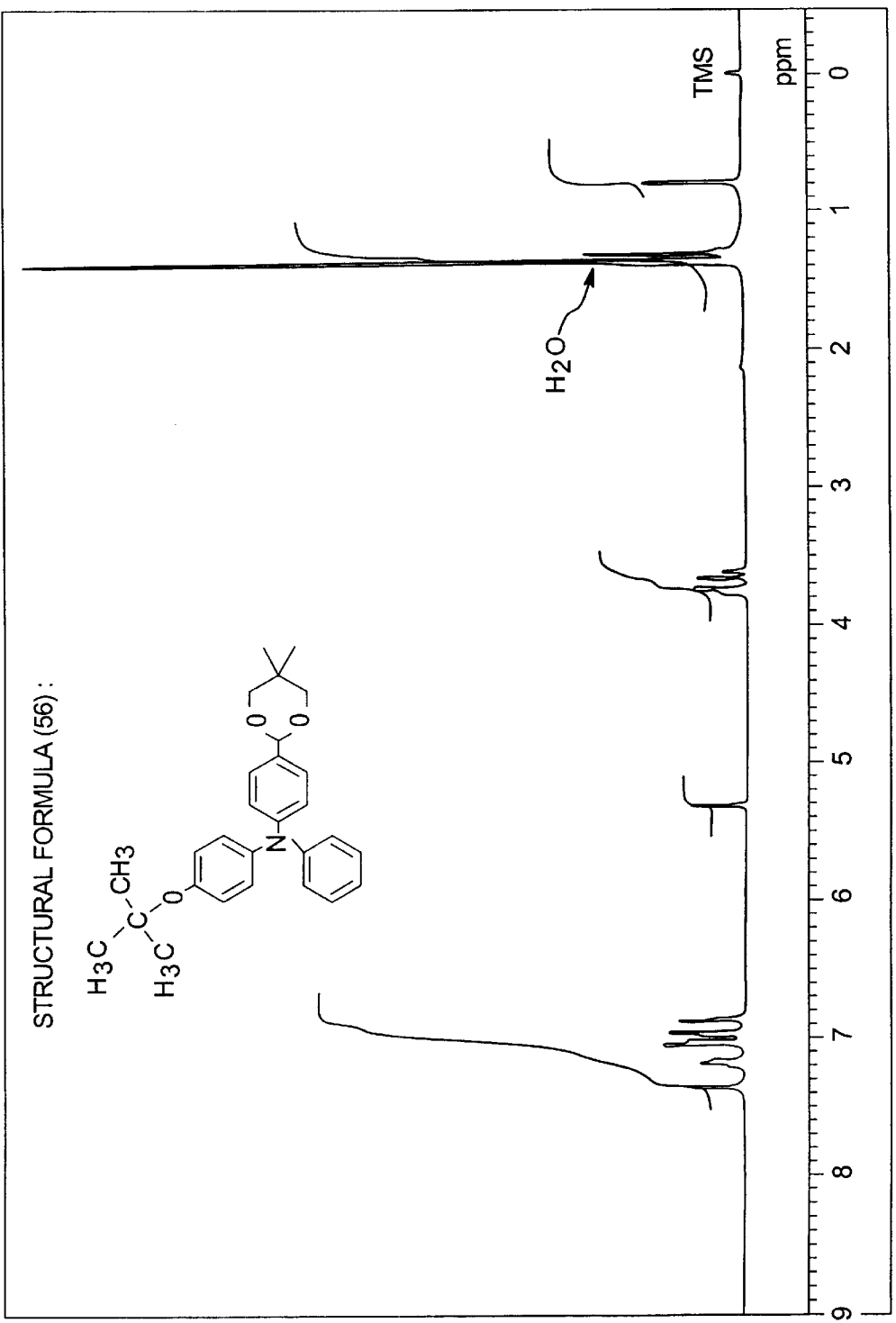
FIG. 16 is an ¹HNMR spectral diagram of an acetal compound of structural formula (56), which is a synthetic intermediate of the invention.

The $^1$HNMR spectra of the intermediate (56) are shown in FIG. 16.

(4) Preparation of Intermediate (57)

1.44 g (3.34 mmols) of compound (56) and 0.084 g (0.334 mmols) of TPPS (pyridinium p-toluenesulfonate) were dissolved in a mixed solvent of 60 ml of acetone and 10 ml of water, followed by refluxing for 3 hours. The solvent was distilled off, followed by extraction with toluene, washing with a saturated saline solution and drying over Na$_2$SO$_4$. 0.940 g of the product (57) was obtained by purification through silica gel chromatography (WAKO-gel, C-300, hexane→hexane:THF=8.1).

This product was identified as the intended product (57) by measurement with $^1$HNMR and FAB-MS (yield of 81%).

$^1$HNMR (CDCl$_3$) δ (ppm): 1.37 (9H, s), 6.96 (4H, d), 7.07 (2H, d), 7.16 (2H, m), 7.33 (2H, m), 7.66 (2H, d), 9.79 (1H, s).

Figure 17:
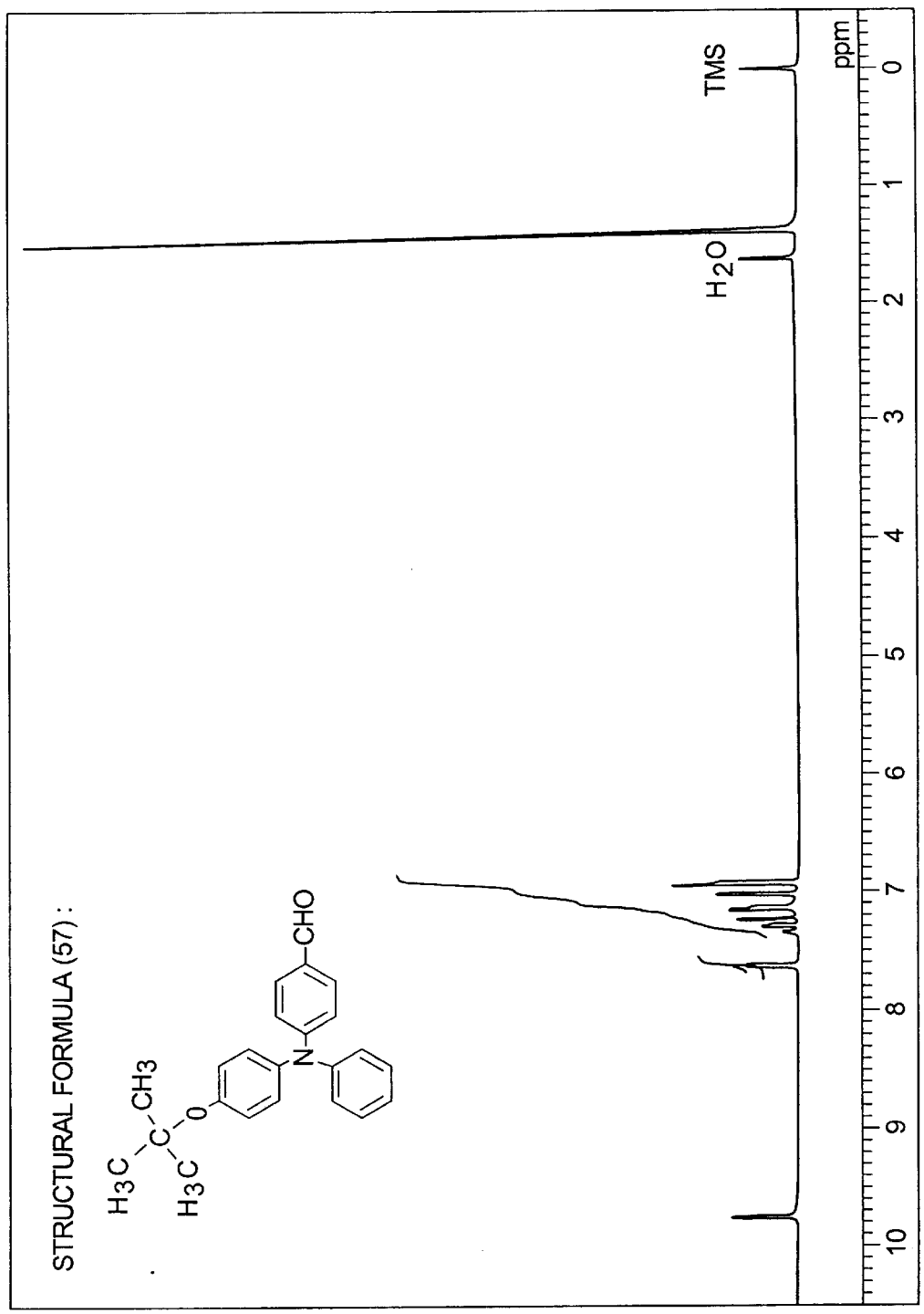
FIG. 17 is an ¹HNMR spectral diagram of an aldehyde compound of structural formula (57), which is a synthetic intermediate of the invention.

The $^1$NMR spectra of the intermediate (56) are shown in FIG. 17.

(5) Preparation of bis(aminostyryl)benzene Compound ((16)-9)

9.54 mmols of NaH (dispersed in a 60% mineral oil) was washed twice with hexane, and suspended in 10 ml of anhydrous THF (tetrahydrofuran), followed by dropping of 50 ml of an anhydrous THF solution of 1.59 mmols of phosphonic acid ester (58) and 0.940 g (2.72 mmols) of compound (57) on an ice bath in an atmosphere of nitrogen in 1 hour, followed by agitation on an ice bath for 3 hours and further agitation at room temperature for 12 hours. The reaction mixture was quenched with a small amount of ice pieces, extraction with toluene, and drying over Na$_2$SO$_4$. The resulting solid matter was purified by silica gel chromatography (WAKO-gel C-300, toluene) and recrystallized from toluene to obtain 0.856 g of product ((16) -9).

Figure 18:
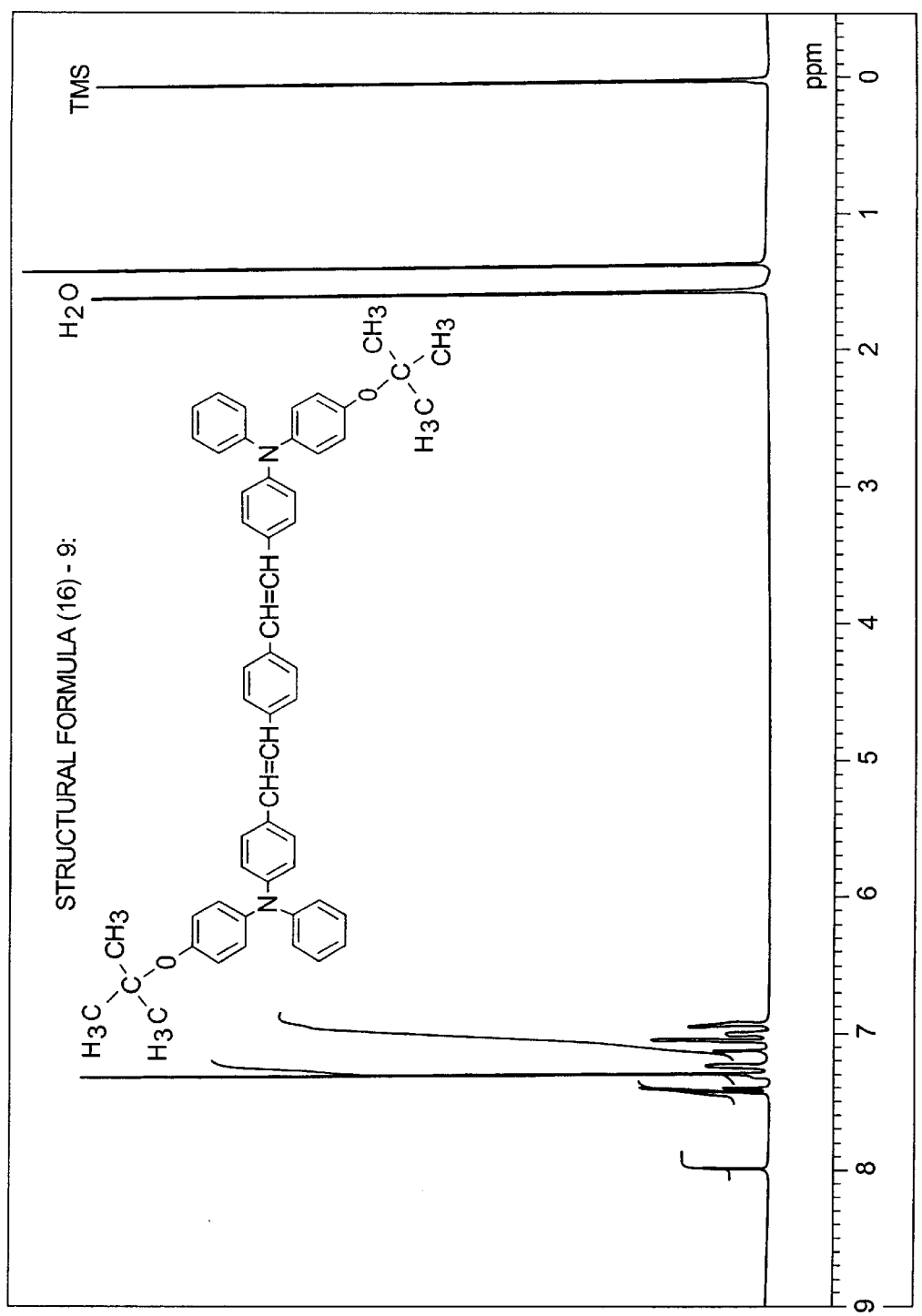
FIG. 18 is an ¹HNMR spectral diagram of a bis (aminostyryl)benzene compound of structural formula (16)-9 of the invention.

This product was identified as product ((16)-9) by measurement with $^1$HNMR and FAB-MS (yield of 66%). The ¹HNMR spectra of the product are shown in FIG. 18 and indicated below.

¹HNMR (CDCl$_3$) δ (ppm): 1.37 (18H, s), 6.92 (4H, d), 7.00–7.32 (22H, m), 7.42 (4H, d), 7.98 (2H, s).

The visible light absorption maximum of the toluene solution of this substance was at 481 nm and the fluorescent maximum wavelength was at 540 nm.

EXAMPLE 18

Preparation of bis(aminostyryl)benzene Compound

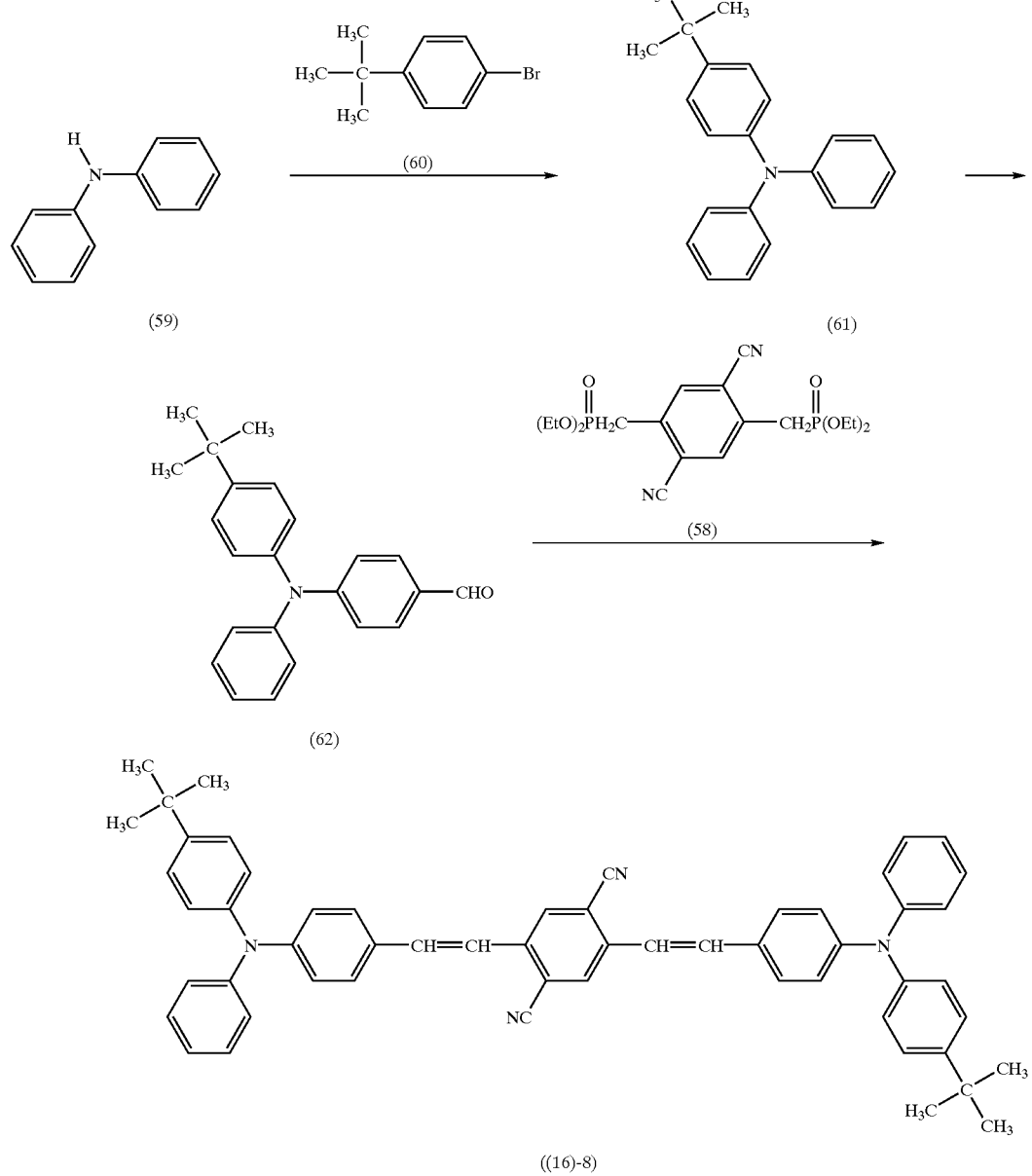

8.45 g (88.0 mmols) of t-BuONa was refluxed at 120° C. for 3 hours. The reaction mixture was cooled, to which water was added, followed by extraction with toluene three times, drying and concentrating the resultant organic layer with anhydrous sodium sulfate. The resultant residue was purified through column chromatography to quantitatively obtain 18.4 g of triarylamine (61) as colorless crystals.

This product was identified as the intended product (61) by measurement with ¹HNMR and FAB-MS.

¹HNMR (CDCl$_3$) δ (ppm): 1.32 (9H, s), 6.98–7.09 (8H, m), 7.19–7.27 (6H, m).

(1) Preparation of Intermediate (61)

Figure 19:
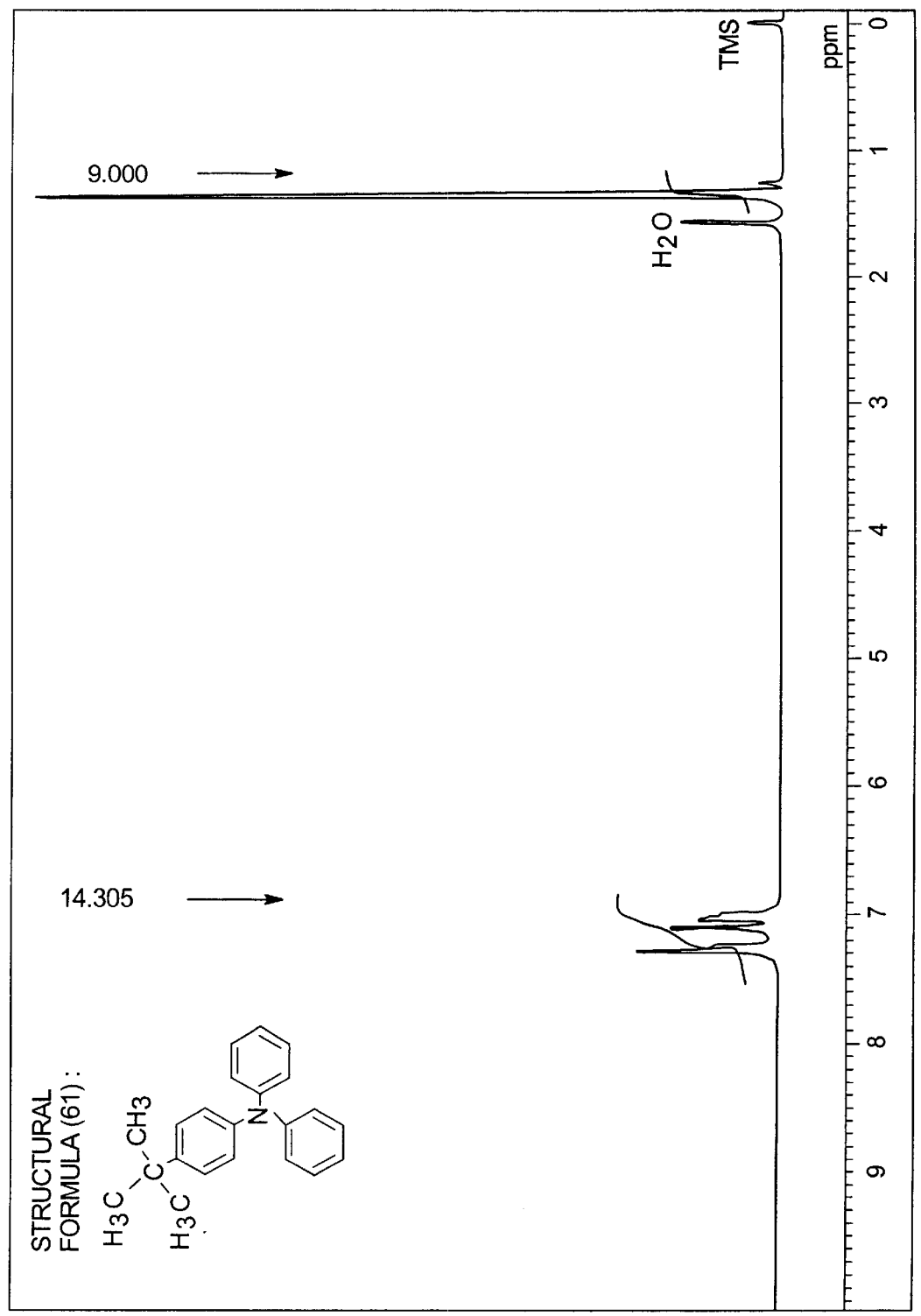
FIG. 19 is an ¹HNMR spectral diagram of an amine compound of structural formula (61), which is a synthetic intermediate of the invention.

A xylene suspension (200 ml) of 12.5 g (58.7 mmols) of 1-bromo-4-t-butylbenzene (60), 9.93 g (58.7 mmols) of diphenylamine (59), 263 mg (1.17 mmols) of Pd(OAc)$_2$, 1.43 g (4.69 mmols) of tris(2-methylphenyl)phosphine, and The ¹HNMR spectra of the product are shown in FIG. 19.
(2) Preparation of Intermediate (62)

27.5 g (179 mmols) of phosphorus oxychloride was dropped in 100 ml of DMF and agitated at 120° C. for 5 minutes. The resultant red solution was cooled down to room temperature, to which 18.0 g (59.7 mmols) of the triarylamine (61) was added. The resultant mixture was agitated at 80° C. After concentration of the mixture under reduced pressure, this mixture was carefully poured into NaNCO$_3$/ice. The resulting mixture was extracted with ethyl acetate three times, and the resultant organic layer was dried over Na$_2$SO$_4$ and concentrated. The residue was purified through column chromatography to obtain 6.69 g of diarylaminobenzaldehyde (62) as light yellow crystals.

This product was identified as the intended product (62) by measurement with $^1$HNMR and FAB-MS (yield of 34%).

$^1$HNMR (CDCl$_3$) δ (ppm): 1.33 (9H, s), 6.99 (2H, d), 7.08 (2H, d), 7.17 (3H, m), 7.33 (4H, m), 7.66 (2H, d), 9.80 (1H, s).

Figure 20:
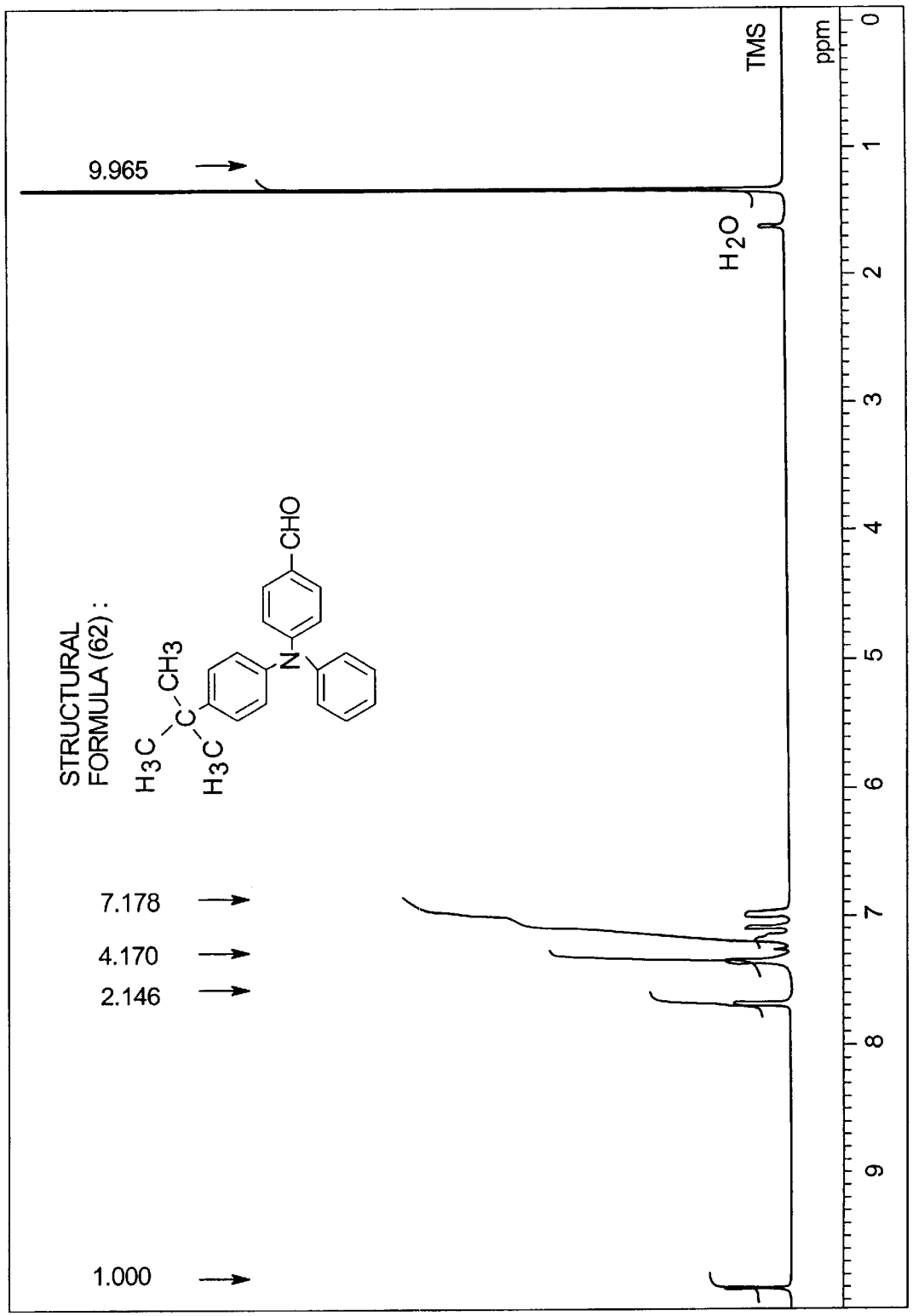
FIG. 20 is an ¹HNMR spectral diagram of an aldehyde compound of structural formula (62), which is a synthetic intermediate of the invention.

The $^1$HNMR spectra of this product are shown in FIG. 20.

(3) Preparation of bis(aminostyryl)benzene Compound (Structural Formula (16)-8)

9.54 mmols of NaH (dispersed in a mineral oil at 60%) was washed with hexane twice, and suspended in 10 ml of anhydrous THF, followed by agitation on an ice bath in an atmosphere of nitrogen. 40 ml of an anhydrous THF solution of 1.59 mmols of compound (58) and 1.26 g (3.82 mmols) of compound (62) was dropped in the NaH suspension in 15 minutes, followed by agitation on an ice bath for 6 hours and for further 6 hours at room temperature. The resultant reaction mixture was quenched with a small amount of ice pieces, washed with a saturated saline solution, and dried over Na$_2$SO$_4$. As a result, there was obtained 1.11 g of the product ((16)-8) by purification through silica gel chromatography (WAKO-gel C-300, toluene) and recrystallized from toluene.

Figure 21:
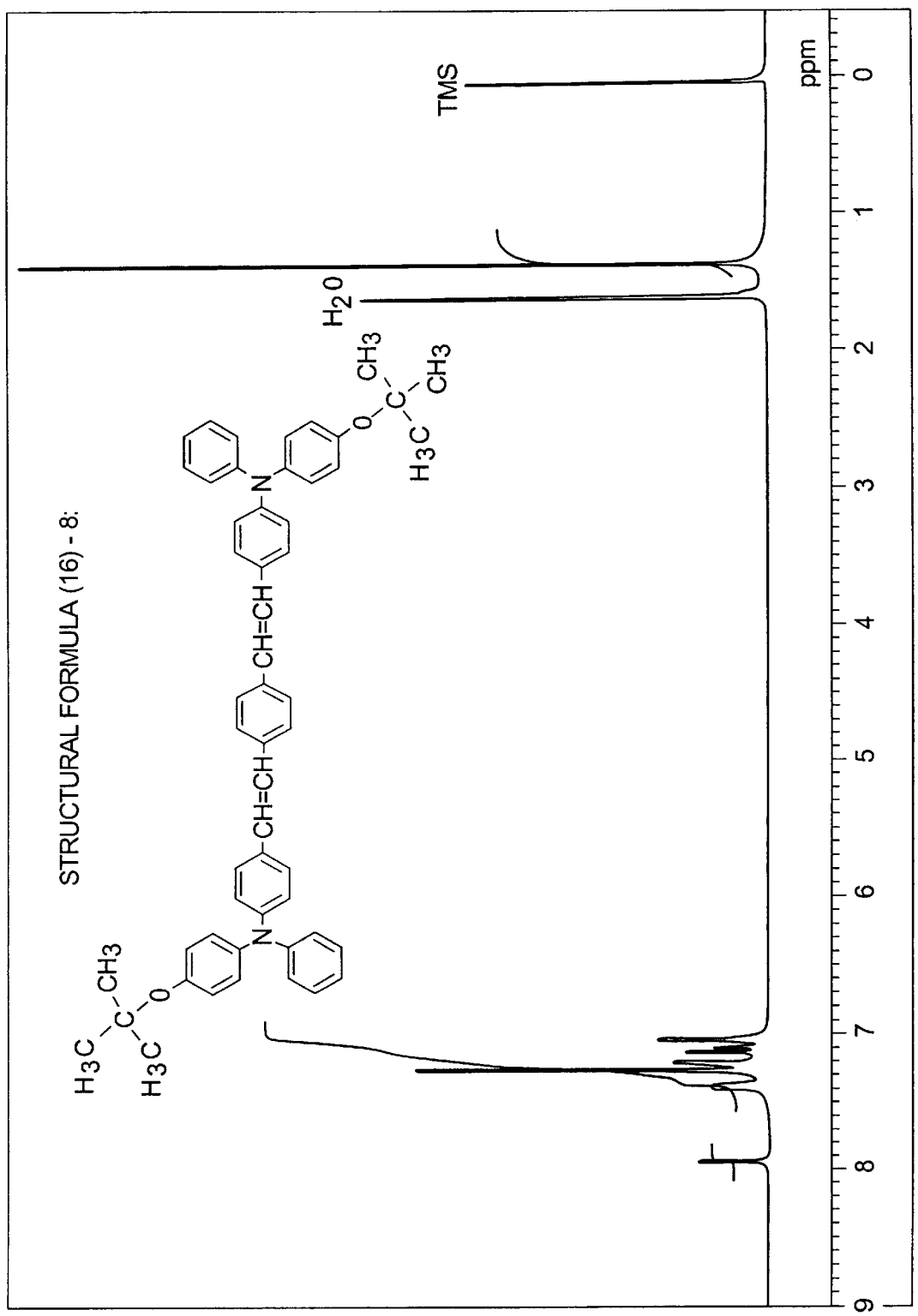
FIG. 21 is an ¹HNMR spectral diagram of a bis (aminostyryl)benzene compound of structural formula (16)-8 of the invention.

This product was identified as product ((16)-8) by measurement with $^1$HNMR and FAB-MS (yield of 90%). The $^1$HNMR spectra of the product are shown in FIG. 21 and indicated below.

$^1$HNMR (CDCl$_3$) δ (ppm): 1.33 (2H, s), 7.02–7.07 (10H, m), 7.14 (4H, d), 7.22–7.32 (8H, m), 7.33 (4H, d), 7.99 (2H, s).

The visible light absorption maximum of the toluene solution of this substance was at 479 nm and the fluorescent maximum wavelength was at 535 nm.

EXAMPLE 19

Preparation of bis(aminostyryl)benzene Compound (Structural Formula (16)-3

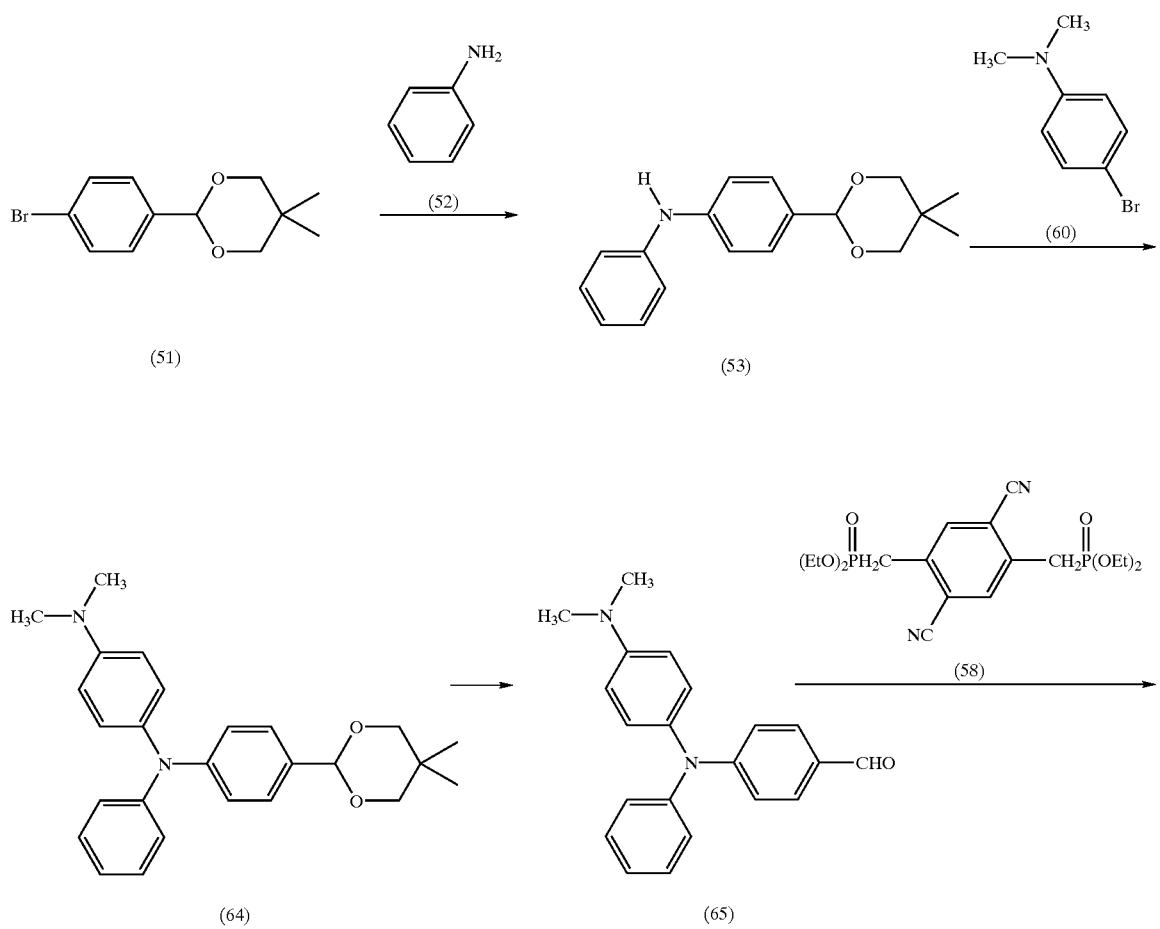

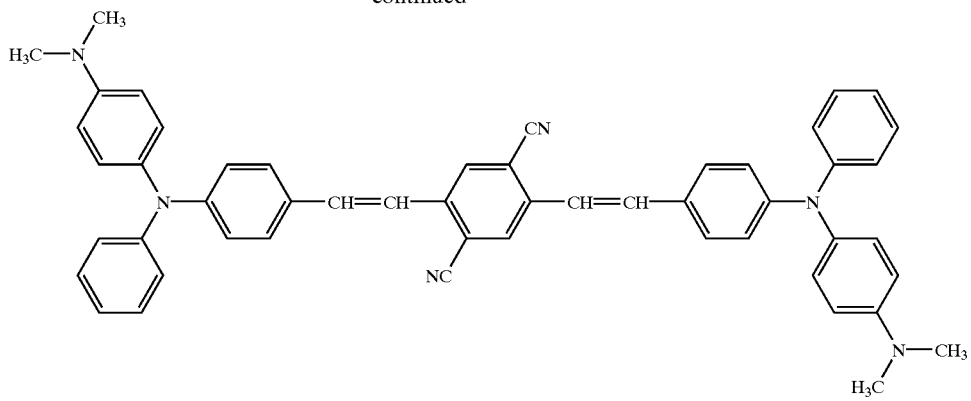

((16)-3)

(1) Preparation of Intermediate (64)

In order to prepare the intended product ((16)-3), 2.85 g (10.1 mmols), prepared in the same manner as in Example 17, 2.00 g (10.0 mmols) of 4bromo-N,N-dimethylaniline (63), 1.20 g (12.0 mmols) of t-BuONa and 0.066 g (0.29 mmols) of $Pd(OAc)_2$ were dissolved in 150 ml of xylene, into which 12.0 ml (0.40 mmole) of 0.1 M P(t-Bu)$_3$ was dropped while refluxing in an atmosphere of nitrogen, followed by further refluxing for 9 hours. 2.28 g of yellow crystals of the intended product (64) were obtained by purification through silica gel chromatography (Wakogel C-300, THF:hexane=1:10).

This product was identified as the intended product (64) by measurement with $^1$HNMR and FAB-MS (yield of 57%).

$^1$HNMR (CDCl$_3$) δ (ppm): 0.74 (3H, s), 1.17 (3H, s), 2.89 (6H, s), 3.62 (4H, q), 5.32 (1H, s), 6.72 (2H, d), 6.86 (7H, m), 7.20–7.27 (4H, m).

Figure 22:
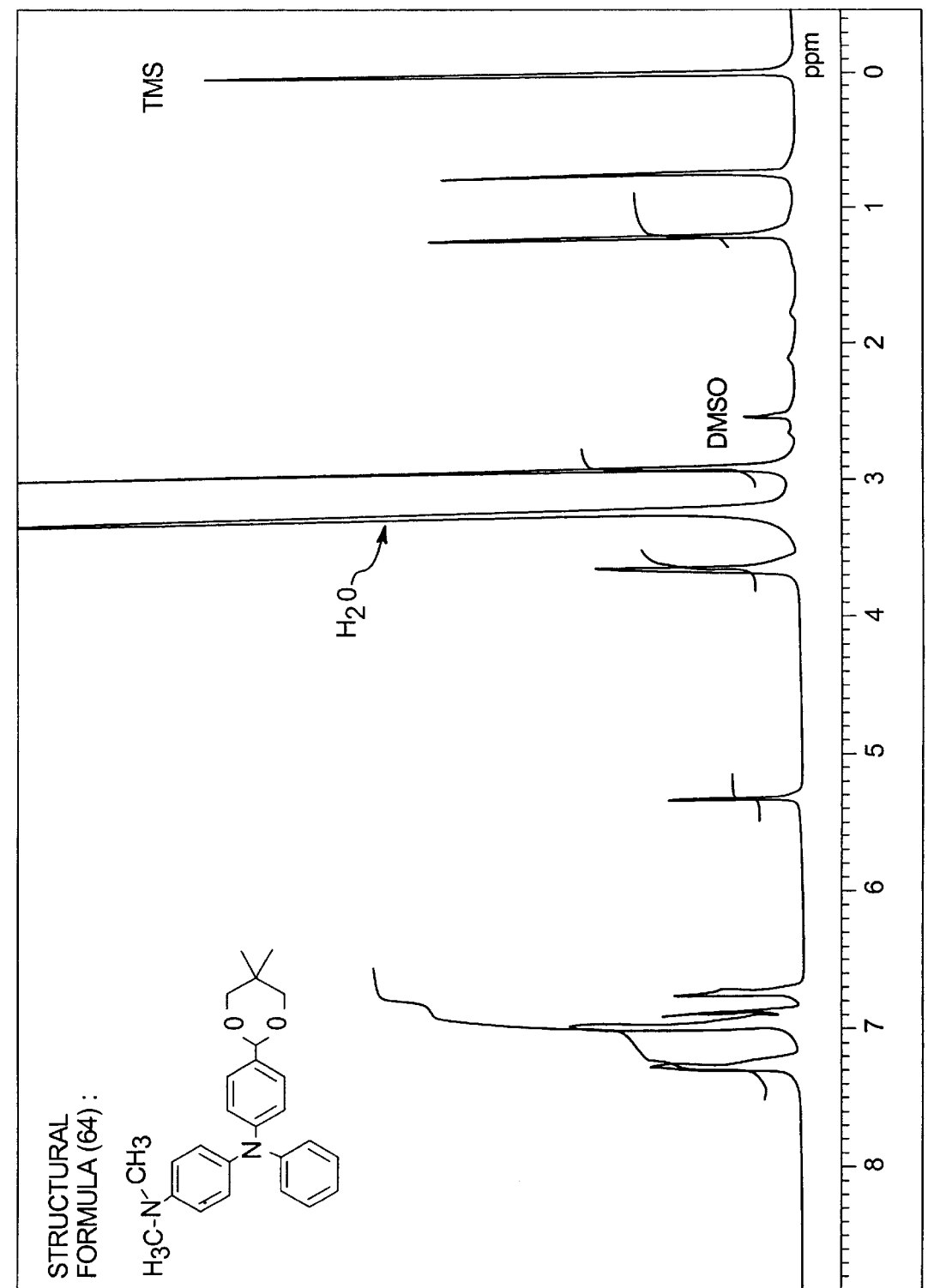
FIG. 22 is an ¹HNMR spectral diagram of an acetal compound of structural formula (64), which is a synthetic intermediate of the invention.

The $^1$HNMR spectra of this product are shown in FIG. 22.

(2) Preparation of Intermediate (65)

2.28 g (5.71 mmols) of compound (64) and 0.133 g (0.700 mmols) of p-toluenesulfonic acid monohydrate were dissolved in 300 ml of acetone and 25 ml of water and refluxed for 2 hours. After removal of the acetone by distillation, the mixture was dried over $Na_2SO_4$, followed by purification through silica gel chromatography (Wakogel C-300, toluene to obtain 1.67 g of the intended product as yellow crystals.

This product was identified as the intended product (65) by measurement with $^1$HNMR and FAB-MS (yield of 92%).

$^1$HNMR (CDCl$_3$) δ (ppm): 2.97 (6H, s), 6.71 (2H, d), 6.93 (2H, s), 7.07–7.34 (7H, m), 7.63 (2H, d), 9,76 (1H, s).

Figure 23:
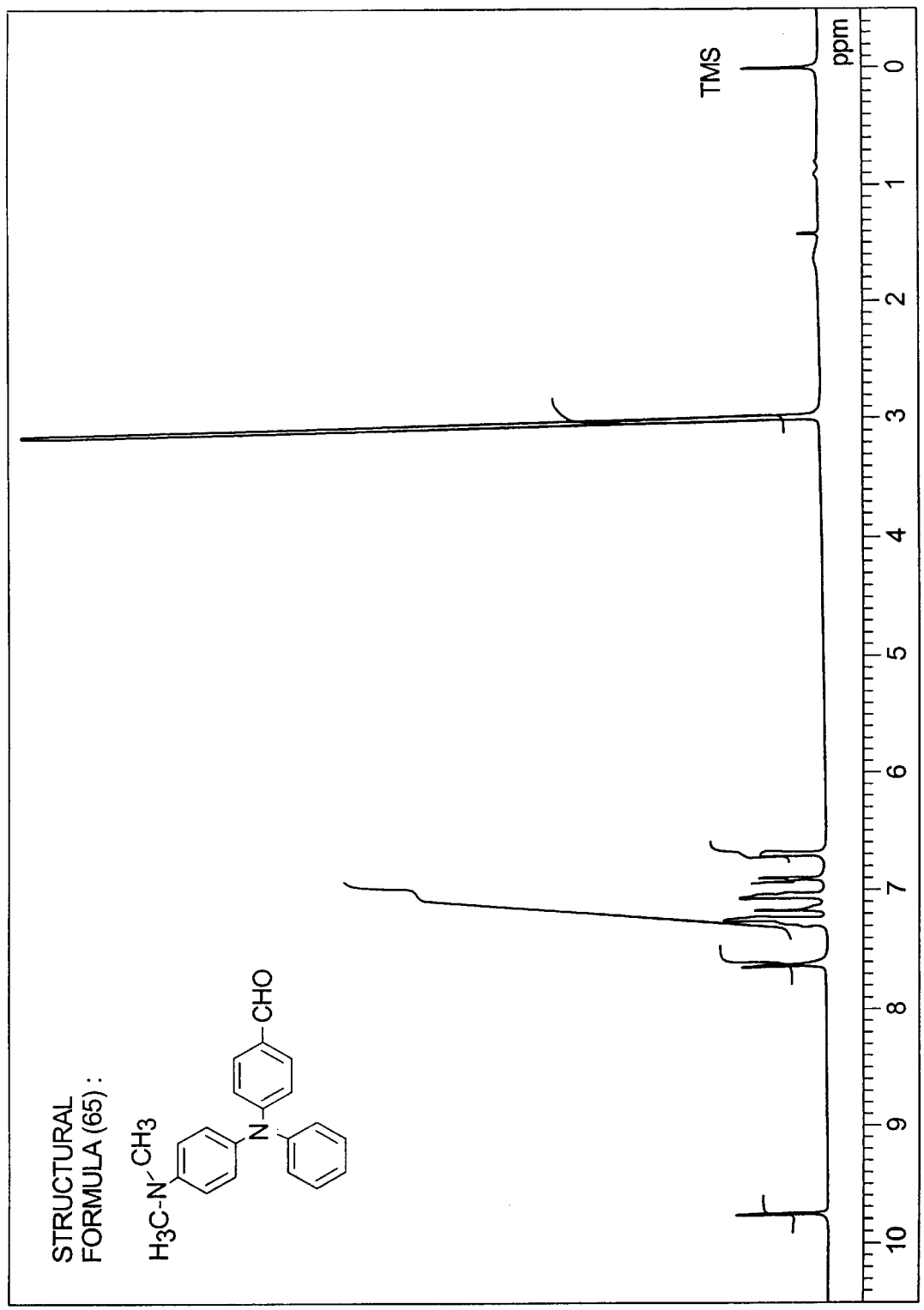
FIG. 23 is an ¹HNMR spectral diagram of an aldehyde compound of structural formula (65), which is a synthetic intermediate of the invention.

The $^1$HNMR spectra of this product are shown in FIG. 23.

(3) Preparation of bis(aminostyryl)benzene Compound (Structural Formula (16)-3)

9.54 mmols of NaH (dispersed in a mineral oil at 60%) was washed with hexane twice, and suspended in 10 ml of anhydrous THF, followed by agitation on an ice bath in an atmosphere of nitrogen. 70 ml of an anhydrous TrY solution of 1.59 mmole of compound (59) and 1.14 g (3.60 mmols) of compound (65) was dropped in the NaH in 15 minutes, followed by agitation at room temperature for 12 hours. The resultant reaction mixture was quenched with a small amount or ice pieces, washed with a saturated saline solution, and dried over $Na_2SO_4$. As a result, there was obtained 1.02 g of the product ((16)-3) by purification through alumina column chromatography (300 mesh size, toluene:THF=5:1) and recrystallized from toluene hexane.

Figure 24:
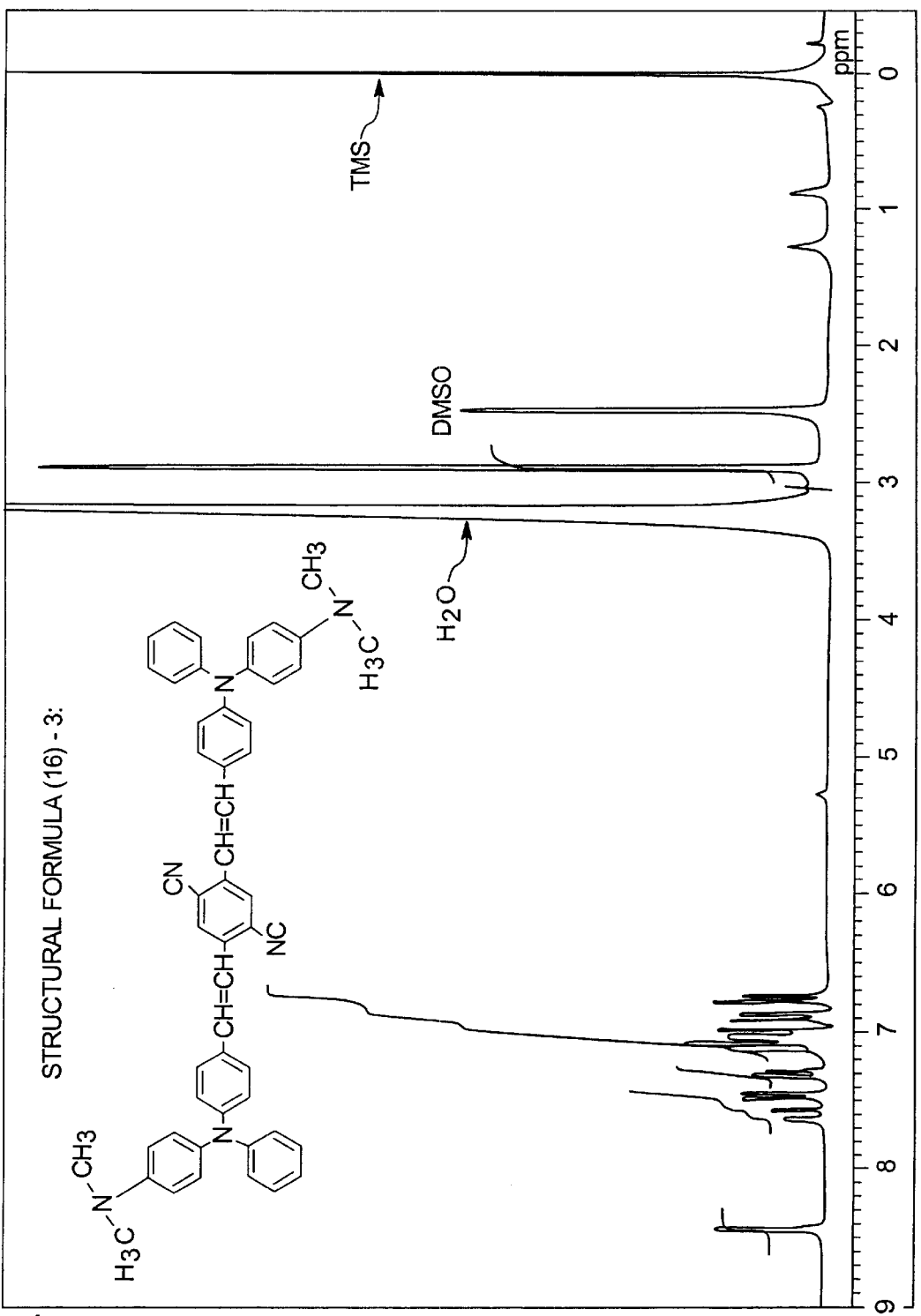
FIG. 24 is an ¹HNMR spectral diagram of a bis (aminostyryl)benzene compound of structural formula (16)-3 which is a synthetic intermediate of the invention.

This product was identified as product ((16)-3) by measurement with $^1$HNMR and FAB-MS (yield of 88%). The $^1$HNMR spectra of the product are shown in FIG. 24 and indicated below.

$^1$HNMR (DMSO-d6) δ (ppm): 2.91 (12H, s), 6.75 (4H, d), 6.68 (4H, s), 6.98–7.13 (12H, m), 7.30 (4H, d), 7.47 (4H, d), 7.59 (2H, d), 8.42 (2H, s).

The visible light absorption maximum of the toluene solution of this product was at 499 nm and the fluorescent maximum wavelength was at 620 nm.

EXAMPLE 20

Preparation of 1,4-bis[2-[4-(N-4-methoxyphenyl-N-phenyl)aminophenyl]ethenyl]-2,3,5,6-tetrafluorobenzene (Structural Formula (40)-1

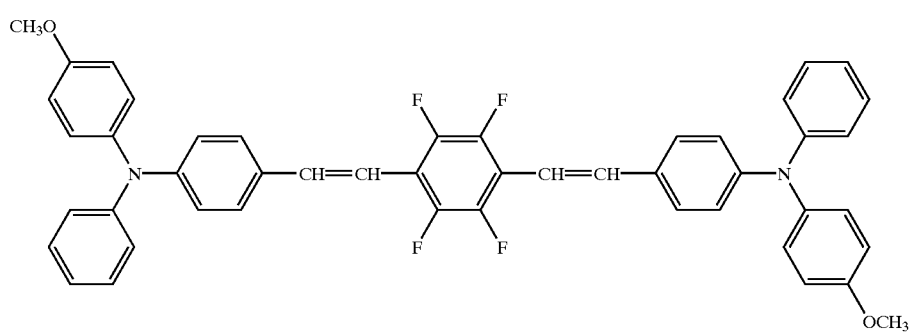

((40)-1)

47.6 mg (0.105 mmols) of 2,3,5,6-tetrafluorobenzene-1,4-diyl-bis(diethyl methanephosphonate) was added to 3 ml of a tetrahydrofuran (THF) suspension of 104 mg (2.50 mmols) of sodium hydride (suspended in a mineral oil at 60%), followed by agitation at room temperature for 10 minutes. 108 mg (0.356 mmols) of (N-4-methoxyphenyl-N-phenylamino)benzaldehyde was added to the mixture and agitated at room temperature for 5 hours. After addition of 0.5 ml of methanol to the mixture, a saturated ammonium chloride aqueous solution was added to the resulting mixture, followed by extraction with ethyl acetate three times.

The resultant organic layer was washed with water and then with a saturated saline solution, dried over anhydrous sodium sulfate and filtered. The filtrate was concentrated under reduced pressure to obtain a residue, which was purified through column chromatography (silica gel, developing solution: hexane/ethyl acetate=5/1) to obtain 66.9 mg of the product ((40)-1) (yield of 85%) as yellowish orange crystals. The identification of the product was performed by measurement with $^1$HNMR and FAB-MS.

The visible light absorption maximum of the THF solution of this product was at 438 nm and the fluorescent maximum wavelength was at 542 nm.

EXAMPLE 21

Preparation of 1,4-bis[2-[4-(N-diphenyl)aminophenyl]ethenyl]-2,3,5,6-tetrafluorobenzene (Structural Formula (40)-2>

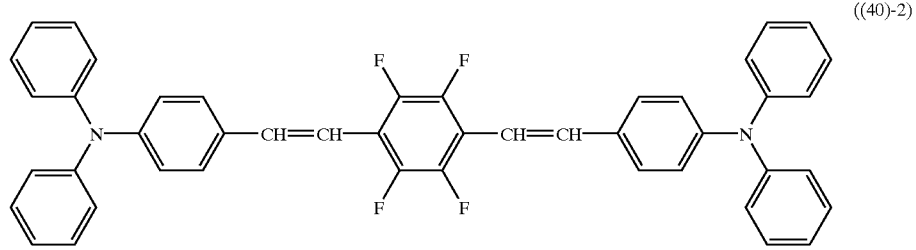

((40)-2)

The compound was prepared in the same manner as in Example 20 using 153 mg (3.84 mmols) of sodium hydride (suspended in a mineral oil at 60%), 115 mg (0.256 mmols) of (2,3,5,6-tetrafluorobenzene)-1,4-diyl-bis(diethyl methanephosphonate), and 245 mg (0.897 mmols) of N,N-diphenylaminobenzaldehyde.

As a result, there was obtained 150 mg of the product (structural formula (40)-2) (yield of 85%) as yellowish orange crystals. The identification of the product was performed by measurement with $^1$HNMR and FAB-MS.

The visible light absorption maximum of the THF solution of this product was at 428 nm and the fluorescent maximum wavelength was at 522 nm.

EXAMPLE 22

Preparation of 1,4-bis[2-[4-(N-4-methylphenyl-N-phenyl)aminophenyl]ethenyl]-2,3,5,6-tetrafluorobenzene (Structural Formula (40)-3

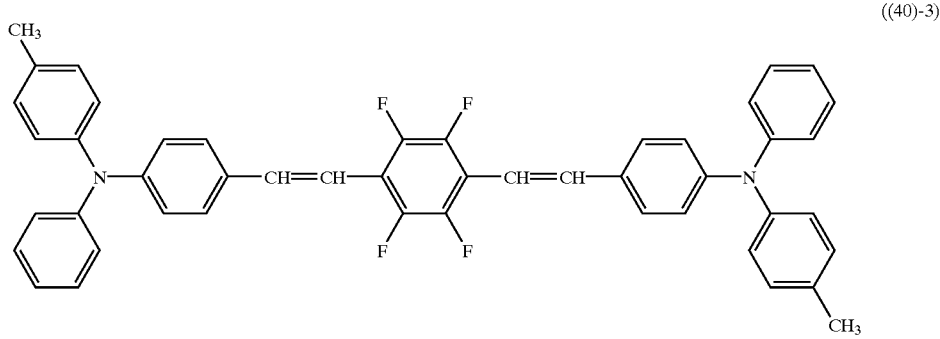

((40)-3)

The compound was prepared in the same manner as in Example 20 using 160 mg (4.01 mmols) of sodium hydride (suspended in a mineral oil at 60%), 90.3 mg (0.201 mmols) of (2,3,5,6-tetrafluorobenzene)-1,4-diyl-bis(diethyl methanephosphonate), and 202 mg (0.702 mmols) of [4-(N-4-methylphenyl)-N-phenyl]aminobenzaldehyde.

As a result, there was obtained 115 mg of the product (structural formula (40)-3) (yield of 80%) as yellowish orange crystals. The identification of the product was performed by measurement with $^1$HNMR and FAB-MS.

The visible light absorption maximum of the THF solution of this product was at 433 nm and the fluorescent maximum wavelength was at 532 nm.

EXAMPLE 23

Preparation of 1,4-bis[2-[4-(N-4-t-butylphenyl-N-phenyl)aminophenyl]ethenyl]-2,3,5,6-tetrafluorobenzene (Structural Formula (40)-4

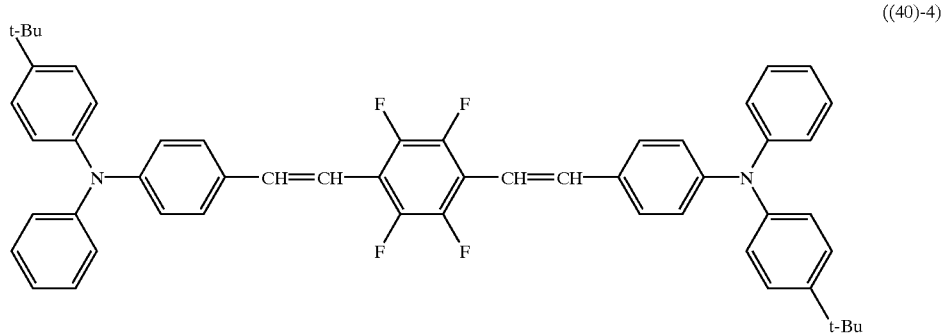

((40)-4)

The compound was prepared in the same manner as in Example 20 using 185 mg (44.3 mmol) of sodium hydride (suspended in a mineral oil at 60%), 69.7 mg (0.155 mmols) of (2,3,5,6-tetrafluorobenzene)-1,4-diyl-bis(diethyl methanephosphonate), and 203 mg (0.619 mmols) of [4-(N-t-butylphenyl)-N-phenyl]aminobenzaldehyde.

As a result, there was obtained 74.3 mg of the product (structural formula (40)-4) (yield of 60%) as yellowish orange crystals. The identification of the product was performed by measurement with $^1$HNMR and FAB-MS.

The visible light absorption maximum of the THF solution of this product was at 433 nm and the fluorescent maximum wavelength was at 532 nm.

EXAMPLE 24

Preparation of 1,4-bis[2-[4-(N-4-t-butoxyphenyl-N-phenyl)aminophenyl]ethenyl]-2,3,5,6-tetrafluorobenzene (Structural Formula (40)-5

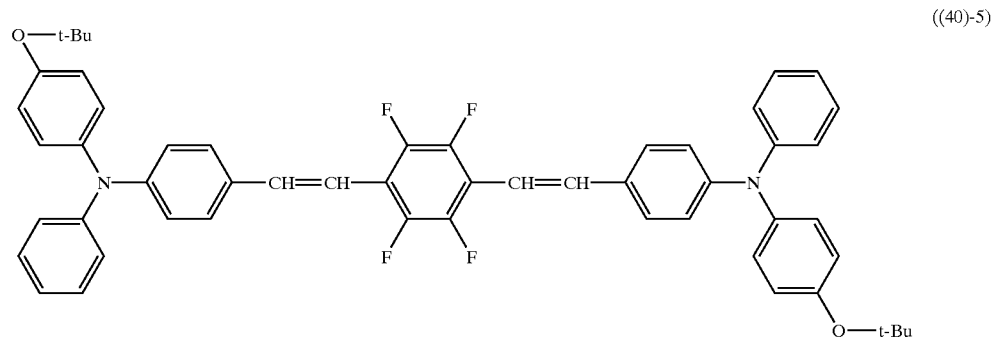

((40)-5)

The compound was prepared in the same manner as in Example 20 using 113 mg (2.93 mmols) of sodium hydride (suspended in a mineral oil at 60%), 45.5 mg (0.101 mmols) of (2,3,5,6-tetrafluorobenzene)-1,4-diyl-bis(diethyl methanephosphonate), and 132 mg (0.385 mmols) of [N-4-t-butoxyphenyl]-N-phenyl] aminobenzaldehyde.

As a result, there was obtained 54.8 mg of the product (structural formula (40)-5) (yield of 65%) as yellowish orange crystals. The identification of the product was performed by measurement with ¹HNMR and FAB-MS.

The visible light absorption maximum of the THF solution of this product was at 435 nm and the fluorescent maximum wavelength was at 537 nm.

EXAMPLE 25

Preparation of 1,4-bis[2-[4-(N,N-bis(4-methylphenyl)aminophenyl]ethenyl]-2,3,5,6-tetrafluorobenzene (Structural Formula (40)-6

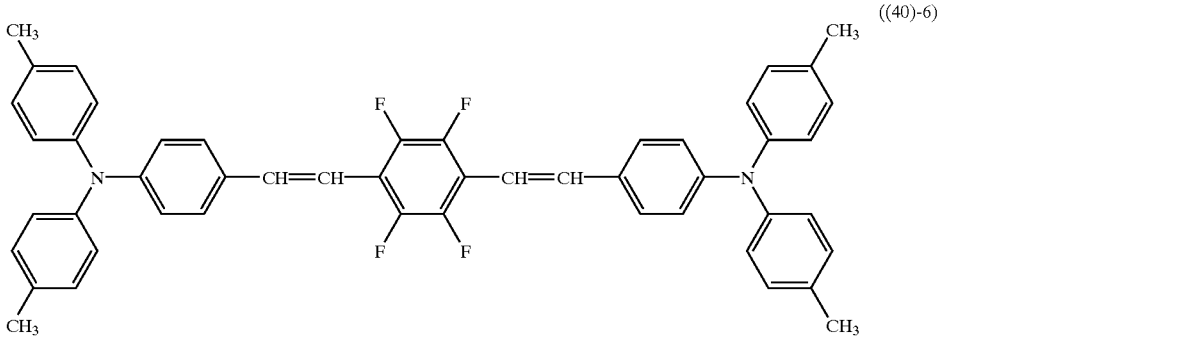

((40)-6)

The compound was prepared in the same manner as in Example 20 using 237 mg (5.78 mmols) of sodium hydride (suspended in a mineral oil at 60%), 260 mg (0.579 mmols) of (2,3,5,6tetrafluorobenzene)-1,4-diyl-bis(diethyl methanephosphonate), and 522 mg (1.73 mmols) of [bis-N-(4-methylphenyl)]aminobenzaldehyde.

As a results there was obtained 241 mg of the product (structural formula (40)-6) (yield of 56%) as yellowish orange crystals. The identification of the product was performed by measurement with ¹HNMR and FAB-MS.

The visible light absorption maximum of the THF solution of this product was at 440 nm and the fluorescent maximum wavelength was at 537 nm.

EXAMPLE 26

Preparation of 1,4-bis[2-[4-(N,N-bis(4-methoxyphenyl)aminophenyl]ethenyl]-2,3,5,6-tetrafluorobenzene (Structural Formula (40)-7

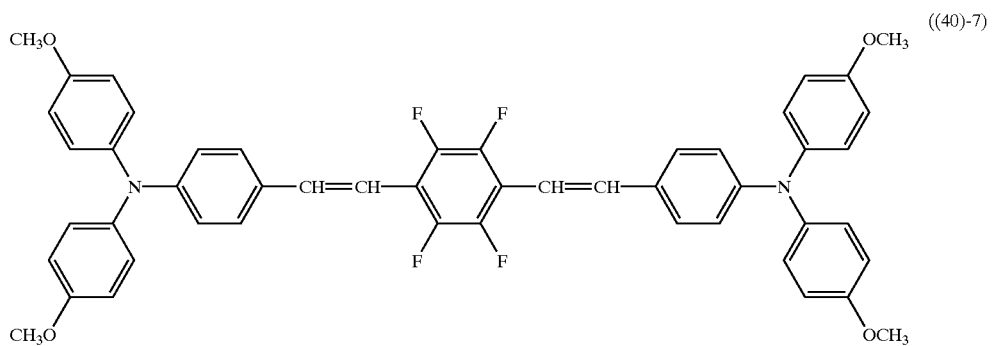

((40)-7)

The compound was prepared in the same manner as in Example 20 using 186 mg (4.65 mmols) of sodium hydride (suspended in a mineral oil at 60%), 110 mg (0.245 mmols) of (2,3,5,6-tetrafluorobenzene)-1,4-diyl-bis(diethyl methanephosphonate), and 253 mg (0.759 mmols) of [bis-N-(4-methoxyphenyl)]aminobenzaldehyde.

As a result, there was obtained 118 mg of the product (structural formula (40)-7) (yield of 62%) as yellowish orange crystals. The identification of the product was performed by measurement with $^1$HNMR and FAB-MS.

The visible light absorption maximum of the THF solution of this product was at 446 nm and the fluorescent maximum wavelength was at 560 nm.

EXAMPLE 27

This example illustrates fabrication of an organic electroluminescent device having a single hetero structure using, at a hole transport luminescent material, a compound of the following structural formula (16)-1. which is a compound of the general formula (I) wherein $R^1$ and $R^4$ independently represent a 3-ethoxyphenyl group, and $R^6$ and $R^8$ independently represent a cyano group respectively, vacuum deposited at a deposition rate of 1 nm/second to form, for example, a 50 nm thick Mg film and a 150 nm thick Ag film. In this way, an organic electroluminescent device as shown in FIG. 47 was fabricated in Example 27.

Figure 25:
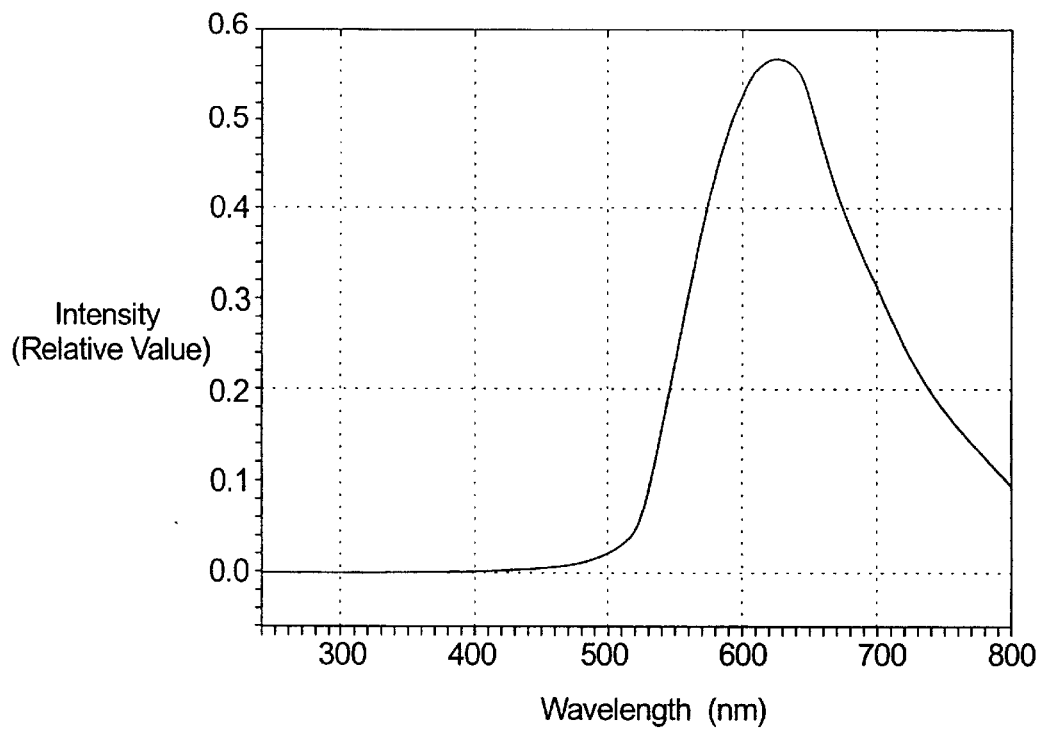
FIG. 25 is an emission spectrogram of an organic electroluminescent device of Example 27 of the invention.
Figure 27:
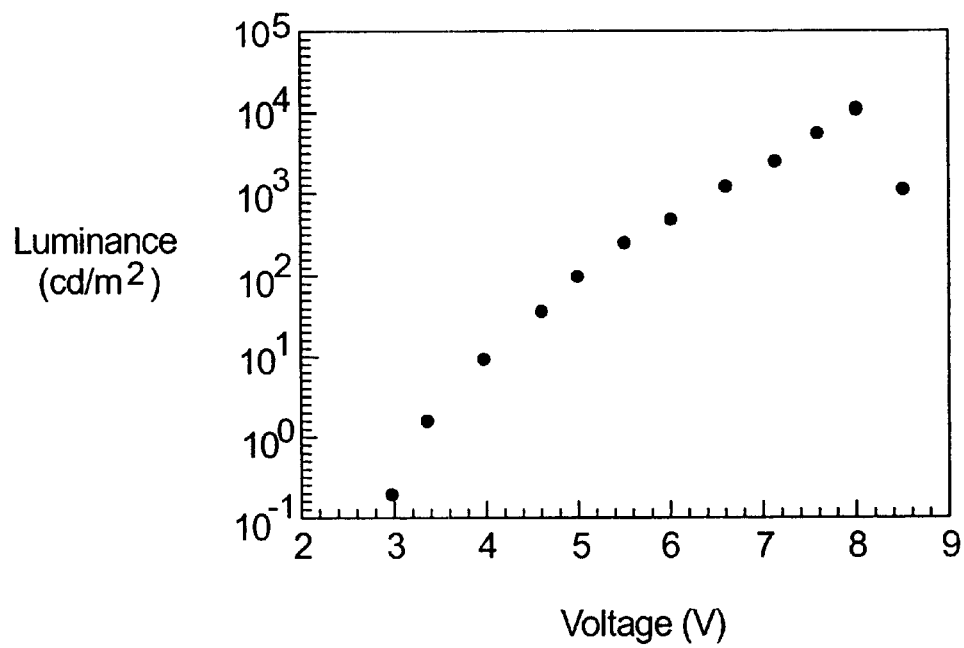
FIG. 27 is a graph showing a voltage-luminance characteristic of the organic electroluminescent device of Example 27 of the invention.

Luminescent characteristics of the device were evaluated by applying a forward bias DC voltage to the thus fabricated organic electroluminescent device of Example 27 in an atmosphere of nitrogen. The luminescent color was red, and the device was then subjected to spectral measurement, with the result that, as shown in FIG. 25, spectra having a luminescent peak at 620 nm were obtained. The spectral measurement was performed by use of a spectroscope made by Otsuka Electronic Co., Ltd. and using a photodiode array as a detector. Moreover, when the device was subjected to voltage-luminance measurement, there could be obtained a luminance of 10,000 cd/m$^2$ at 8 V as is particularly shown in FIG. 27.

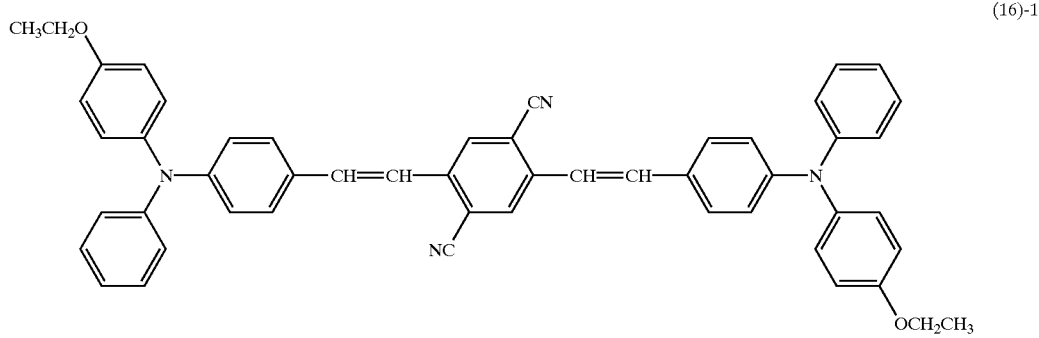

(16)-1

A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, closely to the substrate. The compound of the above structural formula (16)-1 was subjected to vacuum deposition at a vacuum of 10$^{-4}$ Pa or below to form, for example, a 50 nm thick hole transport layer (serving also as a luminescent layer). The deposition rate was at 0.1 nm/second.

Further, Alq$_3$ (tris(-quinolinol)aluminium) of the following structural formula was provided as an electron transport material and was deposited in contact with the hole transport layer. The electron transport layer made of Alq$_3$ was set at a thickness, for example, of 50 nm, and the deposition rate was at 0.2 nm/second.

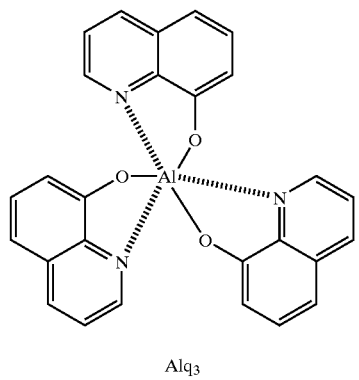

Alq$_3$

A built-up film of Mg and Ag provided as a cathode material was used. To this end, Mg and Ag were, After the fabrication of the organic electroluminescent device, the device was allowed to stand over one month in an atmosphere of nitrogen, no device degradation was observed. In addition, when the device was subjected to forced degradation wherein continuous light emission was carried out at an initial luminance of 300 cd/m$^2$ while keeping a current at a given level. As a consequence, it took 4,000 hours before the luminance was reduced to half.

EXAMPLE 28

This example illustrates fabrication of an organic electroluminescent device having a single hetero structure using, as an electron transport luminescent material, a compound of the structural formula (16)-1, which is a compound of the general formula (1) wherein $R^1$ and $R^4$ independently represent a 3-ethoxyphenyl group, and $R^6$ and $R^8$ independently represent a cyano group.

A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, closely to the substrate. α-NPD (α-naphthylphenyldiamine) of the following structural formula was subjected to vacuum deposition at a vacuum of 10$^{-4}$ Pa or below to form, for example, a 50 nm thick hole transport layer. The deposition rate was at 0.1 nm/second.

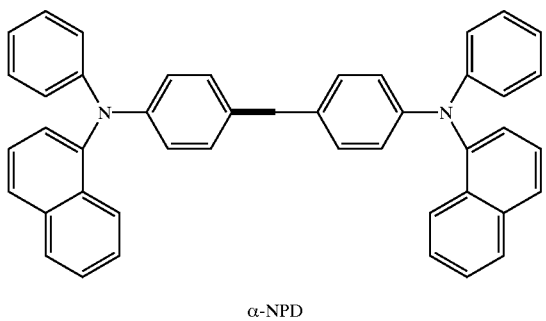

α-NPD

Further, the compound of the structural formula (16)-1 used as an electron transport material was vacuum deposited in contact with the hole transport layer. The thickness of the electron transport layer (serving also as a luminescent layer) composed of the compound of the structural formula (16)-1 was set, for example, at 50 nm, and the deposition rate was at 0.2 nm/second.

A built-up film of Mg and Ag provided as a cathode material was used. More particularly, Mg and Ag were, respectively, vacuum deposited at a deposition rate of 1 nm/second to form, for example, a 50 nm thick Mg film and a 150 nm thick Ag film. In this way, an organic electroluminescent device of Example 28 as shown in FIG. 47 was fabricated.

Figure 26:
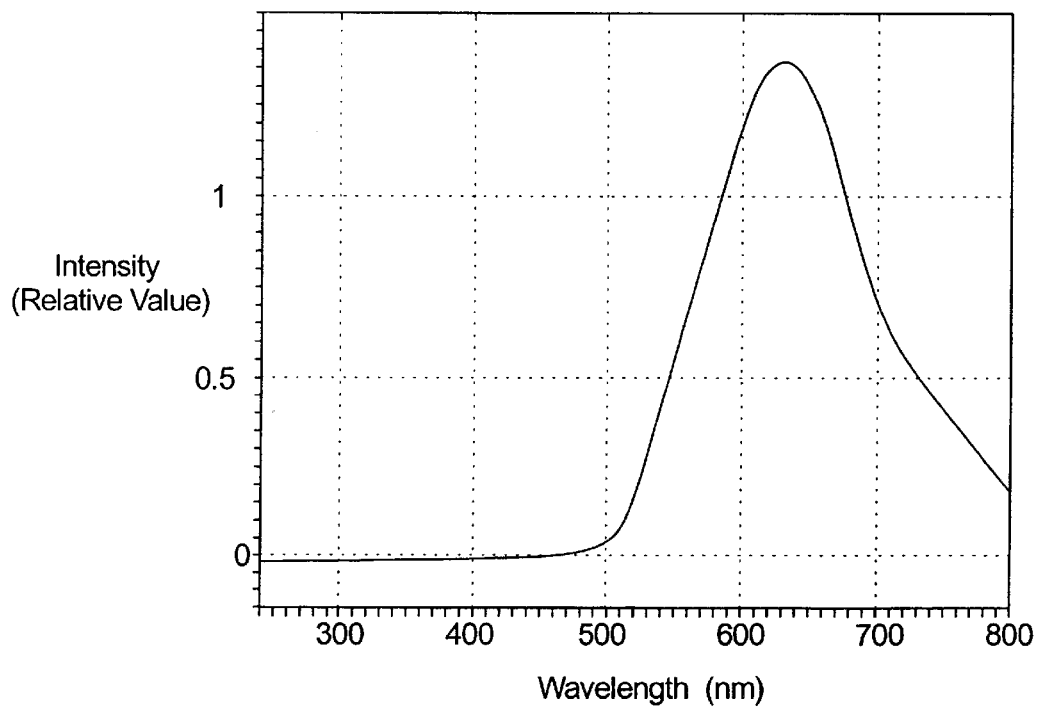
FIG. 26 is an emission spectrogram of an organic electroluminescent device of Example 28 of the invention.
Figure 28:
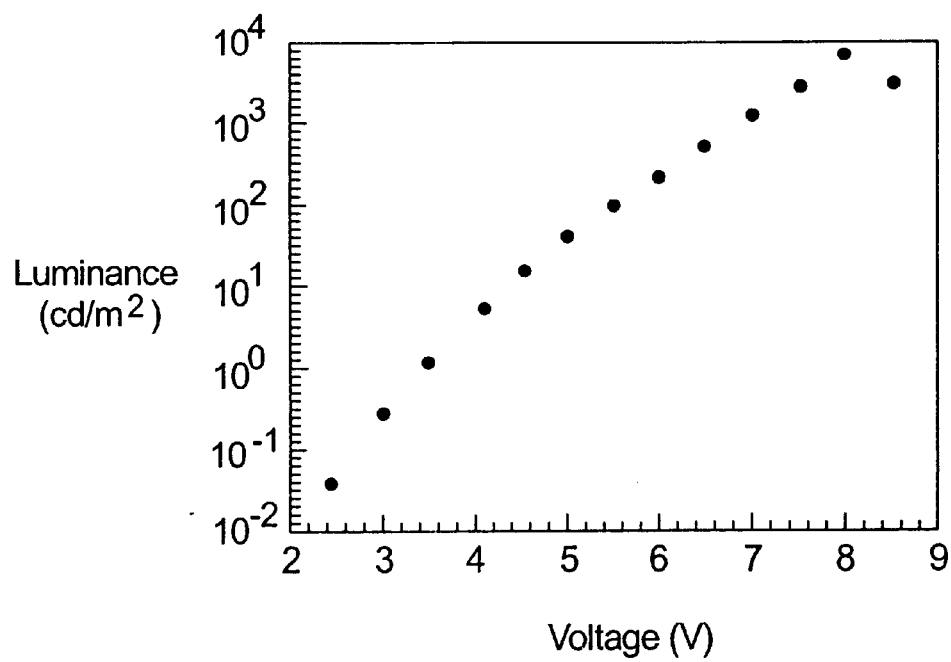
FIG. 28 is a graph showing a voltage-luminance characteristic of the organic electroluminescent device of Example 29 of the invention.

Luminescent characteristics were evaluated by applying a forward bias DC voltage to the thus fabricated organic electroluminescent device of Example 28 in an atmosphere of nitrogen. The luminescent color was red, and the device was then subjected to spectral measurement as in Example 27, with the result that, as shown in FIG. 26, spectra having a luminescent peak at 620 nm were obtained. Moreover, when the device was subjected to voltage-luminance measurement, there could be obtained a luminance of 8,000 cd/m$^2$ at 8 V as is particularly shown in FIG. 28.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m$^2$ while keeping a current at a given level. As a consequence, it took 3,500 hours before the luminance was reduced to half.

EXAMPLE 29

This example illustrates fabrication of an organic electroluminescent device having a double hetero structure using, as a luminescent material, a compound of the structural formula (16)-1, which is a compound of the general formula (I) wherein $R^1$ and $R^4$ independently represent a 3-ethyoxyphenyl group, and $R^6$ and $R^8$ independently represent a cyano group.

A 30 mm×30 mm glass substrate, which had been formed with a 100 nm thick anode made of ITO on one surface thereof, was set in a vacuum deposition apparatus. A metallic mask having a plurality of 2.0 mm×2.0 mm unit openings was placed, as a deposition mask, near the substrate, followed by subjecting A-NPD of the afore-indicated structural formula to vacuum deposition at a vacuum of 10$^{-4}$ Pa or below to form, for example, a 30 nm thick hole transport layer. The deposition rate was at 0.2 nm/second.

Further, the compound of the afore-indicated structural formula (16)-1 used as a luminescent material was vacuum deposited in contact with the hole transport layer. The thickness of the luminescent layer composed of the compound of the structural formula (16)-1 was set, for example, at 30 nm, and the deposition rate was at 0.2 nm/second.

Moreover, Alq$_3$ of the afore-indicated structural formula used as an electron transport material was vacuum deposited in contact with the luminescent layer. The thickness of the Alq$_3$ layer was set, for example, at 30 nm, and the deposition rate was at 0.2 nm/second.

A built-up film of Mg and Ag provided as a cathode material was used. More particularly, Mg and Ag were, respectively, vacuum deposited at a deposition rate of 1 nm/second to form, for example, a 50 nm thick Mg film and a 150 nm thick Ag film. In this way, an organic electroluminescent device of Example 29 as shown in FIG. 48 was fabricated.

Luminescent characteristics were evaluated by applying a forward bias DC voltage to the thus fabricated organic electroluminescent device of Example 29 in an atmosphere of nitrogen. The luminescent color was red, and the device was subjected to spectral measurement, with the result that spectra having a luminescent peak at 620 nm were obtained. Moreover, when the device was subjected to voltage-luminance measurement, there could be obtained a luminance of 11,000 cd/m$^2$ at 8 V.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m$^2$ while passing a current at a given level. As a consequence, it took 5,000 hours before the luminance was reduced to half.

EXAMPLE 30

Example 28 was repeated with respect to the layer arrangement and the film formation procedures except that TPD (triphenyldiamine derivative) of the following structural formula was used as a hole transport material in place of α-NPD, thereby fabricating an organic electroluminescent device.

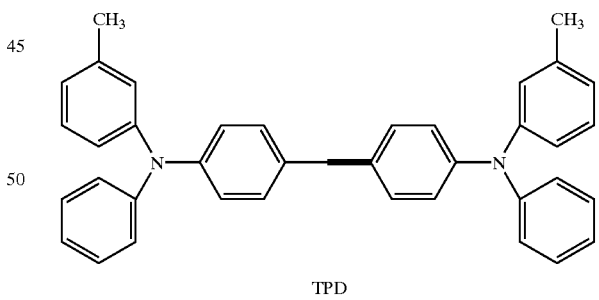

TPD

The organic electroluminescent device of this example assumed red luminescence, like Example 29. The results of spectral measurement reveal that spectra were in coincidence with those of the organic electroluminescent device of Example 29.

EXAMPLE 31

The general procedure of Example 27 was repeated using, as d hole transport luminescent material, the compound of the following structural formula (16)-2, which corresponds to a compound of the general formula (II) wherein $R^{14}$, $R^{15}$, $R^{16}$ and $R^{17}$ independently represent a 3-methoxyphenyl group, and $R^{19}$ and $R^{23}$ independently represent a cyano group, thereby fabricating an organic electroluminescent device having a single hetero structure.

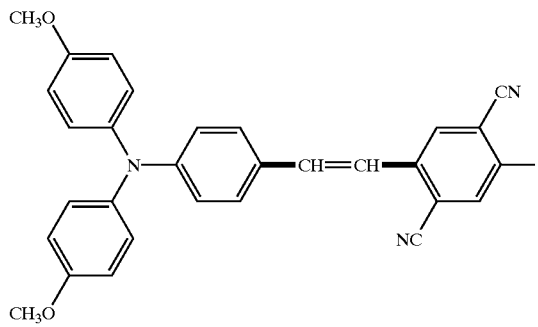 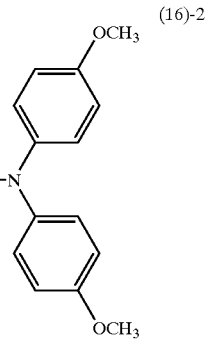

(16)-2

Figure 29:
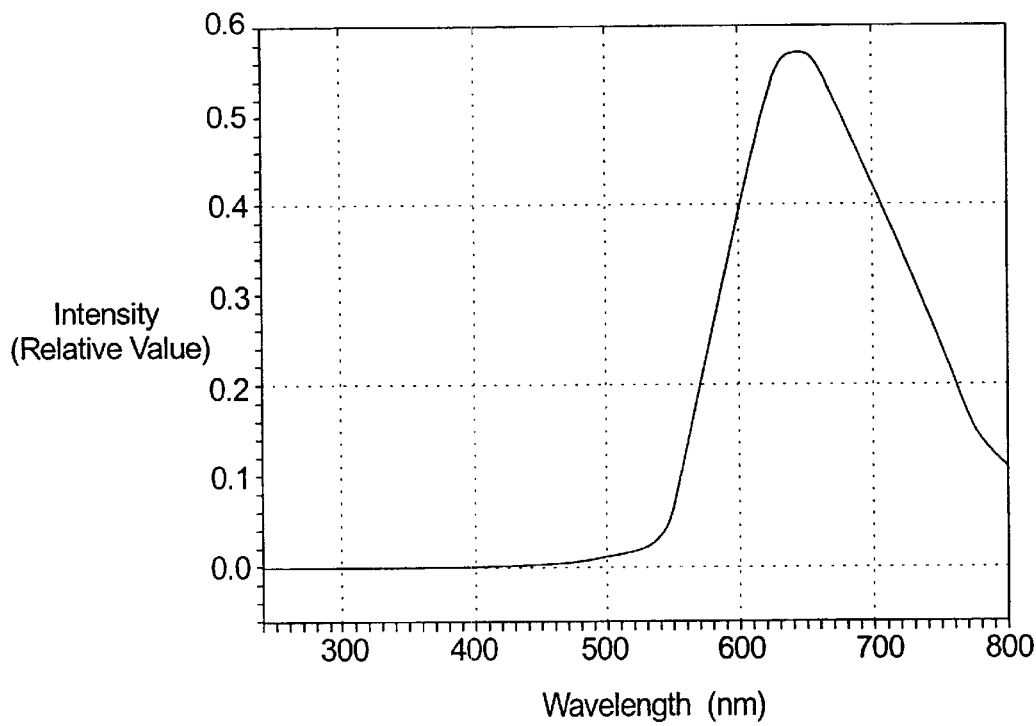
FIG. 29 is an emission spectrogram of an organic electroluminescent device of Example 31 of the invention.
Figure 31:
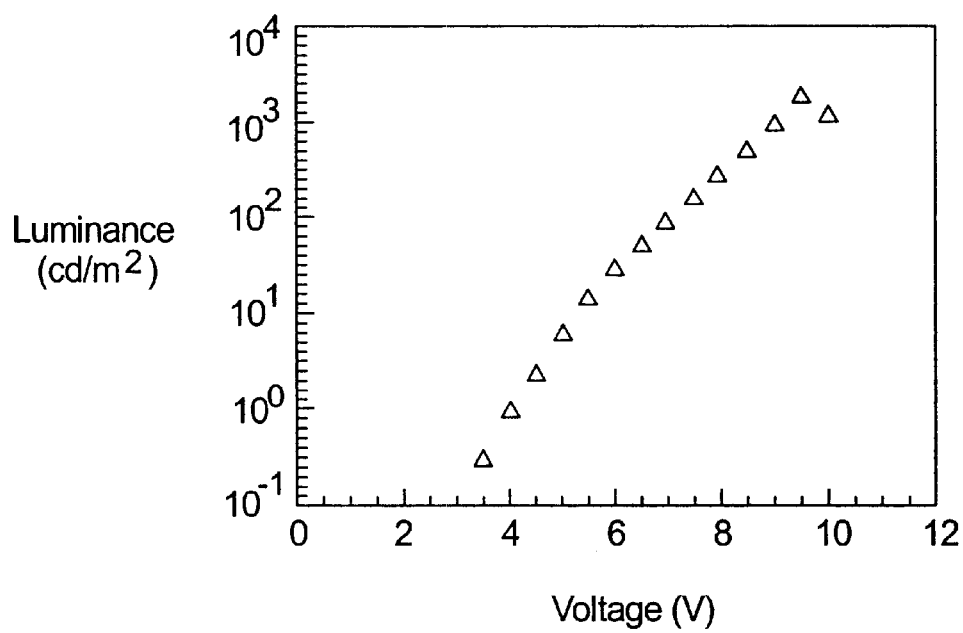
FIG. 31 is a graph showing a voltage-luminance characteristic of the organic electroluminescent device of Example 31 of the invention.

Luminescent characteristics were evaluated by applying a forward bias DC voltage to the thus fabricated organic electroluminescent device of this example in an atmosphere of nitrogen. The luminescent color was red, and the device was subjected to spectral measurement, with the result that spectra having a luminescent peak at 650 nm were obtained as shown in FIG. 29. The spectral measurement was performed by use of a spectroscope made by Otsuka Electronic Co., Ltd. and using a photodiode array as a detector Moreover, when the device was subjected to voltage-luminance measurement, there could be obtained a luminance of 1.200 cd/m$^2$ at 9.5 V as is particularly shown in FIG. 31.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 200 cd/m$^2$ while passing a current at a given level. As a consequence, it took 1,000 hours before the luminance was reduced to half.

EXAMPLE 32

The general procedure of Example 28 was repeated using, as a hole transport luminescent material, the compound of the afore-indicated structural formula (16)-2, which corresponds to a compound of the general formula (II) wherein $R^{14}$, $R^{15}$, $R^{16}$ and $R^{17}$ independently represent a 3-methoxyphenyl group, and $R^{19}$ and $R^{21}$ independently represent a cyano group, thereby fabricating an organic electroluminescent device having a single hetero structure.

Figure 30:
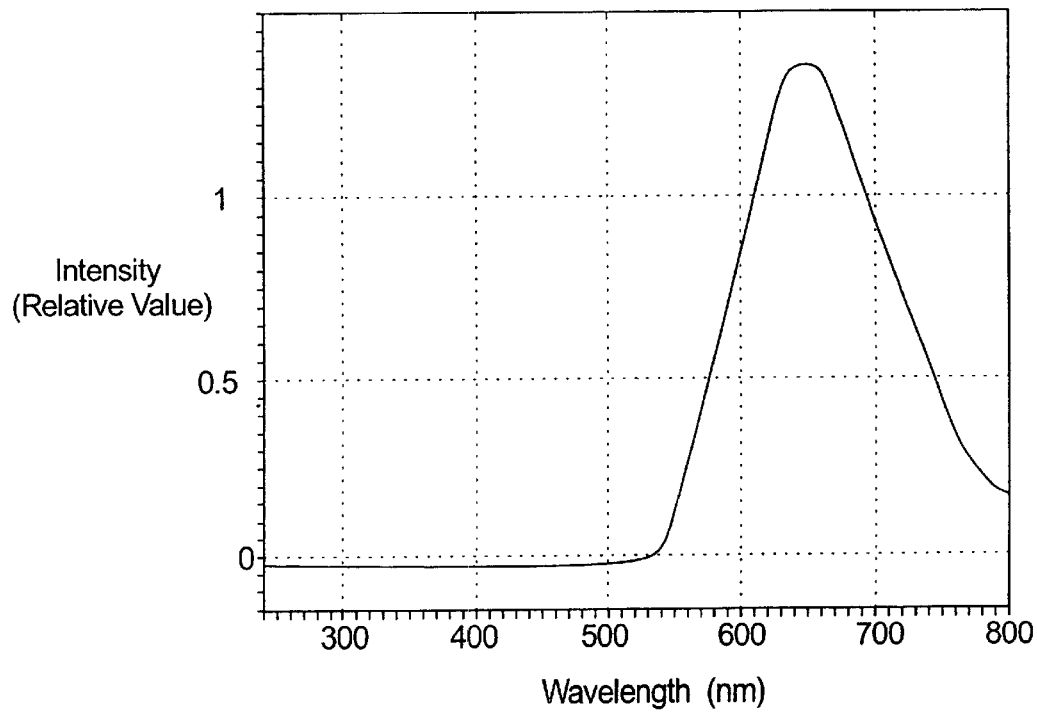
FIG. 30 is an emission spectrogram of an organic electroluminescent device of Example 32 of the inventions
Figure 32:
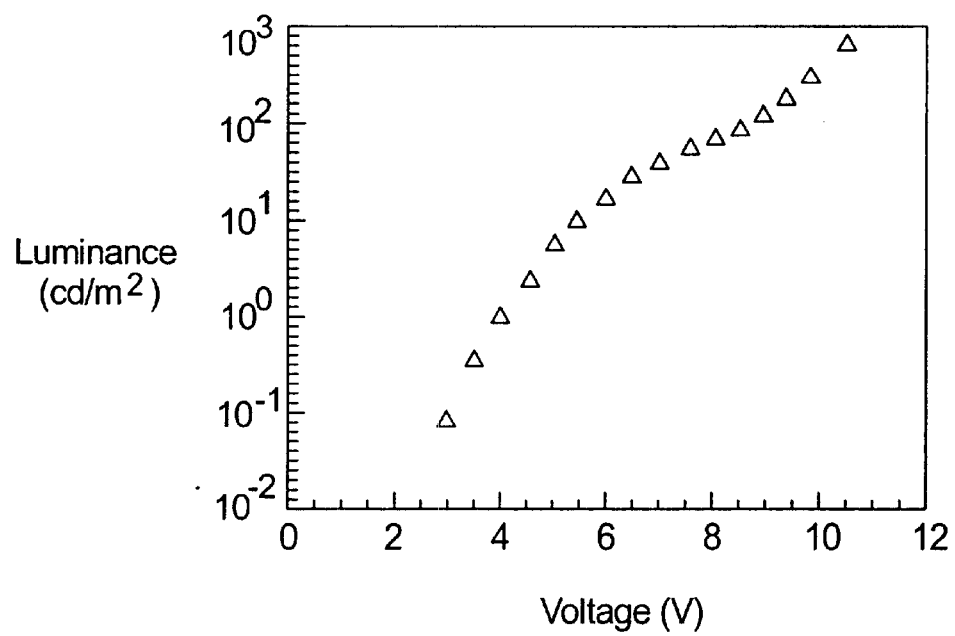
FIG. 32 is a graph showing a voltage-luminance characteristic of the organic electroluminescent device of Example 32 of the invention.

Luminescent characteristics were evaluated by applying a forward bias DC voltage to the thus fabricated organic electroluminescent device of this example in an atmosphere of nitrogen. The luminescent color was red, and the device was subjected to spectral measurement in the same manner as in Example 29, with the result that spectra having a luminescent peak at 650 nm were obtained as shown in FIG. 30. Moreover, when the device was subjected to voltage-luminance measurement, there could be obtained a luminance of 600 cd/m$^2$ at 10.5 V as is particularly shown in FIG. 32.

After the fabrication of the organic electroluminescent device, the device was allowed to stand over one month in an atmosphere of nitrogen. no degradation of the device was observed. In addition, when the device was subjected to forced degradation wherein continuous light emission was carried out at an initial luminance of 200 cd/m$^2$ while passing a current at a given level. As a consequence, it took 700 hours before the luminance was reduced to half.

EXAMPLE 33

The general procedure of Example 29 was repeated using, as a luminescent material, the compound of the aforeindicated structural formula (16)-2, which corresponds to a compound of the general formula (II) wherein $R^{14}$, $R^{15}$, $R^{16}$ and $R^{17}$ independently represent a 3-methoxyphenyl group, and $R^{19}$ and $R^{21}$ independently represent a cyano group, thereby fabricating an organic electroluminescent device having a double hetero structure.

Luminescent characteristics were evaluated by applying a forward bias DC voltage to the thus fabricated organic electroluminescent device of this example in an atmosphere of nitrogen. The luminescent color was red, and the device was subjected to spectral measurement, with the result that spectra having a luminescent peak at 650 nm were obtained. Moreover, when the device was subjected to voltage-luminance measurement, there could be obtained a luminance of 1,800 cd/m$^2$ at 8.5 V.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 200 cd/m$^2$ while passing a current at a given level. As a consequence, it took 1,500 hours before the luminance was reduced to half.

EXAMPLE 34

Example 32 was repeated with respect to the layer arrangement and the film formation procedures except that TPD (triphenyldiamine derivative) of the afore-indicated structural formula was used as a hole transport material in place of α-NPD, thereby fabricating an organic electroluminescent device.

The organic electroluminescent device of this example assumed red luminescence, like Example 32. The results of spectral measurement reveal that spectra were in coincidence with those of the organic electroluminescent device of Example 33.

EXAMPLE 35

The general procedure of Example 27 was repeated using, as a hole transport luminescent material, the compound of the following structural formula (16)-3, which corresponds to a compound of the general formula (iii) wherein $R^{27}$ and $R^{30}$ independently represent a 3-dimethylaminophenyl group, and $R^{32}$ and $R^{34}$ independently represent a cyano group, thereby fabricating an organic electroluminescent device having a single hetero structure.

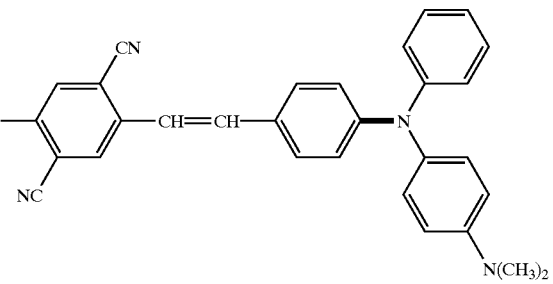

(16)-3

Figure 33:
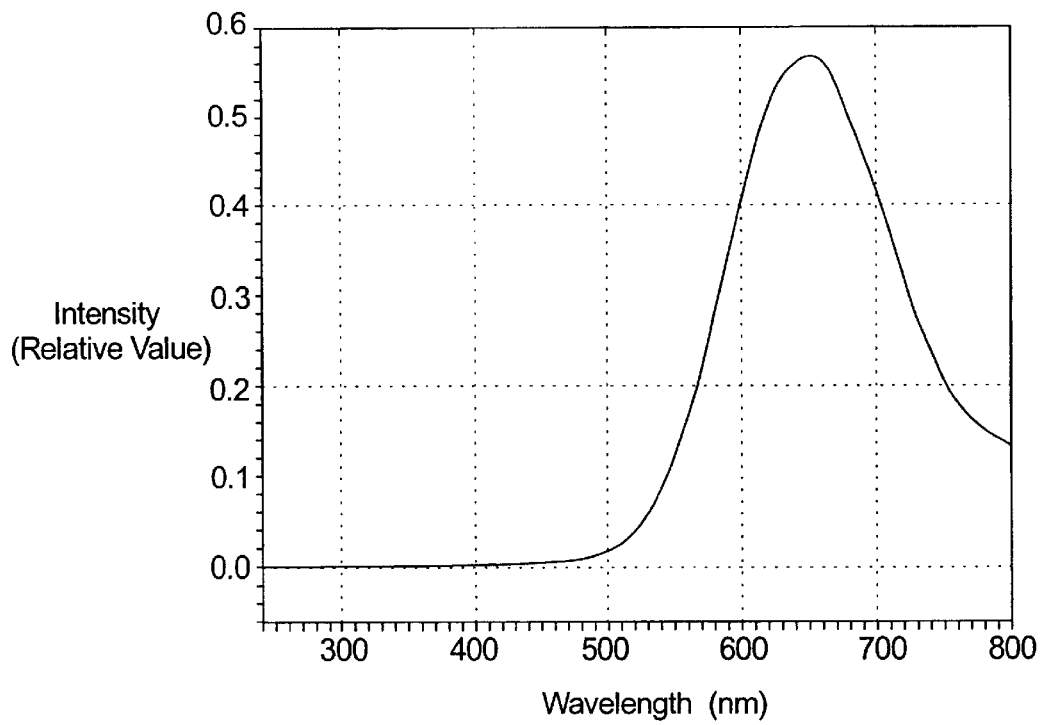
FIG. 33 is an emission spectrogram of an organic electroluminescence of Example 35 of the invention.
Figure 35:
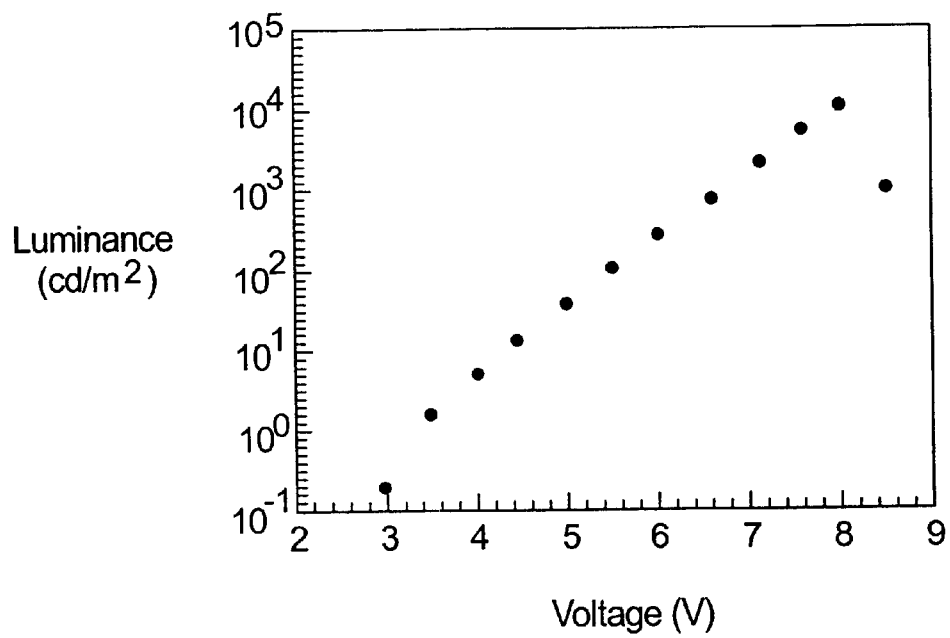
FIG. 35 is a graph showing a voltage-luminance characteristic of the organic electroluminescent device of Example 35 of the invention.

Luminescent characteristics were evaluated by applying a forward bias DC voltage to the thus fabricated organic electroluminescent device of this example in an atmosphere of nitrogen. The luminescent color was red, and the device was subjected to spectral measurement, with the result that spectra having a luminescent peak at 640 nm were obtained as shown in FIG. 33. The spectral measurement was performed by use of a spectroscope made by Otauka Electronic Co., Ltd. and using a photodiode array as a detector. Moreover, when the device was subjected to voltage-luminance measurement, there could be obtained a luminance of 6,000 cd/m² at 8 V, as shown in FIG. 35.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m² while passing a current at a given level. As a consequence, it took 3,800 hours before the luminance was reduced to half.

EXAMPLE 36

The general procedure of Example 28 was repeated using, as an electron transport luminescent material, the compound of the afore-indicated structural formula (16)-3, which corresponds to a compound of the general formula (III) wherein $R^{27}$ and $R^{30}$ independently represent a 3-dimethylaminophenyl group, and $R^{32}$ and $R^{34}$ independently represent a cyano group, thereby fabricating an organic electroluminescent device having a single hetero structure.

Figure 34:
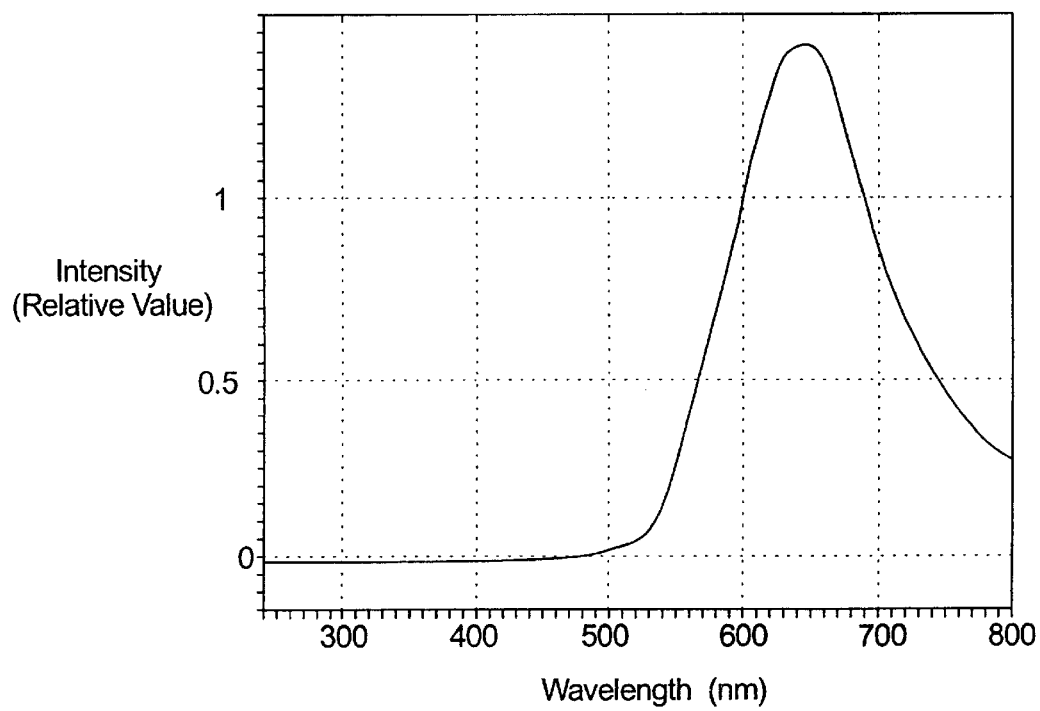
FIG. 34 is an emission spectrogram of an organic electroluminescence of Example 36 of the invention.
Figure 36:
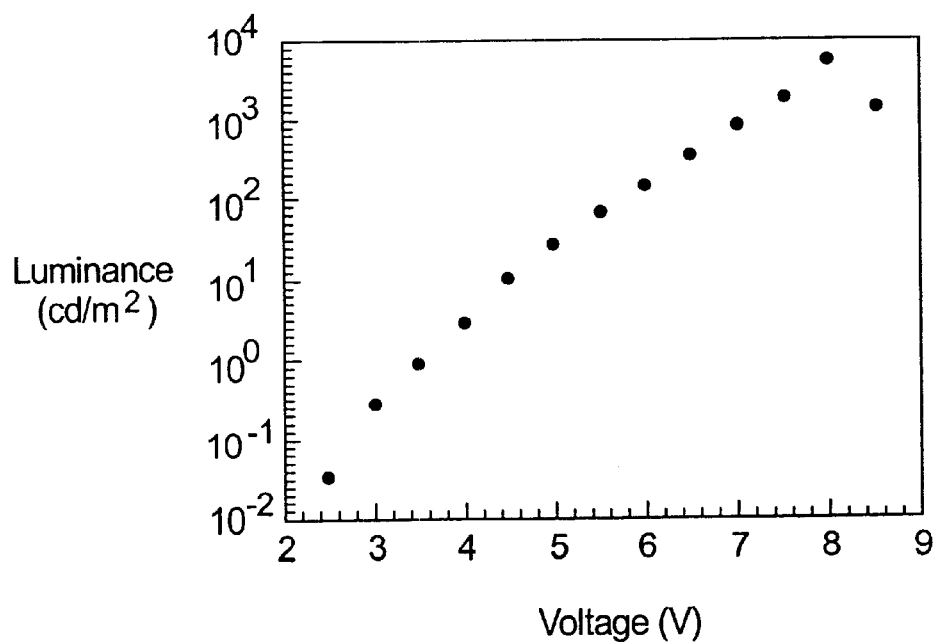
FIG. 36 is a graph showing a voltage luminance characteristic of the organic electroluminescent device of Example 36 of the invention.

Luminescent characteristics were evaluated by applying a forward bias DC voltage to the thus fabricated organic electroluminescent device of this example in an atmosphere of nitrogen. The luminescent color was red, and the device was subjected to spectral measurement in the same manner as in Example 28, with the result that spectra having a luminescent peak at 640 nm were obtained as shown in FIG. 34. Moreover, when the device was subjected to voltage-luminance measurement, there could be obtained a luminance of 5,300 cd/m² at 8 V, as shown in FIG. 36.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m² while passing a current at a given level. As a consequence, it took 3,200 hours before the luminance was reduced to half.

EXAMPLE 37

The general procedure of Example 29 was repeated using, as a luminescent material, the compound of the afore-indicated structural formula (16)-3, which corresponds to a compound of the general formula (III) wherein $R^{27}$ and $R^{30}$ independently represent a 3-dimethylaminophenyl group, and $R^{32}$ and $R^{34}$ independently represent a cyano group, thereby fabricating an organic electroluminescent device having a double hetero structure.

Luminescent characteristics were evaluated by applying a forward bias DC voltage to the thus fabricated organic electroluminescent device of this example in an atmosphere of nitrogen. The luminescent color was red, and the device was subjected to spectral measurement, with the result that spectra having a luminescent peak at 640 nm were obtained. Moreover, when the device was subjected to voltage-luminance measurement, there could be obtained a luminance of 6,800 cd/m² at 8 V.

After the fabrication of the organic electroluminescent device, the device was allowed to stand over one month in an atmosphere of nitrogen, no degradation of the device was observed. In addition, when the device was subjected to forced degradation wherein continuous light emission was carried out at an initial luminance of 300 cd/m² while passing a current at a given level. As a consequence, it took 4,500 hours before the luminance was reduced to half.

EXAMPLE 38

Example 36 was repeated with respect to the layer arrangement and the film formation procedures, but TPD (triphenyldiamine derivative) of the afore-indicated structural formula was used as a hole transport material in place of α-NPD, thereby fabricating an organic electroluminescent device.

The organic electroluminescent device of this example assumed red luminescence, like Example 36. The results of spectral measurement reveal that spectra were in coincidence with those of the organic electroluminescent device of Example 36.

EXAMPLE 39

The general procedure of Example 27 was repeated using, as a hole transport luminescent material, a compound of the following structural formula (16)-4, which corresponds to a compound of the general formula (IV) wherein $R^{41}$ and $R^{42}$ independently represent an unsubstituted phenyl group, $R^{40}$ and $R^{43}$ independently represent an unsubstituted naphthyl group, and $R^{45}$ and $R^{47}$ independently represent a cyano group, thereby fabricating an organic electroluminescent device having a single hetero structure.

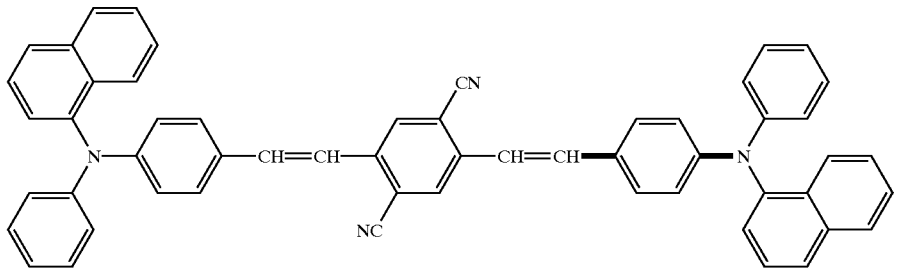

(16)-4

Figure 37:
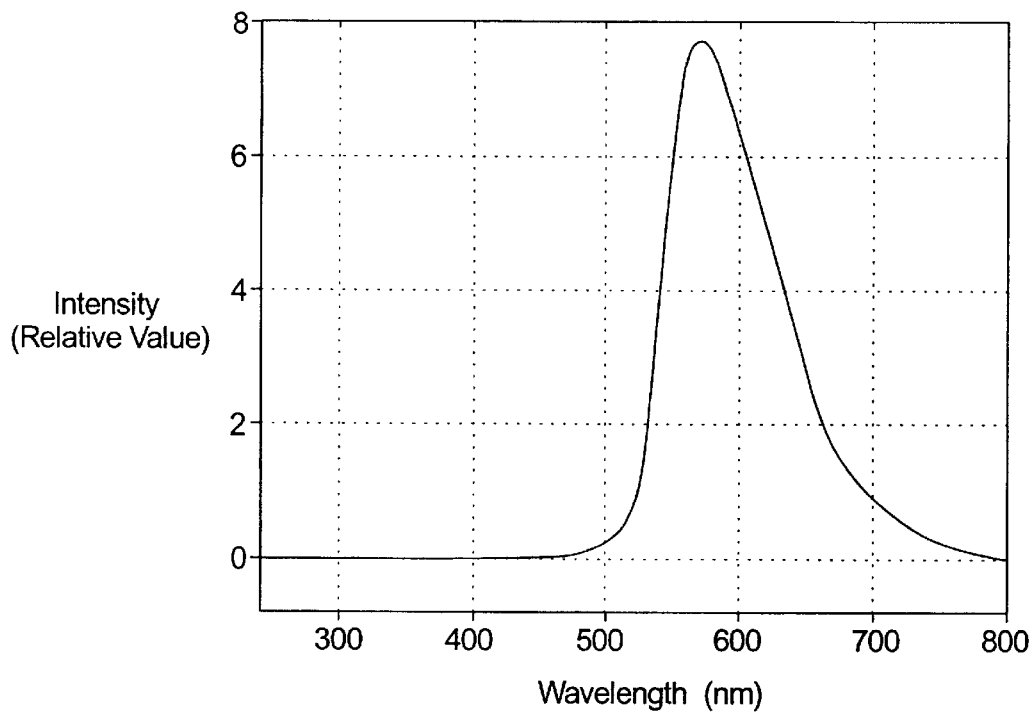
FIG. 37 is an emission spectrogram of an organic electroluminescent device of Example 39 of the invention.
Figure 40:
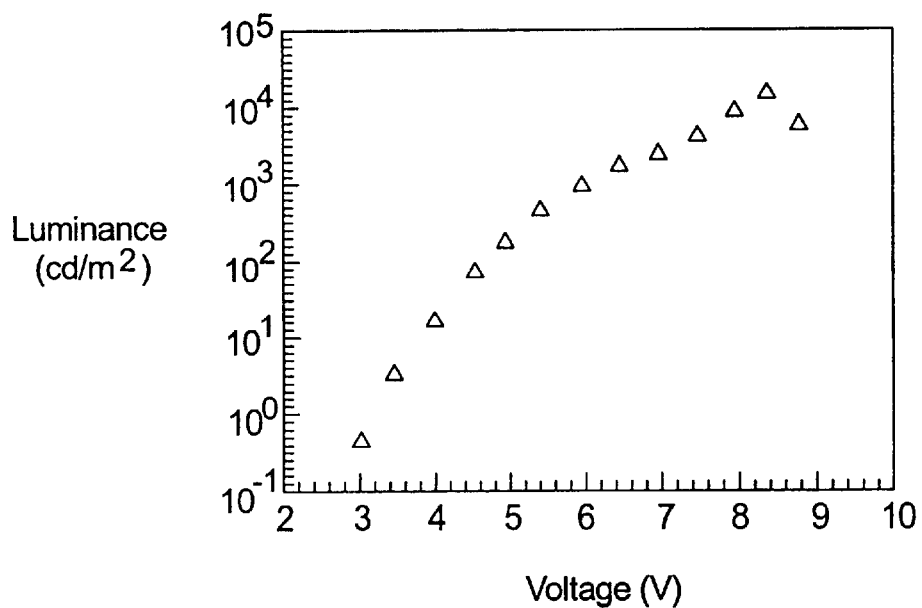
FIG. 40 is a graph showing a voltage-luminance characteristic of the organic electroluminescent device of Example 39 of the invention.

Luminescent characteristics of the device were evaluated by applying a forward bias DC voltage to the thus fabricated organic electroluminescent device of this example in an atmosphere of nitrogen. The luminescent color was yellow, and the device was then subjected to spectral measurement, with the result that, as shown in FIG. 37, spectra having a luminescent peak at 578 nm were obtained. The spectral measurement was performed by use of a spectroscope made by Otsuka Electronic Co., Ltd. and using a photodiode array as a detector. Moreover, when the device was subjected to voltage-luminance measurement, there could be obtained a luminance of 6,500 cd/m$^2$ at 8 V as is particularly shown in FIG. 40.

After the fabrication of the organic electroluminescent device, the device was allowed to stand over one month in an atmosphere of nitrogen, no device degradation was observed. In addition, when the device was subjected to forced degradation wherein continuous light emission was carried out at an initial luminance of 300 cd/m$^2$ while keeping a current at a given level. As a consequence, it took 4,000 hours before the luminance was reduced to half.

EXAMPLE 40

The general procedure of Example 28 was repeated using, as an electron transport luminescent material, a compound of the afore-indicated structural formula (16)-4, which corresponds to a compound of the general formula (IV) wherein $R^{41}$ and $R^{42}$ independently represent an unsubstituted phenyl group, $R^{40}$ and $R^{43}$ independently represent an unsubstituted naphthyl group, and $R^{45}$ and $R^{47}$ independently represent a cyano group, thereby fabricating an organic electroluminescent device having a single hetero structure.

Figure 38:
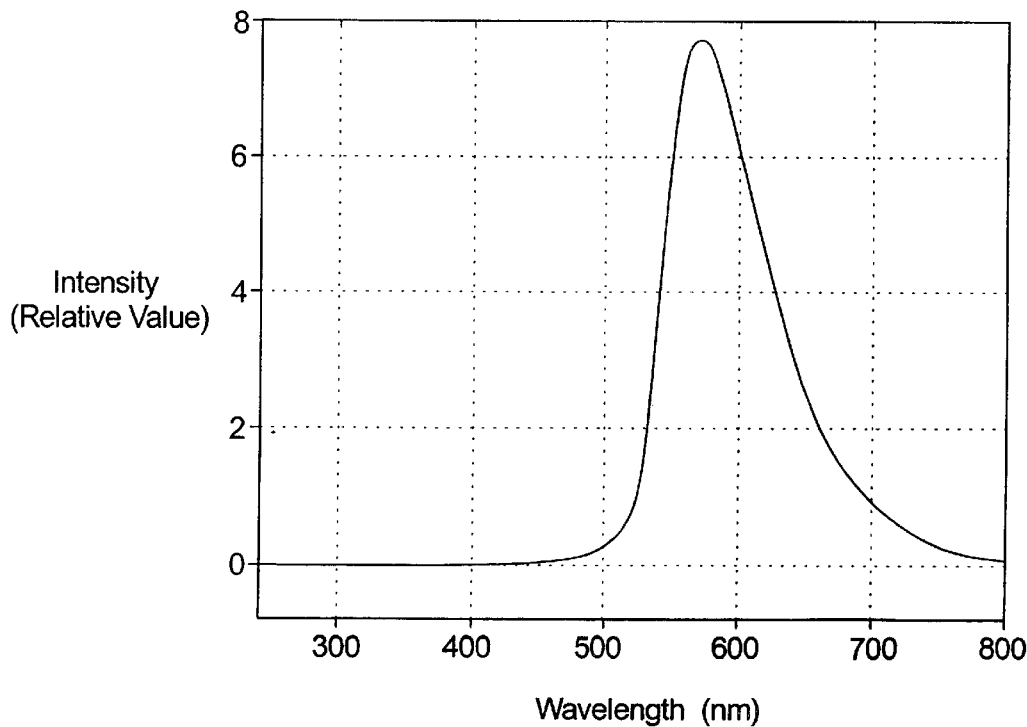
FIG. 38 in an emission spectrogram of an organic electroluminescent device of Example 40 of the invention.
Figure 41:
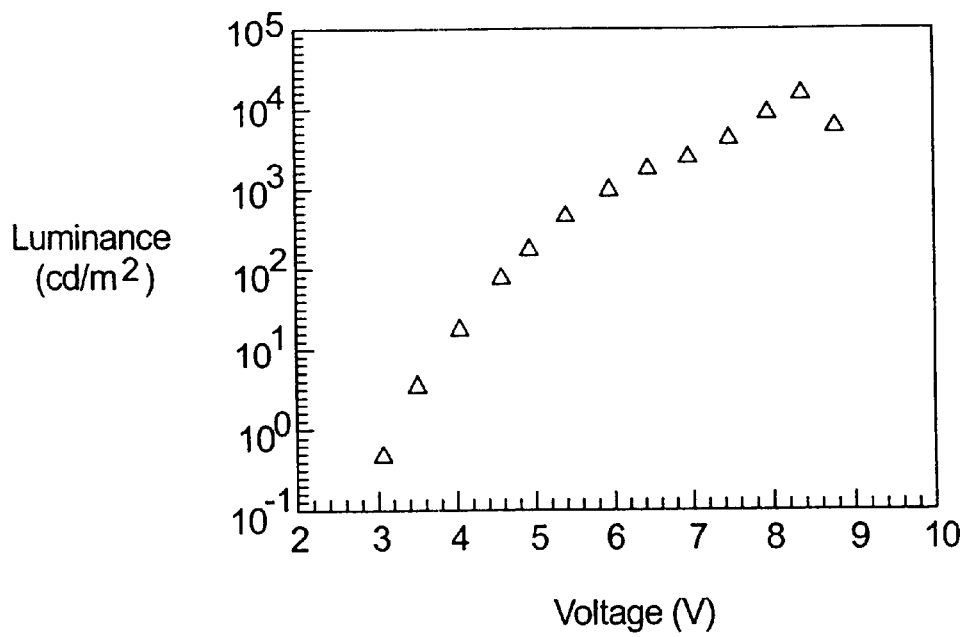
FIG. 41 is a graph showing a voltage-luminance characteristic of the organic electroluminescent device of Example 40 of the invention.

Luminescent characteristics of the device were evaluated by applying a forward bias DC voltage to the thus fabricated organic electroluminescent device of this example in an atmosphere of nitrogen. The luminescent color was yellow, and the device was then subjected to spectral measurement in the same manner as in Example 39, with the result that, as shown in FIG. 38, spectra having a luminescent peak at 578 nm were obtained. Moreover, when the device was subjected to voltage-luminance measurement, there could be obtained a luminance of 5,900 cd/m$^2$ at 8 V as is particularly shown it FIG. 41.

After the fabrication of the organic electroluminescent device, the device was allowed to stand over one month in an atmosphere of nitrogen, no device degradation was observed. In addition, when the device was subjected to forced degradation wherein continuous light emission was carried out at an initial luminance of 300 cd/m$^2$ while keeping a current at a given level. As a consequence, it took 3,500 hours before the luminance was reduced to half.

EXAMPLE 41

The general procedure of Example 29 was repeated using, as a luminescent material, a compound of the afore-indicated structural formula (16)-4, which corresponds to a compound of the general formula (IV) wherein $R^{41}$ and $R^{42}$ independently represent an unsubstituted phenyl group, $R^{40}$ and $R^{43}$ independently represent an unsubstituted naphthyl group, and $R^{45}$ and $R^{47}$ independently represent a cyano group, thereby fabricating an organic electroluminescent device having a double hetero structure.

Figure 39:
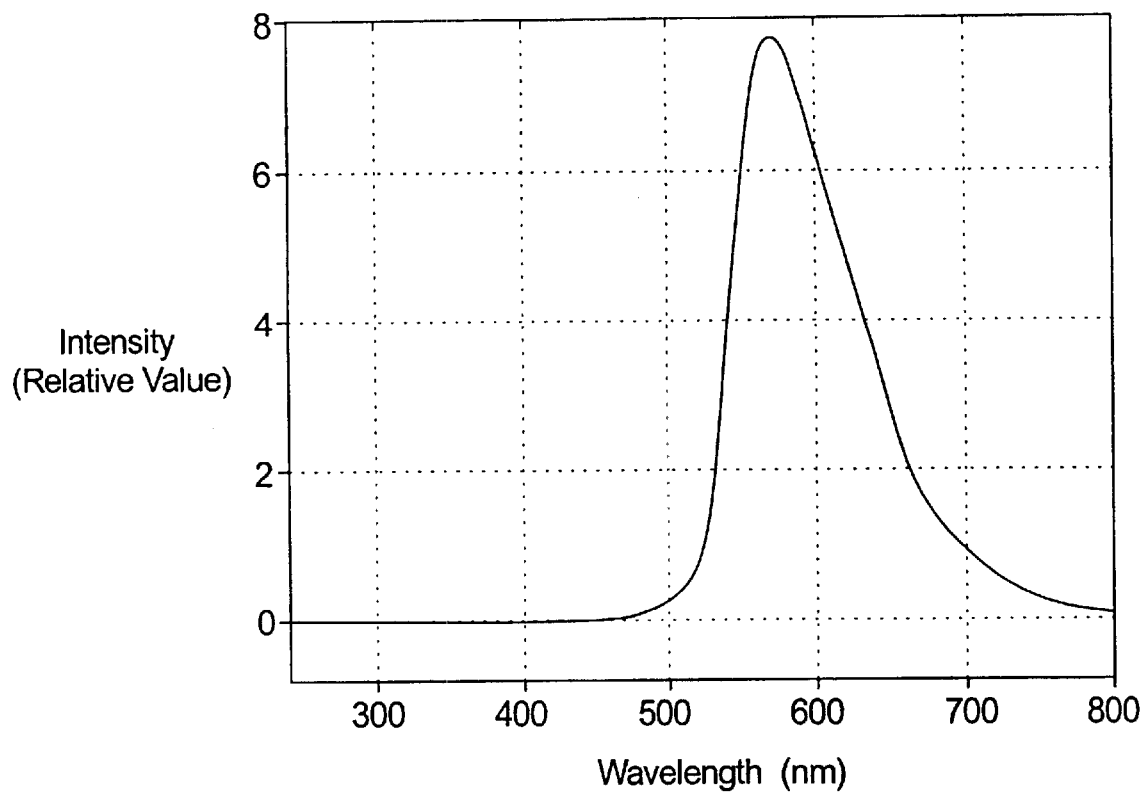
FIG. 39 is an emission spectrogram of an organic electroluminescent device of Example 41 of the invention.
Figure 42:
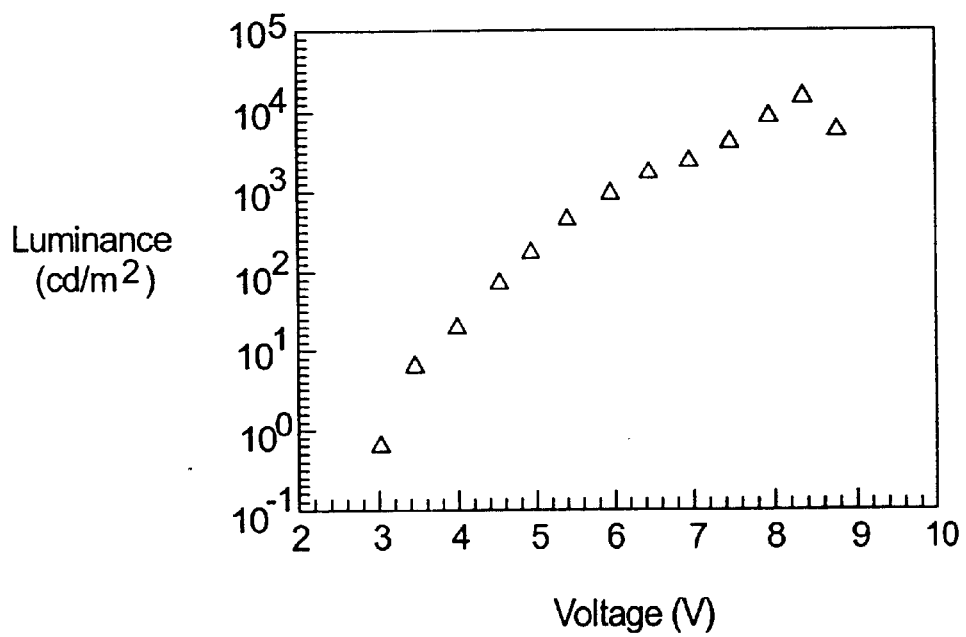
FIG. 42 is a graph showing a voltage-luminance characteristic of the organic electroluminescent device of Example 41 of the invention.

Luminescent characteristics of the device were evaluated by applying a forward bias DC voltage to the thus fabricated organic electroluminescent device of this example in an atmosphere of nitrogen. The luminescent color was yellow, and the device was then subjected to spectral measurement, with the result that, as shown in FIG. 39, spectra having a luminescent peak at 578 nm were obtained. Moreover, when the device was subjected to voltage-luminance measurement, there could be obtained a luminance of 7,500 cd/m$^2$ at 8 V as is particularly shown in FIG. 42.

After the fabrication of the organic electroluminescent device, the device was allowed to stand over one month in an atmosphere of nitrogen, no device degradation was observed. In addition, when the device was subjected to forced degradation wherein continuous light emission was carried out at an initial luminance of 300 cd/m$^2$ while keeping a current at a given level. As a consequence, it took 5,000 hours before the luminance was reduced to half.

EXAMPLE 42

Example 40 was repeated with respect to the layer arrangement and the film formation procedures except that TPD (triphenyldiamine derivative) of the afore-indicated structural formula was used as a hole transport material in place of α-NPD, thereby fabricating an organic electroluminescent device.

The organic electroluminescent device of this example assumed yellow luminescence, like Example 40. The results of spectral measurement reveal that spectra were in coincidence with those of the organic electroluminescent device of Example 40.

EXAMPLE 43

The general procedure of Example 28 was repeated using, as an electron transport luminescent material, the compound of the following structural formula (16)-8, which corresponds to a compound of the general formula (I) wherein $R^1$ and $R^4$ independently represent an unsubstituted phenyl group, and $R^2$ and $R^3$ independently represent a t-butyl group, thereby fabricating an organic electroluminescent device having a single hetero structure.

EXAMPLE 44

The general procedure of Example 43 was repeated using, as an electron transport luminescent material, the compound of the following structural formula (16)-9, which corresponds to a compound of the general formula (I) wherein $R^1$ and $R^4$ independently represent an unsubstituted phenyl group, and $R^2$ and $R^3$ independently represent a tertiary butoxy group, thereby fabricating an organic electroluminescent device having a single hetero structure.

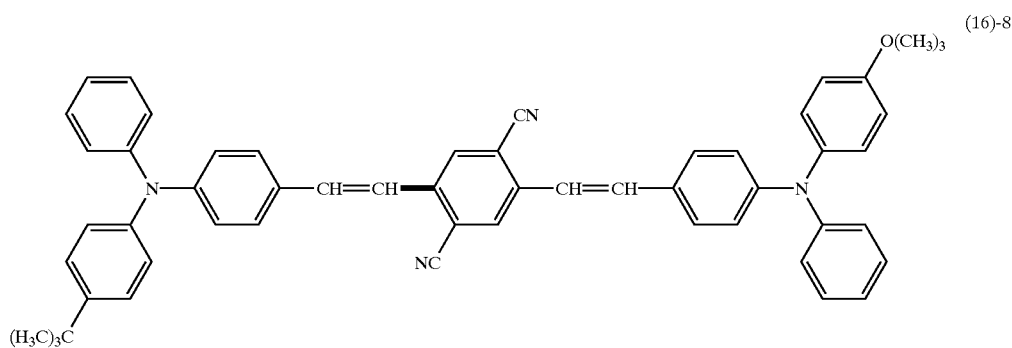

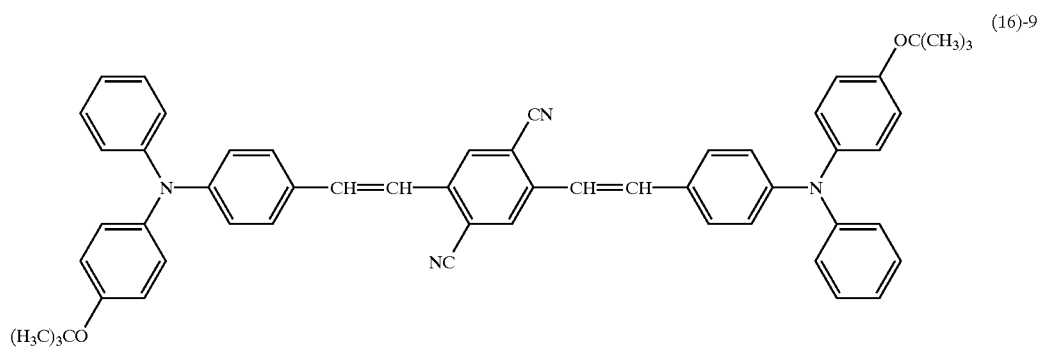

Figure 43:
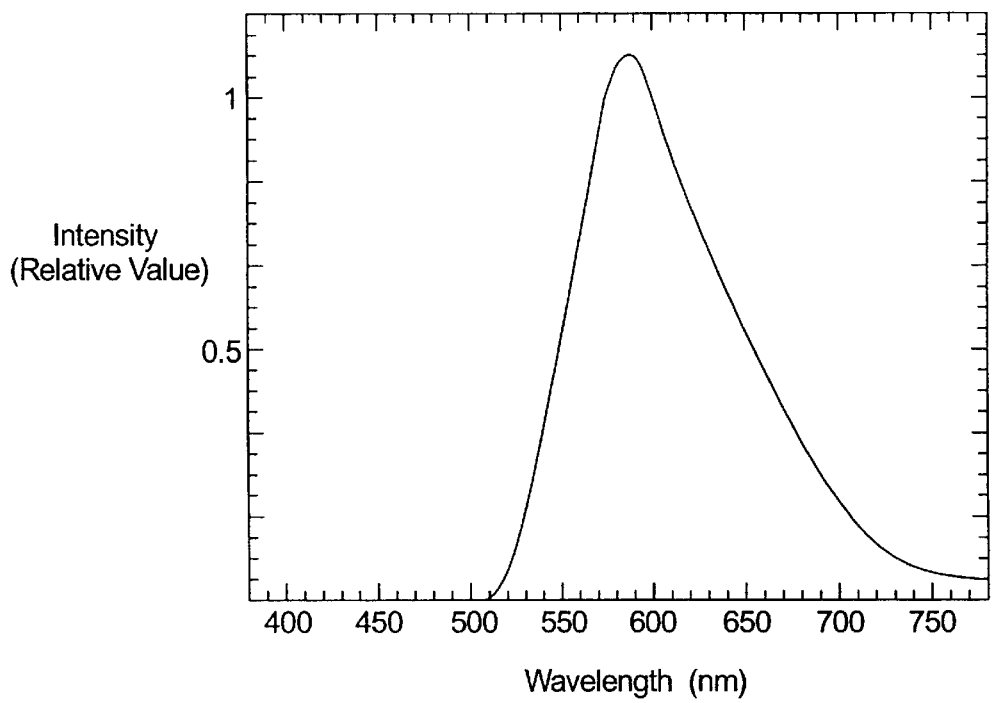
FIG. 43 is an emission spectrogram of an organic electroluminescent device of Example 43 of the invention.

Luminescent characteristics were evaluated by applying a forward bias DC Voltage to the thus fabricated organic electroluminescent device of this example in an atmosphere of nitrogen. The luminescent color was orange, and the device was subjected to spectral measurement in the same manner as in Example 39, with the result that spectra having a luminescent peak at 590 nm were obtained as shown in FIG. 43. Moreover, when the device was subjected to voltage-luminance measurement, there could be obtained a luminance of 300 cd/m² at 8 V.

Figure 44:
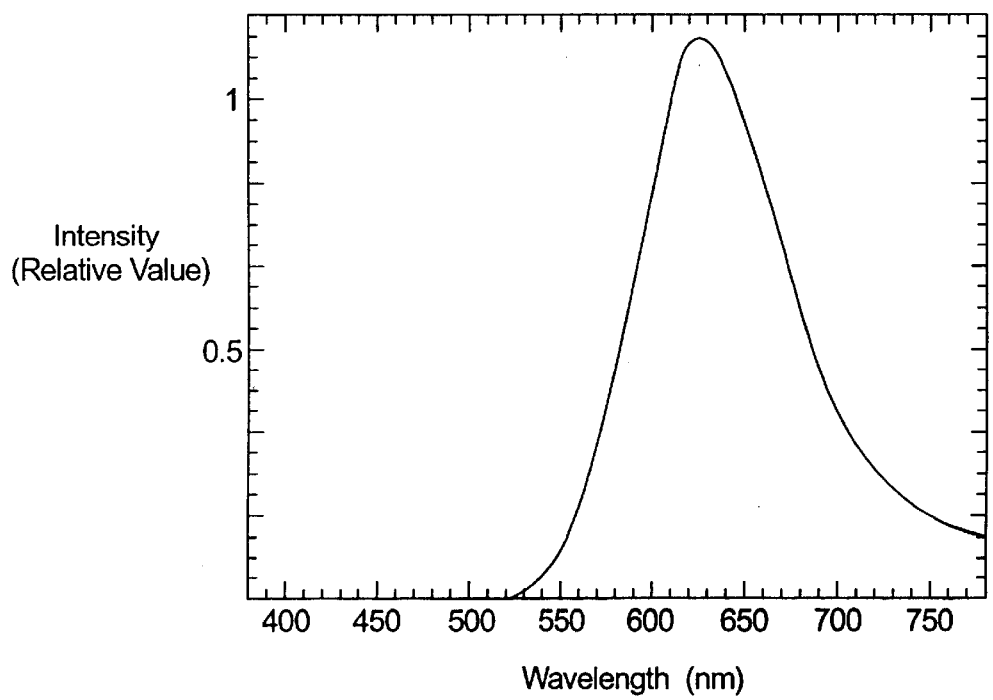
FIG. 44 is an emission spectrogram of an organic electroluminescent device of Example 44 of the invention.

Luminescent characteristics were evaluated by applying a forward bias DC voltage to the thus fabricated organic electroluminescent device of this example in an atmosphere of nitrogen. The luminescent color was red, and the device was subjected to spectral measurement in the same manner as in Example 39, with the result that spectra having a luminescent peak at 628 nm were obtained as shown in FIG. 44. Moreover, when the device was subjected to voltage-luminance measurement, there could be obtained a luminance of 15 cd /m² at 7.5 V.

After the fabrication of the organic electroluminescent device, the device was allowed to stand over one month in an atmosphere of nitrogen, no degradation of the device was observed.

After the fabrication of the organic electroluminescent device, the device was allowed to stand over one month in an atmosphere of nitrogen, no degradation of the device was observed.

EXAMPLE 45

Preparation of bis(aminostyryl)benzene Compound of the Following Formula

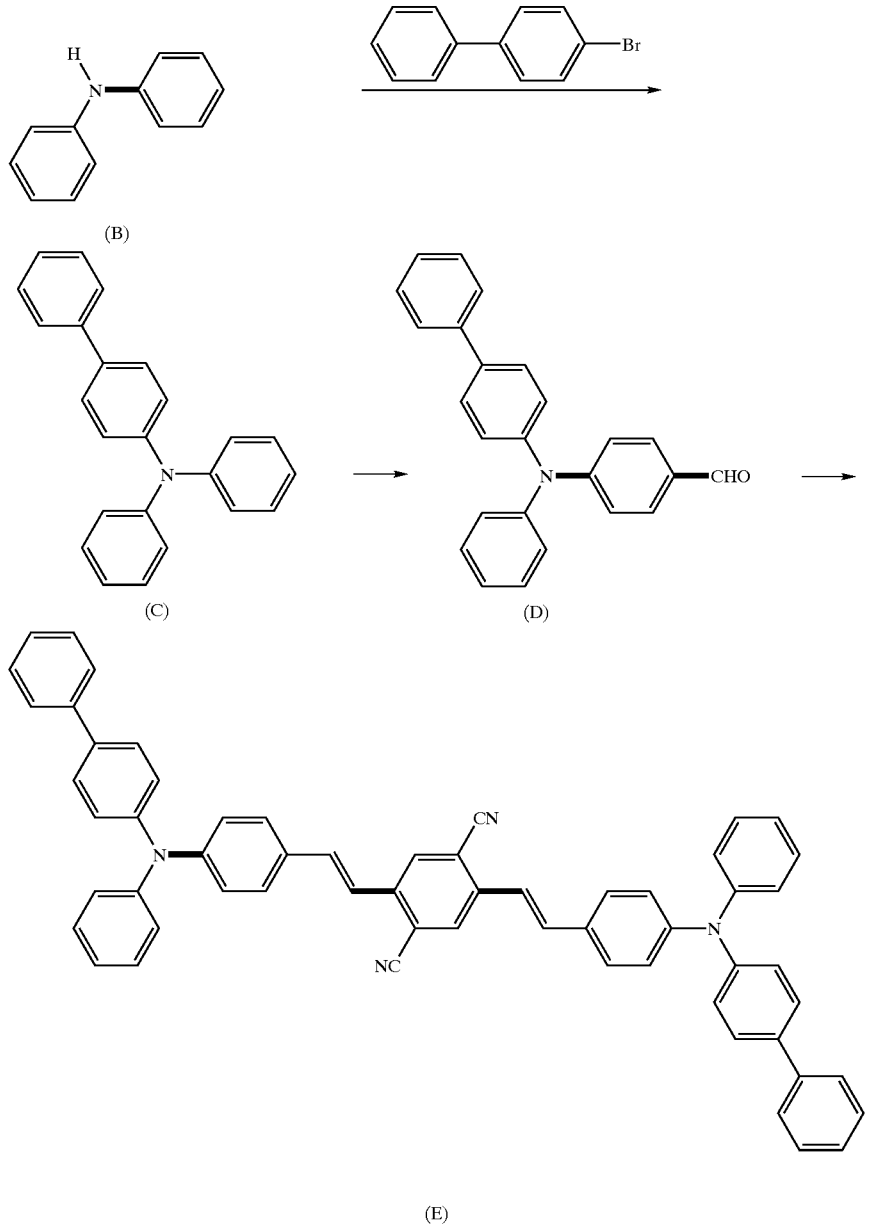

(1) Preparation of Intermediate (C) of the Above Formula 0.72 g (4.29 mmols) of N,N-diphenylamine (B), 1.00 g (4.29 mmols) of 4-bromobiphenyl, 0.495 g (5.15 mmols) of sodium t-butoxide, 10 mg (2 mole %) of palladium (II) acetate, and 0.105 g (8 mole %) of tris(a-methylphenyl)phosphine were suspended in 50 ml of xylene and refluxed in an atmosphere of nitrogen for 5 hours.

Insoluble matters were removed from the reaction solution by filtration, followed by separation and purification through silica gel chromatography (Wako-gel C-300, toluene:hexane=1:9) to obtain 1.00 g of colorless crystals.

This product was subjected to measurements of $^1$H NMR and FAB-MS and identified as the intended product (C) (yield: 72%).

$^1$HNMR (CDCl$_3$) δ (ppm): 7.10 (2H, t), 7.15 (6H, d), 7.20–7.32 (5H, m), 7.38–7.50 (4H, m), 7.58 (2H, d).

Figure 50:
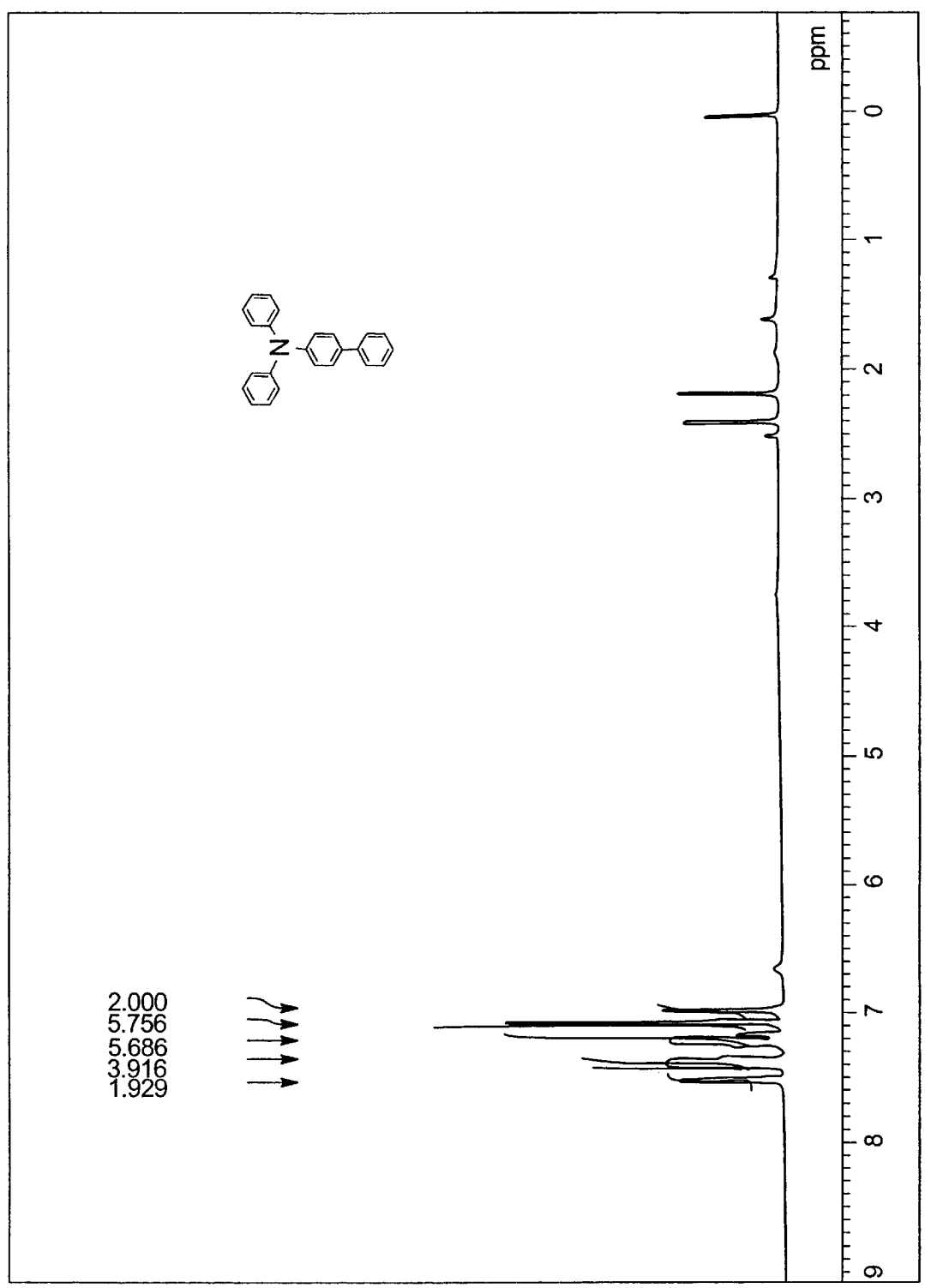
FIG. 50 is an $^1$HNMR spectral diagram of a synthetic intermediate (C) of the invention.

The spectra of $^1$HNMR are shown in FIG. 50.

(2) Preparation of Intermediate (D)

1.72 g (11.2 mmols) of phosphorus oxychloride was dropped in 5 ml of DMF under ice-cooling conditions, followed by heating at 120° C. for 5 minutes under agitation. The resultant red solution was cooled down to room temperature, in which 20 ml of a DMF solution of 1.00 g (3.10 mmols) of the triarylamine (C) was dropped, followed by agitation at 50° C. for 3 hours and subsequently at 100° C. for 5 hours. The resultant reaction mixture was concentrated under reduced pressure, and carefully poured into NaHCO$_3$/water. The resulting solution wag extracted with ethyl acetate, and the resultant organic phase was dried over anhydrous sodium sulfate and concentrated.

The residue was separated and purified through silica gel chromatography (Wako-gel C-300, THF:hexane=2:8) to obtain an oily substance (D).

This product was subjected to measurements of ¹HNMR and FAB-MS and identified as the intended product (D)

¹HNMR (CDCl₃) δ (ppm): 7.00–7.60 (16H, m), 7.70 (2H, d), 9.82 (1H, s).

Figure 51:
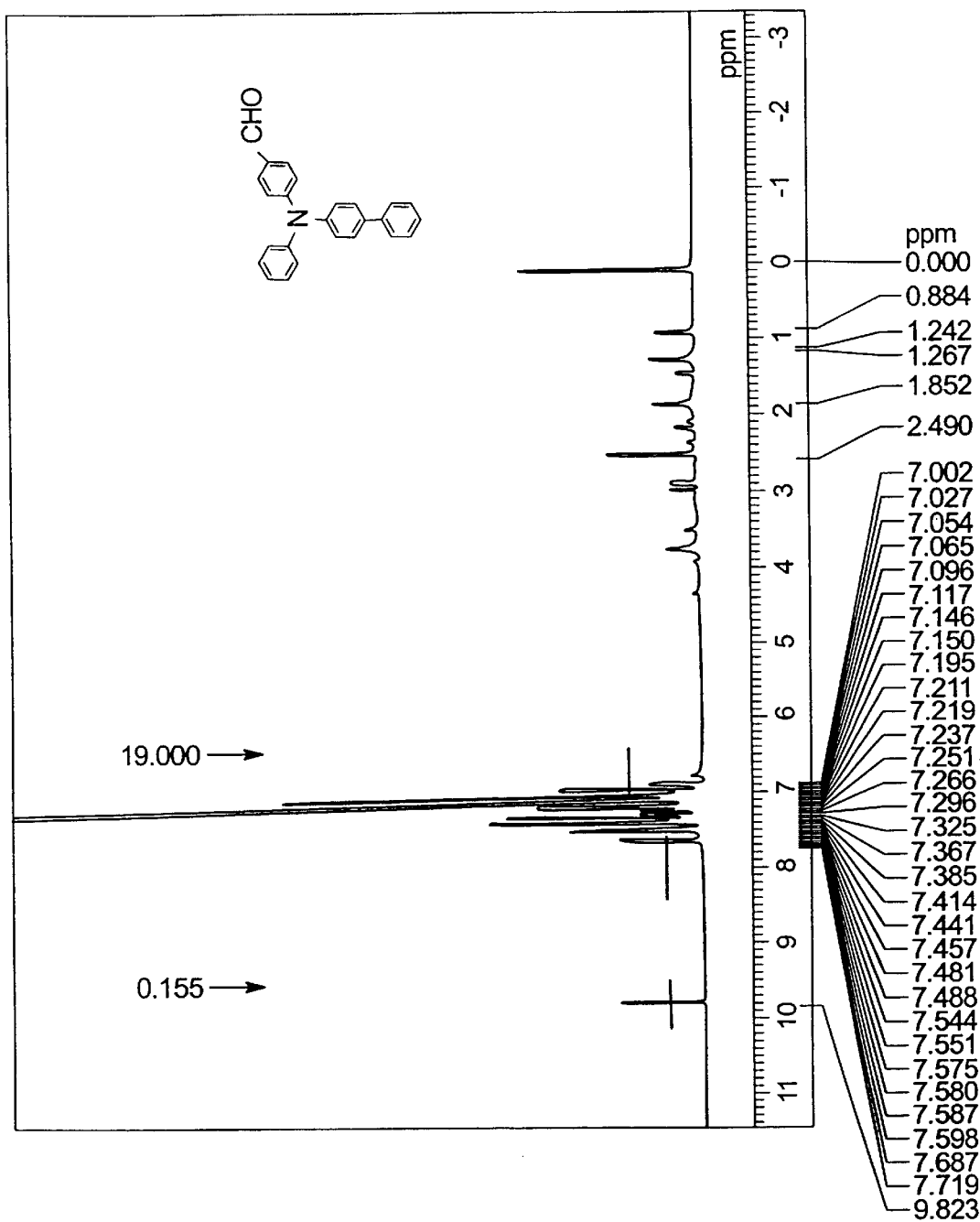
FIG. 51 is an $^1$HNMR spectral diagram of a synthetic intermediate (D) of the invention.

The spectra of ¹HNMR are shown in FIG. 51.

(3) Preparation of bis(aminostyryl)benzene Compound (E)

75 mg (1.9 mmols) of sodium hydride was weighed and placed in a reaction container, washed twice with hexane, suspended in 10 ml of moisture-free THF and agitated in an atmosphere of nitrogen on an iced water bath for 30 minutes. 0.656 g (1.87 mmols) of compound No. 58 was dropped in 1.0 ml of the moisture-free THF solution in 1 hour, followed by agitation at room temperature for 1 hour. The reaction mixture was quenched with a small amount of ice pieces, extracted with ethyl acetate, extracted with ethyl acetate, washed with a saline solution, and dried over anhydrous sodium sulfate.

Separation and purification through silica gel chromatography (Wako-gel C-300, toluene:hexane=6:4) resulted in 0.300 g of orange crystals.

This product was subjected to measurements of ¹HNMR and FAB-MS and identified as the,intended product (E).

¹HNMR (CDCl₃) δ (ppm): 7.10 (SH, d), 7.13≧7.32 (14H, d), 7.40–7.61 (12H, m), 8.00 (2H, s)

Figure 52:
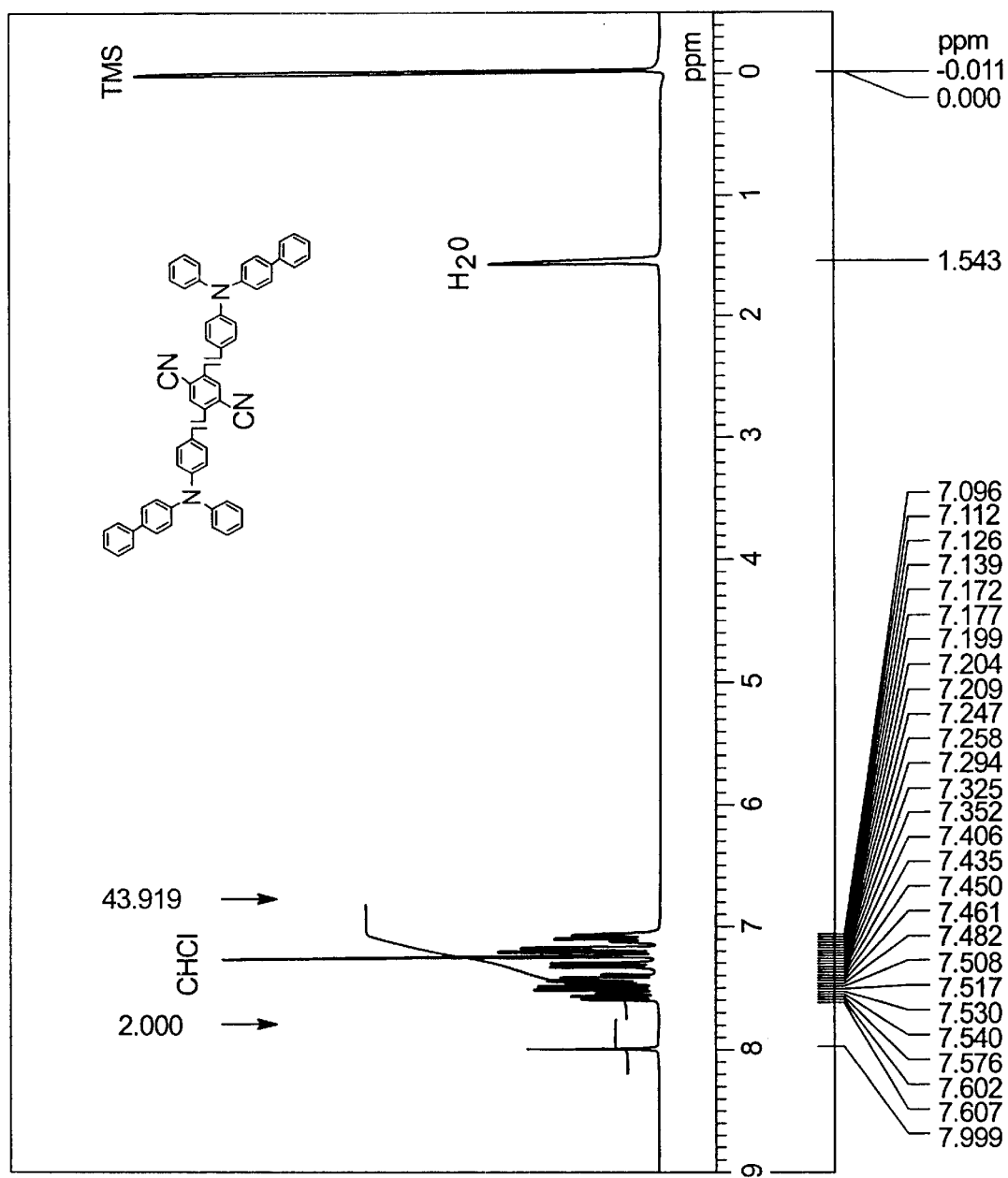
FIG. 52 is an $^1$HNMR spectral diagram of a synthetic intermediate (E) of the invention.

The spectra of ¹HNMR are shown in FIG. 52.

The visible light absorption maximum and fluorescence wavelength maximum of a chloroform solution of the product were, respectively, at 482 nm and 566 nm.

As will be seen from the foregoing, the first and second compounds of the invention can be effectively utilized as an organic luminescent material capable of exhibiting intense yellow to red or green to red luminescent colors, which depend on the types of introduced substituents and have high glass transition point and melting point. In additions these compounds are excellent in heat resistance and are electrically, thermally or chemically stable, and can readily form an amorphous vitreous state. Moreover, they are sublimable in nature and are able to form a uniform amorphous film by vacuum deposition or the like. The compounds of the invention can be prepared in an ordinary and highly efficient manner through synthetic intermediates.

What is claimed is:

1. A bis(aminostyryl)benzene compound of the following formula [I], [II], [III] or [IV]:

[I]

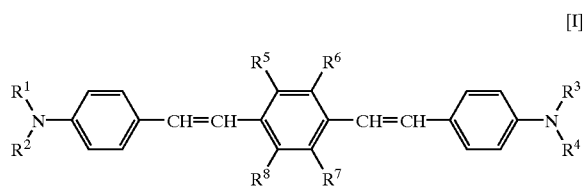

wherein $R^2$ and $R^3$ independently represent an unsubstituted aryl group, and $R^1$ and $R^4$ independently represent an aryl group represented by the following formula (1)

(1)

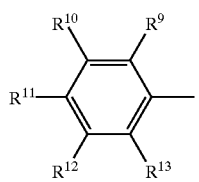

in which $R^9$, $R^{10}$, $R^{11}$, $R^{12}$ and $R^{13}$ may be the same or different and at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^5$, $R^6$, $R^7$ and $R^8$ may be the same or different and at least one thereof represents a member selected from a cyano group and a nitro group, and the others independently represent a hydrogen atom, a cyano group, a nitro group or a halogen atom;

[II]

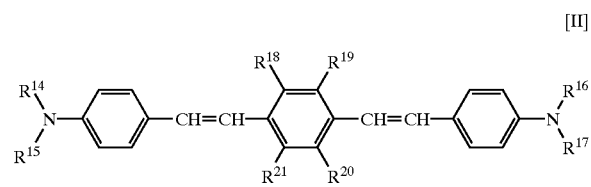

wherein $R^{14}$, $R^{15}$, $R^{16}$ and $R^{17}$ may be the same or different and independently represent an aryl group of the following formula (2)

(2)

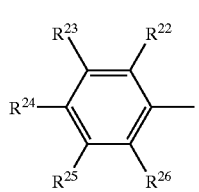

in which $R^{22}$, $R^{23}$, $R^{24}$, $R^{25}$ and $R^{26}$ may be the same or different, and at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{18}$, $R^{19}$, $R^{20}$ and $R^{21}$ may be the same or different and at least one thereof represents a member selected from a cyano group and a nitro group, and the others independently represent a hydrogen atom, a cyano group, a nitro group or a halogen atom;

[III]

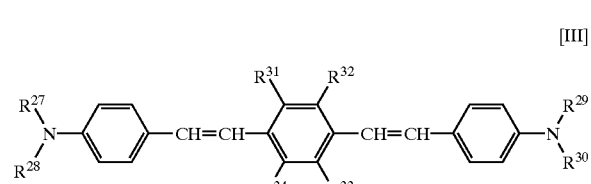

wherein at least one of $R^{27}$, $R^{28}$, $R^{29}$ and $R^{30}$ represents an aryl group of the following formula (3) and the others independently represent an unsubstituted aryl group

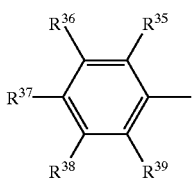

(3)

in which $R^{35}$, $R^{36}$, $R^{37}$, $R^{38}$ and $R^{39}$ may be the same or different and at least one thereof is a group selected from a dialkylamino or dialkenylamino group whose alkyl or alkenyl moiety has from 1 to 4 carbon atoms, a dicyclohexylamino group, and a diphenylamino group, and the others represent a hydrogen atom, and $R^{31}$, $R^{32}$, $R^{33}$ and $R^{34}$ may be same or different and at least one thereof represents a group selected from a cyano group and a nitro group, and the others independently represent a hydrogen atom, a cyano group, a nitro group or a halogen atom; or

[IV]

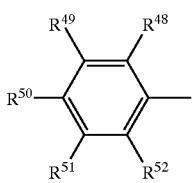

wherein $R^{41}$ and $R^{42}$ may be the same or different and independently represent an aryl group of the following formula (4)

(4)

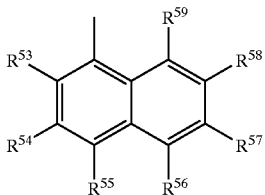

in which $R^{48}$, $R^{49}$, $R^{50}$, $R^{51}$ and $R^{52}$ may be the same or different and independently represent a hydrogen atom provided that at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{40}$ and $R^{43}$ may be the same or different and independently represent an aryl group of the following (5)

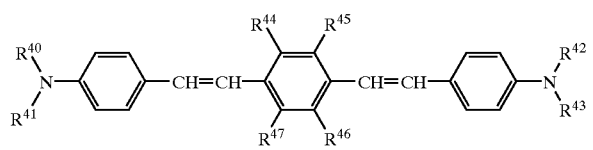

in which $R^{53}$, $R^{54}$, $R^{55}$, $R^{56}$, $R^{57}$, $R^{58}$ and $R^{59}$ may be the same or different and independently represent a hydrogen atom, or at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{44}$, $R^{45}$, $R^{46}$ and $R^{47}$ may be the same or different and at least one thereof represents a member selected from a cyano group and a nitro group, and the others independently represent a hydrogen atom, a cyano group, a nitro group or a halogen atom.

2. A bis(aminostyryl)benzene compound according to claim 1, wherein said compound is of the following formula

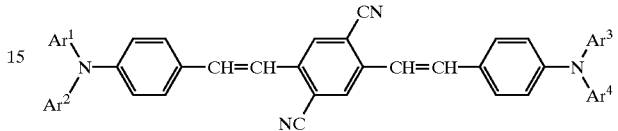

wherein $Ar^1$, $Ar^2$, $Ar^3$ and $Ar^4$ may be the same or different and independently represent an aryl group which may have a substituent, and if a substituent is present, such an aryl group is one selected from those aryl groups of the following formulas (6), (7), (8) and (9)

(6)

(7)

(8)

(9)

wherein $R^{60}$ represents an alkyl or alkenyl group having from 1 to 4 carbon atoms, a cyclohexyl group or a phenyl group, provided that where $Ar^1$, $Ar^2$, $Ar^3$ and $Ar^4$ are all the aryl group of the formula (6), $R^{60}$ represents an alkyl or alkenyl group having from 1 to 4 carbon atoms, a cyclohexyl group or a phenyl group, $R^{61}$ and $R^{62}$ independently represent an alkyl or alkenyl group having from 1 to 4 carbon atoms, a cyclohexyl group or a phenyl group, $R^{63}$ and $R^{64}$ may be the same or different and independently represent an alkyl or alkenyl group having from 1 to 4 carbon atoms, a cyclohexyl group or a phenyl group, n is an integer of 0 to 5, m is an integer of 0 to 3, and l is an integer of 0 to 4.

3. A bis(aminostyryl)benzene compound according to claim 2, wherein said compound is of the following formula (10), (11), (12), (13), (14), (15) or (15'):

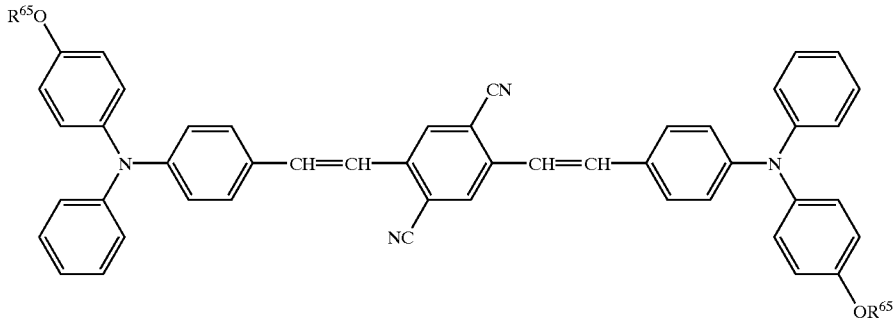
(10)
wherein $R^{65}$ represents an alkyl or alkenyl group having from 1 to 4 carbon atoms, a cyclohexyl group or a phenyl group;
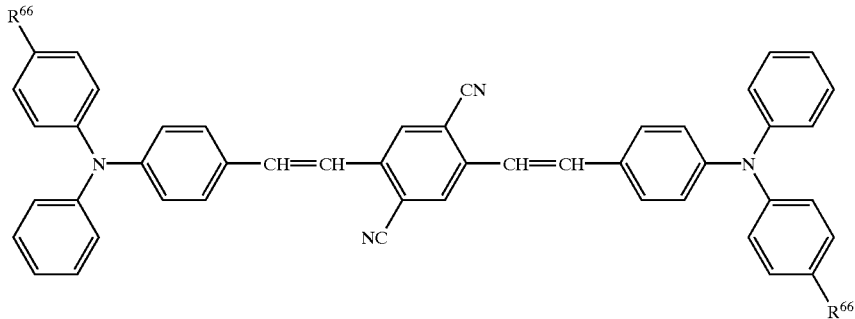
(11)
wherein $R^{66}$ represents an alkyl or alkenyl group having from 1 to 4 carbon atoms, a cyclohexyl group or a phenyl group;
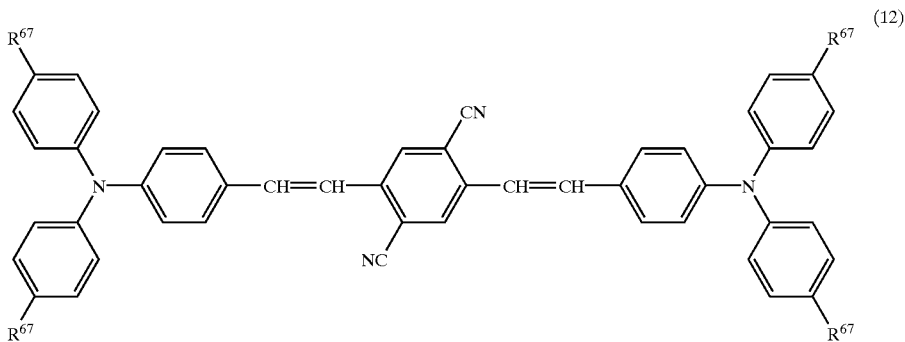
(12)

wherein R⁶⁷ represents an alkyl or alkenyl group having from 1 to 4 carbon atoms, a cyclohexyl group or a phenyl group;

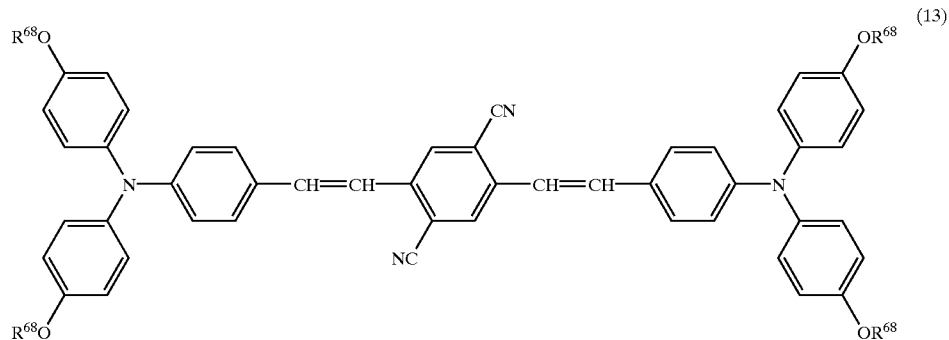

(13)

wherein R⁶⁸ represents an alkyl or alkenyl group having from 1 to 4 carbon atoms, a cyclohexyl group or a phenyl group;

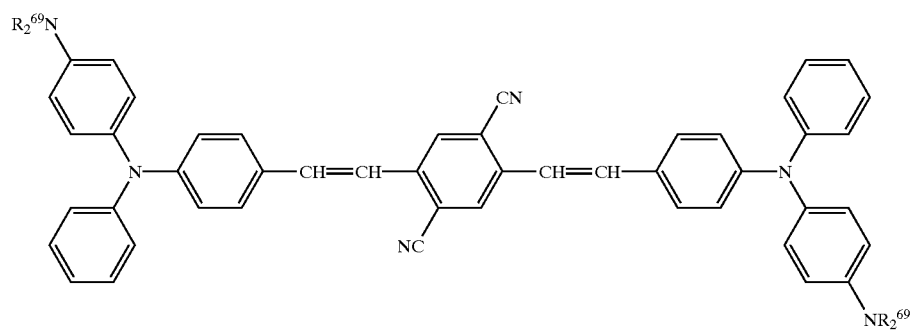

(14)

wherein R⁶⁹ represents an alkyl or alkenyl group having from 1 to 4 carbon atoms, a cyclohexyl group or a phenyl group;

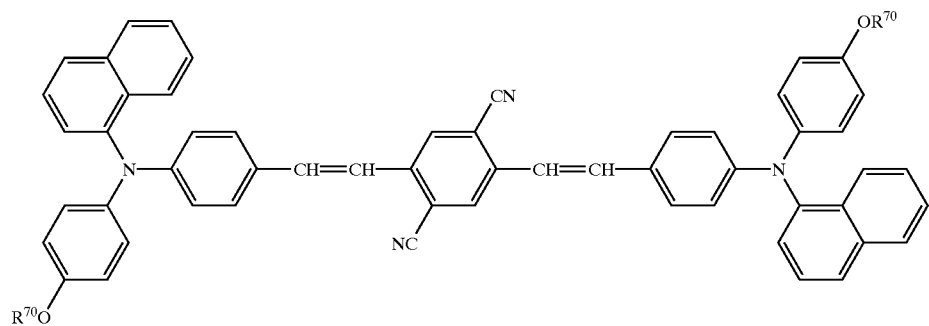

(15)

wherein R⁷⁰ represents an alkyl or alkenyl group having from 1 to 4 carbon atoms, a cyclohexyl group or a phenyl group; or

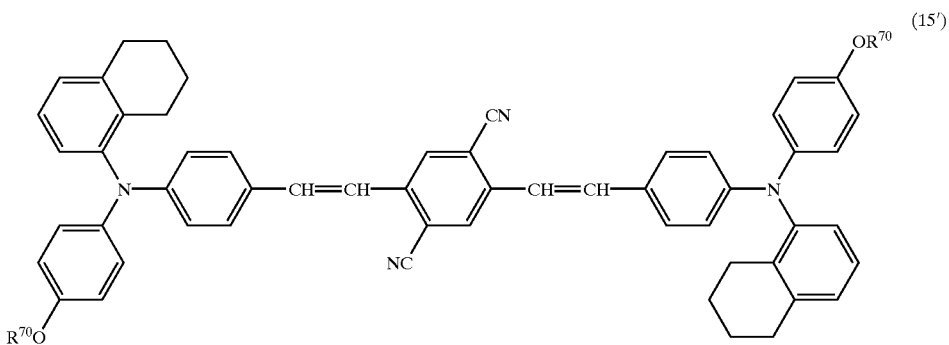
(15′)
wherein $R^{70}$ represents an alkyl or alkenyl group having from 1 to 4 carbon atoms, a cyclohexyl group or a phenyl group.
4. A bis(aminostyryl)benzene compound according to claim 2, wherein said compound is of the following structural formula (16)-1, (16)-2, (16)-3, (16)-4, (16)-5, (16)-6, (16)-7, (16)-8, (16)-9, (16)-10, (16)-11, (16)-12 or (16)-13:
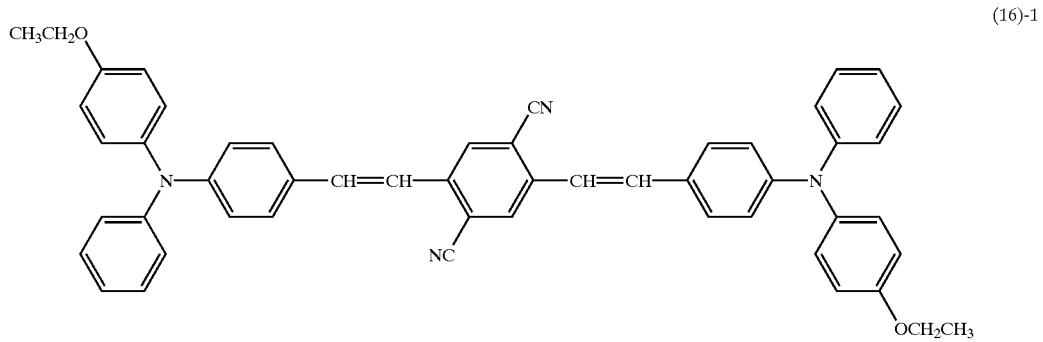
(16)-1
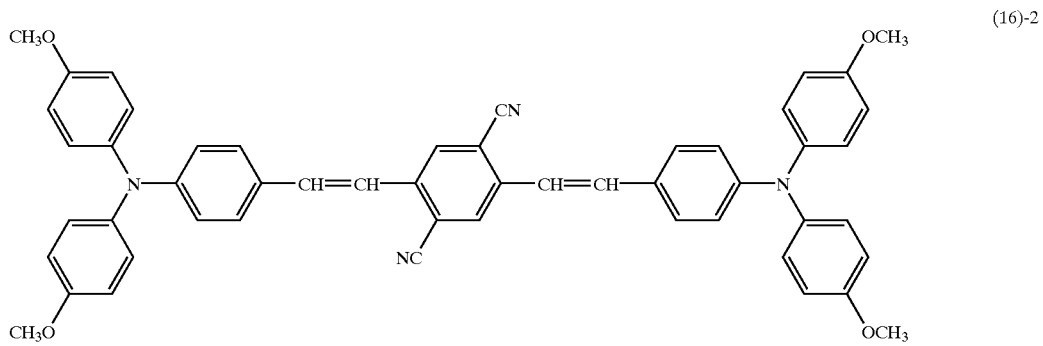
(16)-2
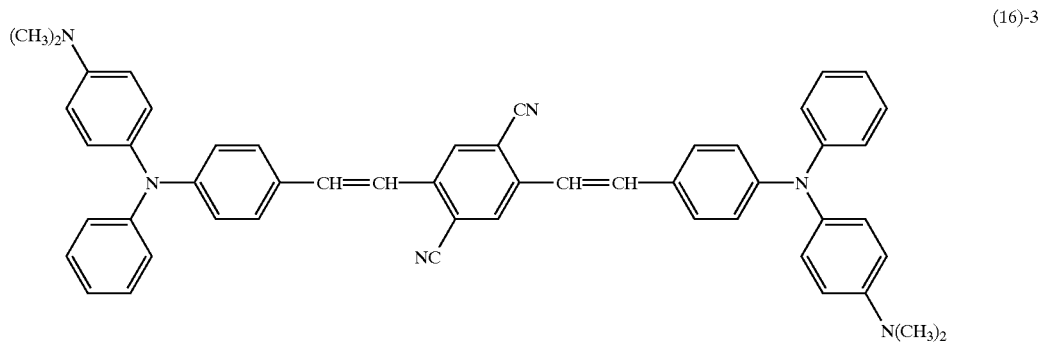
(16)-3

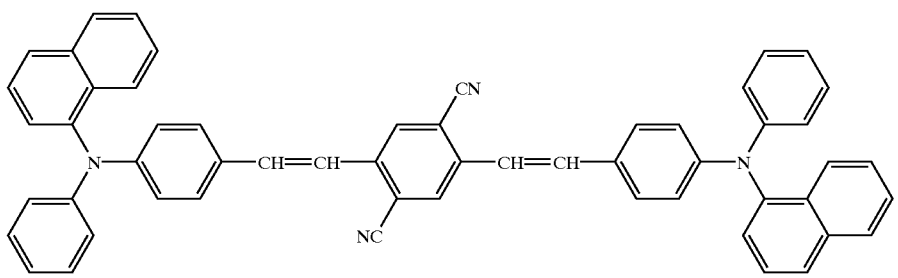
(16)-4
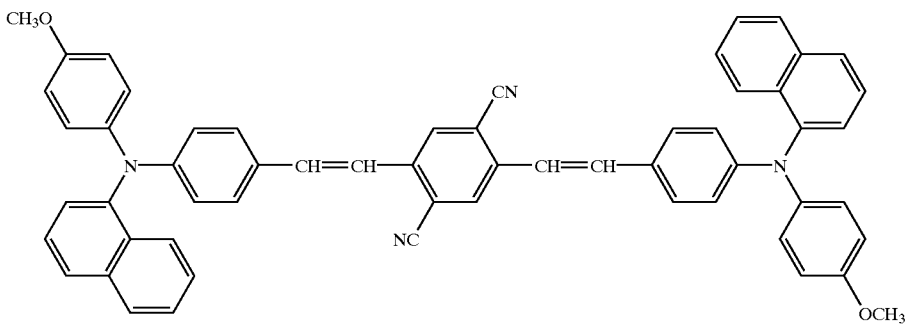
(16)-5
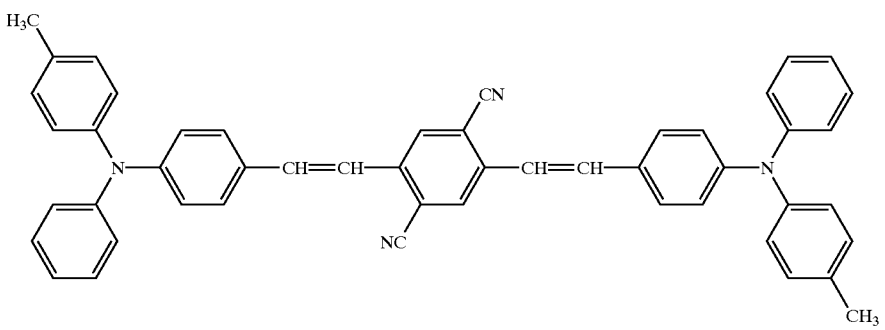
(16)-6
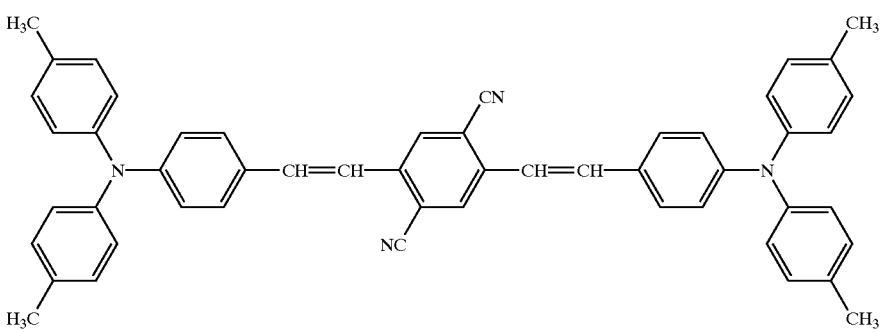
(16)-7
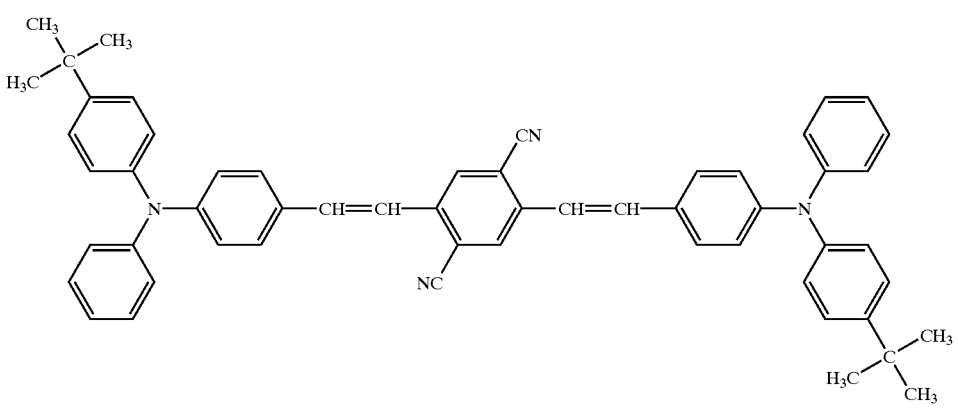
(16)-8

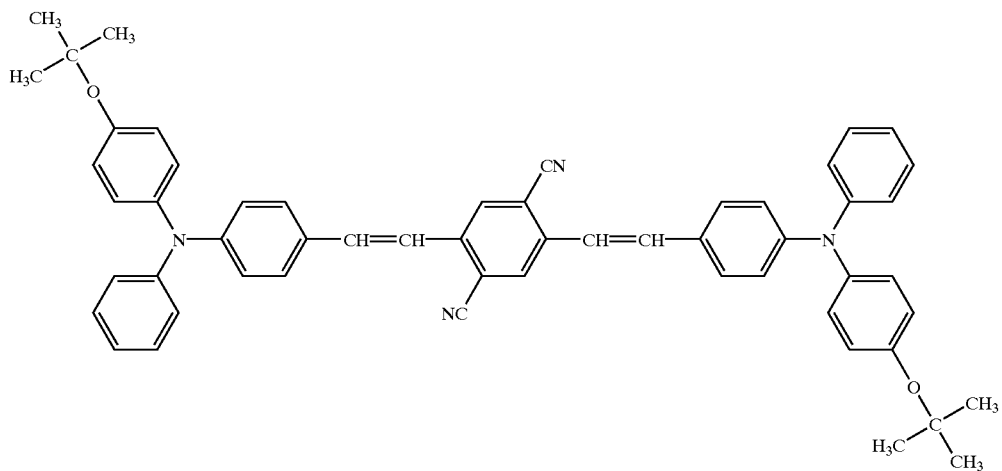
(16)-9
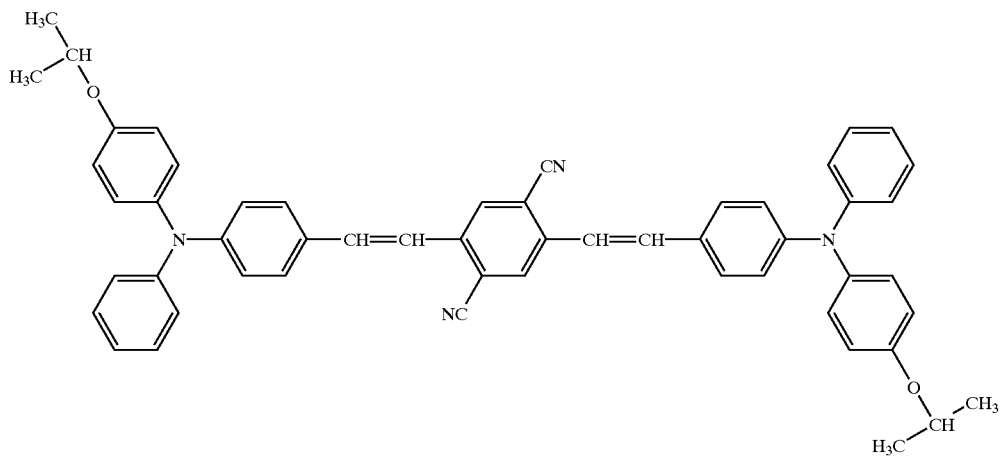
(16)-10
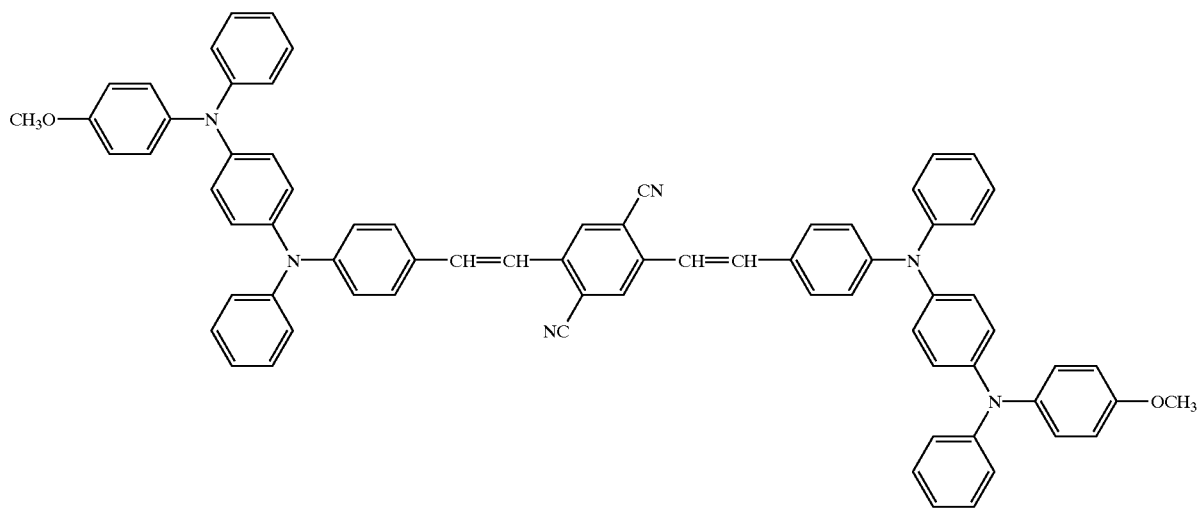
(16)-11

-continued

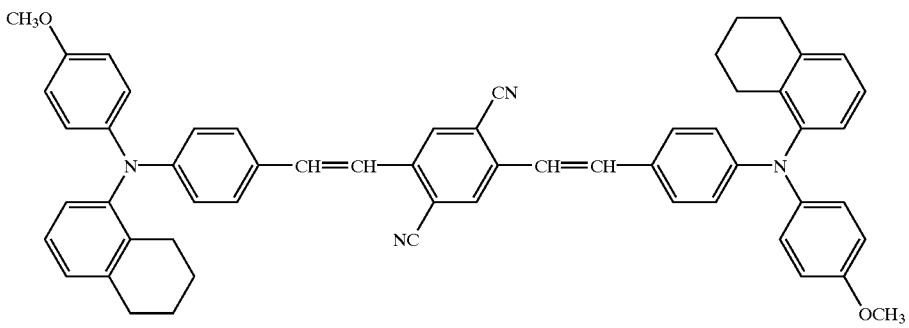

(16)-12

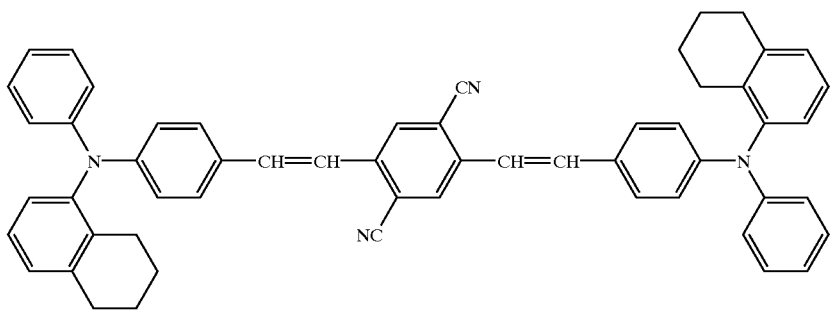

(16)-13

5. A bis(aminostyryl)benzene compound of the following formula [XIX]

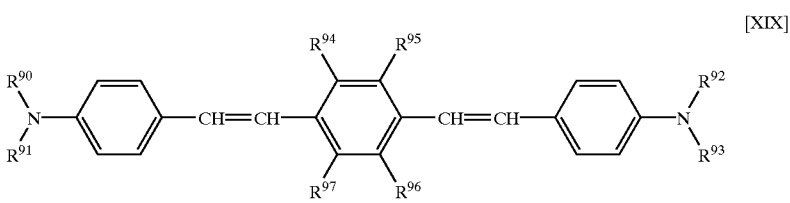

[XIX]

wherein $R^{90}$, $R^{91}$, $R^{92}$ and $R^{93}$ are groups, which may be the same or different, provided that at least one thereof represents an aryl group of the following formula (40) and the others independently represent an unsubstituted aryl group

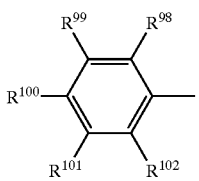

(40)

$R^{98}$, $R^{99}$, $R^{100}$, $R^{101}$ and $R^{102}$ may be the same or different and at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{94}$, $R^{95}$, $R^{96}$ and $R^{97}$ may be the same or different and at least one thereof represents a fluorine atom and the others independently represent a hydrogen atom, a cyano group, a nitro group or a halogen atom.

6. A bis(aminostyryl)benzene compound according to claim 5, wherein said compound is of the following formula [XX]

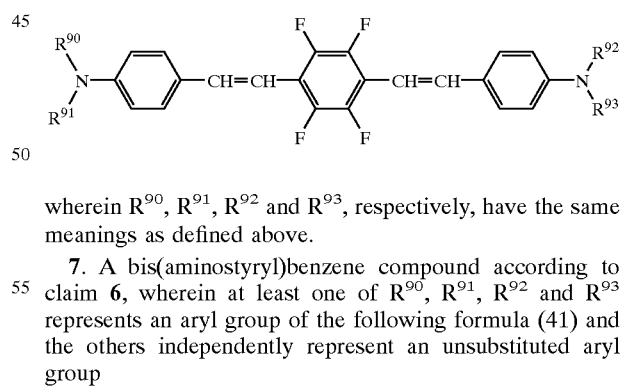

[XX]

wherein $R^{90}$, $R^{91}$, $R^{92}$ and $R^{93}$, respectively, have the same meanings as defined above.

7. A bis(aminostyryl)benzene compound according to claim 6, wherein at least one of $R^{90}$, $R^{91}$, $R^{92}$ and $R^{93}$ represents an aryl group of the following formula (41) and the others independently represent an unsubstituted aryl group

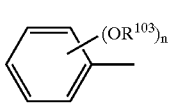

(41)

wherein at least one of $R^{103}$'s represents a hydrocarbon group (i.e. an alkyl or alkenyl group) having from 1 to 4 carbon atoms, a cyclohexyl group or a phenyl group and the other represents a hydrogen atom, and n is an integer of 0 to 5.

8. A bis(aminostyryl)benzene compound according to claim 7, wherein said compound consists of a compound of the following formula (42)

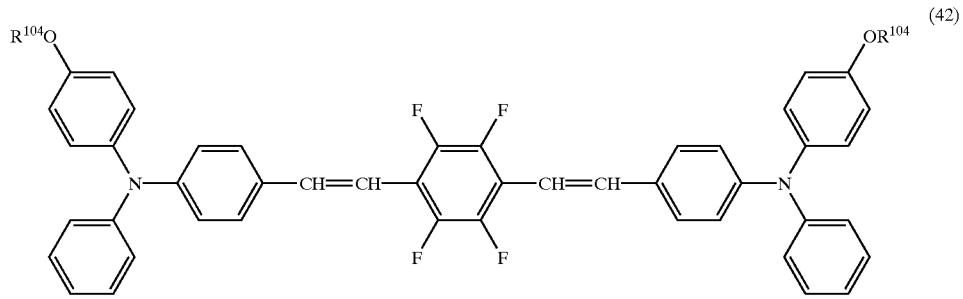

wherein at least one of $R^{104}$'s represents an alkyl or alkenyl group having from 1 to 4 carbon atoms, a cyclohexyl group or a phenyl group and the others independently represent a hydrogen atom, if present.

9. A bis(aminostyryl)benzene compound according to claim 6, wherein said compound is of the following structural formula (40)-1, (40)-2, (40)-3, (40)-4, (40)-5, (40)-6 or (40)

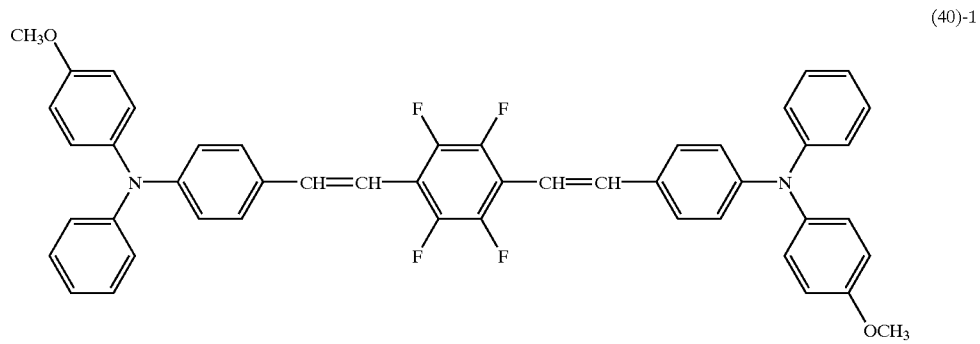

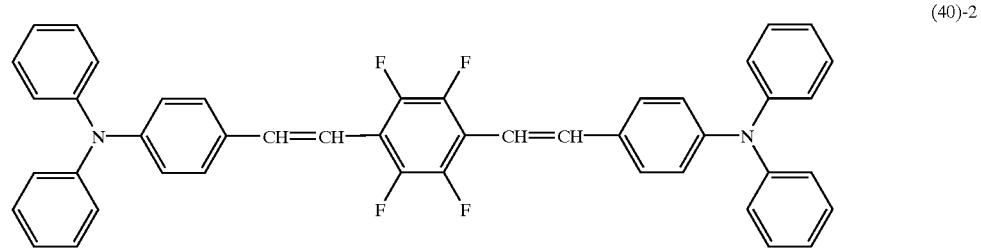

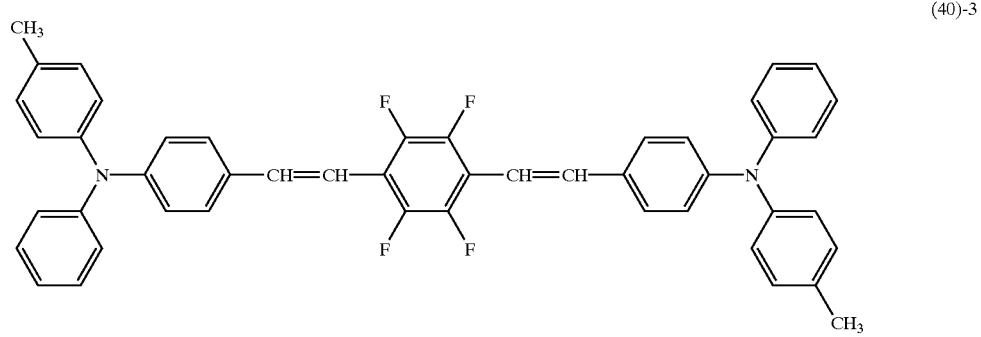

-continued
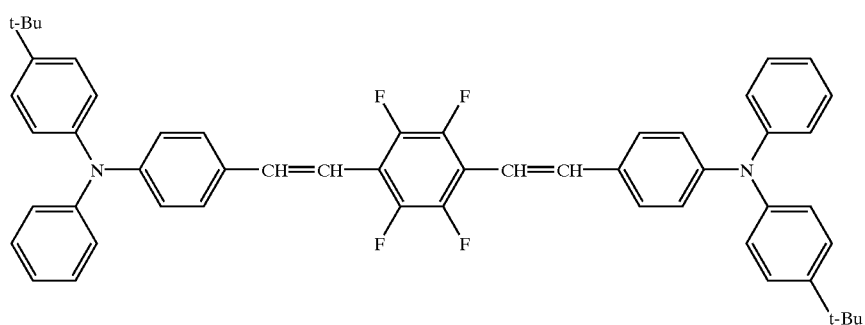
(40)-4
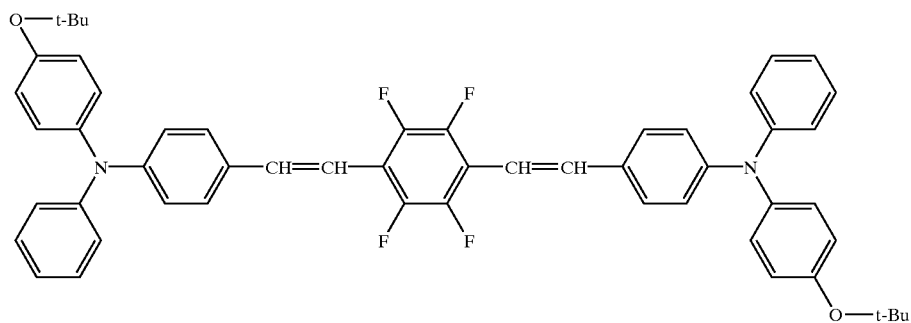
(40)-5
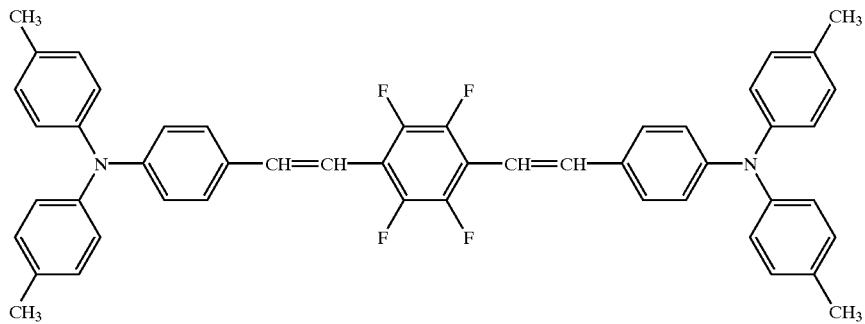
(40)-6
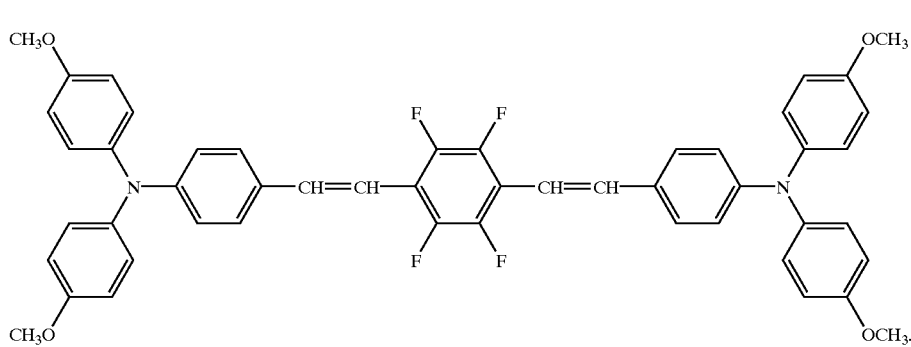
(40)-7

10. A process for preparing a bis(aminostyryl)benzene compound of the following formula [II], [III], [III] or [IV]:

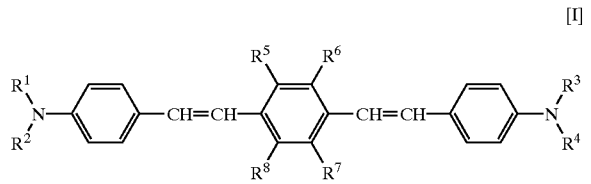

wherein $R^2$ and $R^3$ independently represent an unsubstituted aryl group, and $R^1$ and $R^4$ independently represent an aryl group represented by the following formula (1)

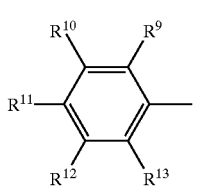

in which $R^9$, $R^{10}$, $R^{11}$, $R^{12}$ and $R^{13}$ may be the same or different and at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^5$, $R^6$, $R^7$ and $R^8$ may be the same or different and at least one thereof represents a member selected from a cyano group and a nitro group, and the others independently represent a hydrogen atom, a cyano group, a nitro group or a halogen atom;

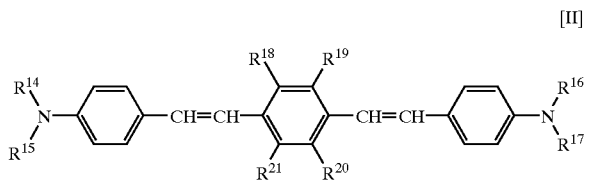

wherein $R^{14}$, $R^{15}$, $R^{16}$ and $R^{17}$ may be the same or different and independently represent an aryl group of the following formula (2)

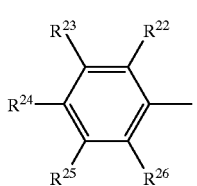

in which $R^{22}$, $R^{23}$, $R^{24}$, $R^{25}$ and $R^{26}$ may be the same or different, and at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{18}$, $R^{19}$, $R^{20}$ and $R^{21}$ may be the same or different and at least one thereof represents a member selected from a cyano group and a nitro group, and the others independently represent a hydrogen atom, a cyano group, a nitro group or a halogen atom;

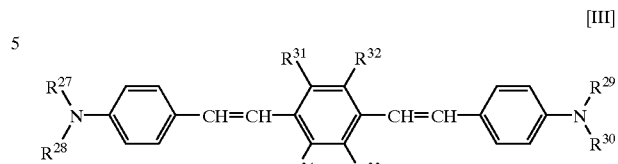

wherein at least one of $R^{27}$, $R^{28}$, $R^{29}$ and $R^{30}$ represents an aryl group of the following formula (3) and the others independently represent an unsubstituted aryl group

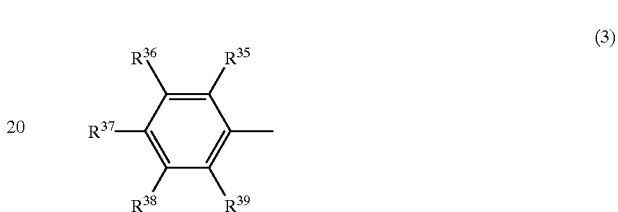

in which $R^{35}$, $R^{36}$, $R^{37}$, $R^{38}$ and $R^{39}$ may be the same or different and at least one thereof is a group selected from a dialkylamino or dialkenylamino group whose alkyl or alkenyl moiety has from 1 to 4 carbon atoms, a dicyclohexylamino group, and a diphenylamino group, and the others represent a hydrogen atom, and $R^{31}$, $R^{32}$, $R^{33}$ and $R^{34}$ may be the same or different and at least one thereof represents a group selected from a cyano group and a nitro group, and the others independently represent a hydrogen atom, a cyano group, a nitro group or a halogen atom; or

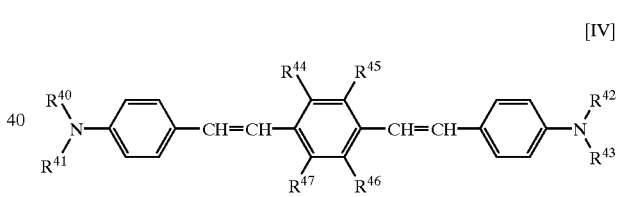

wherein $R^{41}$ and $R^{42}$ may be the same or different and independently represent an aryl group of the following formula (4)

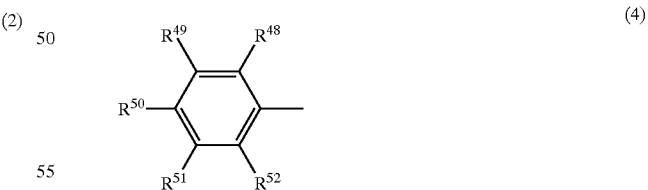

in which $R^{48}$, $R^{49}$, $R^{50}$, $R^{51}$ and $R^{52}$ may be the same or different and independently represent a hydrogen atom provided that at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{40}$ and $R^{43}$ may be the same or different and independently represent an aryl group of the following (5)

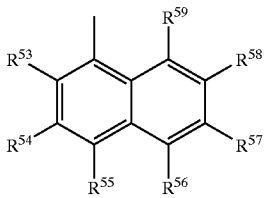

in which $R^{53}$, $R^{54}$, $R^{55}$, $R^{56}$, $R^{57}$, $R^{58}$ and $R^{59}$ may be the same or different and independently represent a hydrogen atom, or at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbon atoms, a cyclohexyl group, and a phenyl group, and the others represent a hydrogen atom, and $R^{44}$, $R^{45}$, $R^{46}$ and $R^{47}$ may be the same or different and at least one thereof represents a member selected from a cyano group and a nitro group, and the others independently represent a hydrogen atom, a cyano group, a nitro group or a halogen atom, which process comprising subjecting at least one of 4-(N,N-diarylamino)benzaldehydes of the following formulas [V] and [VI] to condensation with a diphosphonic acid ester of the following formula [VII] or a diphosphonium salt of the following formula [VIII]:

[V]

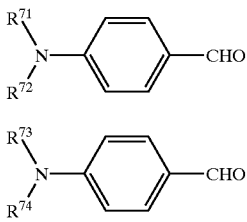

[VI]

wherein $R^{71}$ and $R^{72}$ independently represent an aryl group corresponding to or as defined before with respect to $R^1$, $R^2$, $R^{14}$, $R^{15}$, $R^{27}$, $R^{28}$, $R^{40}$ or $R^{41}$, and $R^{73}$ and $R^{74}$ independently represent an aryl group corresponding to or as defined before with respect to $R^3$, $R^4$, $R^{16}$, $R^{17}$, $R^{29}$, $R^{30}$, $R^{42}$ or $R^{43}$; and

[VII]

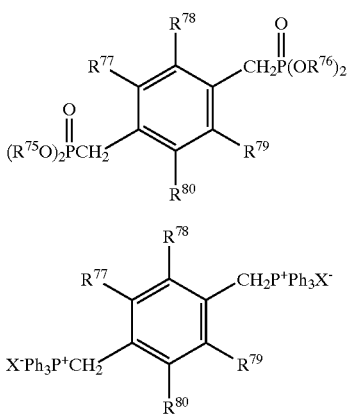

[VIII]

wherein $R^{75}$ and $R^{76}$ may be the same or different and independently represent a hydrocarbon group, $R^{77}$, $R^{78}$, $R^{79}$ and $R^{80}$ independently represent a group corresponding to or defined before with respect to $R^5$, $R^6$, $R^7$, $R^8$, $R^{18}$, $R^{19}$, $R^{20}$, $R^{21}$, $R^{31}$, $R^{32}$, $R^{33}$, $R^{34}$, $R^{44}$, $R^{45}$, $R^{46}$ or $R^{47}$, and X represents a halogen atom.

11. A process for preparing a bis(aminostyryl)benzene compound according to claim 10, wherein the condensation is carried out under the usual conditions of the Wadsworth-Emmons or Wittig reaction wherein said diphosphonic acid ester and/or said diphosphonium salt is treated with a base in a solvent to form a carbo anion, and said carbo anion is condensed with said 4-(N,N-diarylamino)benzaldehyde.

12. A process according to claim 10, wherein said bis(aminostyryl)benzene compound is of the following formula

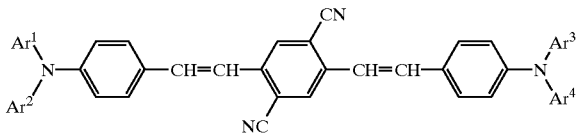

wherein $Ar^1$, $Ar^2$, $Ar^3$ and $Ar^4$ may be the same or different and independently represent an aryl group which may have a substituent, and if a substituent is present, such an aryl group is one selected from those aryl groups of the following formulas (6), (7), (8) and (9)

(6)

(7)

(8)

(9)

wherein $R^{60}$ represents an alkyl or alkenyl group having from 1 to 4 carbon atoms, a cyclohexyl group or a phenyl group, provided that where $Ar^1$, $Ar^2$, $Ar^3$ and $Ar^4$ are all the aryl group of the formula (6), $R^{60}$ represents an alkyl or alkenyl group having from 1 to 4 carbon atoms, a cyclohexyl group or a phenyl. group, $R^{61}$ and $R^{62}$ independently represent an alkyl or alkenyl group having from 1 to 4 carbon atoms, a cyclohexyl group or a phenyl group, $R^{63}$ and $R^{64}$ may be the same or different and independently represent an alkyl or alkenyl group having from 1 to 4 carbon atoms, a cyclohexyl group or a phenyl group, n is an integer of 0 to 5, m is an integer of 0 to 3, and l is an integer of 0 to 4, which process comprising subjecting at least one of 4-(N,N-diarylamino)benzaldehydes of the following formulas (17) and (18) and a diphosphonic acid ester of the following formula (19) or a diphosphonium salt of the following formula (20) to condensation reaction

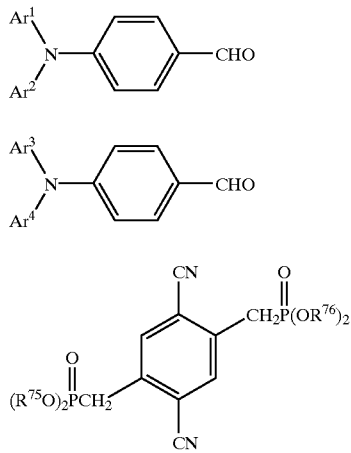

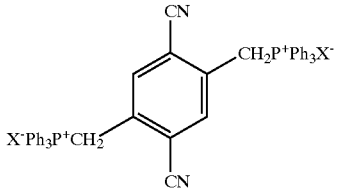

wherein $Ar^1$, $Ar^2$, $Ar^3$, $Ar^4$, $R^{75}$, $R^{76}$ and X, respectively, have the same meanings as defined before.

13. A process for preparing a bis(aminostyryl)benzene compound according to claim 10, wherein $R^{75}$ and $R^{76}$ independently represent a saturated hydrocarbon group having from 1 to 4 carbon atoms.

14. A process for preparing a bis(aminostyryl)benzene compound according to claim 10, wherein said compound consists of a member selected from the group consisting of those compounds of the following formulas (10), (11), (12), (13), (14), (15) and (15'):

(10)

wherein $R^{65}$ represents an alkyl or alkenyl group having from 1 to 4 carbon atoms, a cyclohexyl group or a phenyl group;

(11)

wherein $R^{66}$ represents an alkyl or alkenyl group having from 1 to 4 carbon atoms, a cyclohexyl group or a phenyl group;

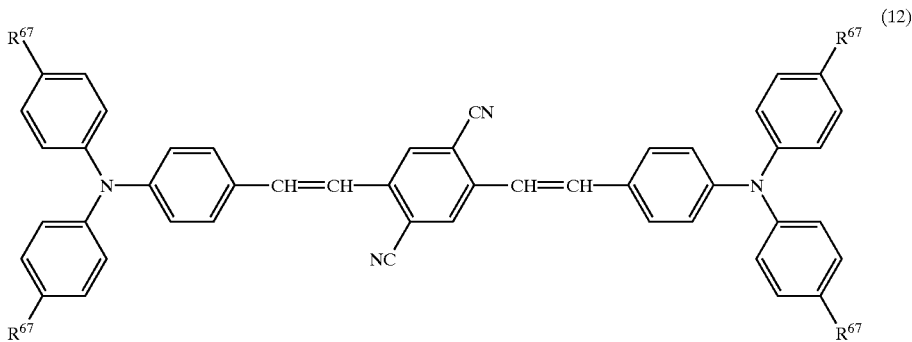
(12)
wherein $R^{67}$ represents an alkyl or alkenyl group having from 1 to 4 carbon atoms, a cyclohexyl group or a phenyl group;
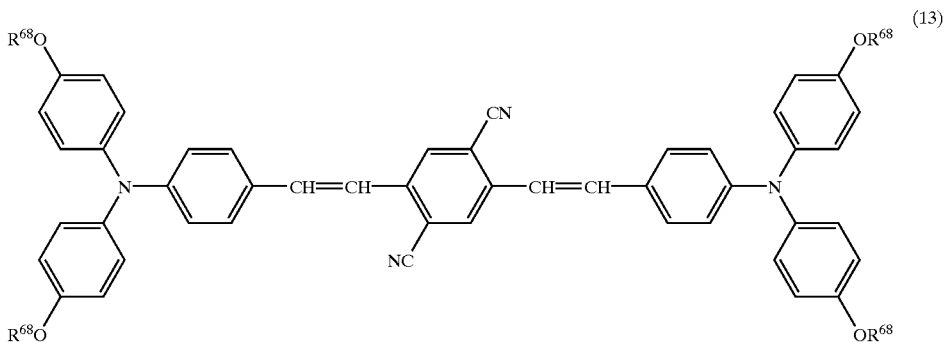
(13)
wherein $R^{68}$ represents an alkyl or alkenyl group having from 1 to 4 carbon atoms, a cyclohexyl group or a phenyl group;
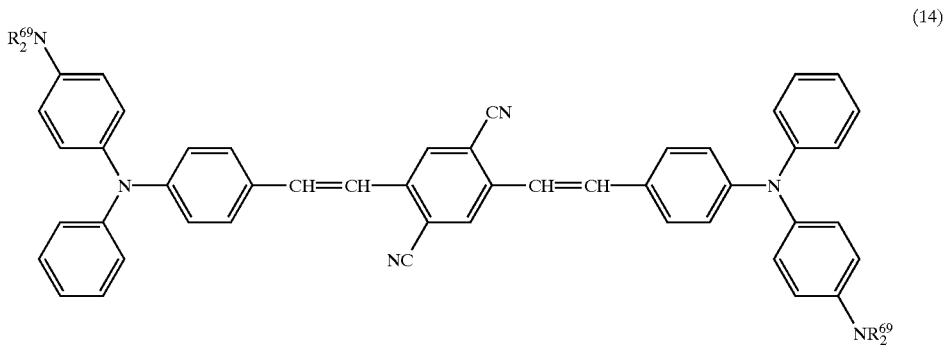
(14)
wherein $R^{69}$ represents an alkyl or alkenyl group having from 1 to 4 carbon atoms, a cyclohexyl group or a phenyl group;

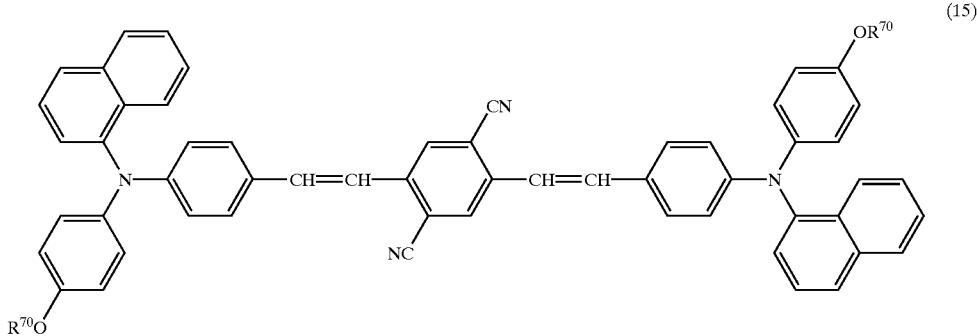
(15)

wherein $R^{70}$ represents an alkyl or alkenyl group having from 1 to 4 carbon atoms, a cyclohexyl group or a phenyl group; and formula (15'):

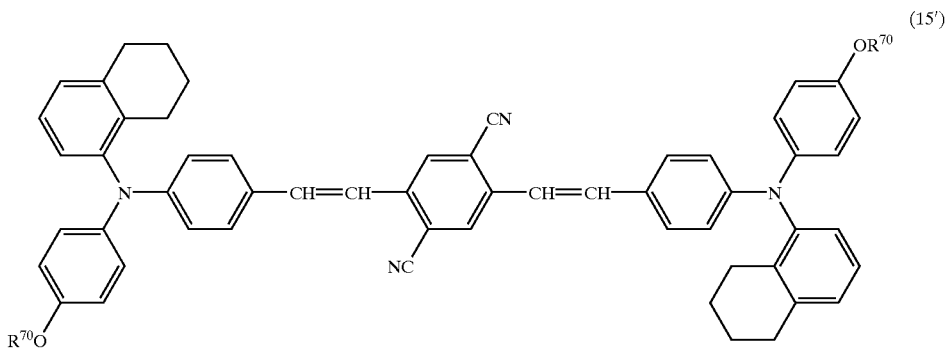
(15')

wherein $R^{70}$ represents an alkyl or alkenyl group having from 1 to 4 carbon atoms, a cyclohexyl group or a phenyl group.

15. A process for preparing a bis(aminostyryl)benzene compound according to claim 10, wherein said compound consists of a member selected front the group consisting of those compounds of the following structural formulas (16)-1, (16)-2, (16)-3, (16)-4, (16)-5, (16)-6, (16)-7, (16)-8, (16)-9, (16)-10, (16)-11, (16)-12 and (16)-13:

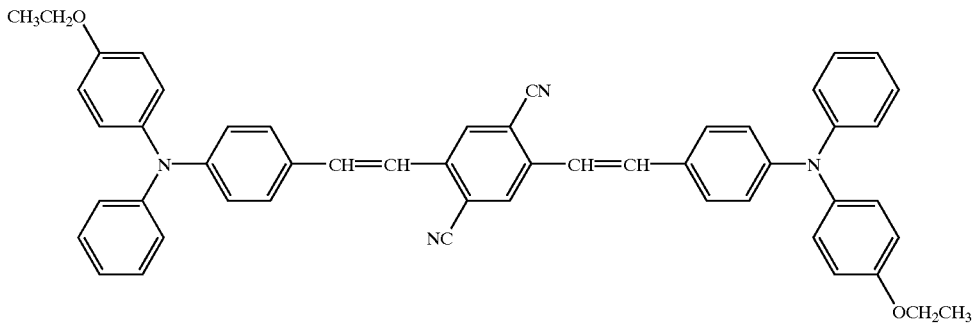
(16)-1

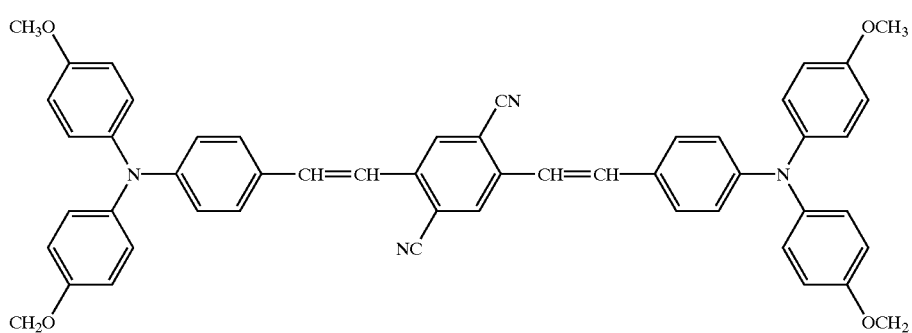
(16)-2
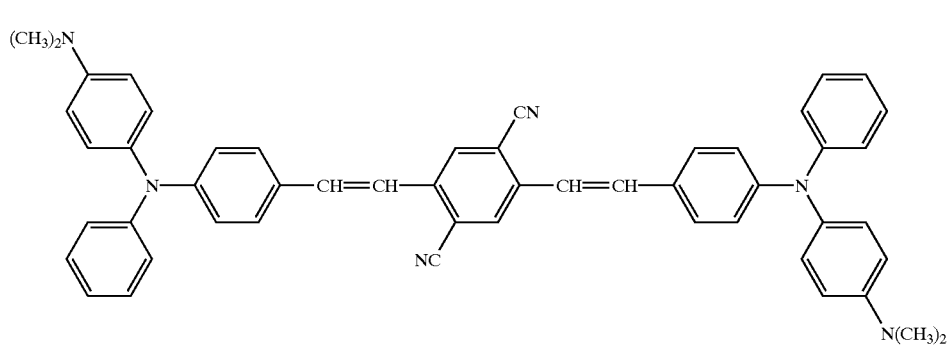
(16)-3
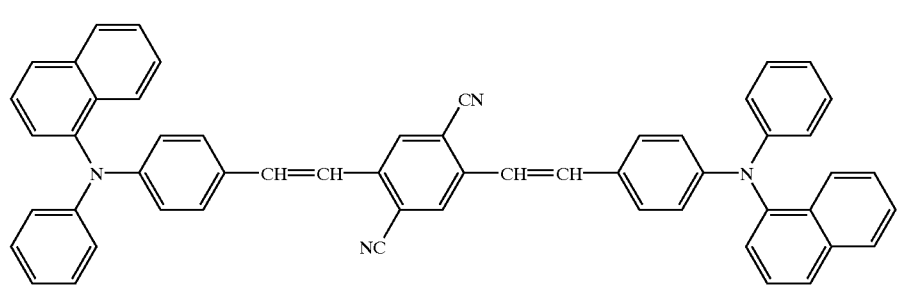
(16)-4
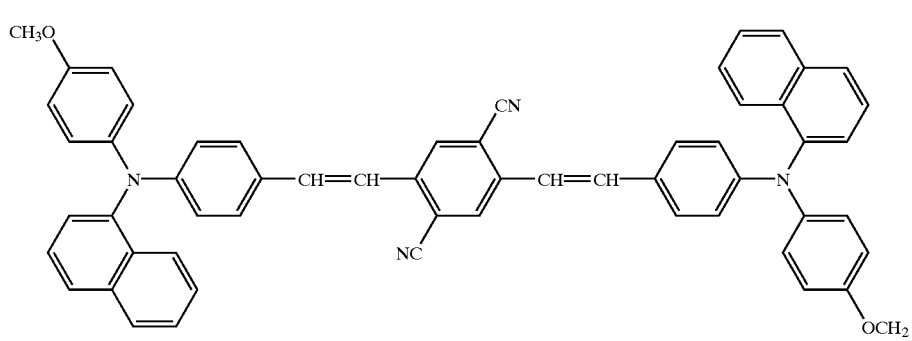
(16)-5

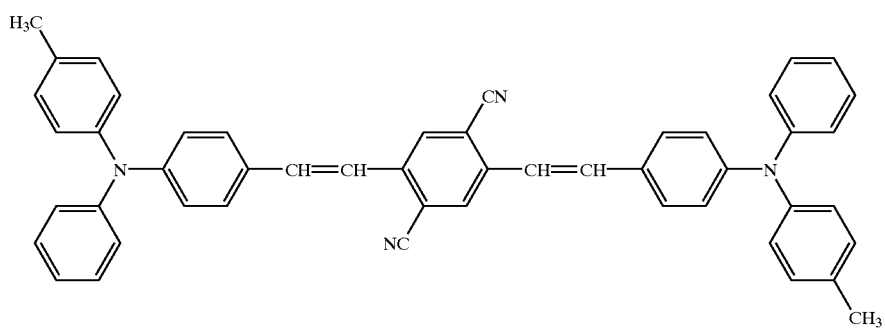
(16)-6
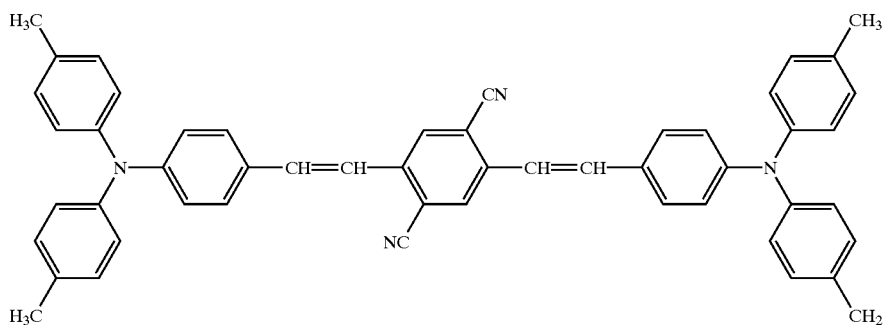
(16)-7
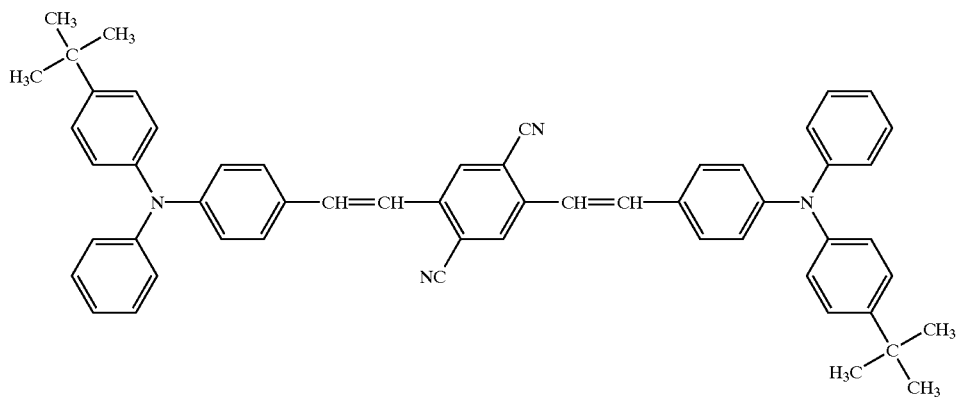
(16)-8
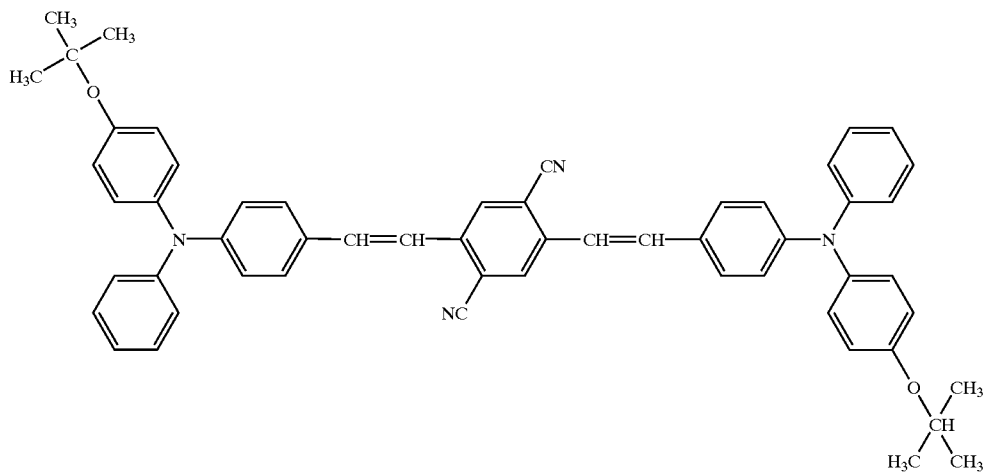
(16)-9

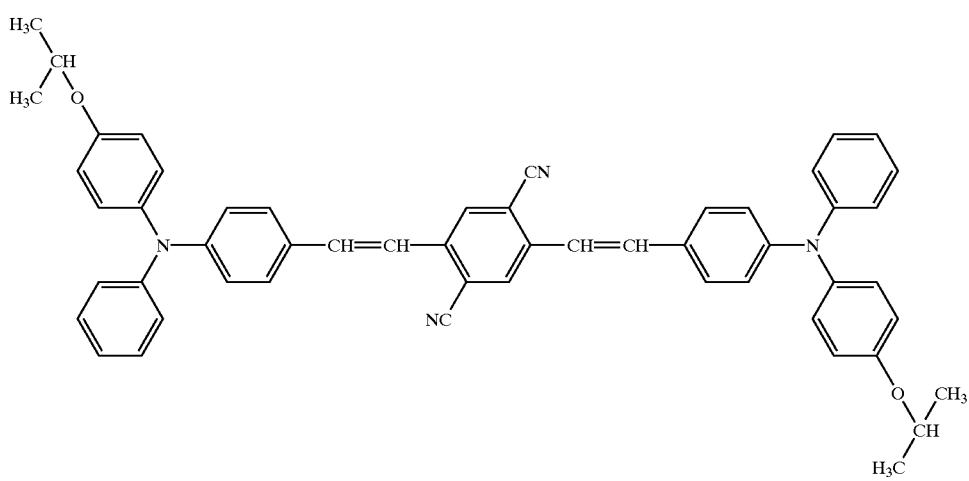
(16)-10
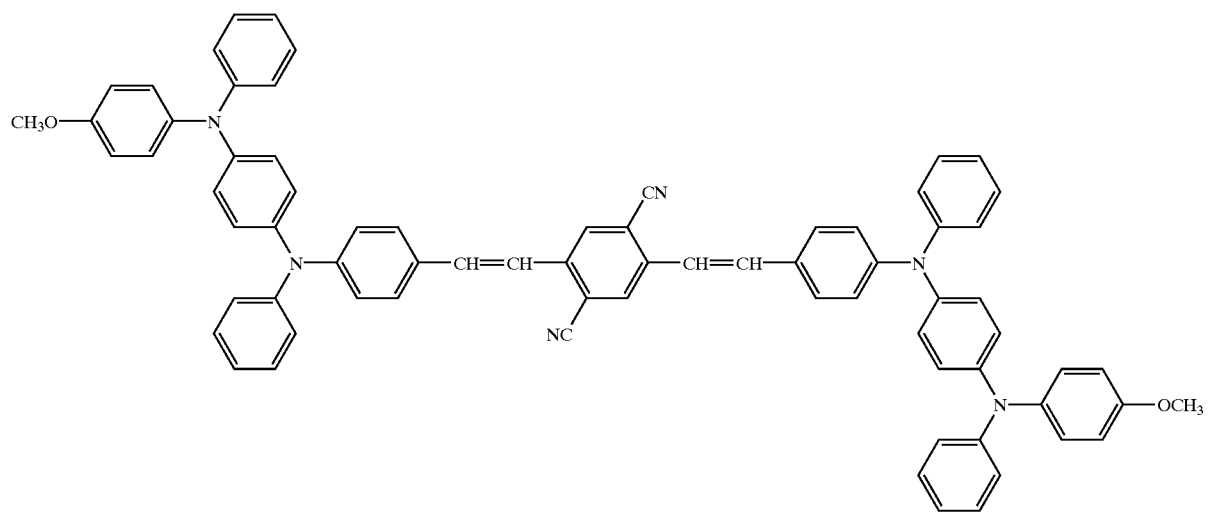
(16)-11
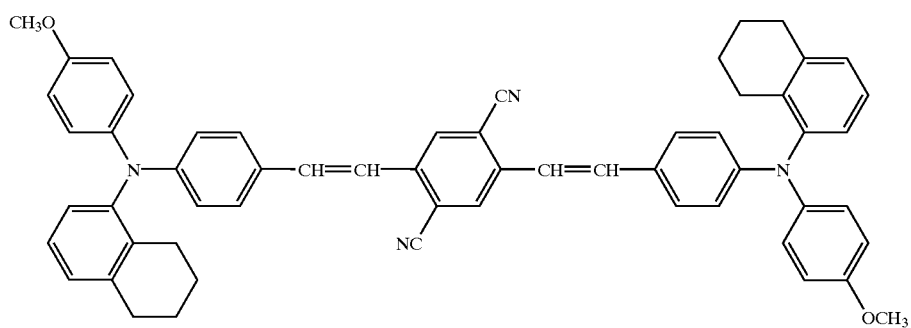
(16)-12
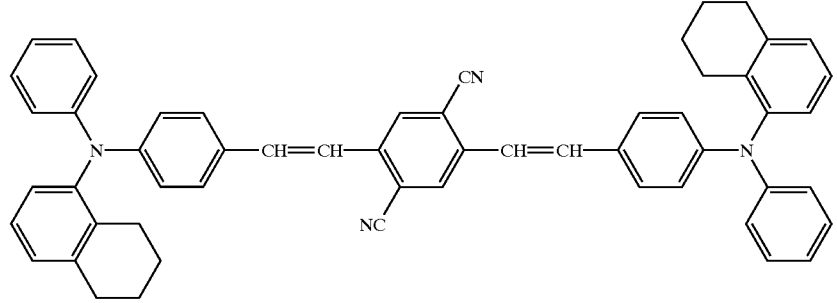
(16)-13

16. A process for preparing a bis(aminostyryl)benzene compound of the following formula [XIX]

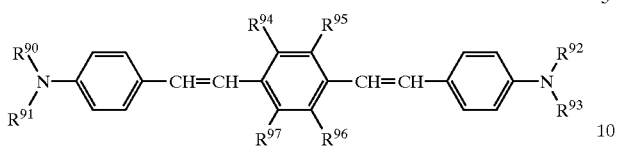

[XIX]

wherein $R^{90}$, $R^{91}$, $R^{92}$ and $R^{93}$ are groups, which may be the same or different, and at least one thereof represents an aryl group of the following formula (40) and the others independently represent an unsubstituted aryl group

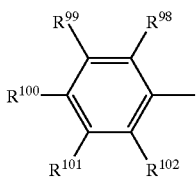

(40)

wherein $R^{98}$, $R^{99}$, $R^{100}$, $R^{101}$ and $R^{102}$ may be the same or different and at least one thereof is a member selected from an alkoxy group having from 1 to 4 carbon atoms, which may be saturated or may have a double bond, a cyclohexyloxy group, a phenoxy group, an alkyl or alkenyl group having from 1 to 4 carbons atoms, a cyclohexyl group, and a phenyl group, and the others represent a hydrogen atom, and $R^{94}$, $R^{95}$, $R^{96}$ and $R^{97}$ may be the same or different and at least one thereof represents a fluorine atom and the others independently represent a hydrogen atom, a cyano group, a nitro group or a halogen atom, the process comprising subjecting at least one of 4-(N,N-diarylamino) benzoaldehydes of the following formulas [V'] and [VI'] to condensation reaction with a diphosphonic acid ester of the following formula [VII'] or a diphosphonium salt of the following formula [VIII']

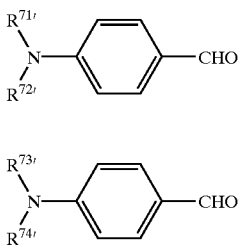

[V']

[VI']

wherein $R^{71}$ and $R^{72}$ independently represent an aryl group corresponding to or as defined before with respect to $R^{90}$ or $R^{91}$, and $R^{73}$ and $R^{74}$ independently represent an aryl group corresponding to or as defined before with respect to $R^{92}$ or $R^{93}$, and

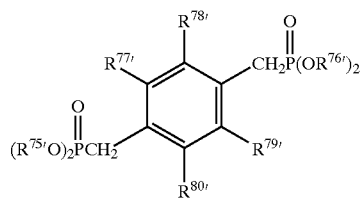

[VII']

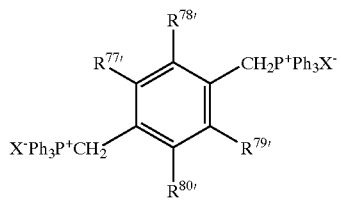

[VIII']

wherein $R^{75}$ and $R^{76}$ may be the same or different and independently represent a hydrocarbon group, $R^{77}$, $R^{78}$, $R^{79}$ and $R^{80}$ independently represent a group corresponding to or defined before with respect to $R^{94}$, $R^{95}$, $R^{96}$ or $R^{97}$, and X represents a halogen atom.

17. A process for preparing a bis(aminostyryl)benzene compound according to claim 16, wherein said compound consists of a bis(aminostyryl)benzene compound of the following formula [XX]

formula [XX]

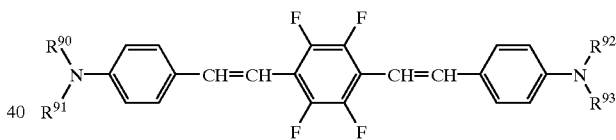

[XX]

wherein $R^{90}$, $R^{91}$, $R^{92}$ and $R^{93}$, respectively, have the same meanings as defined above.

18. A process for preparing a bis(aminostyryl)benzene compound according to claim 17, wherein at least one of $R^{90}$, $R^{91}$, $R^{92}$ and $R^{93}$ represents an aryl group of the following formula (41) and the others independently represent an unsubstituted aryl group

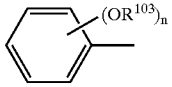

(41)

wherein at least one of $R^{103}$'s represents an alkyl or alkenyl group having from 1 to 4 carbon atoms, a cyclohexyl group or a phenyl group and the other represents a hydrogen atom, and n is an integer of 0 to 5.

19. A process for preparing a bis(aminostyryl)benzene compound according to claim 18, wherein said compound is of the following formula (42)

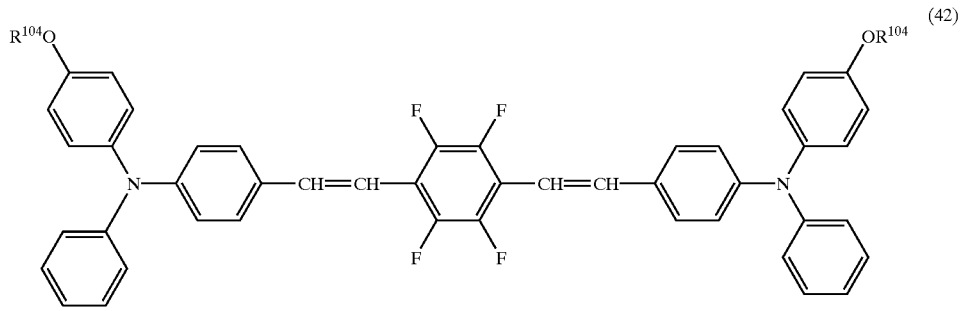

(42)

wherein at least one of $R^{104}$'s represents an alkyl or alkenyl group having from 1 to 4 carbon atoms, a cyclohexyl group or a phenyl group and the others independently represent a hydrogen atom, if present.

20. A process for preparing a bis(aminostyryl)benzene compound according to claim 16, wherein the condensation is carried out under the usual conditions of the Wadsworth-Emmons or Wittig reaction wherein said diphosphonic acid ester and/or said diphosphonium salt is treated with a base in a solvent to form a carbo anion, and said carbo anion is condensed with said 4-(N,N-diarylamino)benzaldehyde.

21. A process for preparing a bis(aminostyryl)benzene compound according to claim 17, wherein said compound is of the following structural formula (40)-1, (40)-2, (40)-3, (40)-4, (40)-5, (40)-6 or (40)-7:

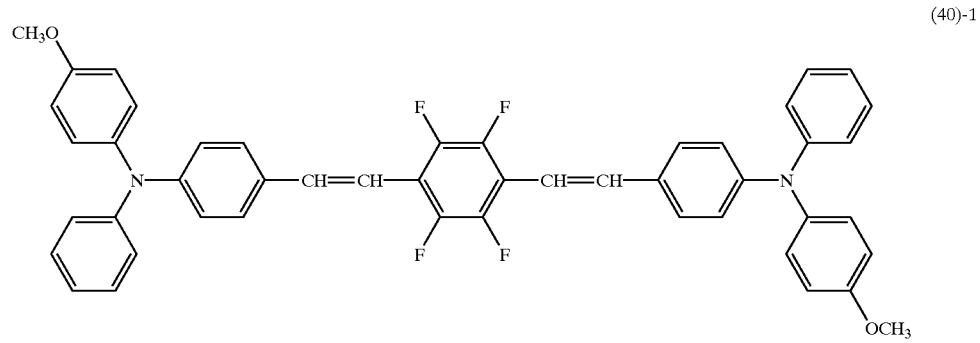

(40)-1

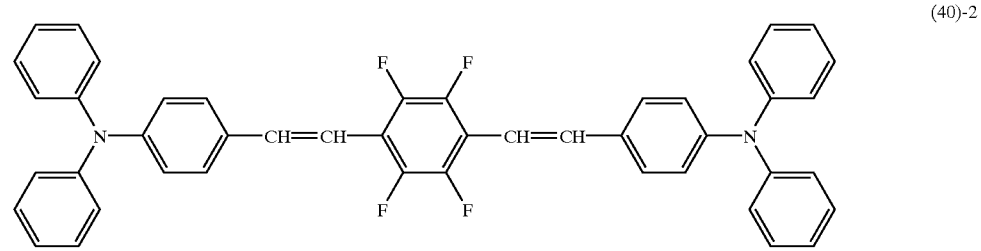

(40)-2

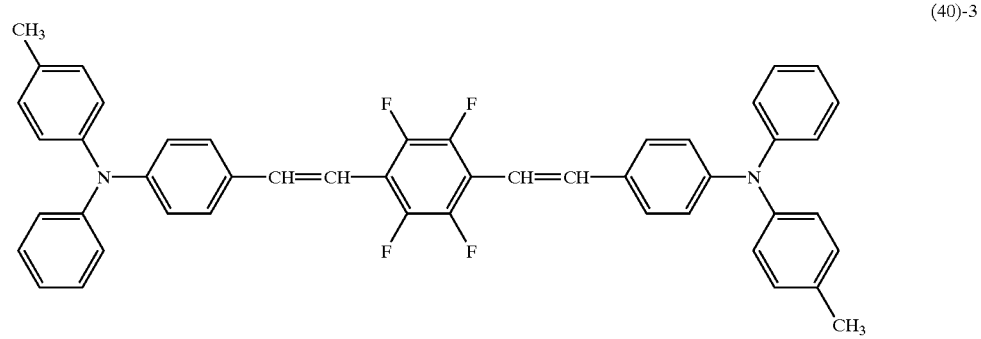

(40)-3

-continued
(40)-4
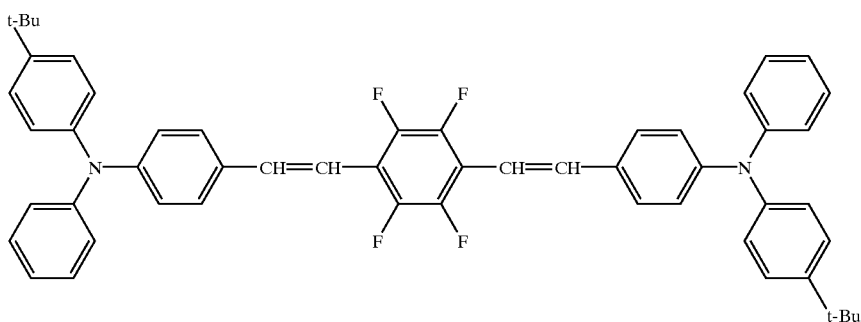
(40)-5
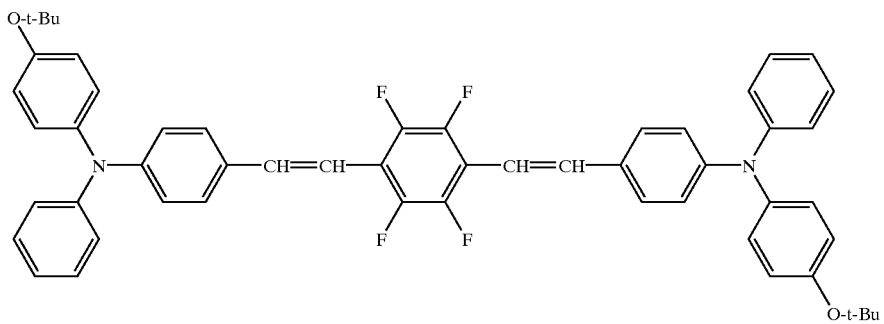
(40)-6
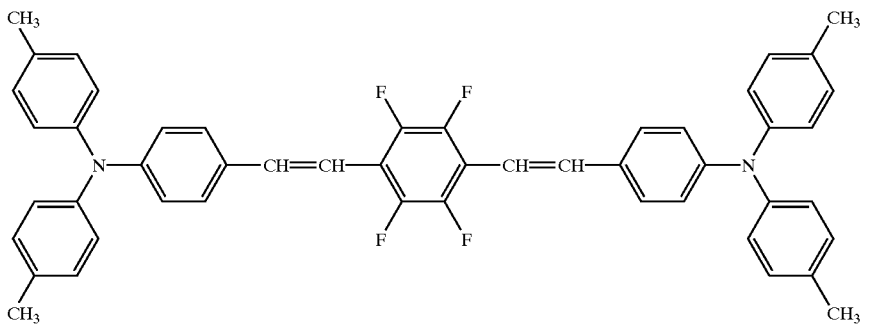
(40)-7
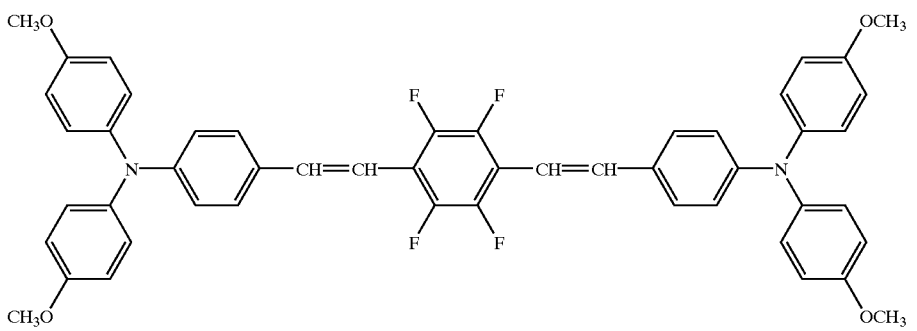
* * * * *